US012767648B2

(12) United States Patent
Lee et al.

(10) Patent No.: US 12,767,648 B2
(45) Date of Patent: Oct. 20, 2026

(54) COMPOUND FOR ORGANIC OPTOELECTRONIC ELEMENT, COMPOSITION FOR ORGANIC OPTOELECTRONIC ELEMENT, ORGANIC OPTOELECTRONIC ELEMENT, AND DISPLAY DEVICE

(71) Applicant: SAMSUNG SDI CO., LTD., Yongin-si (KR)

(72) Inventors: Byoungkwan Lee, Suwon-si (KR); Yoonman Lee, Suwon-si (KR); Sunwoong Shin, Suwon-si (KR); Sangshin Lee, Suwon-si (KR); Kipo Jang, Suwon-si (KR); Ran Namgung, Suwon-si (KR); Seungin Park, Suwon-si (KR); Sung-Hyun Jung, Suwon-si (KR); Ho Kuk Jung, Suwon-si (KR); Youngkyoung Jo, Suwon-si (KR)

(73) Assignee: Samsung SDI Co., Ltd., Yongin-si (KR)

(*) Notice: Subject to any disclaimer, the term of this patent is extended or adjusted under 35 U.S.C. 154(b) by 967 days.

(21) Appl. No.: 17/924,486

(22) PCT Filed: Sep. 1, 2021

(86) PCT No.: PCT/KR2021/011732
§ 371 (c)(1),
(2) Date: Nov. 10, 2022

(87) PCT Pub. No.: WO2022/055169
PCT Pub. Date: Mar. 17, 2022

(65) Prior Publication Data

US 2023/0183190 A1 Jun. 15, 2023

(30) Foreign Application Priority Data

Sep. 9, 2020 (KR) ........................ 10-2020-0115635

(51) Int. Cl.
*C07D 405/04* (2006.01)
*C07D 251/24* (2006.01)
(Continued)

(52) U.S. Cl.
CPC ......... *C07D 405/04* (2013.01); *C07D 251/24* (2013.01); *C07D 409/04* (2013.01);
(Continued)

(58) Field of Classification Search
CPC ............................ H10K 85/622; C07D 251/24
See application file for complete search history.

(56) References Cited

U.S. PATENT DOCUMENTS 5,061,569 A 10/1991 Vanslyke et al.
6,821,643 B1 11/2004 Hu et al.
(Continued)

FOREIGN PATENT DOCUMENTS

CN 108218664 A 6/2018
CN 108368078 A 8/2018
(Continued)

OTHER PUBLICATIONS

Machine-generated English-language translation of CN-108586188-A.*
(Continued)

*Primary Examiner* — Vu A Nguyen
(74) *Attorney, Agent, or Firm* — Lee IP Law, P.C.

(57) ABSTRACT

Disclosed are a compound for an organic optoelectronic device represented by Chemical Formula 1, a composition for an organic optoelectronic device including the same, an organic optoelectronic device and a display device.
Details of Chemical Formula 1 are as described in the specification.

13 Claims, 2 Drawing Sheets

100

(51) Int. Cl.

| | |
|---|---|
| ***C07D 409/04*** | (2006.01) |
| ***H10K 50/11*** | (2023.01) |
| ***H10K 85/60*** | (2023.01) |
| ***H10K 102/00*** | (2023.01) |

(52) U.S. Cl.

CPC ........... *H10K 50/11* (2023.02); *H10K 85/621* (2023.02); *H10K 85/622* (2023.02); *H10K 85/654* (2023.02); *H10K 85/6574* (2023.02); *H10K 85/6576* (2023.02); *H10K 2102/301* (2023.02)

(56) References Cited

U.S. PATENT DOCUMENTS

| | | | | |
|---|---|---|---|---|
| 2010/0194270 | A1 | 8/2010 | Kawamura et al. | |
| 2015/0318486 | A1 | 11/2015 | Kim et al. | |
| 2018/0019409 | A1 | 1/2018 | Ryu et al. | |
| 2018/0090689 | A1 | 3/2018 | Kim et al. | |
| 2018/0337348 | A1 | 11/2018 | Jung et al. | |
| 2019/0198772 | A1 | 6/2019 | Lui et al. | |
| 2021/0257556 | A1* | 8/2021 | Lee | H10K 85/657 |
| 2022/0033414 | A1* | 2/2022 | Jung | H10K 85/624 |
| 2022/0069228 | A1* | 3/2022 | Park | H10K 85/633 |
| 2022/0109110 | A1* | 4/2022 | Park | C07D 401/04 |
| 2022/0131083 | A1* | 4/2022 | Lee | H10K 85/6574 |
| 2022/0263031 | A1* | 8/2022 | Um | C09K 11/02 |
| 2023/0174544 | A1* | 6/2023 | Kim | C07D 409/14 257/40 |

FOREIGN PATENT DOCUMENTS

| | | | | |
|---|---|---|---|---|
| CN | 108586188 | A * | 9/2018 | C07D 311/82 |
| CN | 113277988 | A | 8/2021 | |
| JP | 1993-009471 | A | 1/1993 | |
| JP | 1995-126615 | A | 5/1995 | |
| JP | 1998-095973 | A | 4/1998 | |
| JP | 2010-138121 | A | 6/2010 | |
| JP | 5473600 | B2 | 4/2014 | |
| JP | 5709382 | B2 | 4/2015 | |
| JP | 2020-015691 | A | 1/2020 | |
| JP | 2021-125684 | A | 8/2021 | |
| JP | 2021-145126 | A | 9/2021 | |
| JP | 2021-150643 | A | 9/2021 | |
| JP | 2022-022206 | A | 2/2022 | |
| JP | 2022-032988 | A | 2/2022 | |
| KR | 10-2012-0120885 | A | 11/2012 | |
| KR | 10-1423173 | B1 | 7/2014 | |
| KR | 10-1489992 | B1 | 2/2015 | |
| KR | 10-2015-0050102 | A | 5/2015 | |
| KR | 10-2015-0140241 | A | 12/2015 | |
| KR | 10-2016-0093754 | A | 8/2016 | |
| KR | 10-2017-0096770 | A | 8/2017 | |
| KR | 10-2018-0007617 | A | 1/2018 | |
| KR | 10-1833669 | B1 | 3/2018 | |
| KR | 10-2018-0035076 | A | 4/2018 | |
| KR | 10-2018-0133772 | A | 12/2018 | |
| KR | 10-2019-0007789 | A | 1/2019 | |
| KR | 10-2019-0103765 | A | 9/2019 | |
| KR | 10-2019-0127536 | A | 11/2019 | |
| KR | 10-2020-0005489 | A | 1/2020 | |
| KR | 10-2020-0033049 | A | 3/2020 | |
| KR | 10-2020-0096169 | A | 8/2020 | |
| KR | 10-2021-0098316 | A | 8/2021 | |
| WO | WO 1995/009147 | A1 | 4/1995 | |
| WO | WO 2009/008311 | A1 | 1/2009 | |
| WO | WO 2010/058946 | A2 | 5/2010 | |
| WO | WO 2010/067894 | A1 | 6/2010 | |
| WO | WO 2010/107037 | A1 | 9/2010 | |
| WO | WO 2014/010823 | A1 | 1/2014 | |
| WO | WO 2014/054552 | A1 | 4/2014 | |
| WO | WO 2017/171420 | A1 | 10/2017 | |
| WO | WO-2020159335 | A1 * | 8/2020 | H10K 85/656 |

OTHER PUBLICATIONS

Machine-generated English-language translation of WO-2020159335-A1.*

International Search Report dated Dec. 16, 2021 for PCT/KR2021/011732.

Korean Notice of Allowance dated Jan. 20, 2025.

JP Office Action dated Feb. 26, 2024, for corresponding Japanese Patent Application No. 2023-515653.

Chinese Office action dated Aug. 1, 2024.

Japanese Office action dated Apr. 22, 2025.

Third Party Observation dated Nov. 28, 2023, of the corresponding application Korean Patent Application No. 10-2020-0115635.

European Search Report dated May 8, 2024.

Provisional double patenting rejection from U.S. Appl. No. 17/978,417 dated Jul. 7, 2026.

* cited by examiner

【Figure 1】
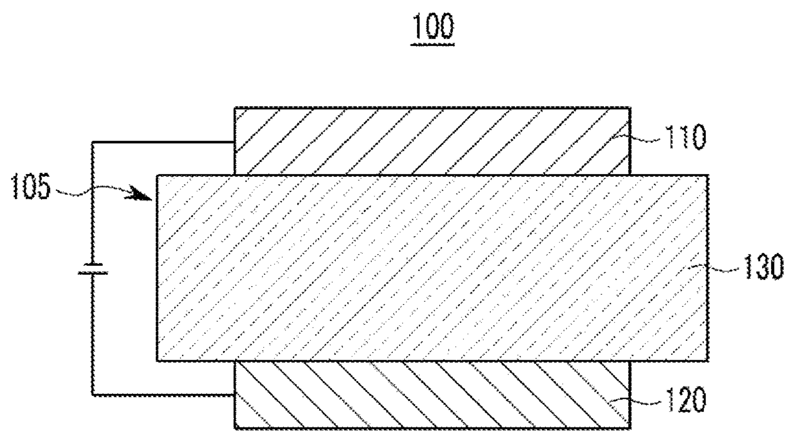
【Figure 2】
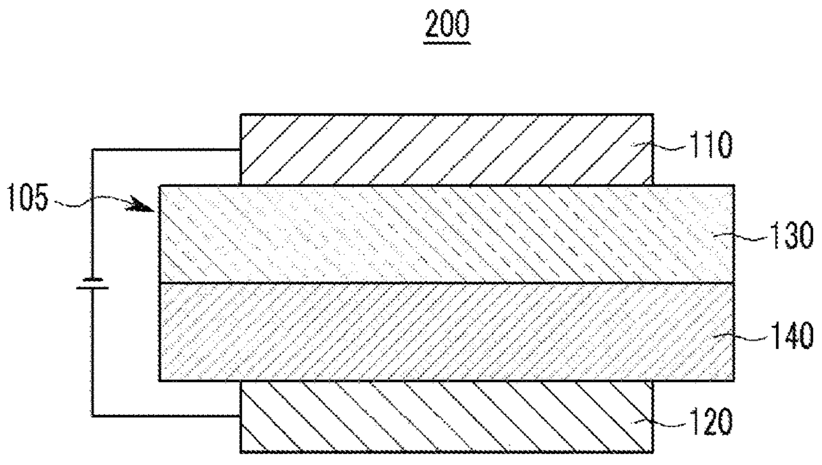

【Figure 3】
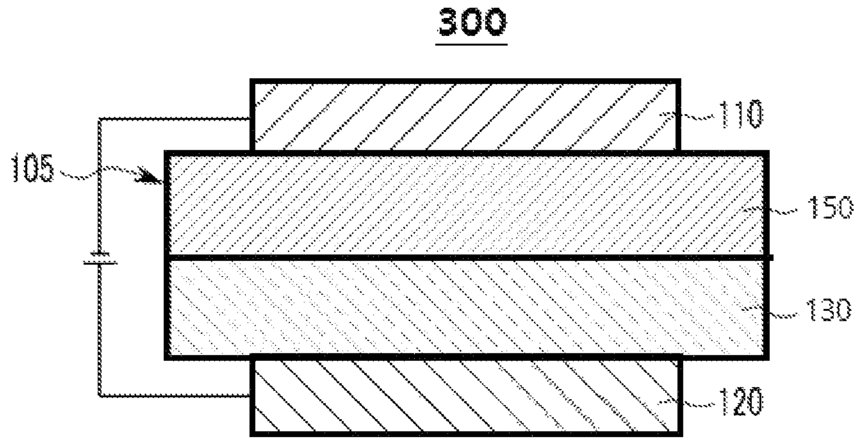
【Figure 4】
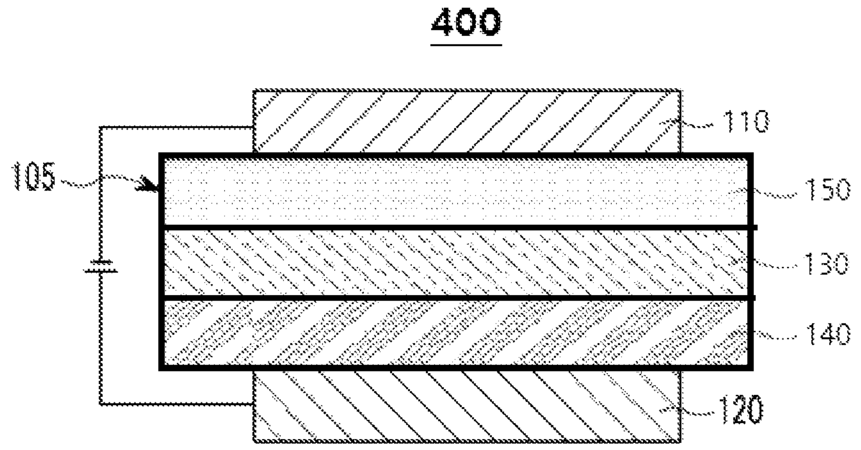

COMPOUND FOR ORGANIC OPTOELECTRONIC ELEMENT, COMPOSITION FOR ORGANIC OPTOELECTRONIC ELEMENT, ORGANIC OPTOELECTRONIC ELEMENT, AND DISPLAY DEVICE

CROSS REFERENCE TO RELATED APPLICATIONS

This is the U.S. national phase application based on PCT Application No. PCT/KR2021/011732, filed Sep. 1, 2021, which is based on Korean Patent Application No. 10-2020-0115635, filed Sep. 9, 2020, the entire contents of all of which are hereby incorporated by reference.

TECHNICAL FIELD

A compound for an organic optoelectronic device, a composition for an organic optoelectronic device, an organic optoelectronic device, and a display device are disclosed.

BACKGROUND ART

An organic optoelectronic device (organic optoelectronic diode) is a device capable of converting electrical energy and optical energy to each other.

Organic optoelectronic devices may be largely divided into two types according to a principle of operation. One is a photoelectric device that generates electrical energy by separating excitons formed by light energy into electrons and holes, and transferring the electrons and holes to different electrodes, respectively and the other is light emitting device that generates light energy from electrical energy by supplying voltage or current to the electrodes.

Examples of the organic optoelectronic device include an organic photoelectric device, an organic light emitting diode, an organic solar cell, and an organic photoconductor drum.

Among them, organic light emitting diodes (OLEDs) are attracting much attention in recent years due to increasing demands for flat panel display devices. The organic light emitting diode is a device that converts electrical energy into light, and the performance of the organic light emitting diode is greatly influenced by an organic material between electrodes.

DISCLOSURE

Technical Problem

An embodiment provides a compound for an organic optoelectronic device capable of implement an organic optoelectronic device having high efficiency and a long life-span.

Another embodiment provides a composition for an organic optoelectronic device including the compound.

Another embodiment provides an organic optoelectronic device including the compound.

Another embodiment provides a display device including the organic optoelectronic device.

Technical Solution

According to an embodiment, a compound for an organic optoelectronic device represented by Chemical Formula 1 is provided.

[Chemical Formula 1]

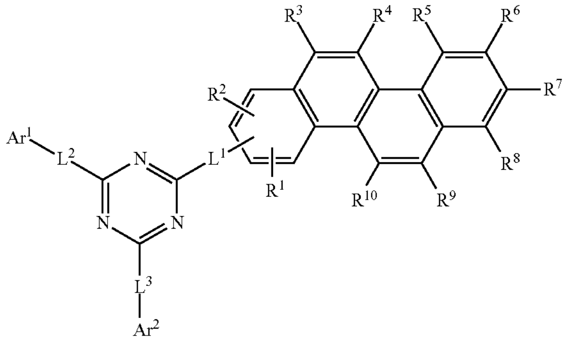

In Chemical Formula 1, $L^1$ to $L^3$ are each independently a substituted or unsubstituted C6 to C30 arylene group, $Ar^1$ and $Ar^2$ are each independently a substituted or unsubstituted C6 to C30 aryl group or a substituted or unsubstituted C2 to C30 heterocyclic group, and $R^1$ to $R^{10}$ are each independently hydrogen, deuterium, a substituted or unsubstituted C1 to C20 alkyl group, or a substituted or unsubstituted C6 to C20 aryl group.

According to another embodiment, composition for an organic optoelectronic device includes a first compound, and a second compound.

The first compound may be the aforementioned compound for an organic optoelectronic device and the second compound may be represented by Chemical Formula 2.

[Chemical Formula 2]

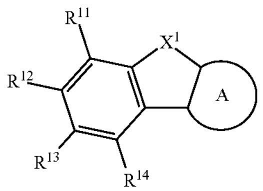

In Chemical Formula 2, $X^1$ is O, S, $NR^a$, $CR^bR^c$, or $SiR_dR_e$, $R^a$, $R^b$, $R^c$, $R^d$, $R^e$, and $R^{11}$ to $R^{14}$ are each independently hydrogen, deuterium, a substituted or unsubstituted amine group, a substituted or unsubstituted C1 to C30 alkyl group, a substituted or unsubstituted C6 to C30 aryl group or a substituted or unsubstituted C2 to C30 heterocyclic group, A is any one selected from the rings of Group II and Group III,

[Group II]

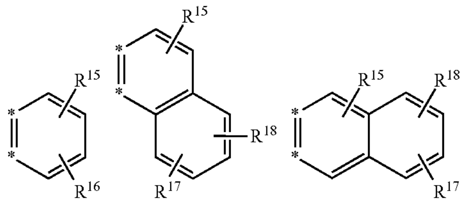

-continued

[Group III]

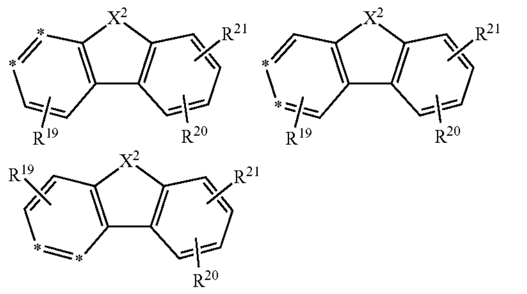

In Group II and Group III,

* is a linking point, $X^2$ is O, S, $NR^f$, $CR^gR^h$, or $SiR^iR^j$, $R^f$, $R^g$, $R^h$, $R^i$, $R^j$, and $R^{15}$ to $R^{21}$ are each independently hydrogen, deuterium, a substituted or unsubstituted amine group, a substituted or unsubstituted C1 to C30 alkyl group, a substituted or unsubstituted C6 to C30 aryl group or a substituted or unsubstituted C2 to C30 heterocyclic group, and at least one of $R^{11}$ to $R^{14}$ and $R^{11}$ to $R^{21}$ is a group represented by Chemical Formula a,

[Chemical Formula a]

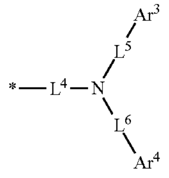

wherein, in Chemical Formula a, $L^4$ to $L^6$ are each independently a single bond, or a substituted or unsubstituted C6 to C30 arylene group, $Ar^3$ and $Ar^4$ are each independently a substituted or unsubstituted amine group, a substituted or unsubstituted C6 to C30 aryl group, or a substituted or unsubstituted C2 to C30 heterocyclic group, and

* is a linking point.

According to another embodiment, an organic optoelectronic device includes an anode and a cathode facing each other, and at least one organic layer between the anode and the cathode, wherein the organic layer includes the compound for an organic optoelectronic device or the composition for an organic optoelectronic device.

According to another embodiment, a display device including the organic optoelectronic device is provided.

Advantageous Effects

An organic optoelectronic device having high efficiency and a long life-span may be realized.

DESCRIPTION OF THE DRAWINGS

FIGS. 1 to 4 are cross-sectional views each illustrating an organic light emitting diode according to embodiments.

DESCRIPTION OF SYMBOLS

100, 200, 300, 400: organic light emitting diode
105: organic layer
110: cathode
120: anode
130: light emitting layer
140: hole transport region
150: electron transport region

BEST MODE

Hereinafter, embodiments of the present invention are described in detail. However, these embodiments are exemplary, the present invention is not limited thereto and the present invention is defined by the scope of claims.

In the present specification, when a definition is not otherwise provided, "substituted" refers to replacement of at least one hydrogen of a substituent or a compound by deuterium, a halogen, a hydroxyl group, an amino group, a substituted or unsubstituted C1 to C30 amine group, a nitro group, a substituted or unsubstituted C1 to C40 silyl group, a C1 to C30 alkyl group, a C1 to C10 alkylsilyl group, a C6 to C30 arylsilyl group, a C3 to C30 cycloalkyl group, a C3 to C30 heterocycloalkyl group, a C6 to C30 aryl group, a C2 to C30 heteroaryl group, a C1 to C20 alkoxy group, a C1 to C10 trifluoroalkyl group, a cyano group, or a combination thereof.

In one example of the present invention, the "substituted" refers to replacement of at least one hydrogen of a substituent or a compound by deuterium, a C1 to C30 alkyl group, a C1 to C10 alkylsilyl group, a C6 to C30 arylsilyl group, a C3 to C30 cycloalkyl group, a C3 to C30 heterocycloalkyl group, a C6 to C30 aryl group, a C2 to C30 heteroaryl group, or a cyano group. In specific example of the present invention, the "substituted" refers to replacement of at least one hydrogen of a substituent or a compound by deuterium, a C1 to C20 alkyl group, a C6 to C30 aryl group, or a cyano group. In specific example of the present invention, the "substituted" refers to replacement of at least one hydrogen of a substituent or a compound by deuterium, a C1 to C5 alkyl group, a C6 to C18 aryl group, or a cyano group. In specific example of the present invention, the "substituted" refers to replacement of at least one hydrogen of a substituent or a compound by deuterium, a cyano group, a methyl group, an ethyl group, a propanyl group, a butyl group, a phenyl group, a biphenyl group, a terphenyl group, or a naphthyl group.

In the present specification, when a definition is not otherwise provided, "hetero" refers to one including one to three heteroatoms selected from N, O, S, P, and Si, and remaining carbons in one functional group.

In the present specification, "an aryl group" refers to a group including at least one hydrocarbon aromatic moiety, and all elements of the hydrocarbon aromatic moiety have p-orbitals which form conjugation, for example a phenyl group, a naphthyl group, and the like, two or more hydrocarbon aromatic moieties may be linked by a sigma bond and may be, for example a biphenyl group, a terphenyl group, a quarterphenyl group, and the like, and two or more hydrocarbon aromatic moieties are fused directly or indirectly to provide a non-aromatic fused ring, for example a fluorenyl group.

The aryl group may include a monocyclic, polycyclic, or fused ring polycyclic (i.e., rings sharing adjacent pairs of carbon atoms) functional group.

In the present specification, "a heterocyclic group" is a generic concept of a heteroaryl group, and may include at least one heteroatom selected from N, O, S, P, and Si instead of carbon (C) in a cyclic compound such as an aryl group, a cycloalkyl group, a fused ring thereof, or a combination thereof. When the heterocyclic group is a fused ring, the entire ring or each ring of the heterocyclic group may include one or more heteroatoms.

For example, "a heteroaryl group" may refer to an aryl group including at least one heteroatom selected from N, O, S, P, and Si. Two or more heteroaryl groups are linked by a sigma bond directly, or when the heteroaryl group includes two or more rings, the two or more rings may be fused. When the heteroaryl group is a fused ring, each ring may include one to three heteroatoms.

More specifically, the substituted or unsubstituted C6 to C30 aryl group may be a substituted or unsubstituted phenyl group, a substituted or unsubstituted naphthyl group, a substituted or unsubstituted anthracenyl group, a substituted or unsubstituted phenanthrenyl group, a substituted or unsubstituted naphthacenyl group, a substituted or unsubstituted pyrenyl group, a substituted or unsubstituted biphenyl group, a substituted or unsubstituted p-terphenyl group, a substituted or unsubstituted m-terphenyl group, a substituted or unsubstituted o-terphenyl group, a substituted or unsubstituted chrysenyl group, a substituted or unsubstituted triphenylene group, a substituted or unsubstituted perylenyl group, a substituted or unsubstituted fluorenyl group, a substituted or unsubstituted indenyl group, a substituted or unsubstituted furanyl group, or combination thereof, but is not limited thereto.

More specifically, the substituted or unsubstituted C2 to C30 heterocyclic group may be a substituted or unsubstituted thiophenyl group, a substituted or unsubstituted pyrrolyl group, a substituted or unsubstituted pyrazolyl group, a substituted or unsubstituted imidazolyl group, a substituted or unsubstituted triazolyl group, a substituted or unsubstituted oxazolyl group, a substituted or unsubstituted thiazolyl group, a substituted or unsubstituted oxadiazolyl group, a substituted or unsubstituted thiadiazolyl group, a substituted or unsubstituted pyridyl group, a substituted or unsubstituted pyrimidinyl group, a substituted or unsubstituted pyrazinyl group, a substituted or unsubstituted triazinyl group, a substituted or unsubstituted benzofuranyl group, a substituted or unsubstituted benzothiophenyl group, a substituted or unsubstituted benzimidazolyl group, a substituted or unsubstituted indolyl group, a substituted or unsubstituted quinolinyl group, a substituted or unsubstituted isoquinolinyl group, a substituted or unsubstituted quinazolinyl group, a substituted or unsubstituted quinoxalinyl group, a substituted or unsubstituted naphthyridinyl group, a substituted or unsubstituted benzoxazinyl group, a substituted or unsubstituted benzthiazinyl group, a substituted or unsubstituted acridinyl group, a substituted or unsubstituted phenazinyl group, a substituted or unsubstituted phenothiazinyl group, a substituted or unsubstituted phenoxazinyl group, a substituted or unsubstituted carbazolyl group, a substituted or unsubstituted dibenzofuranyl group, or a substituted or unsubstituted dibenzothiophenyl group, or a combination thereof, but is not limited thereto.

In the present specification, hole characteristics refer to an ability to donate an electron to form a hole when an electric field is applied and that a hole formed in the anode may be easily injected into the light emitting layer and transported in the light emitting layer due to conductive characteristics according to a highest occupied molecular orbital (HOMO) level.

In addition, electron characteristics refer to an ability to accept an electron when an electric field is applied and that electron formed in the cathode may be easily injected into the light emitting layer and transported in the light emitting layer due to conductive characteristics according to a lowest unoccupied molecular orbital (LUMO) level.

Hereinafter, a compound for an organic optoelectronic device according to an embodiment is described.

A compound for an organic optoelectronic device according to an embodiment is represented by Chemical Formula 1.

[Chemical Formula 1]

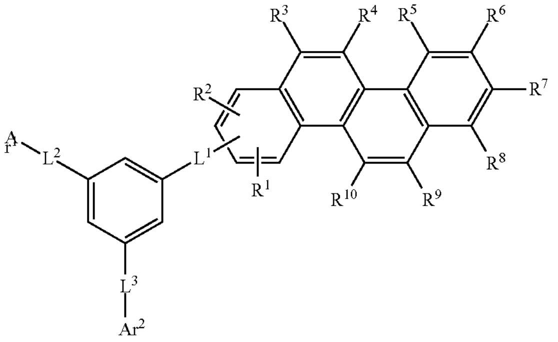

In Chemical Formula 1, $L^1$ to $L^3$ are each independently a single bond, or a substituted or unsubstituted C6 to C30 arylene group, $Ar^1$ and $Ar^2$ are each independently a substituted or unsubstituted C6 to C30 aryl group or a substituted or unsubstituted C2 to C30 heterocyclic group, and $R^1$ to $R^{10}$ are each independently hydrogen, deuterium, a substituted or unsubstituted C1 to C20 alkyl group, or a substituted or unsubstituted C6 to C20 aryl group.

The compound represented by Chemical Formula 1 has a structure in which chrysene is substituted with triazine at the terminal end.

As the chrysene is substituted with triazine at the terminal end, the molecule becomes stable as the conjugation length becomes longer compared with that linked to the center, and thus the molecule may have a long life-span effect. In addition, the life-span may be further maximized by strengthening the stabilization of the rings by fusion of the aromatic rings.

Chemical Formula 1 may be represented by any one of Chemical Formula 1-1 to Chemical Formula 1-4 depending on the specific substitution point of the triazine.

[Chemical Formula 1-1]

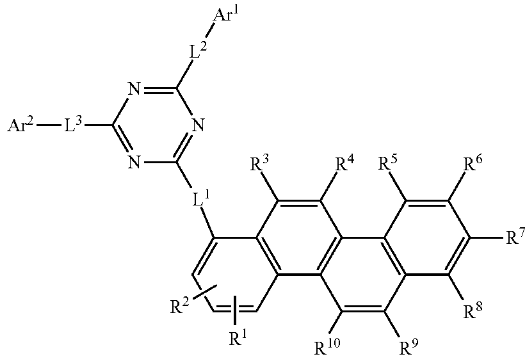

-continued

[Chemical Formula 1-2]

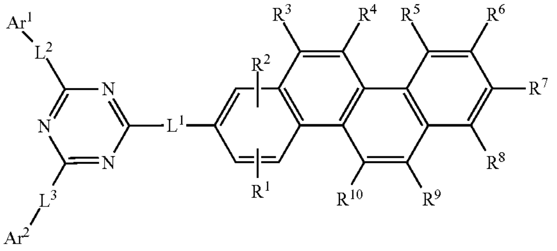

[Chemical Formula 1-3]

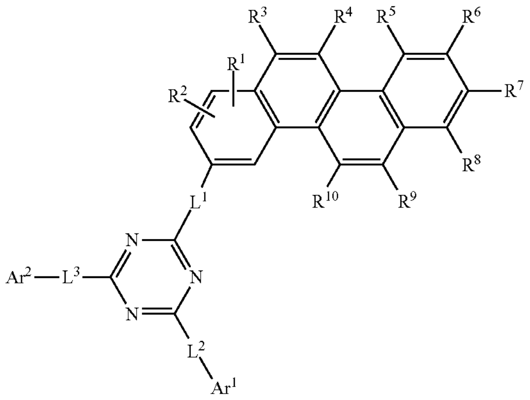

[Chemical Formula 1-4]

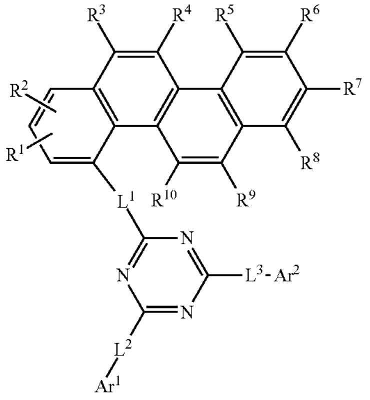

In Chemical Formula 1-1 to Chemical Formula 1-4, $L^1$ to $L^3$, $Ar^1$ and $Ar^2$, and $R^1$ to $R^{10}$ are the same as described above.

The compound for an organic optoelectronic device according to an embodiment may be represented by any one of Chemical Formula 1-1, Chemical Formula 1-2 and Chemical Formula 1-4.

In an embodiment of the present invention, at least one of $Ar^1$ and $Ar^2$ may be a substituted or unsubstituted C10 to C30 aryl group, a substituted or unsubstituted dibenzofuranyl group, or a substituted or unsubstituted dibenzothiophenyl group.

In a more specific embodiment of the present invention, at least one of $Ar^1$ and $Ar^2$ may be a substituted or unsubstituted naphthyl group, a substituted or unsubstituted phenanthrenyl group, a substituted or unsubstituted biphenyl group, a substituted or unsubstituted dibenzofuranyl group, or a substituted or unsubstituted dibenzothiophenyl group.

In an example embodiment of the present invention, $L^1$ to $L^3$ may each independently be a single bond or a substituted or unsubstituted phenylene group.

For example, $L^1$ may be a single bond, $Ar^1$ and $Ar^2$ may each independently be a substituted or unsubstituted phenyl group, a substituted or unsubstituted naphthyl group, a substituted or unsubstituted phenanthrenyl group, a substituted or unsubstituted biphenyl group, a substituted or unsubstituted dibenzofuranyl group, or a substituted or unsubstituted dibenzothiophenyl group, and at least one of $Ar^1$ and $Ar^2$ may be a substituted or unsubstituted naphthyl group, a substituted or unsubstituted phenanthrenyl group, a substituted or unsubstituted biphenyl group, a substituted or unsubstituted dibenzofuranyl group, or a substituted or unsubstituted dibenzothiophenyl group.

For example, $L^1$ may be a substituted or unsubstituted phenylene group, and $Ar^1$ and $Ar^2$ may each independently be a substituted or unsubstituted phenyl group, a substituted or unsubstituted naphthyl group, a substituted or unsubstituted phenanthrenyl group, a substituted or unsubstituted biphenyl group, a substituted or unsubstituted dibenzofuranyl group, or a substituted or unsubstituted dibenzothiophenyl group.

As a more specific example, each of $*-L^2-Ar^1$ and $*-L^3-Ar^2$ may be independently selected from the substituents of Group I.

[Group I]

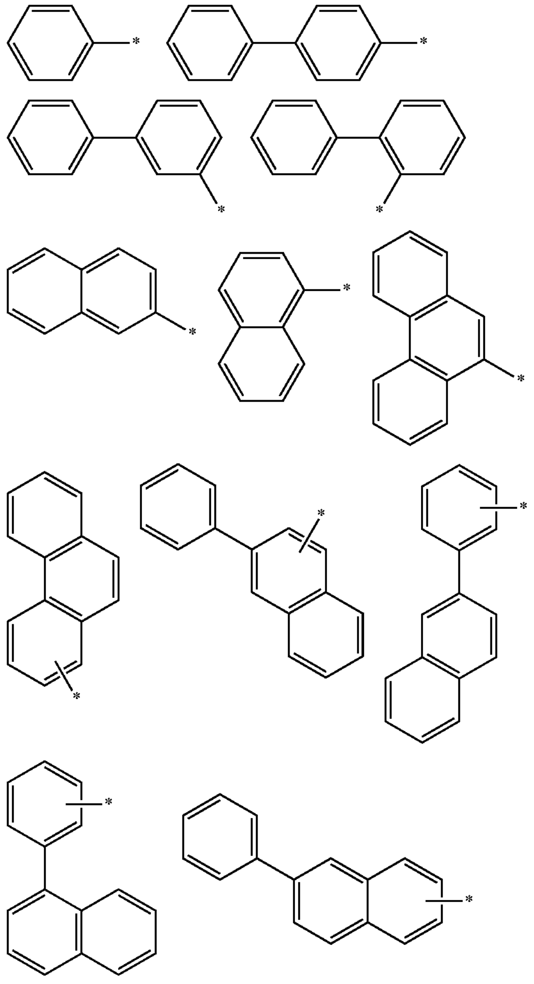

-continued
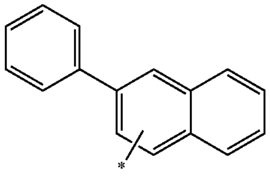
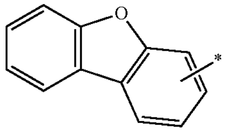
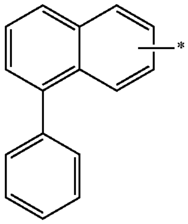
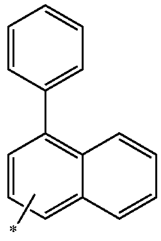
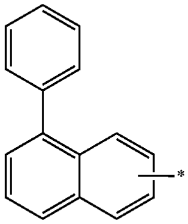
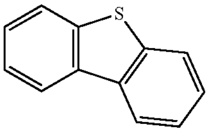
In Group I, * is a linking point.
For example, the compound for an organic optoelectronic device represented by Chemical Formula 1 may be one selected from the compounds of Group 1, but is not limited thereto.
[Group 1]
[1]
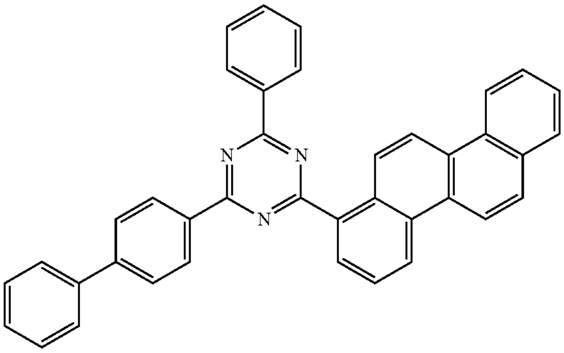
[2]
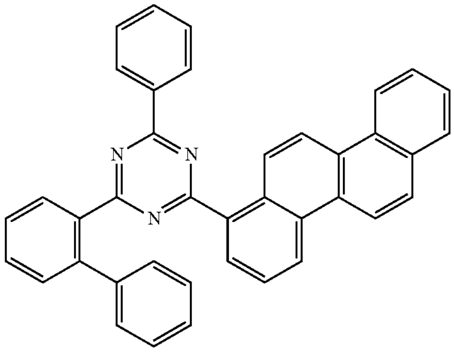
-continued
[3]
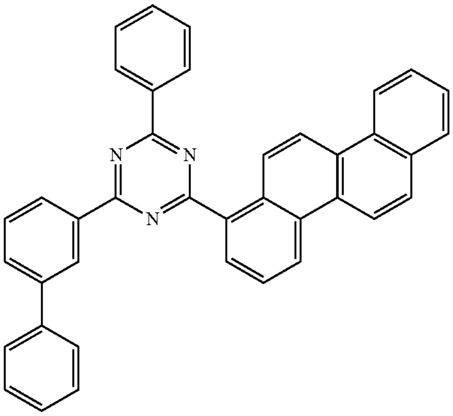
[4]
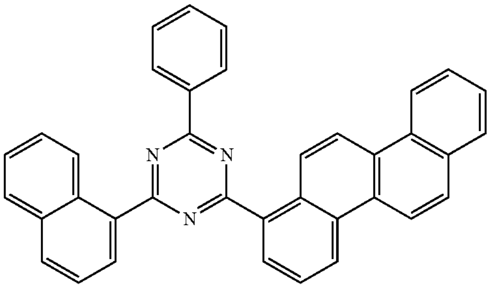
[5]
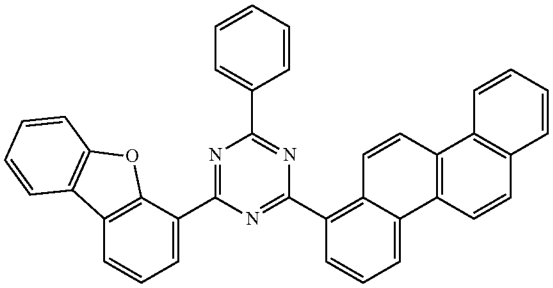
[6]
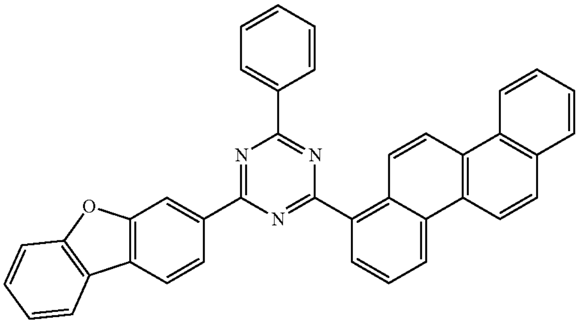

-continued
[7]
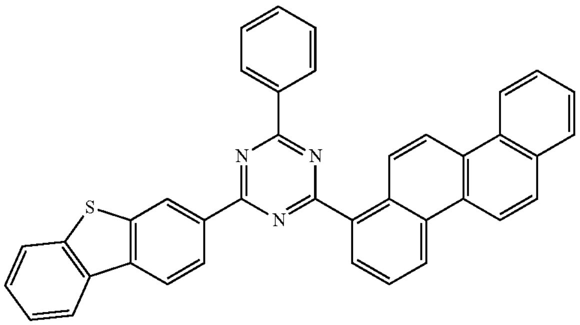
[8]
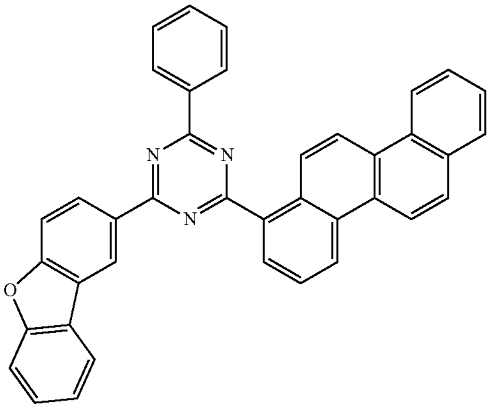
[9]
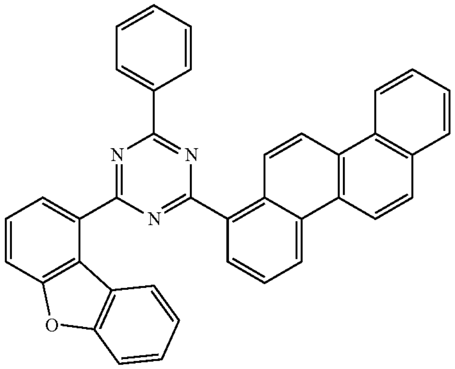
[10]
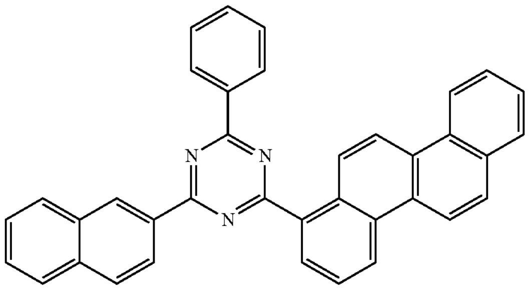
-continued
[11]
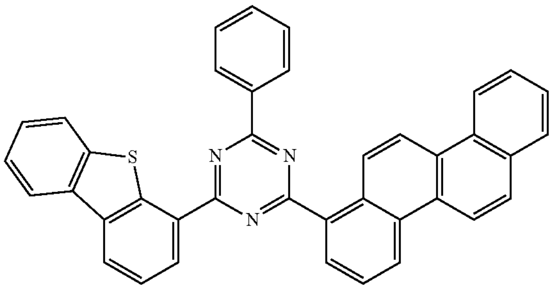
[12]
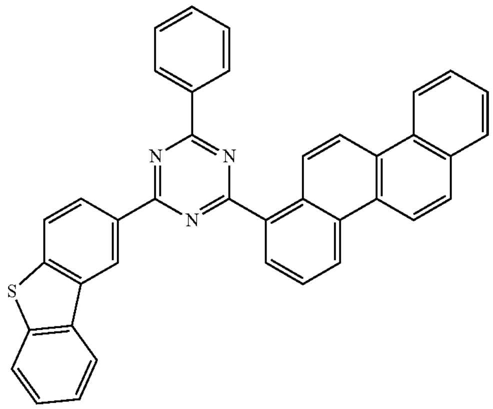
[13]
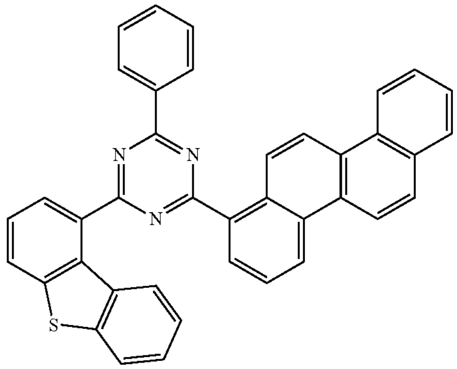
[14]
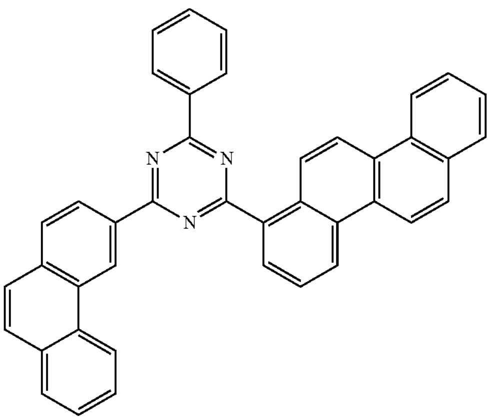

-continued
[15]
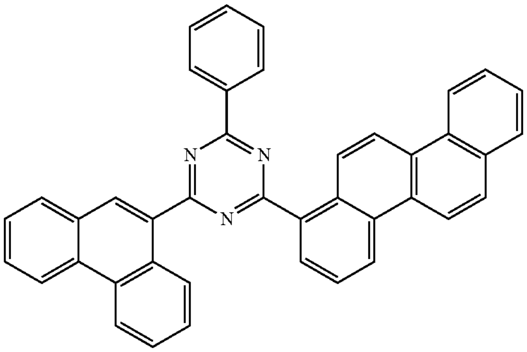
[16]
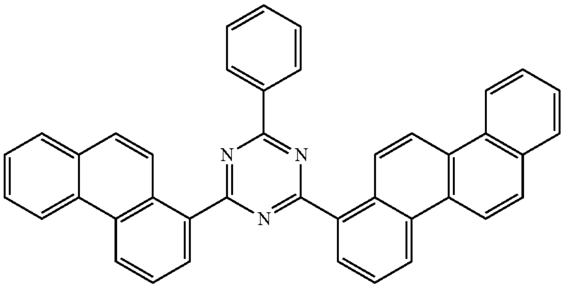
[17]
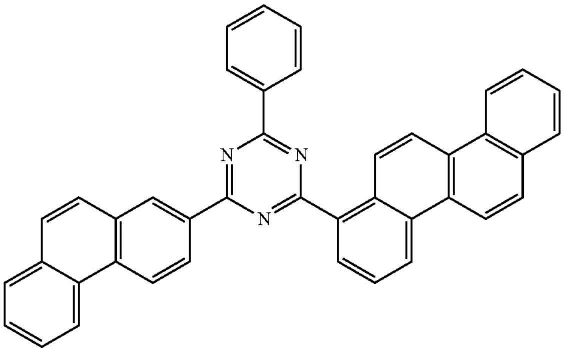
[18]
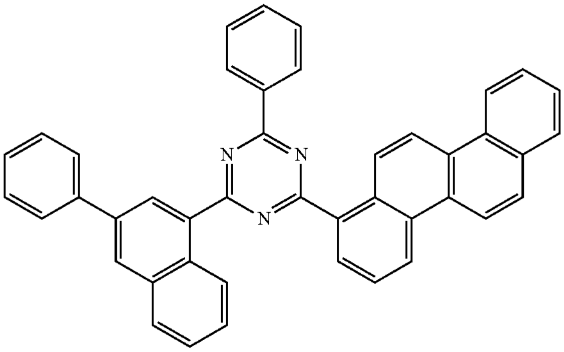
-continued
[19]
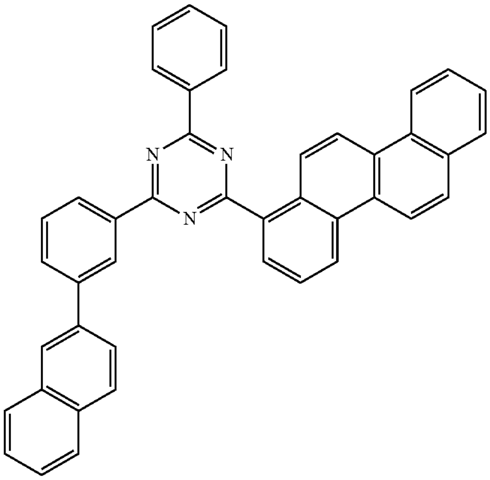
[20]
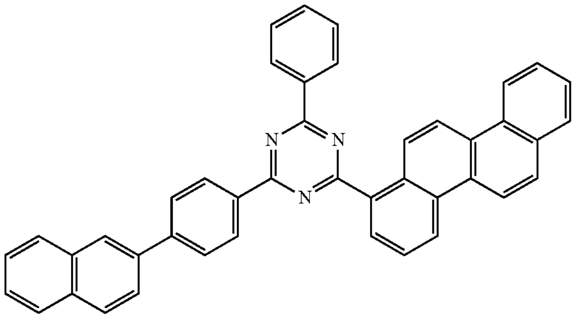
[21]
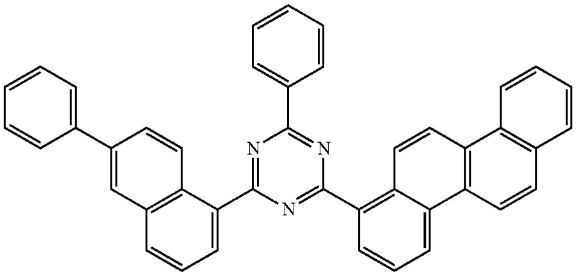
[22]
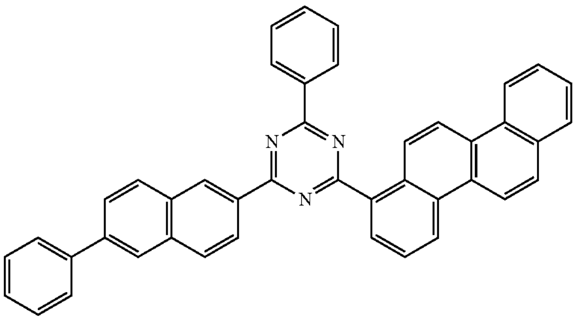

[23]
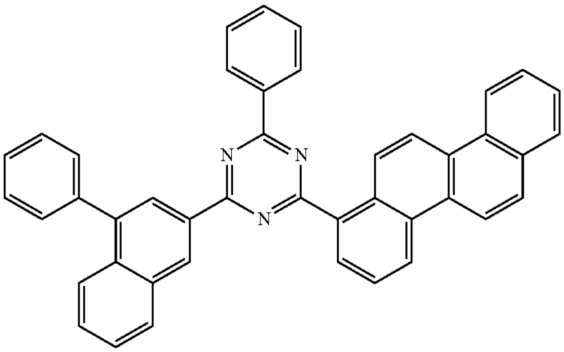
[24]
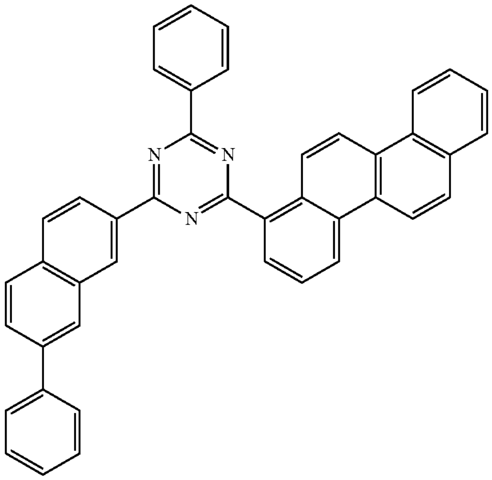
[25]
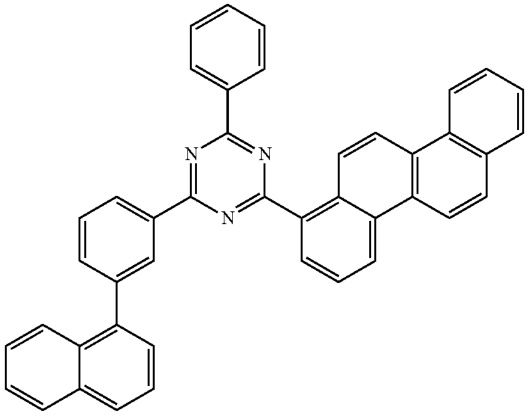
[26]
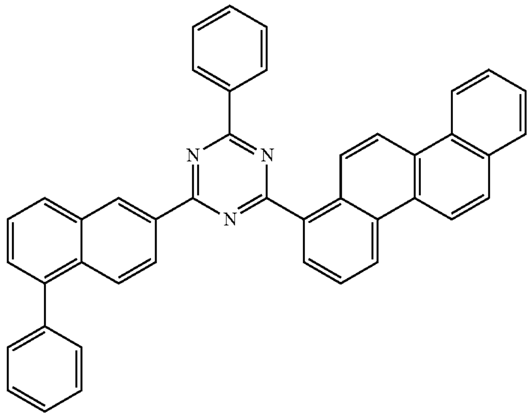
[27]
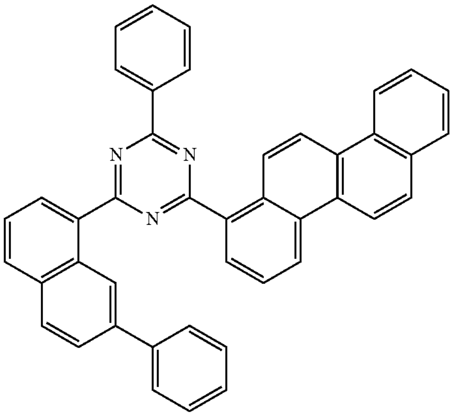
[28]
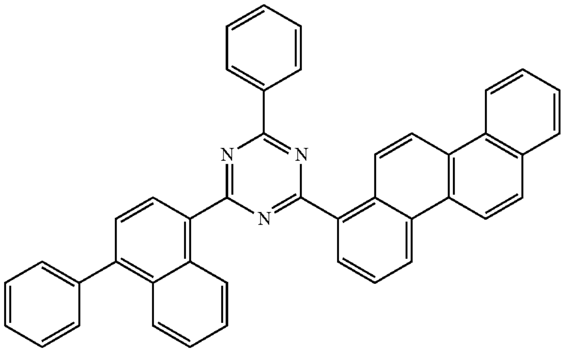
[29]
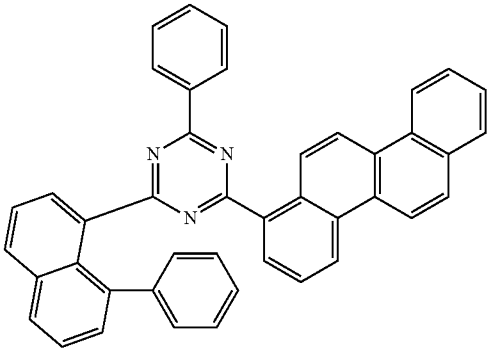

-continued
[30]
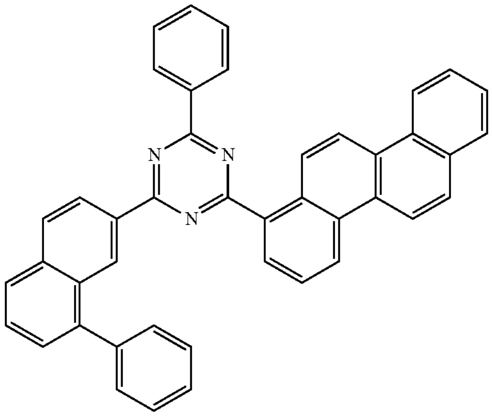
[31]
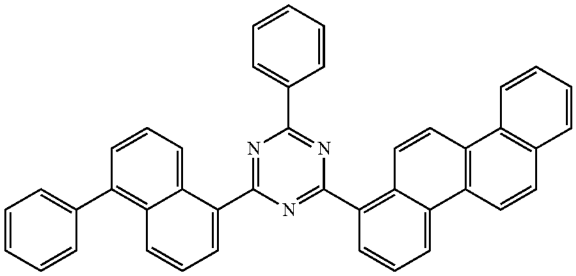
[32]
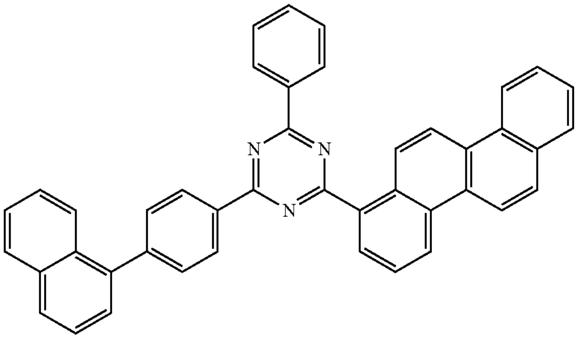
[33]
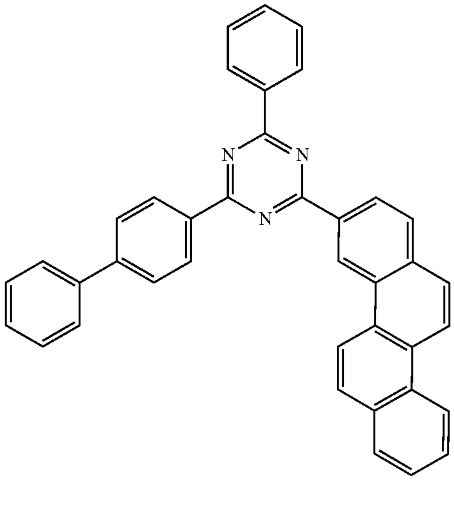
-continued
[34]
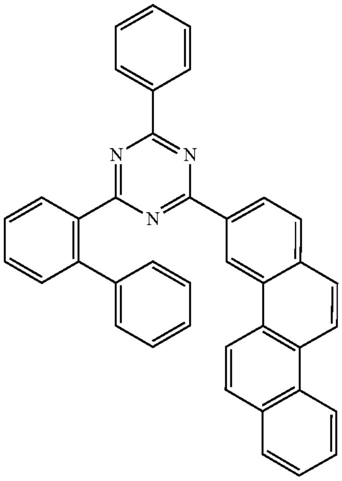
[35]
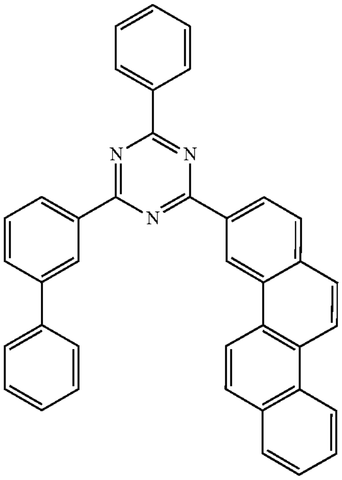
[37]
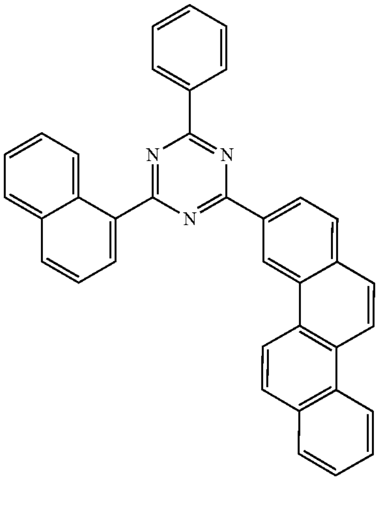

-continued
[38]
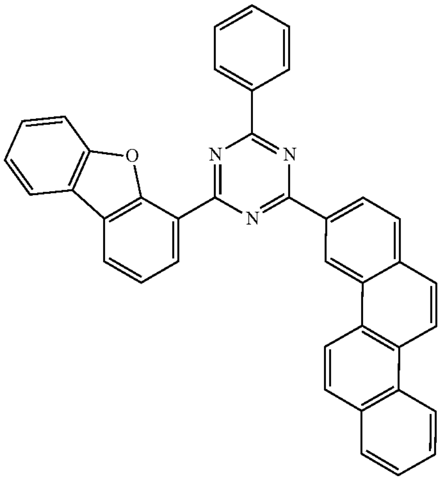
[39]
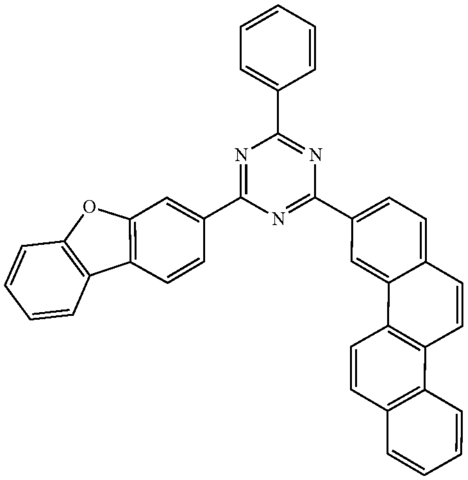
[40]
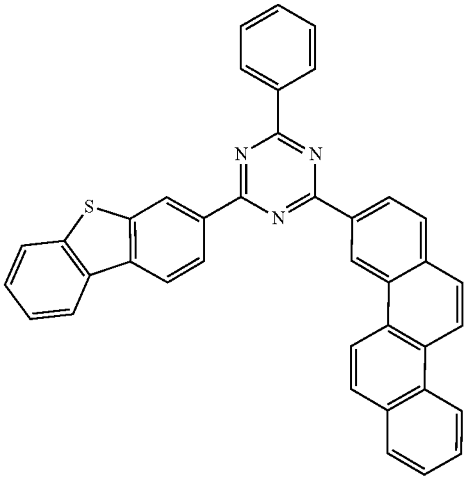
-continued
[41]
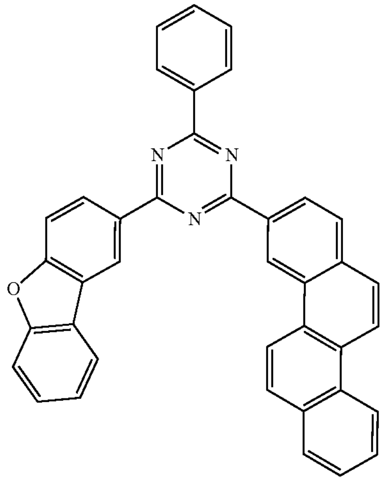
[42]
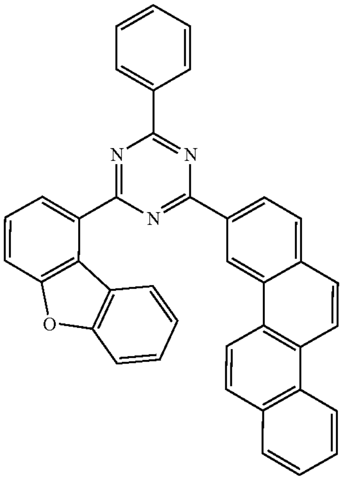
[43]
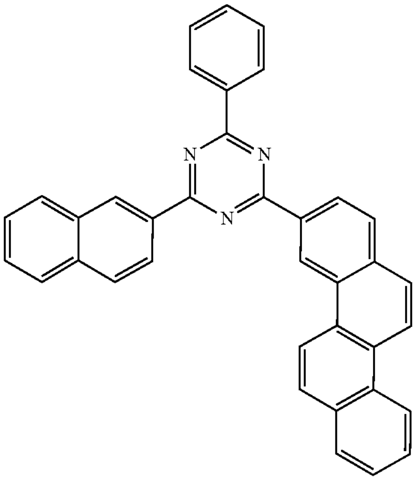

-continued
[44]
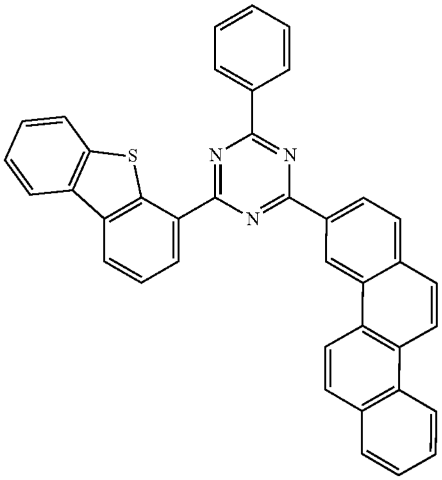
[45]
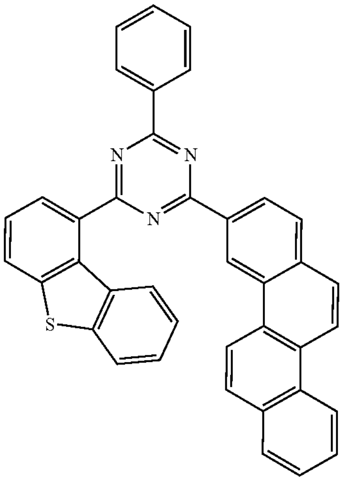
[46]
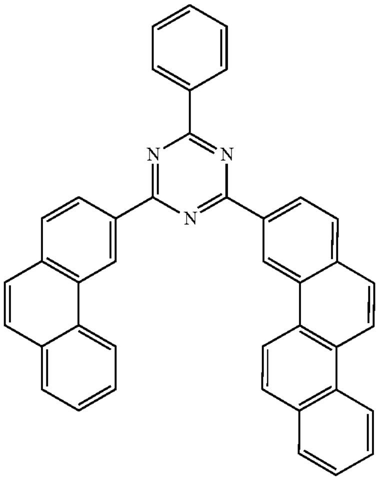
-continued
[47]
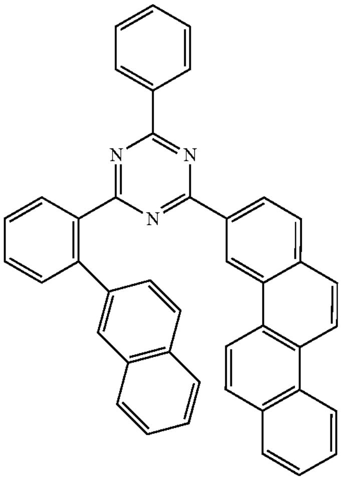
[48]
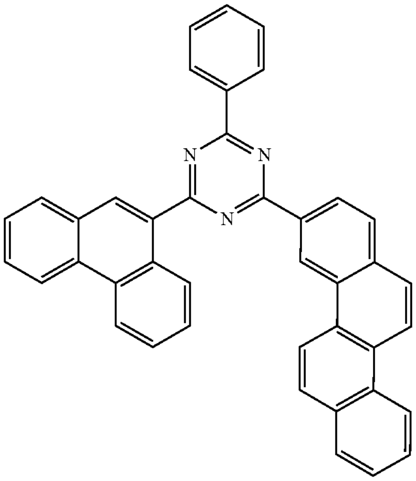
[49]
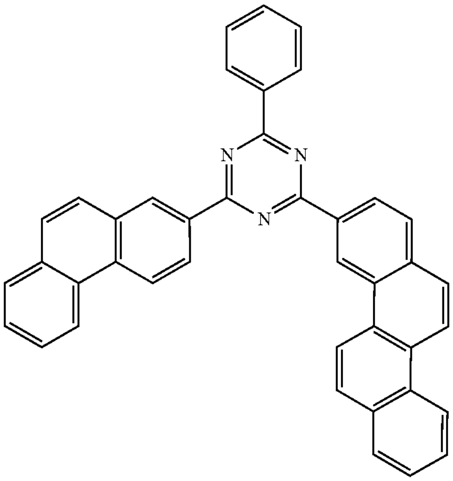

-continued
[50]
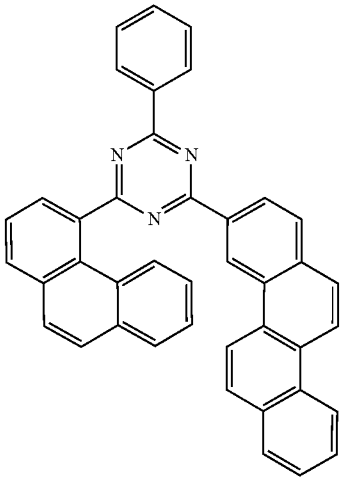
[51]
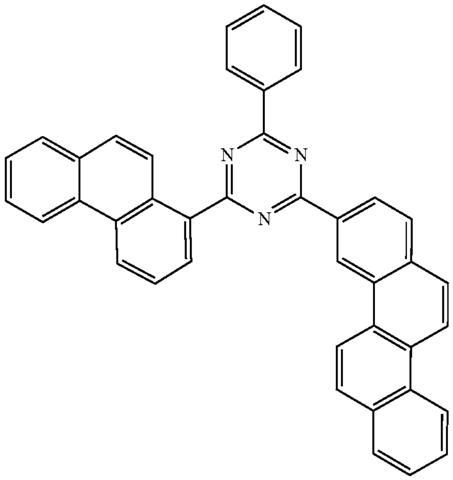
52
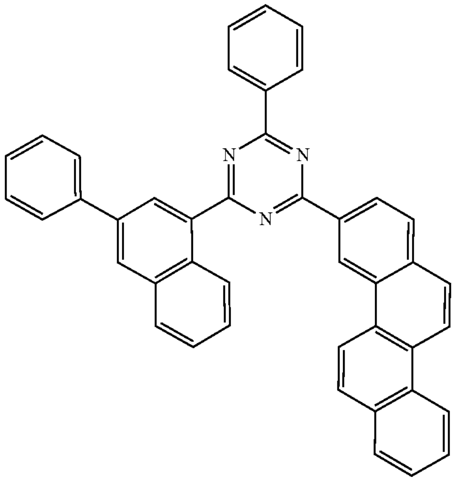
-continued
53
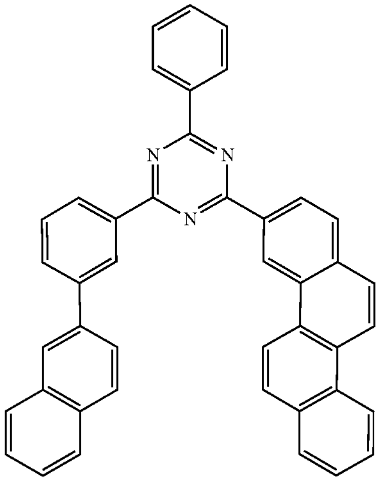
54
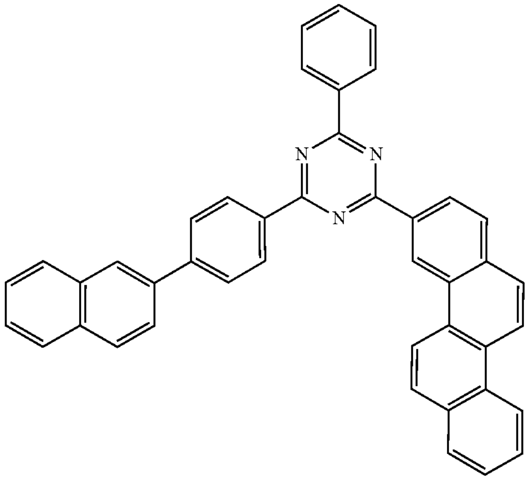
[55]
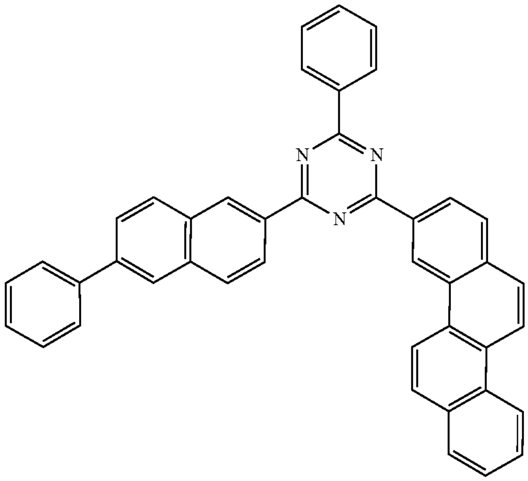

-continued
[56]
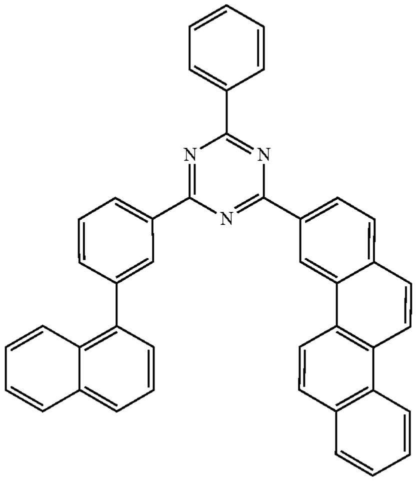
[57]
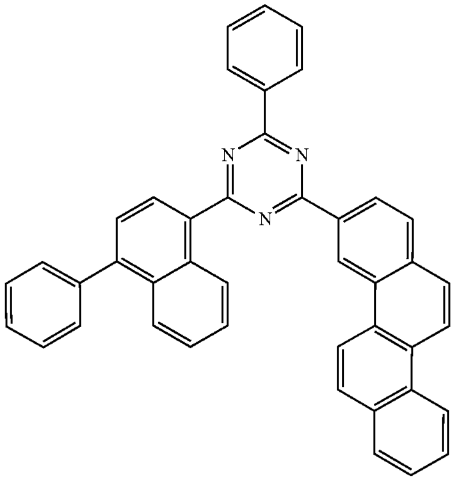
[58]
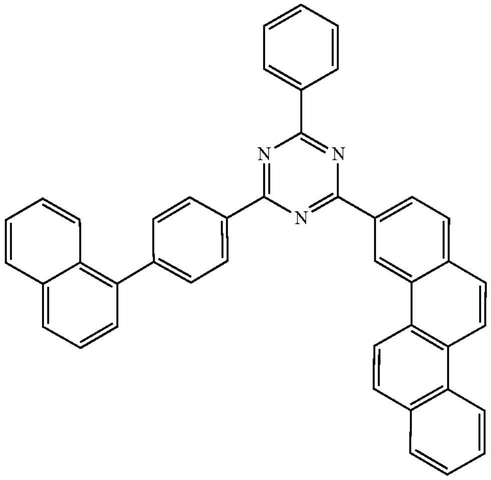
-continued
[59]
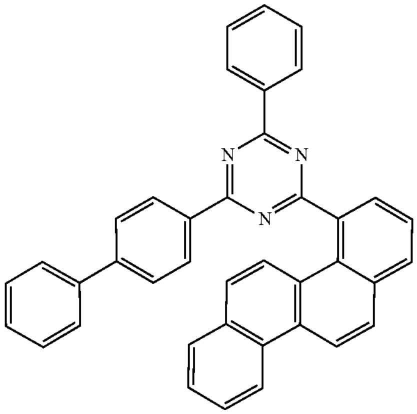
[60]
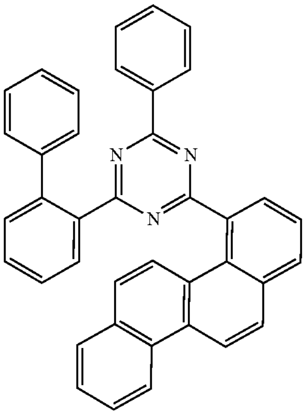
[61]
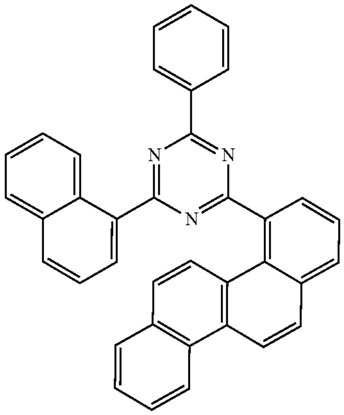

-continued
[62]
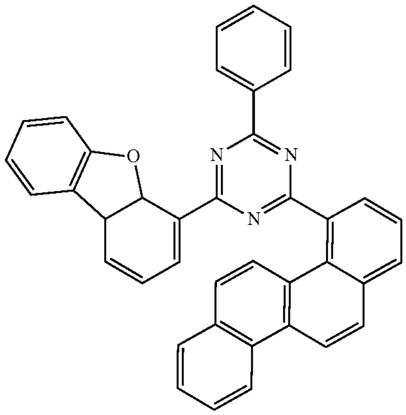
[63]
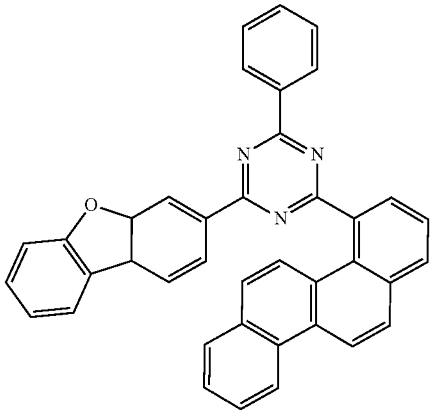
[64]
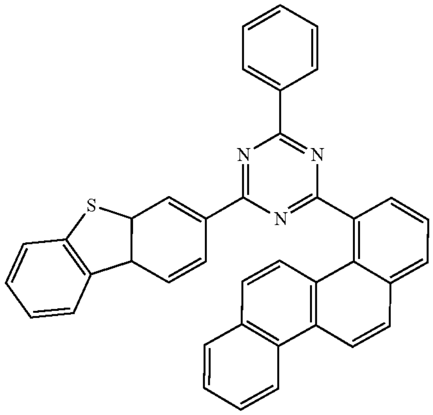
-continued
[65]
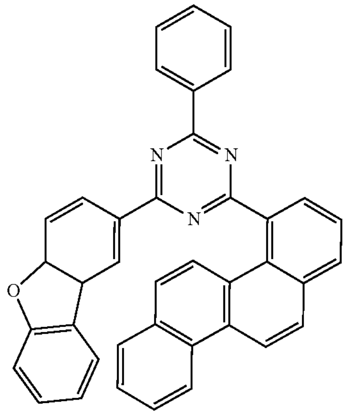
[66]
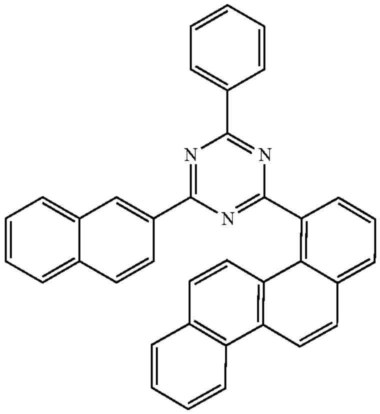
[67]
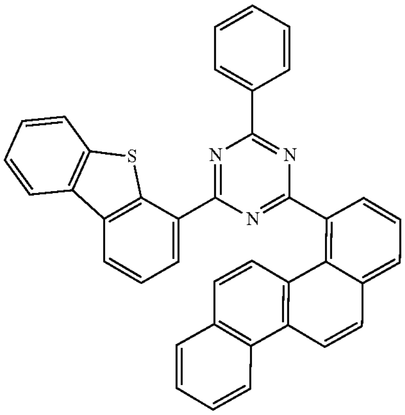

-continued
[68]
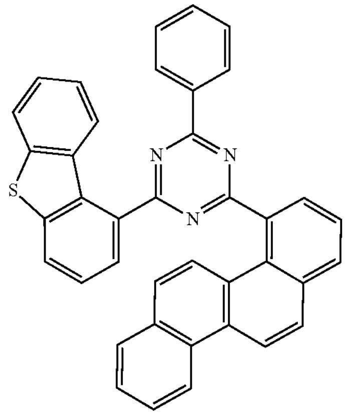
[69]
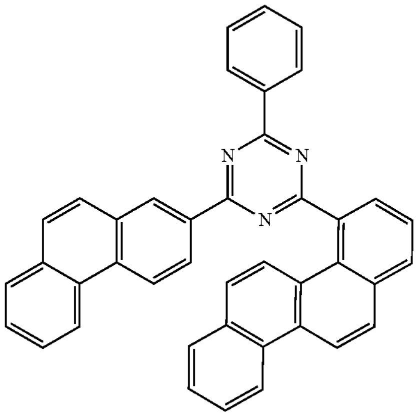
[70]
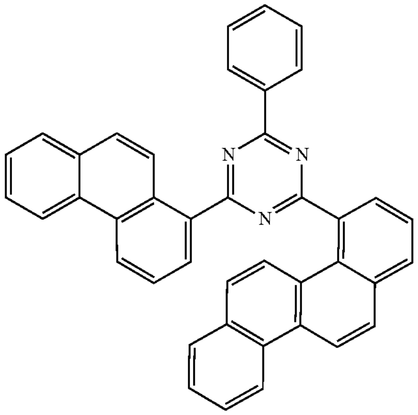
-continued
[71]
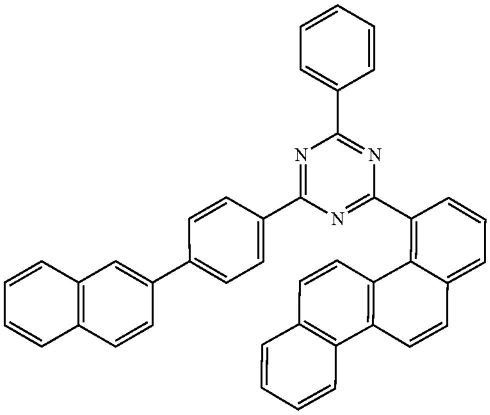
[72]
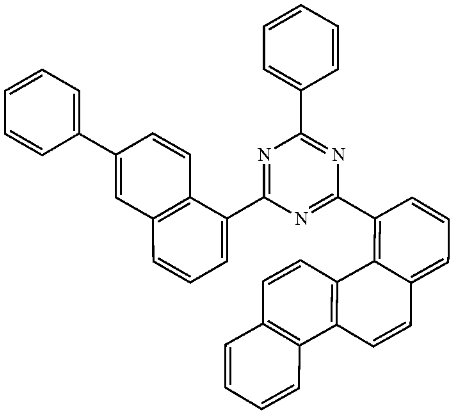
[73]
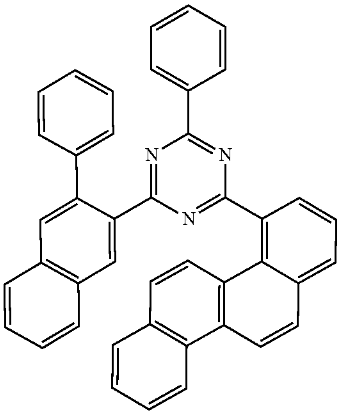

-continued
[74]
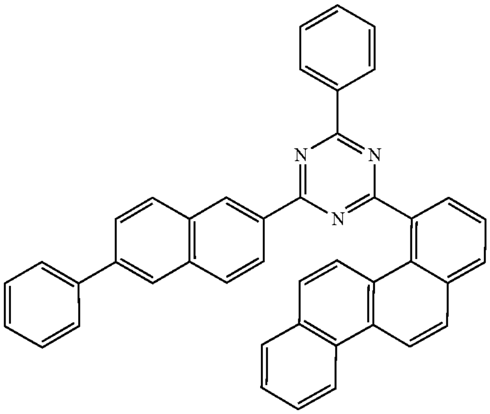
[75]
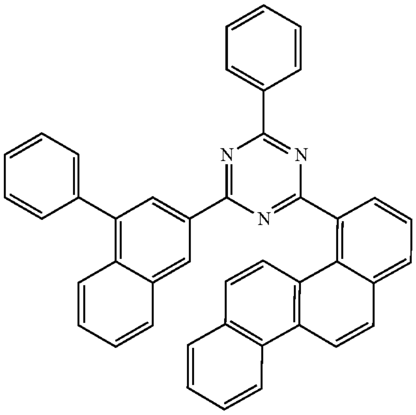
[76]
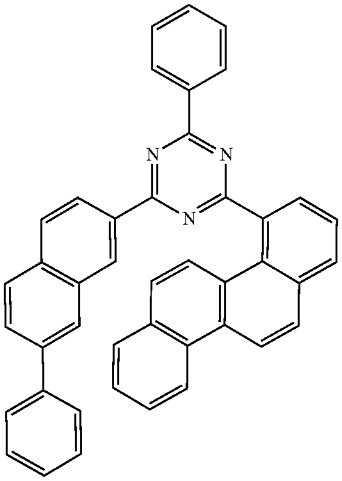
-continued
[77]
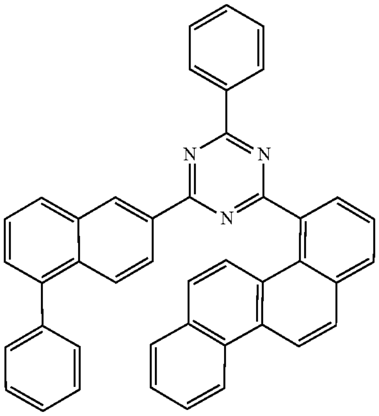
[78]
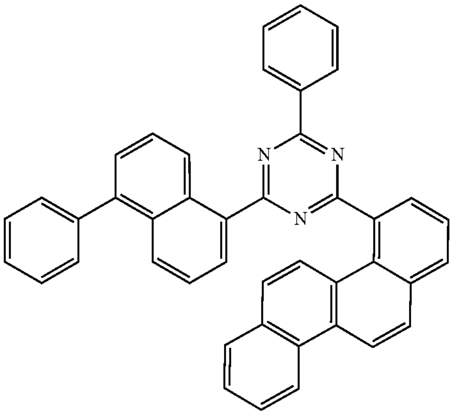
[79]
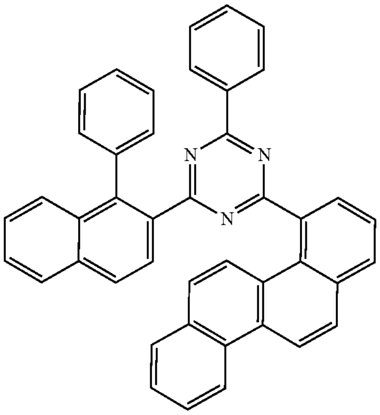

-continued
[80]
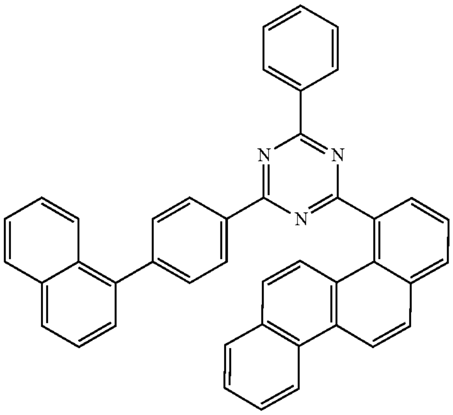
[81]
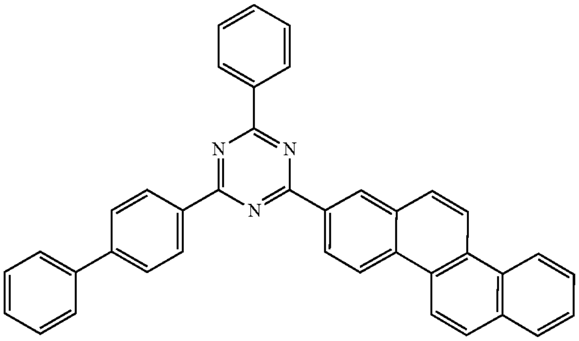
[82]
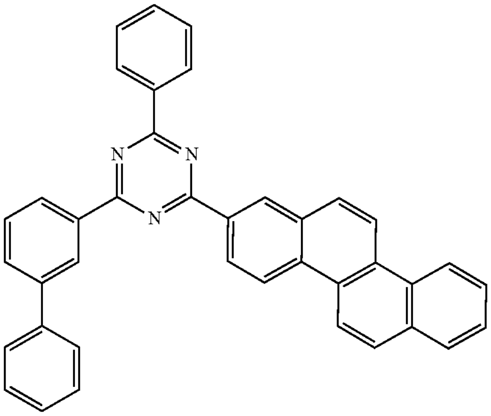
[83]
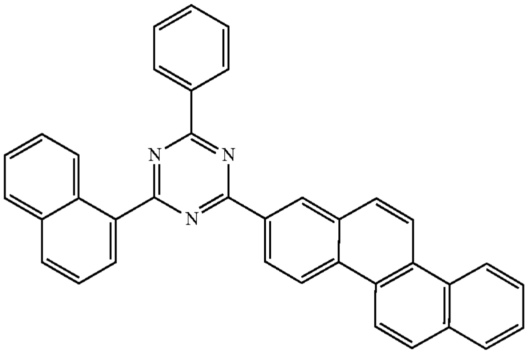
-continued
[84]
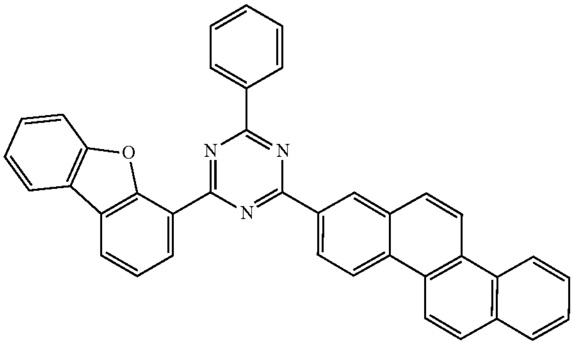
[85]
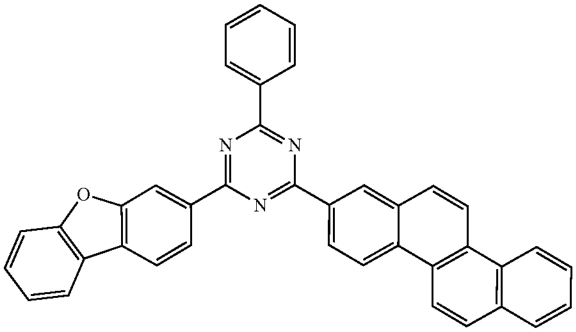
[86]
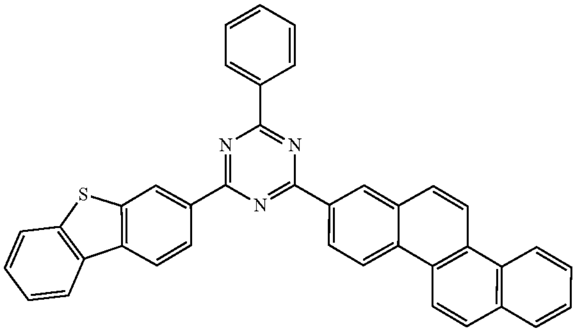
[87]
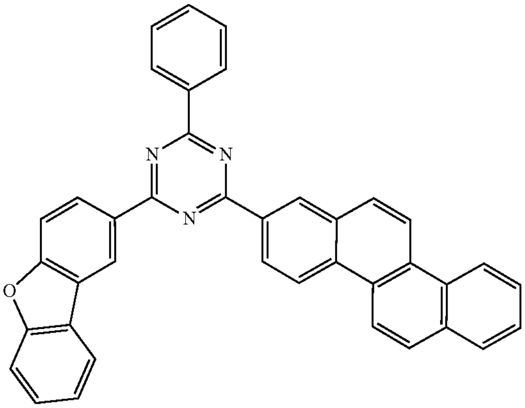

-continued
[88]
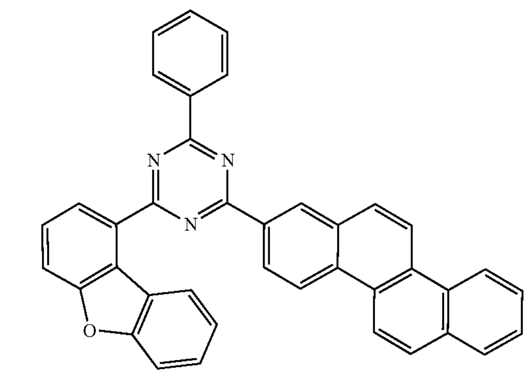
[89]
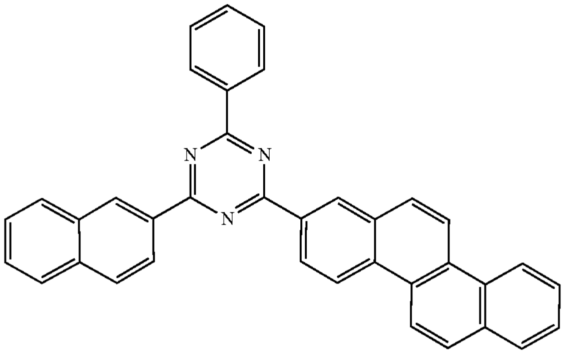
[90]
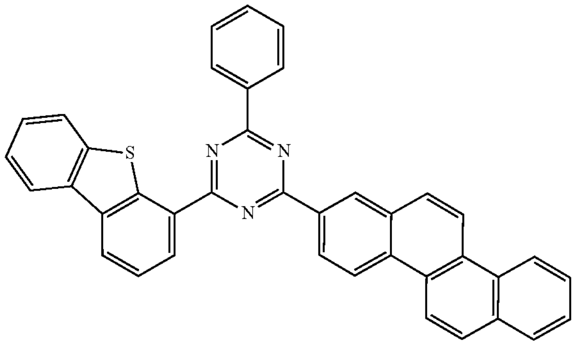
[91]
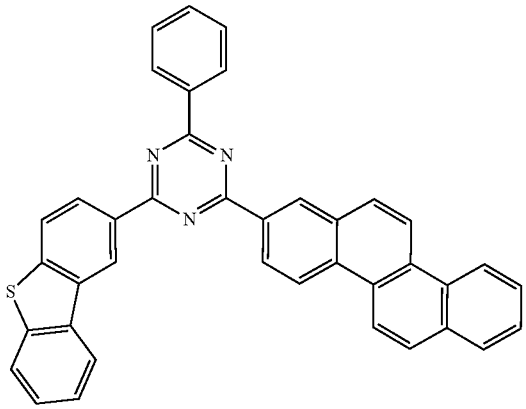
-continued
[92]
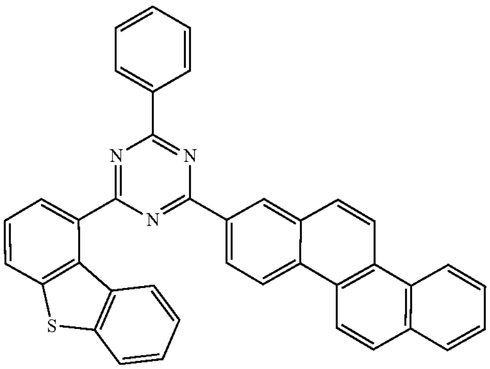
[93]
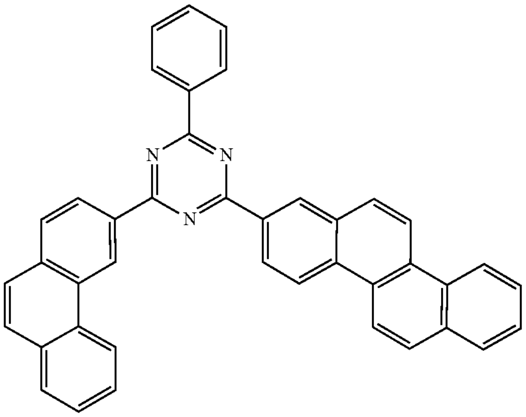
[94]
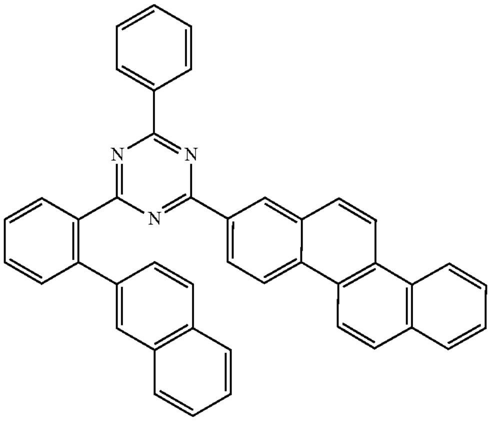
[95]
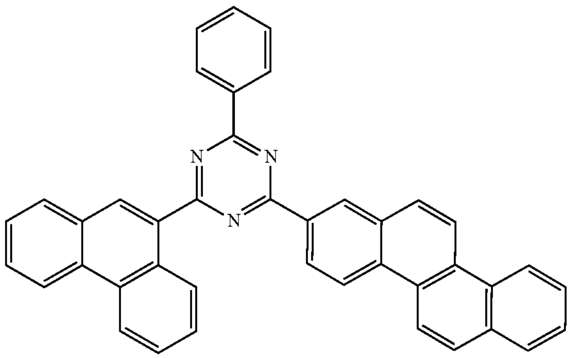

-continued
[96]
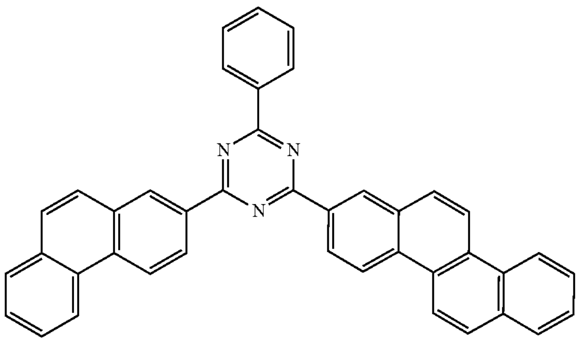
[97]
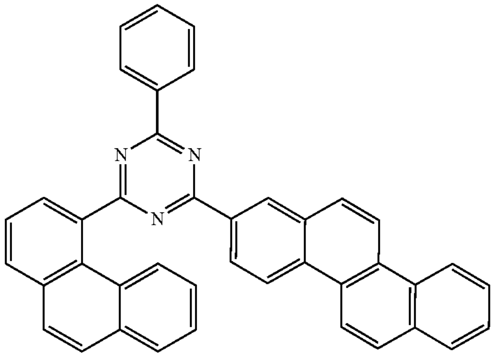
[98]
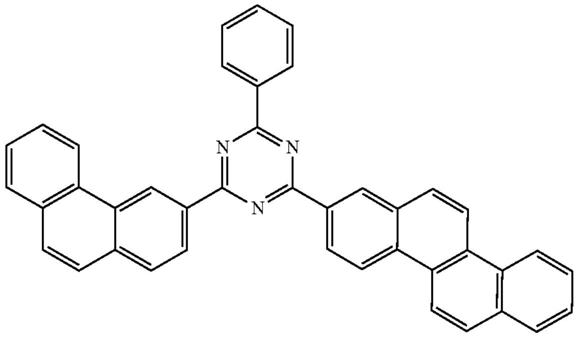
[99]
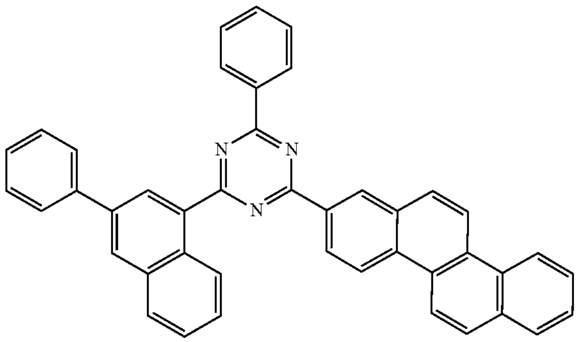
-continued
[100]
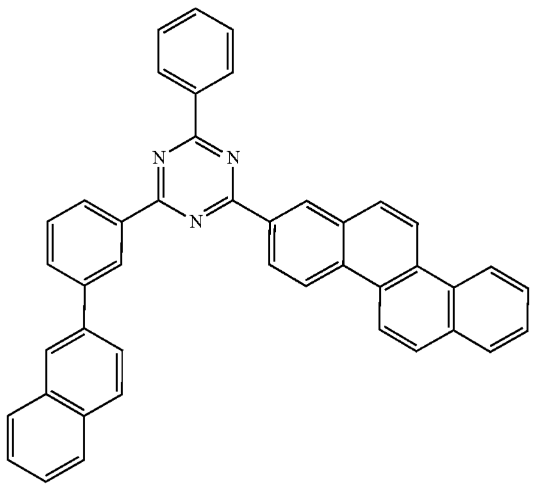
[101]
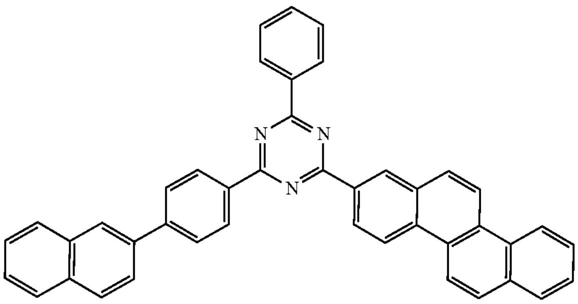
[102]
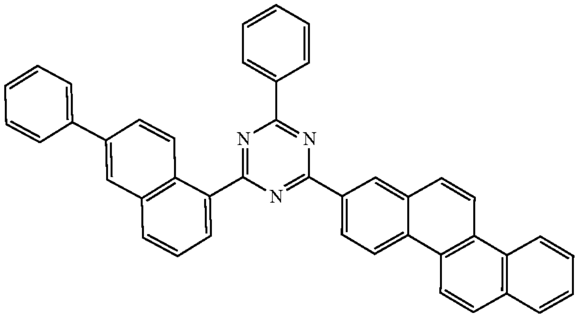
[103]
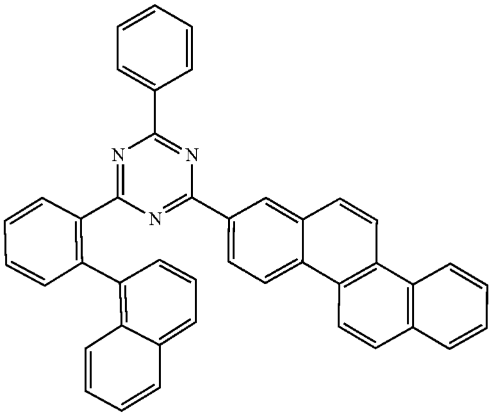

-continued
[104]
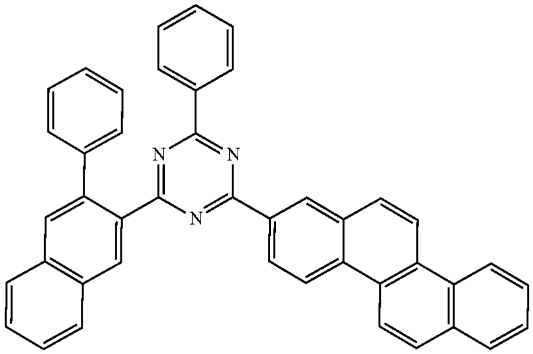
[105]
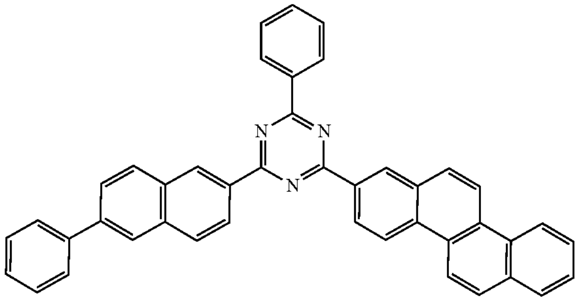
[106]
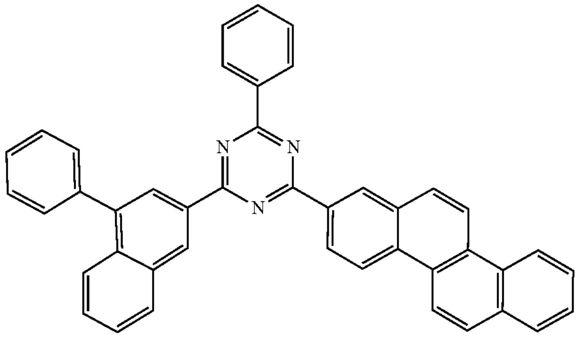
[107]
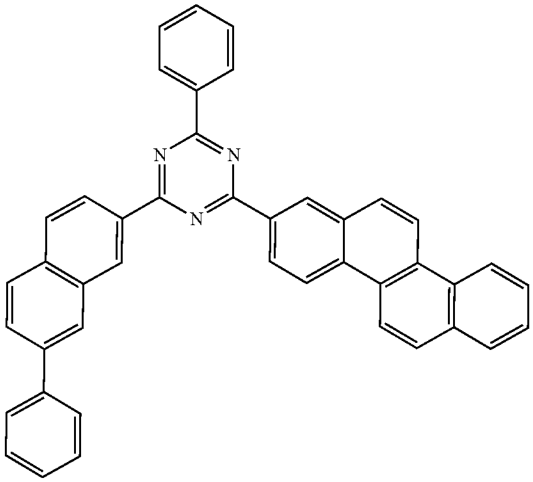
-continued
[108]
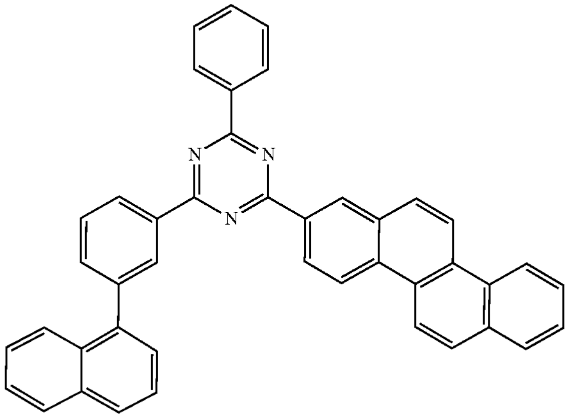
[109]
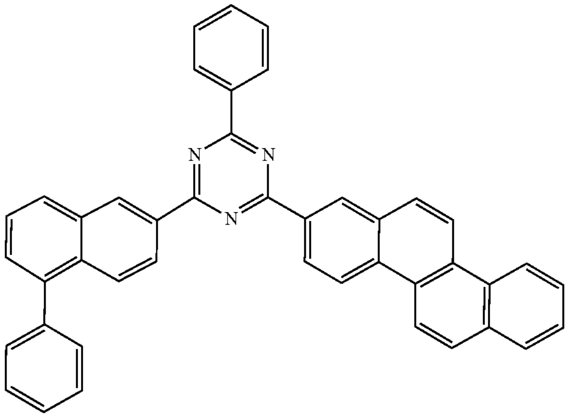
[110]
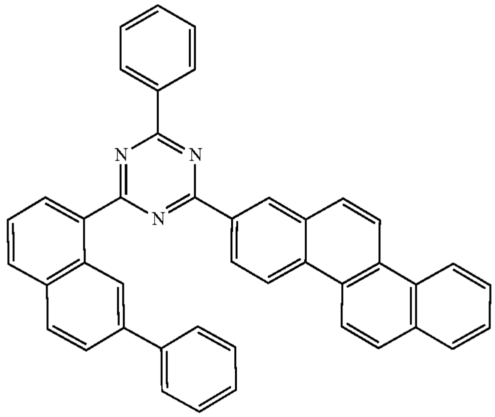

-continued
[111]
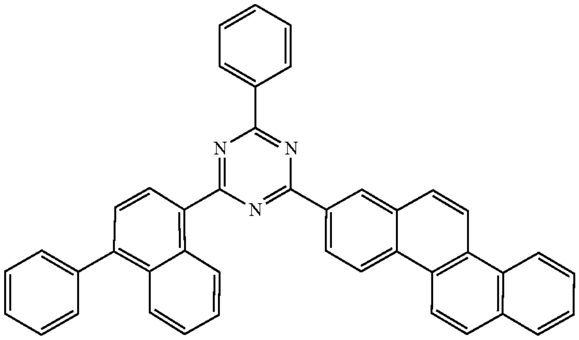
[112]
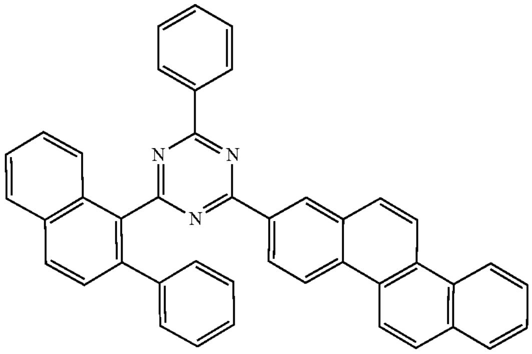
[113]
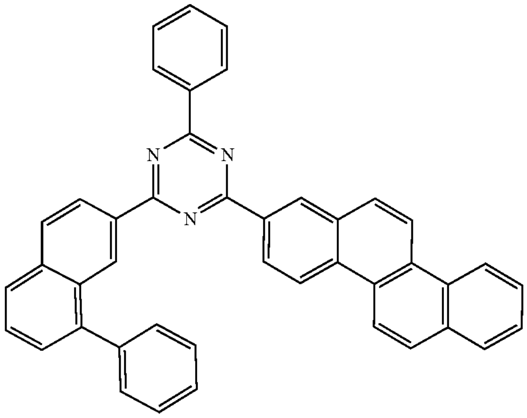
[114]
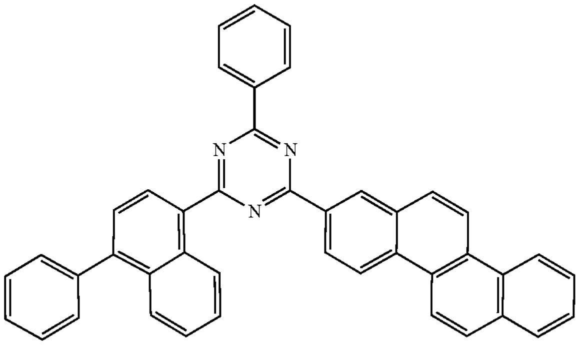
-continued
[115]
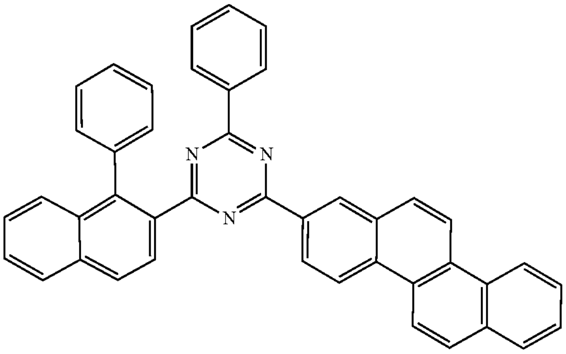
[116]
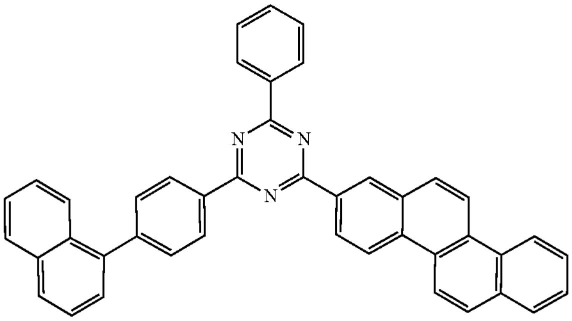
[117]
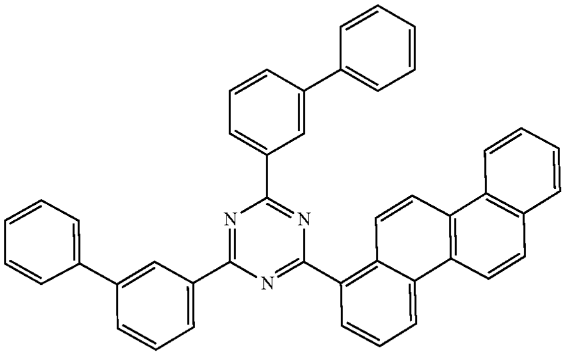
[118]
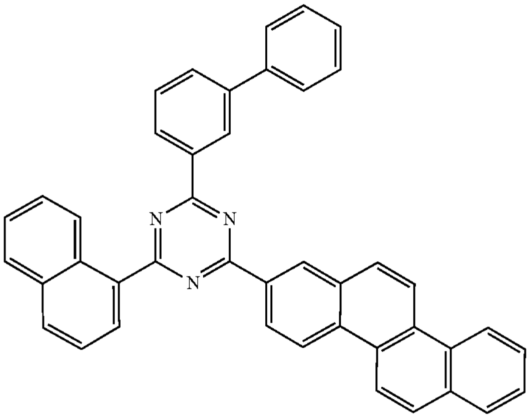

-continued

[119]

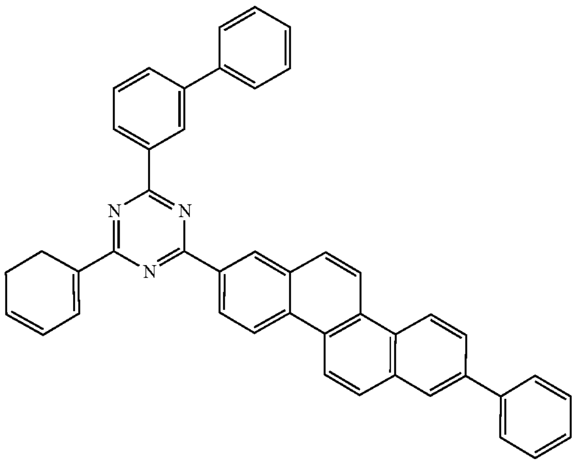

[120]

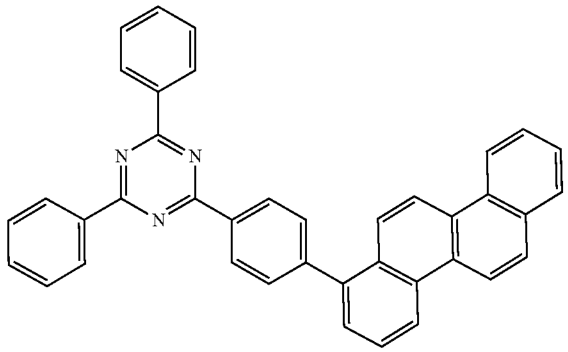

[121]

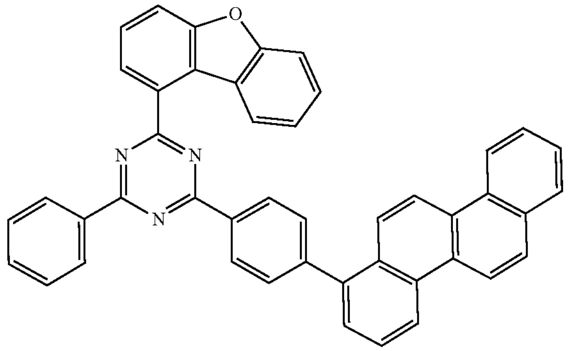

[122]

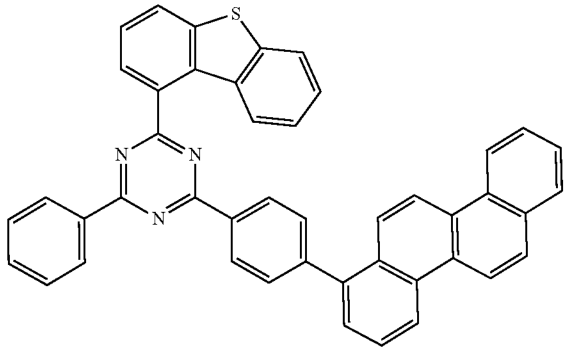

-continued

[123]

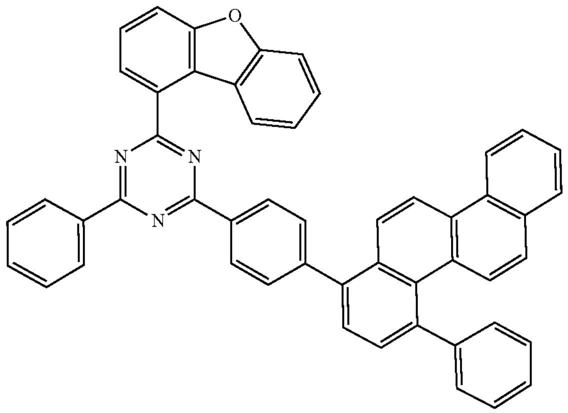

[124]

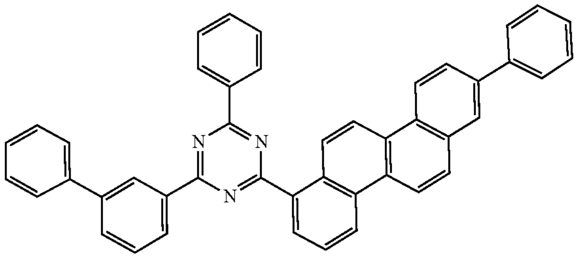

A composition for an organic optoelectronic device according to another embodiment includes a first compound and a second compound, wherein the first compound may be the aforementioned compound for an organic optoelectronic device and the second compound may be represented by Chemical Formula 2

[Chemical Formula 2]

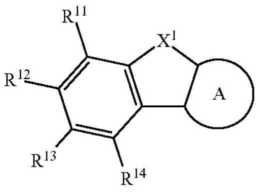

In Chemical Formula 2, $X^1$ is O, S, $NR^a$, $CR^bR^c$ or $SiR^dR^e$, $R^a$, $R^b$, $R^c$, $R^d$, $R^e$, and $R^{11}$ to $R^{14}$ are each independently hydrogen, deuterium, a substituted or unsubstituted amine group, a substituted or unsubstituted C1 to C30 alkyl group, a substituted or unsubstituted C6 to C30 aryl group, or a substituted or unsubstituted C2 to C30 heterocyclic group, and A is any one selected from the rings of Group II and Group III,

[Group II]

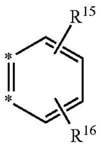

-continued

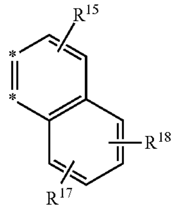

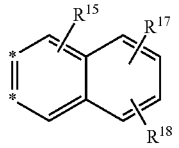

[Group III]

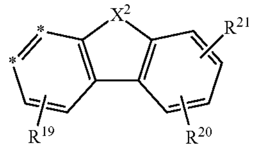

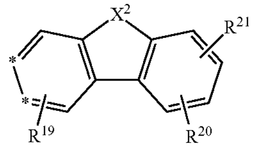

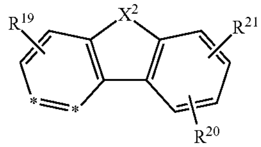

wherein, in Group II and Group III,

* is a linking point, $X^2$ is O, S, $NR^f$, $CR^gR^h$ or $SiR^iR^j$, $R^f$, $R^g$, $R^h$, $R^i$, $R^j$, and $R^{15}$ to $R^{21}$ are each independently hydrogen, deuterium, a substituted or unsubstituted amine group, a substituted or unsubstituted C1 to C30 alkyl group, a substituted or unsubstituted C6 to C30 aryl group, or a substituted or unsubstituted C2 to C30 heterocyclic group, and at least one of $R^{11}$ to $R^{14}$ and $R^{15}$ to $R^{21}$ is a group represented by Chemical Formula a,

[Chemical Formula a]

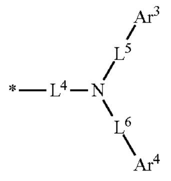

wherein, in Chemical Formula a, $L^4$ to $L^6$ are each independently a single bond, or a substituted or unsubstituted C6 to C30 arylene group, $Ar^3$ and $Ar^4$ are each independently a substituted or unsubstituted amine group, a substituted or unsubstituted C6 to C30 aryl group, or a substituted or unsubstituted C2 to C30 heterocyclic group, and

* is a linking point.

The second compound may have a structure in which carbazole/fused carbazole/fused dibenzofuran/fused dibenzothiophene/fused dibenzosilole is substituted with an amine, and may be for example represented by any one of Chemical Formula 2-I to Chemical Formula 2-IX depending on the type and fusion position of the additional benzene ring.

[Chemical Formula 2-I]

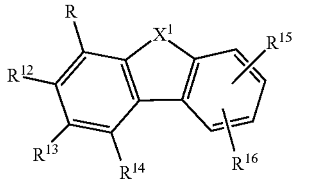

[Chemical Formula 2-II]

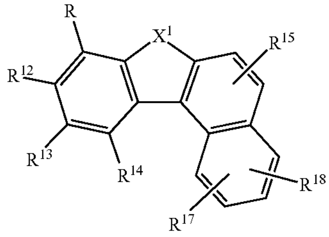

[Chemical Formula 2-III]

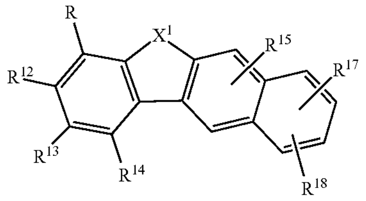

[Chemical Formula 2-IV]

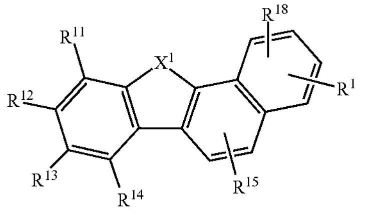

[Chemical Formula 2-V]

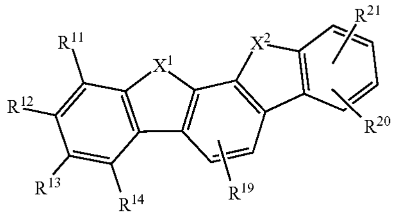

[Chemical Formula 2-VI]

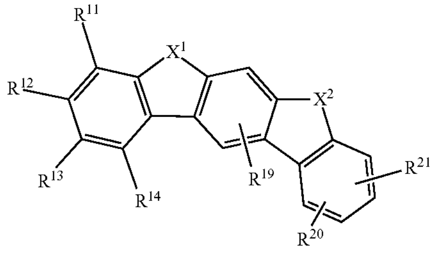

-continued

[Chemical Formula 2-VII]

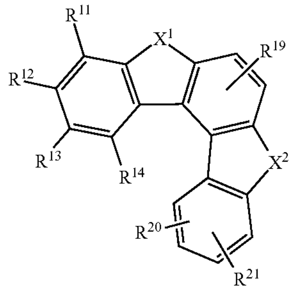

[Chemical Formula 2-VIII]

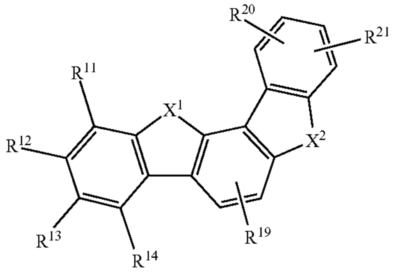

[Chemical Formula 2-IX]

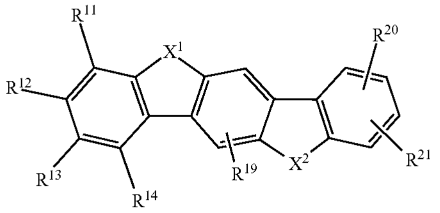

In Chemical Formula 2-I to Chemical Formula 2-IX, $X^1$, $X^2$, and $R^{11}$ to $R^{21}$ are the same as described above.

In addition, the second compound may be represented by one of Chemical Formula 2-IA to Chemical Formula 2-IXA, Chemical Formula 2-IB to Chemical Formula 2-IXB, and Chemical Formula 2-IC to Chemical Formula 2-IIIC depending on a substituted direction of the amine group.

[Chemical Formula 2-IA]

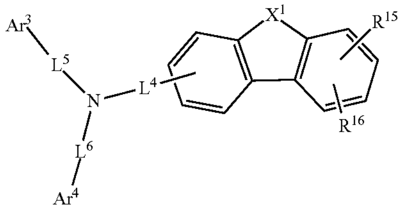

[Chemical Formula 2-IIA]

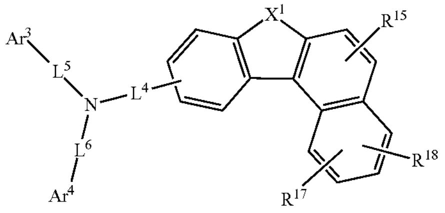

-continued

[Chemical Formula 2-IIIA]

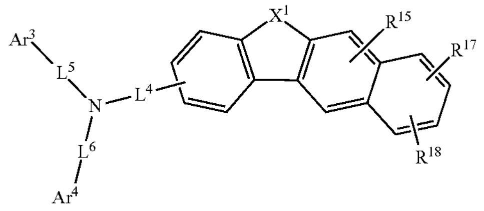

[Chemical Formula 2-IVA]

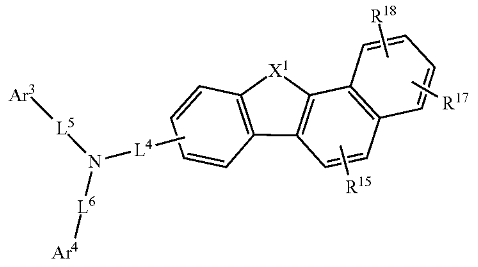

[Chemical Formula 2-VA]

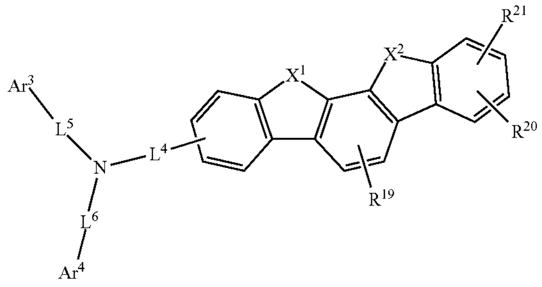

[Chemical Formula 2-VIA]

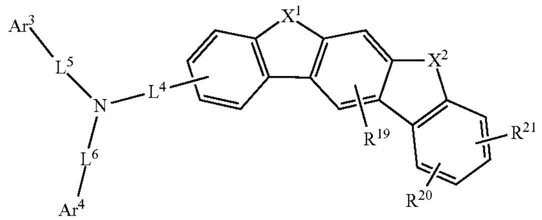

[Chemical Formula 2-VIIA]

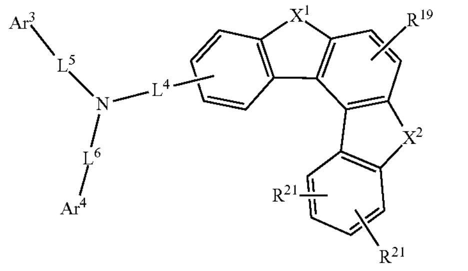

-continued
[Chemical Formula 2-VIIIA]
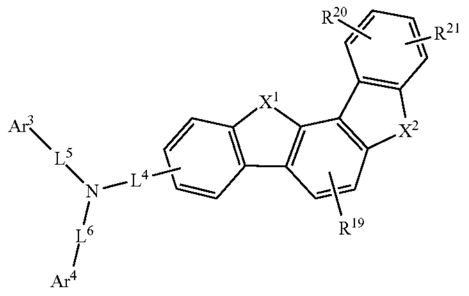
[Chemical Formula 2-IXA]
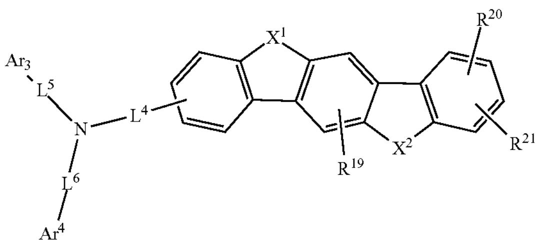
[Chemical Formula 2-IB]
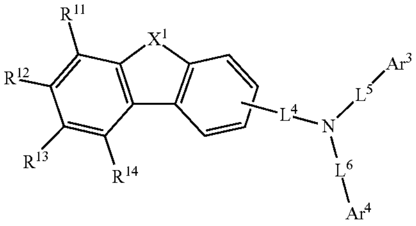
[Chemical Formula 2-IIB]
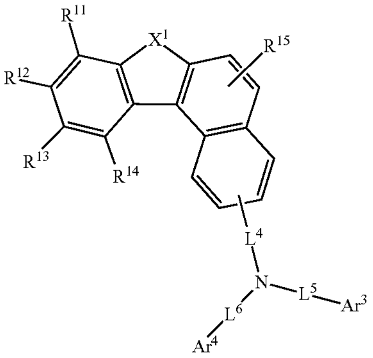
[Chemical Formula 2-IIIB]
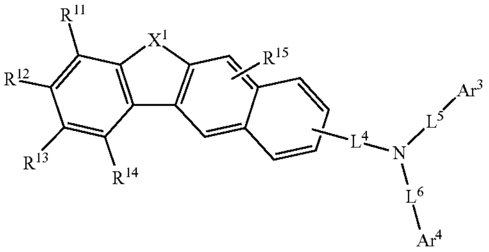
-continued
[Chemical Formula 2-IVB]
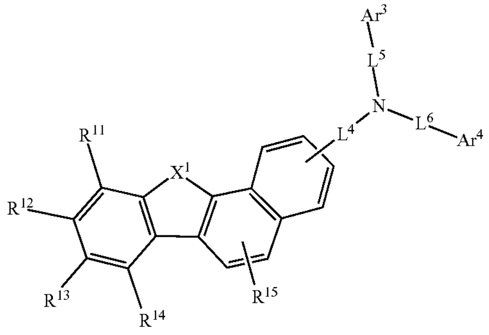
[Chemical Formula 2-VB]
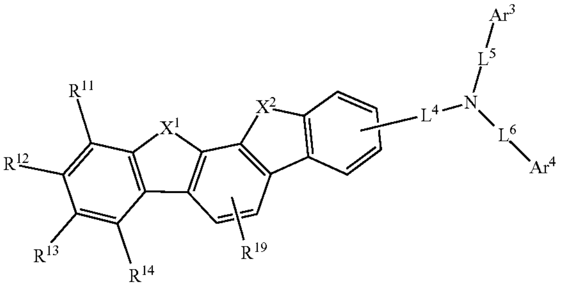
[Chemical Formula 2-VIB]
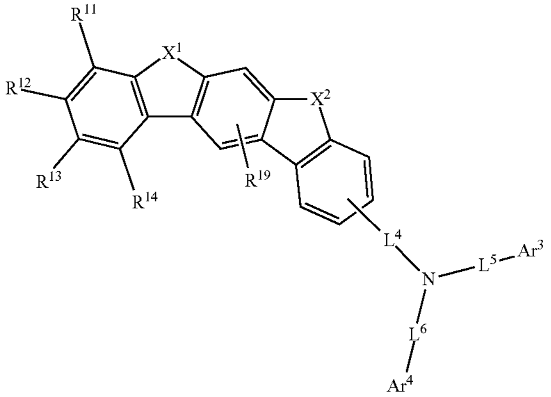
[Chemical Formula 2-VIIB]
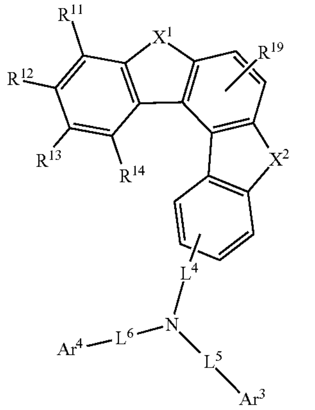

-continued

[Chemical Formula 2-VIIIB]

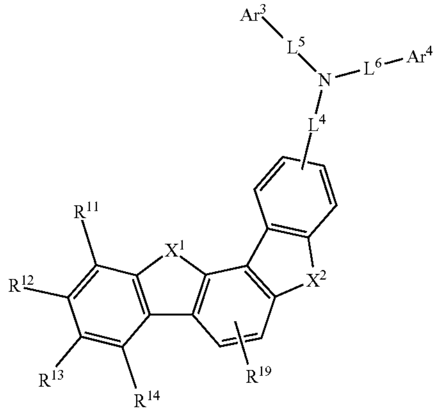

[Chemical Formula 2-IXB]

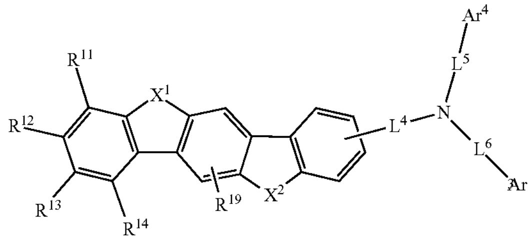

[Chemical Formula 2-IC]

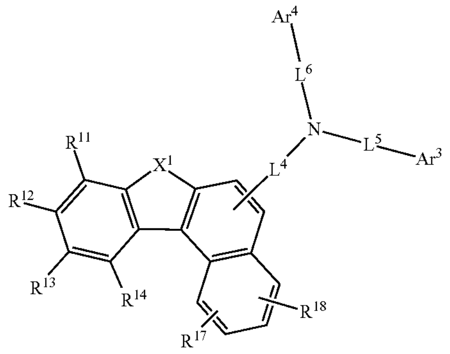

[Chemical Formula 2-IIC]

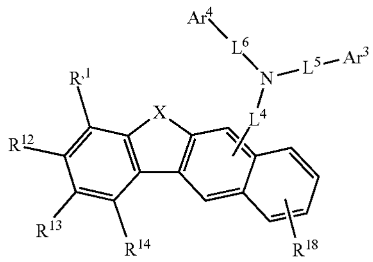

-continued

[Chemical Formula 2-IIIC]

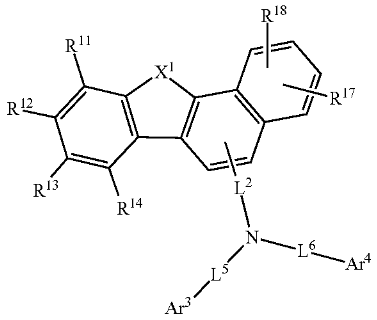

In Chemical Formula 2-IA to Chemical Formula 2-IXA, Chemical Formula 2-IB to Chemical Formula 2-IXB, and Chemical Formula 2-IC to Chemical Formula 2-IIIC, $X^1$, $X^2$, $L^2$ to $L^4$, $Ar^3$, and $A^4$ are the same as described above, and $R^{11}$ to $R^{21}$ are each independently hydrogen, deuterium, a substituted or unsubstituted C1 to C30 alkyl group, or a substituted or unsubstituted C6 to C30 aryl group.

The second compound according to an embodiment may be represented by one of Chemical Formula 2-VIIIA, Chemical Formula 2-IVB and Chemical Formula 2-VIIIB.

For example, in Chemical Formula 2-VIIIA, $X^1$ may be O or S, and $X^2$ may be $CR^gR^h$ or $SiR^iR^j$.

For example, in Chemical Formula 2-VIIIB, $X^1$ may be O or S, and $X^2$ may be $CR^gR^h$ or $SiR^iR^j$.

For example, in Chemical Formula 2-VIIIA, $X^1$ may be $CR^gR^h$ or $SiR^iR^j$, and $X^2$ may be O or S.

For example, in Chemical Formula 2-VIIIB, $X^1$ may be $CR^gR^h$ or $SiR^iR^j$, and $X^2$ may be O or S.

Here, $R^g$, $R^h$, $R^i$, and $R^j$ may each independently represent a substituted or unsubstituted C1 to C10 alkyl group, or a substituted or unsubstituted C6 to C20 aryl group.

The second compound according to a specific embodiment may be represented by any one of Chemical Formula 2-VIIIA-2, Chemical Formula 2-IVB-2, and Chemical Formula 2-VIIIB-2.

[Chemical Formula 2-VIIIA-2]

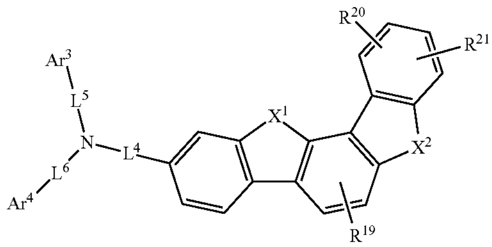

-continued

[Chemical Formula 2-IVB-2]

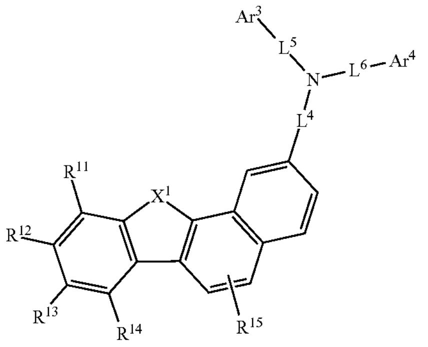

[Chemical Formula 2-VIIIB-2]

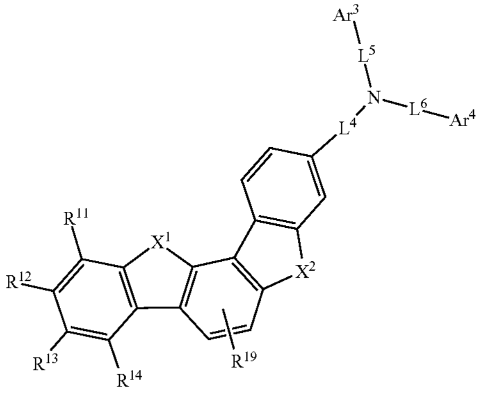

In Chemical Formula 2-VIIIA-2, Chemical Formula 2-IVB-2, and Chemical Formula 2-VIIIB-2, $L^4$ to $L^6$ are each independently a single bond or a substituted or unsubstituted phenylene group, $Ar^3$ and $Ar^4$ are each independently a substituted or unsubstituted phenyl group, a substituted or unsubstituted biphenyl group, or a substituted or unsubstituted naphthyl group, $X^1$ is $NR^a$, O, S, $CR^bR^c$, or $SiR^dR^e$, $X^2$ is O, S, $CR^gR^h$, or $SiR^iR^j$, $R^a$, $R^b$, $R^c$, $R^d$, $R^e$, $R^g$, $R^h$, $R^i$, and $R^j$ are each independently a substituted or unsubstituted C1 to C30 alkyl group, or a substituted or unsubstituted C6 to C30 aryl group, and $R^{11}$ to $R^{15}$ and $R^{19}$ to $R^{21}$ are each independently hydrogen, deuterium, a substituted or unsubstituted C1 to C30 alkyl group, a substituted or unsubstituted C6 to C30 aryl group or a substituted or unsubstituted C2 to C30 heterocyclic group.

For example, $L^5$ and $L^6$ may each independently be a single bond, a substituted or unsubstituted phenylene group, or a substituted or unsubstituted biphenylene group.

For example, $Ar^3$ and $Ar^4$ may each independently be a substituted or unsubstituted phenyl group, a substituted or unsubstituted biphenyl group, a substituted or unsubstituted terphenyl group, a substituted or unsubstituted naphthyl group, a substituted or unsubstituted phenanthrenyl group, a substituted or unsubstituted triphenylene group, a substituted or unsubstituted fluorenyl group, a substituted or unsubstituted carbazolyl group, a substituted or unsubstituted dibenzofuranyl group, a substituted or unsubstituted dibenzothiophenyl group, a substituted or unsubstituted benzofuranofluorenyl group, or a substituted or unsubstituted benzothiophenefluorenyl group.

For example, the second compound may be one selected from the compounds of Group 2, but is not limited thereto.

[Group 2]

A-1

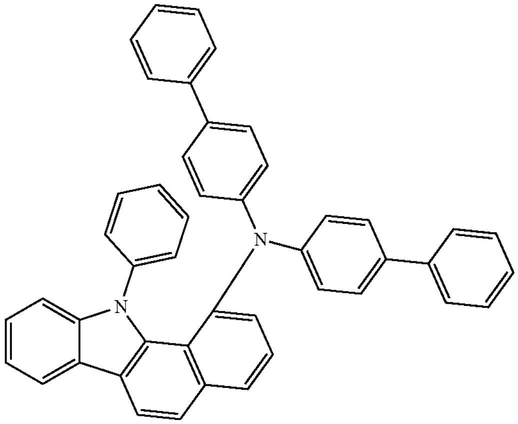

A-2

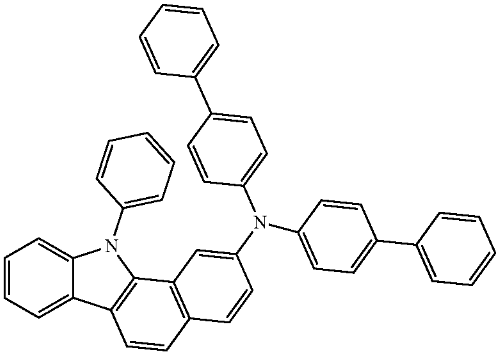

-continued
A-3
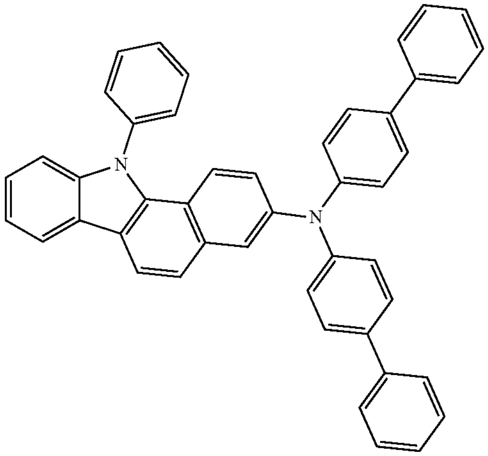
A-4
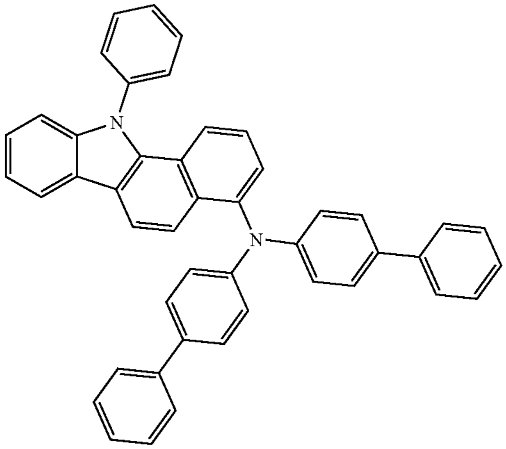
A-5
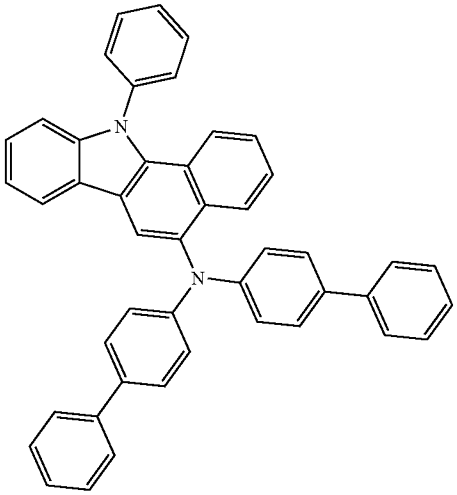
A-6
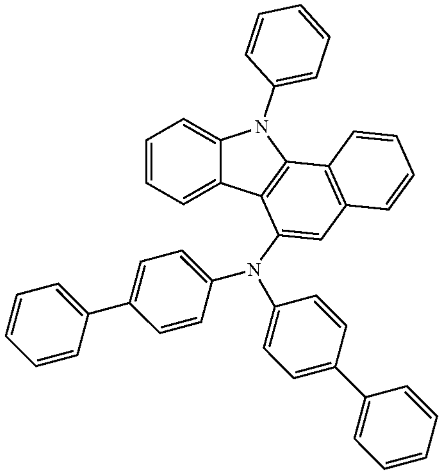
A-7
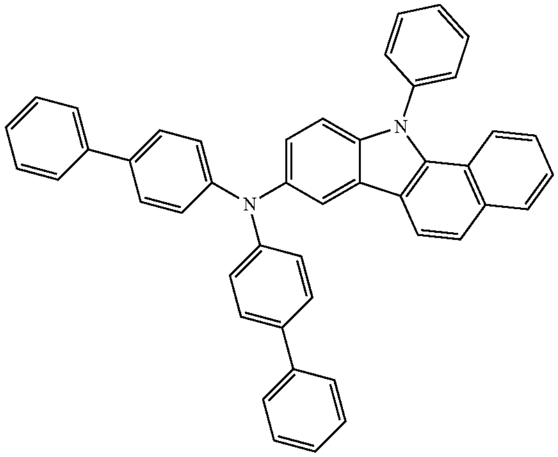
A-8
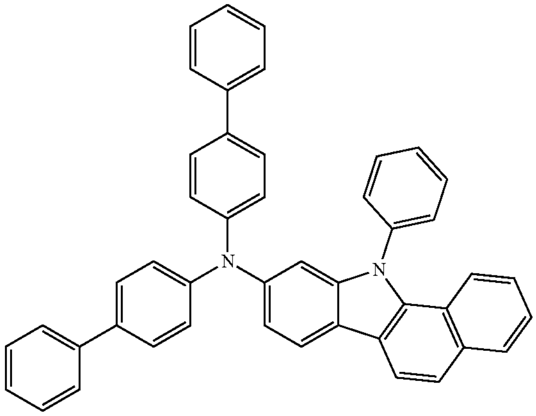

-continued
A-9
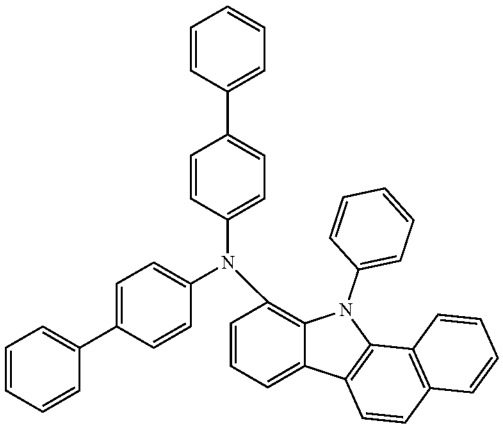
A-10
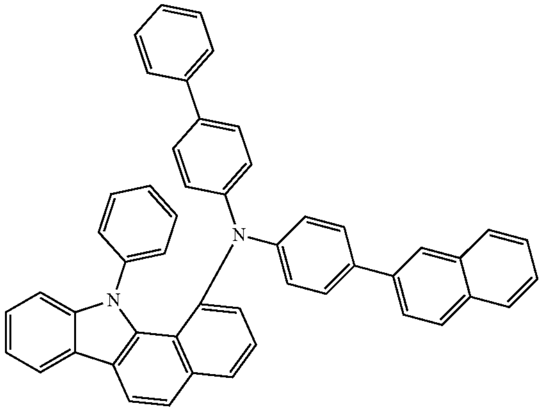
A-11
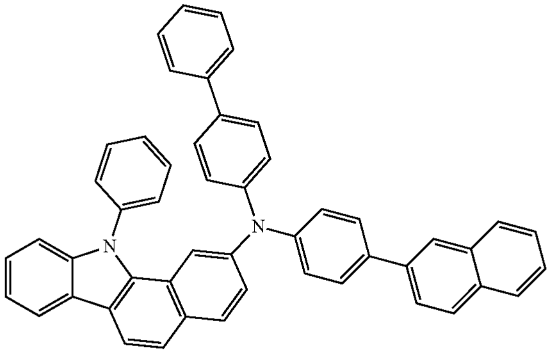
A-12
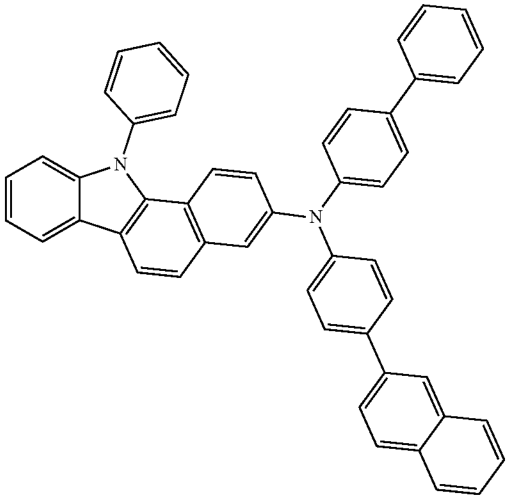
A-13
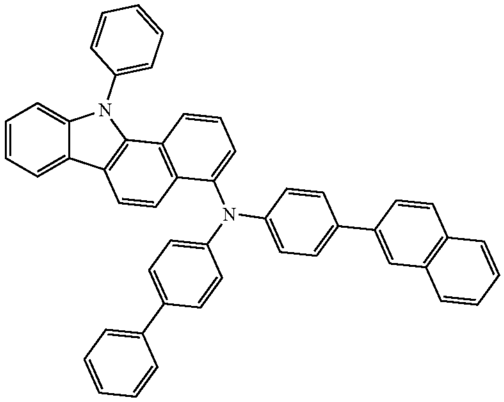
A-14
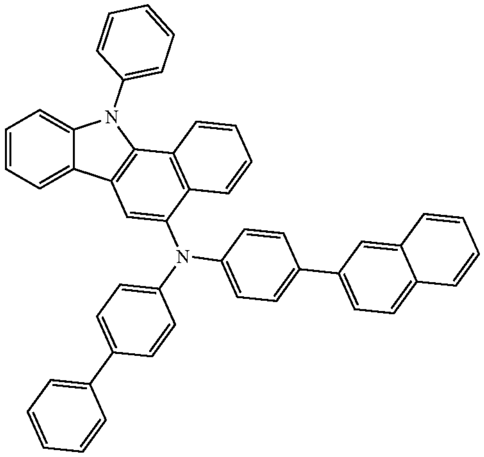

-continued
A-15
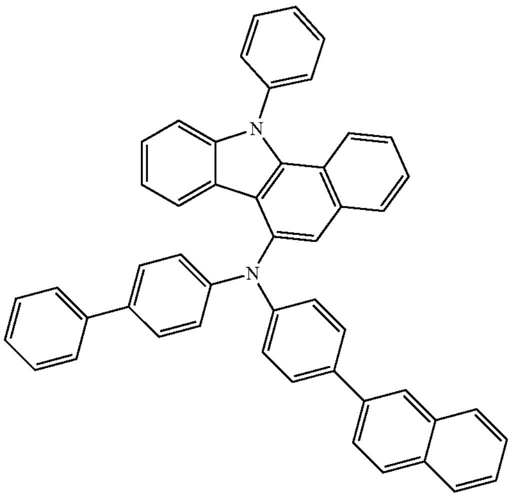
A-16
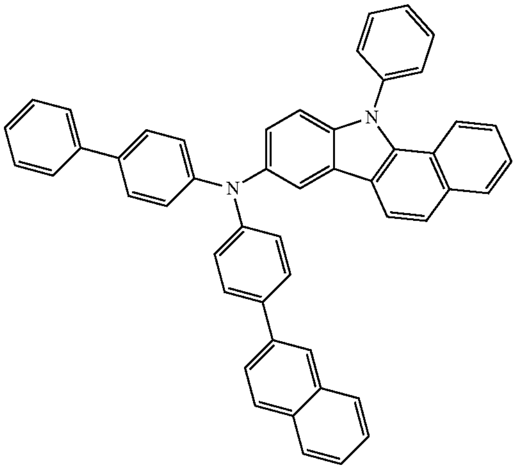
A-17
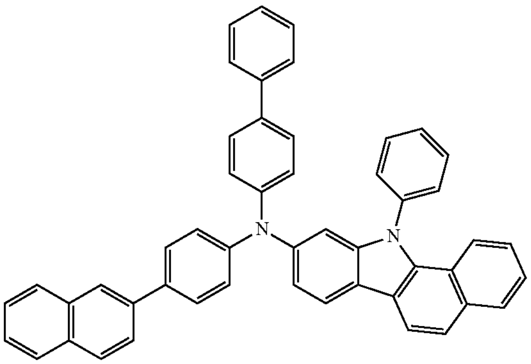
A-18
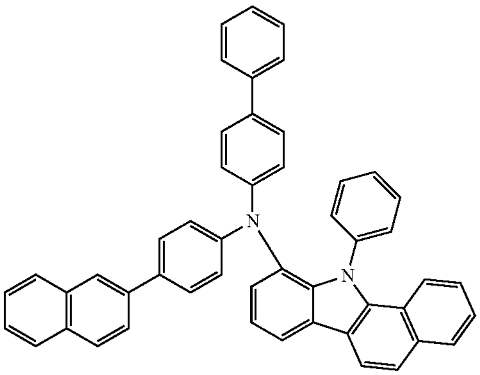
A-19
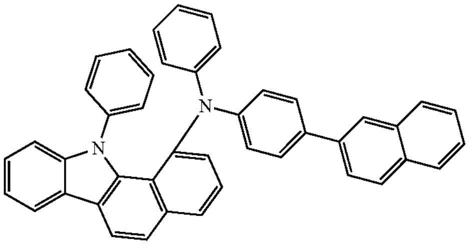
A-20
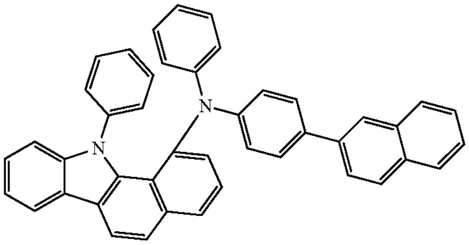
A-21
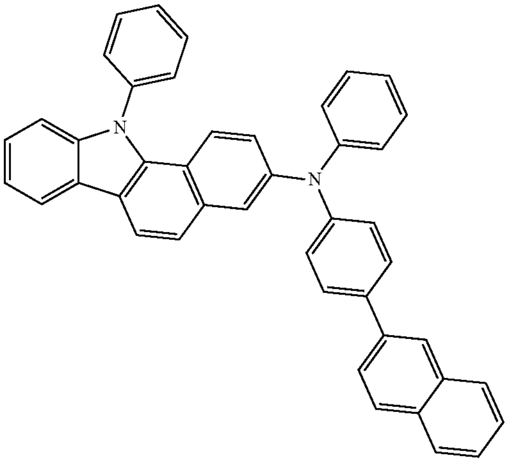
A-22
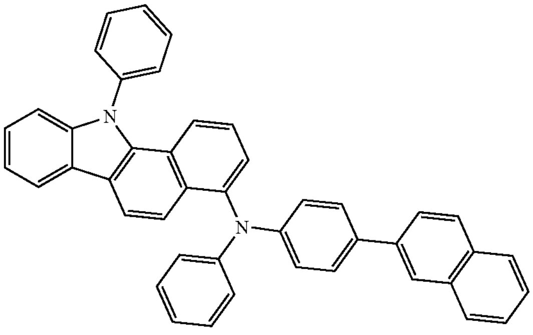

-continued
A-23
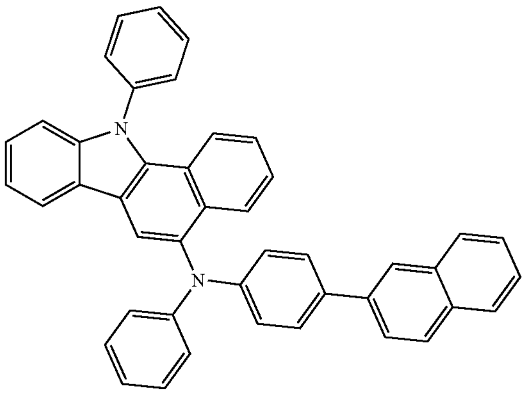
A-24
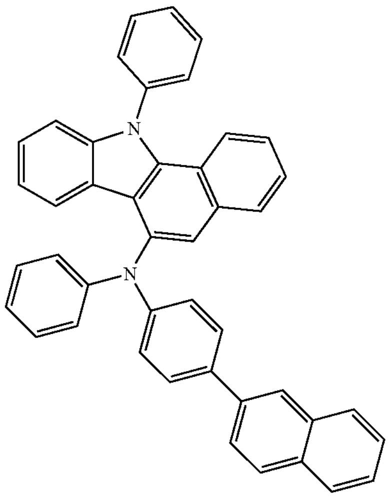
A-25
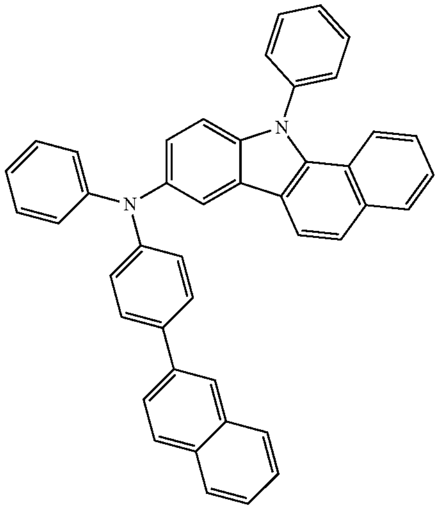
A-26
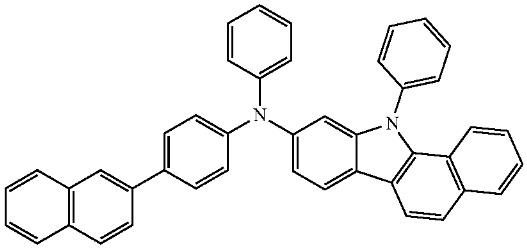
A-27
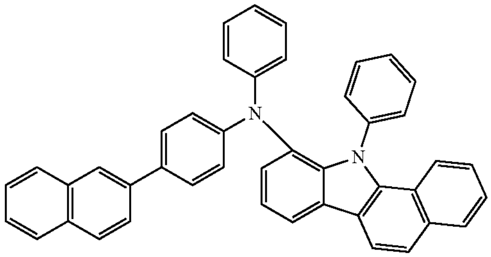
A-28
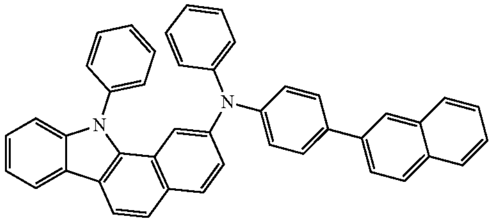
A-45
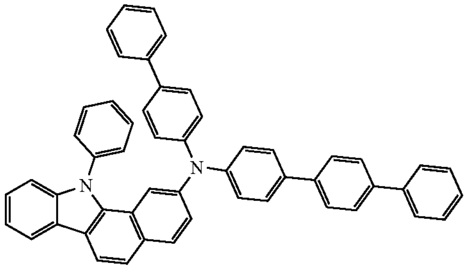
A-46
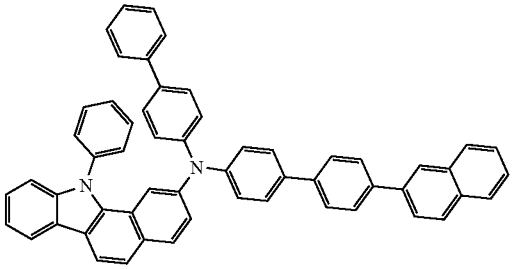

-continued
A-47
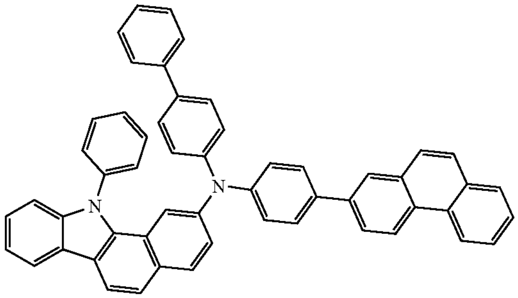
A-48
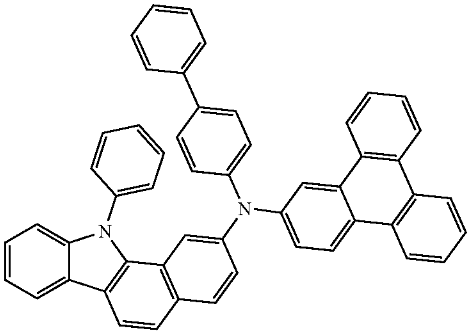
A-49
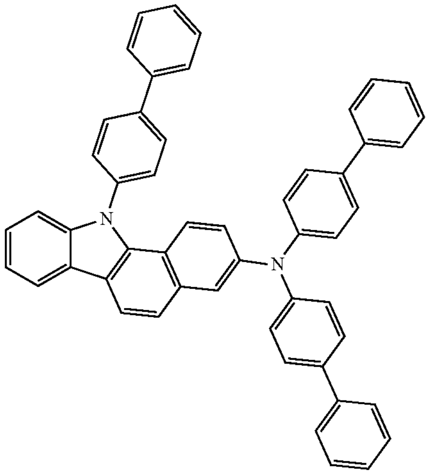
A-50
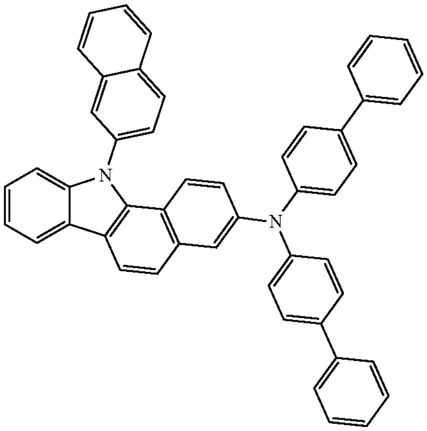
A-51
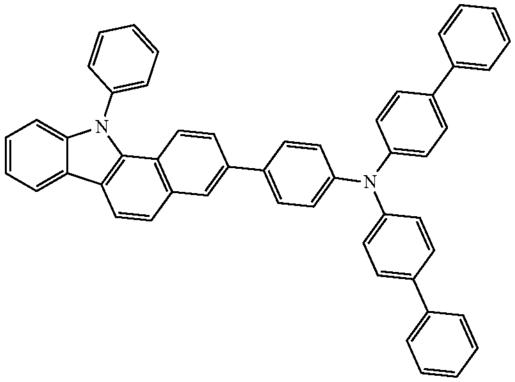
A-52
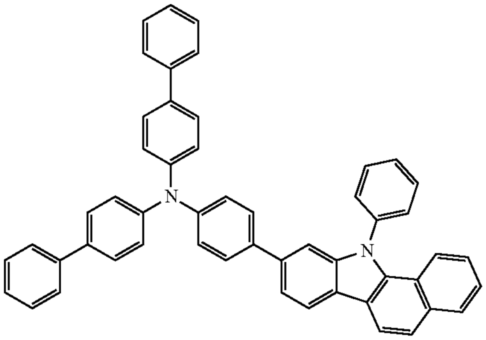
A-53
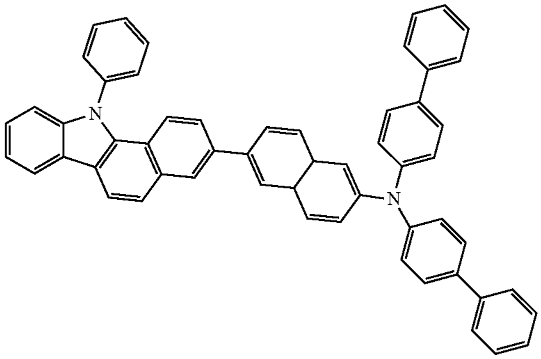

-continued
A-54
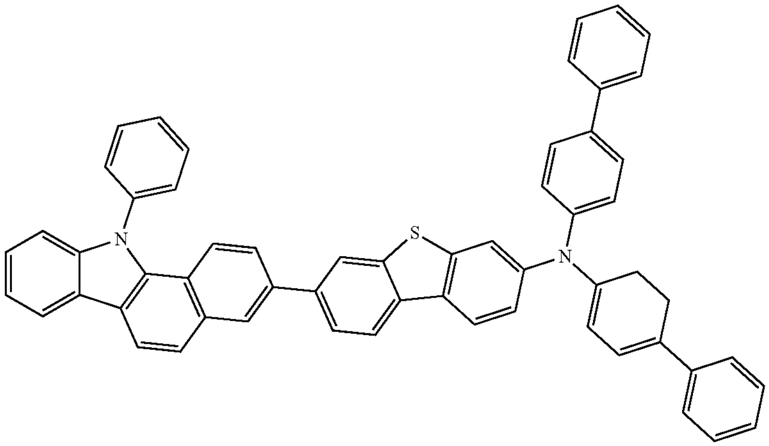
A-55
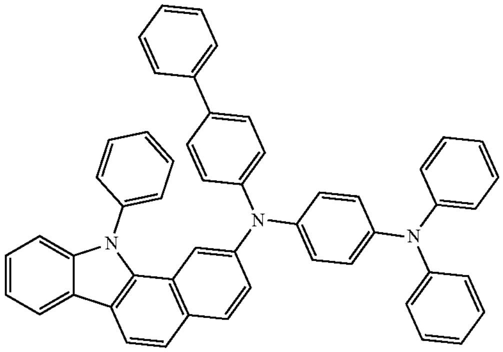
A-56
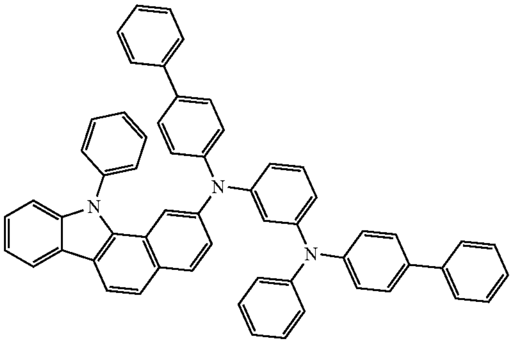
A-57
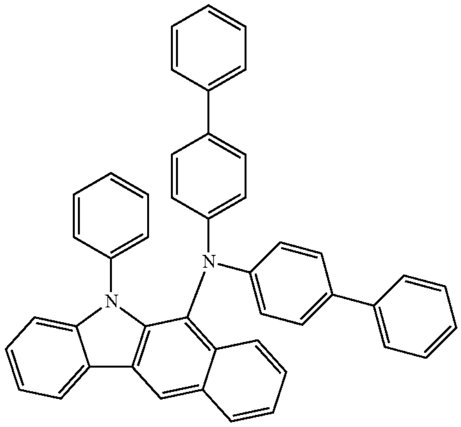
A-58
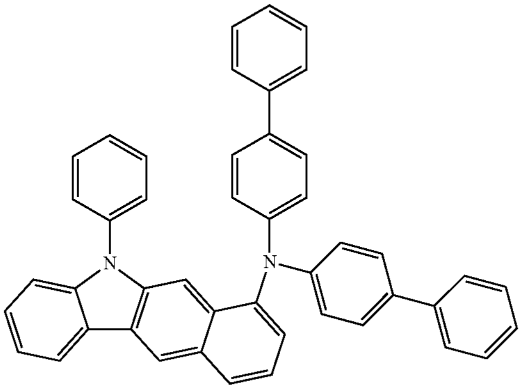

-continued
A-59
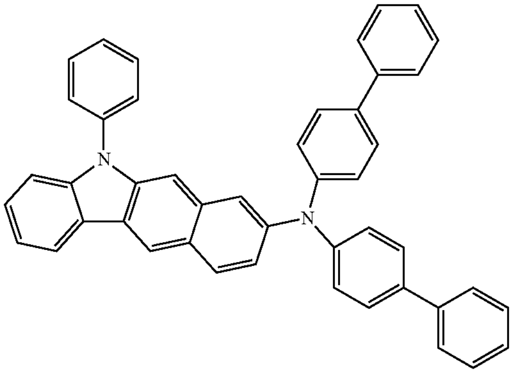
A-60
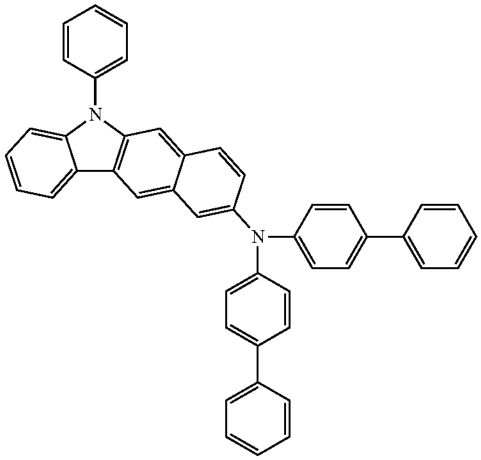
A-61
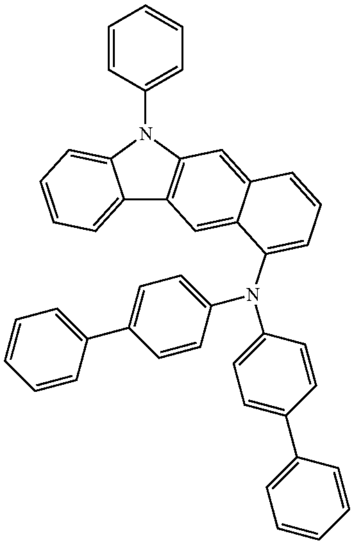
A-62
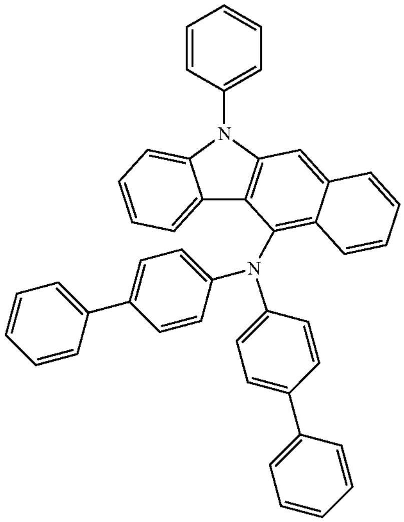
A-63
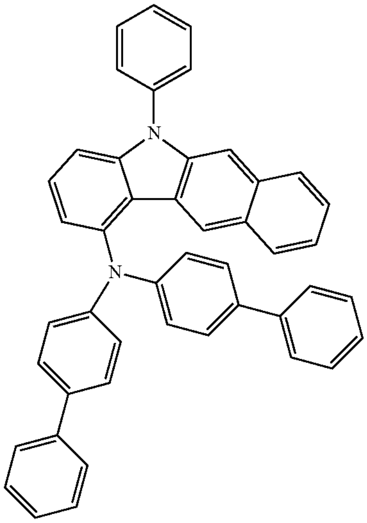
A-64
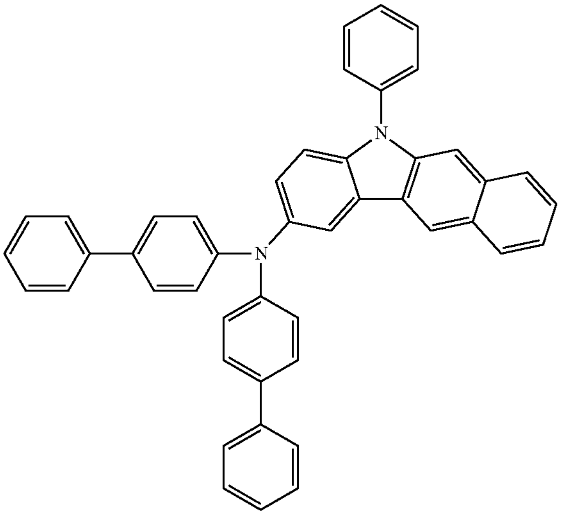

-continued
A-65
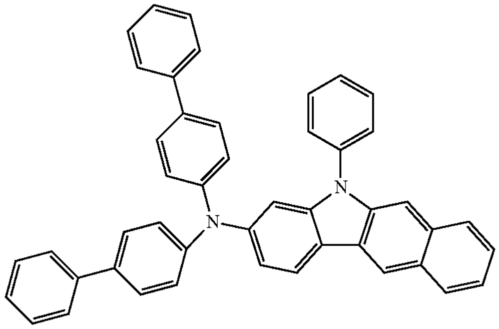
A-66
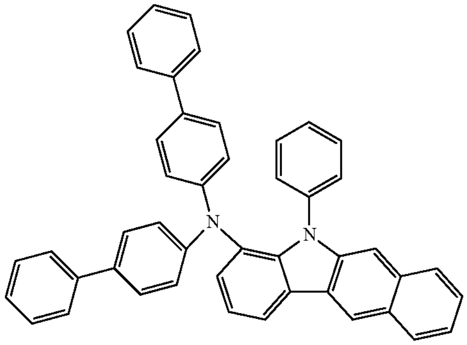
A-67
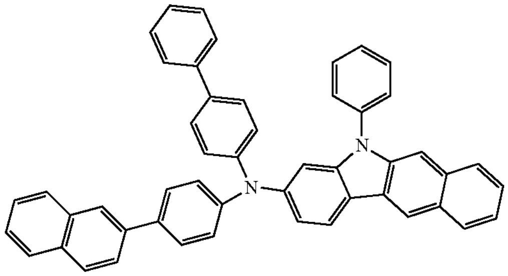
A-68
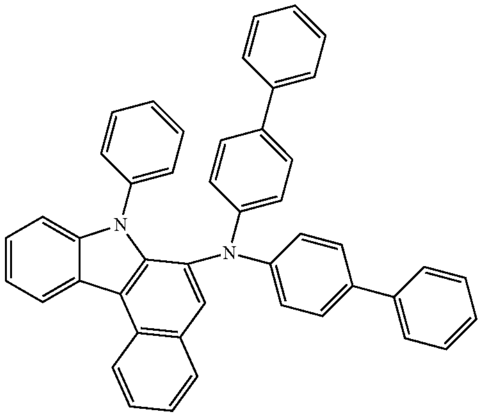
A-69
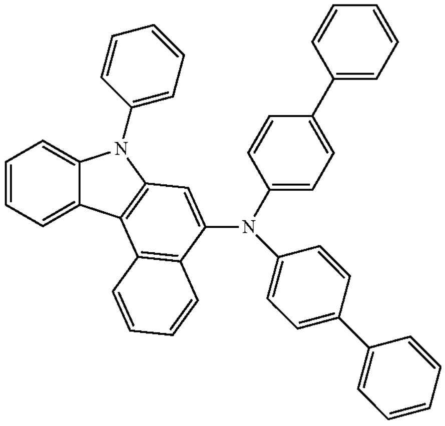
A-70
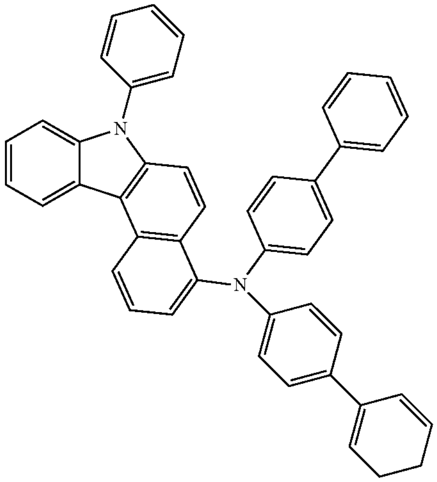

-continued
A-71
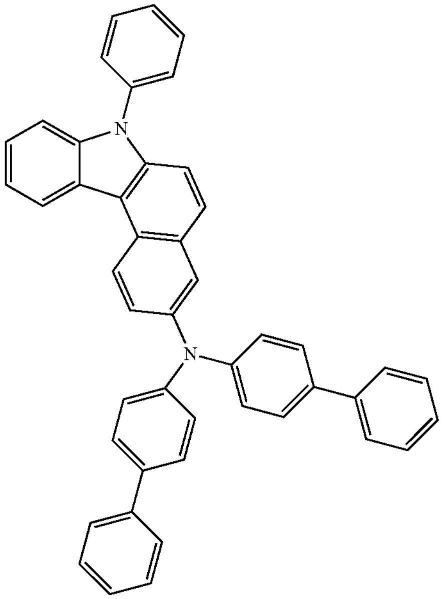
A-72
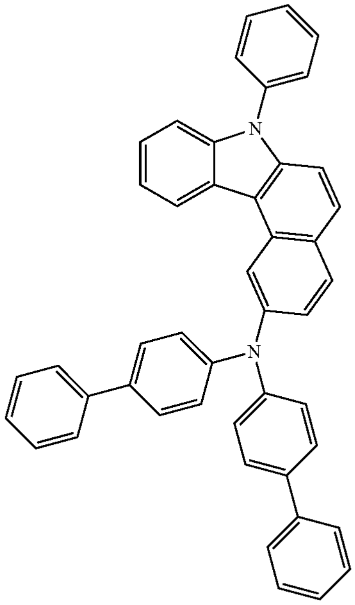
A-73
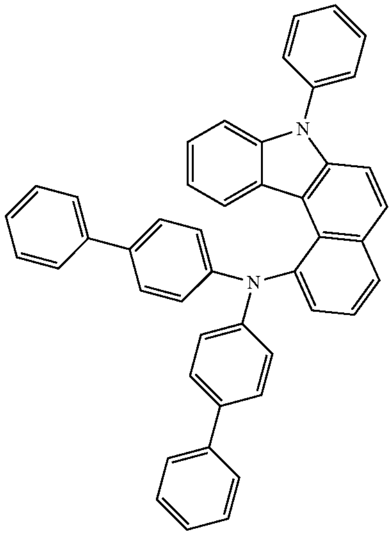
A-74
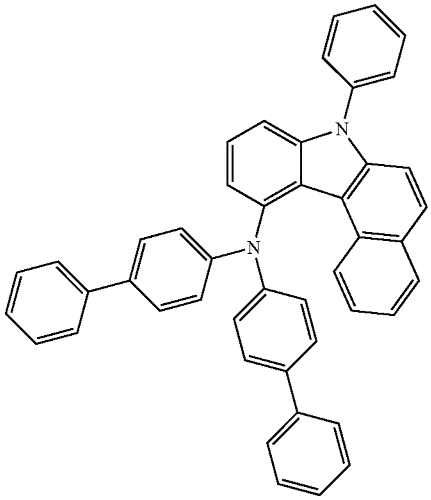
A-75
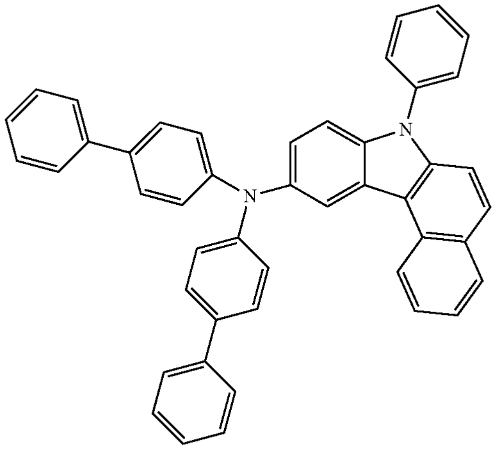
A-76
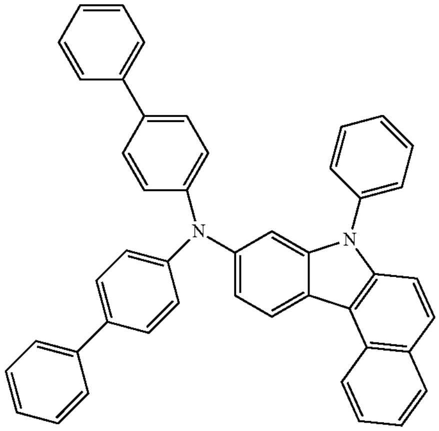

-continued
A-77
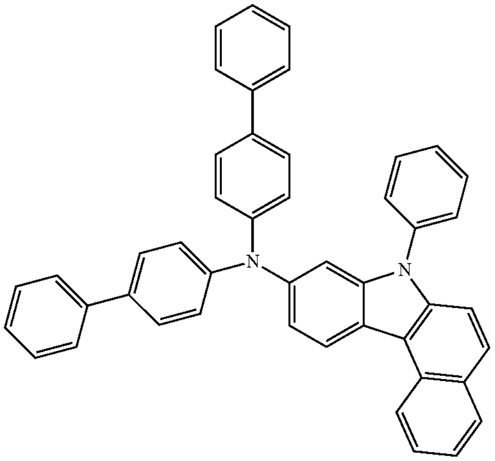
A-78
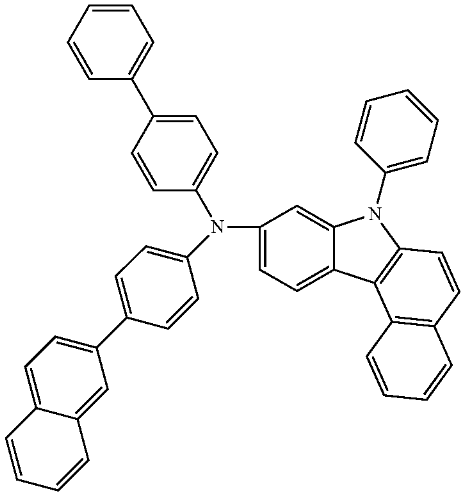
A-79
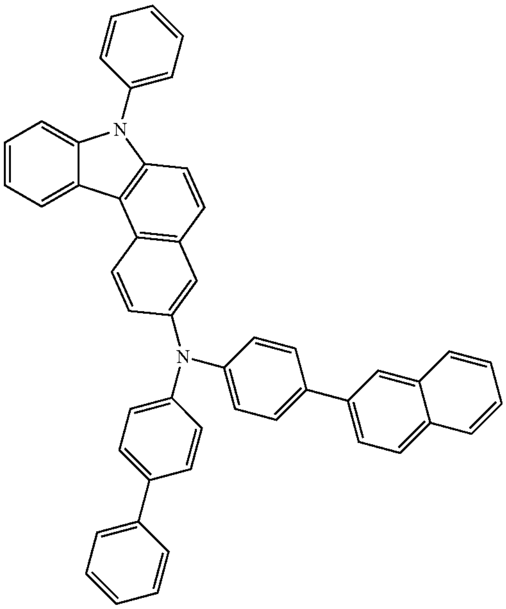
A-80
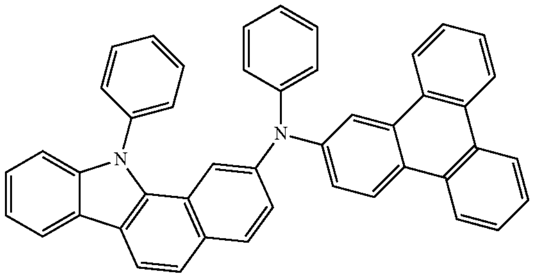
A-81
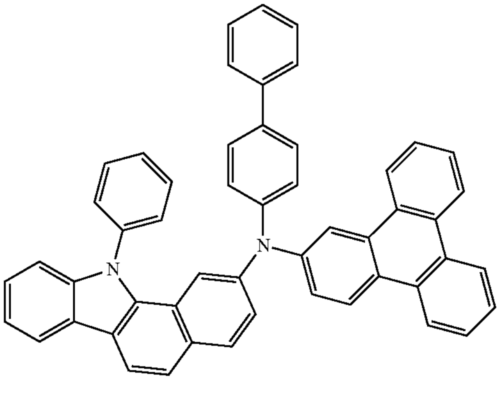
A-82
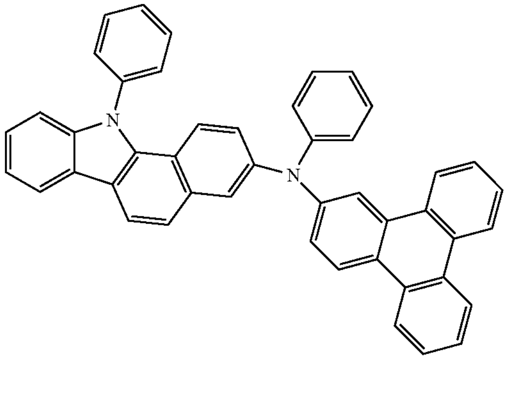

-continued
A-83
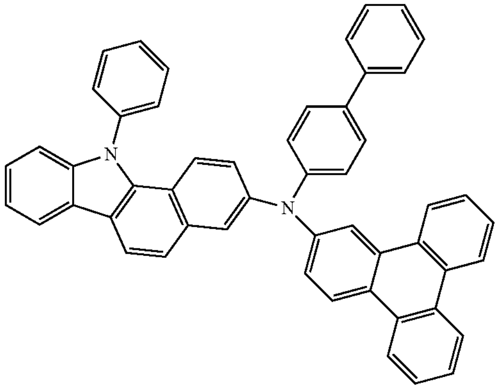
A-84
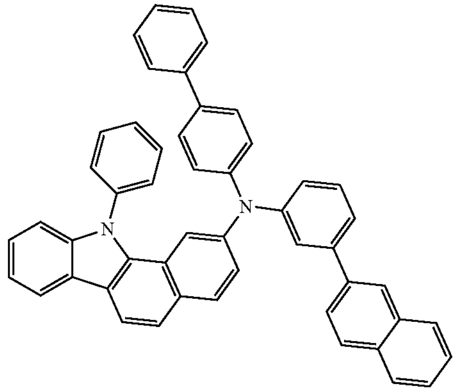
[2-1]
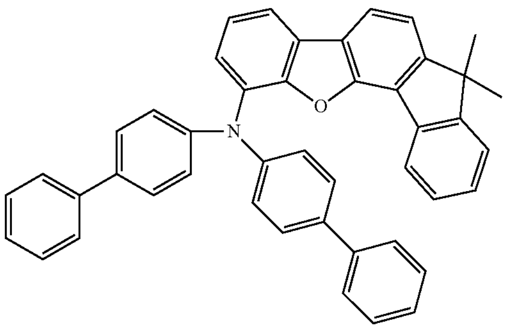
[2-2]
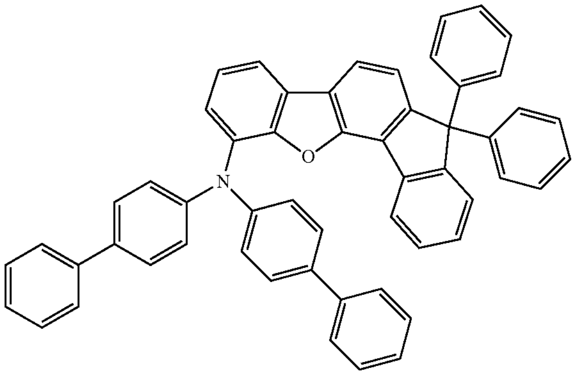
[2-3]
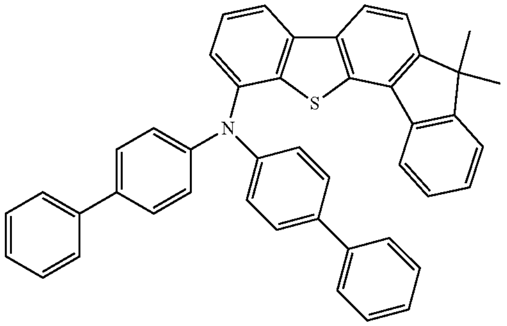
-continued
[2-4]
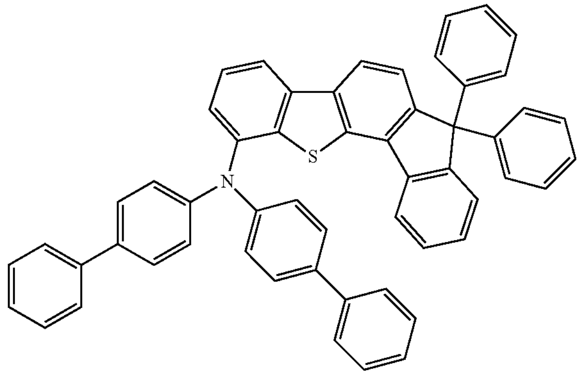
[2-5]
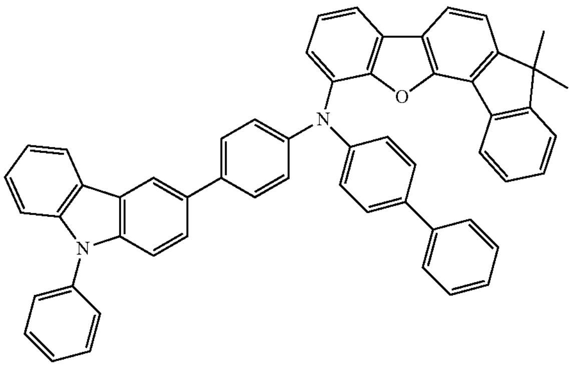
[2-6]
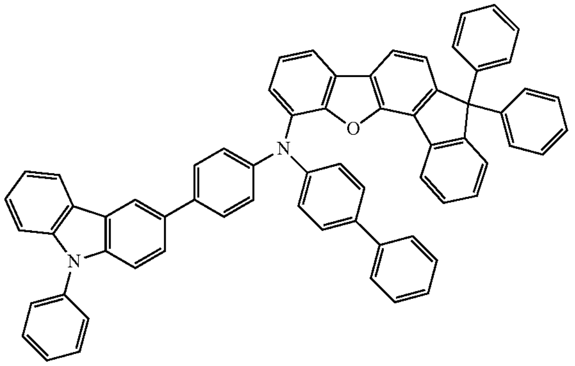

-continued
[2-7]
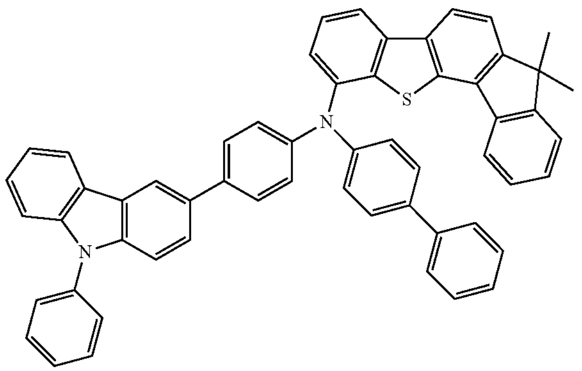
[2-8]
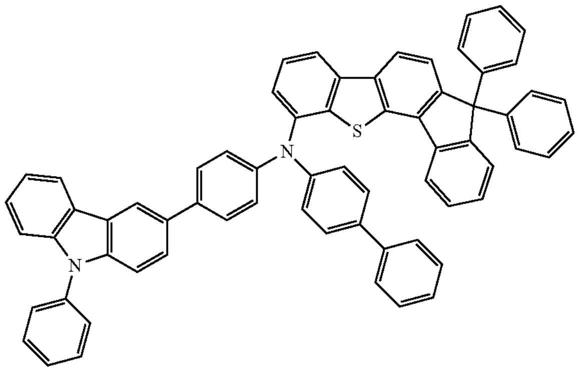
[2-9]
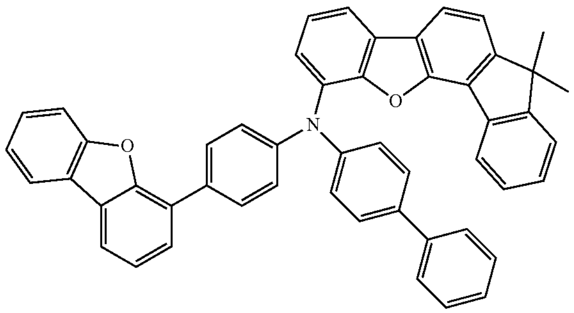
[2-10]
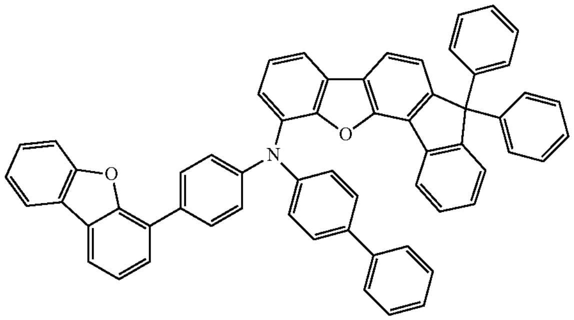
-continued
[2-11]
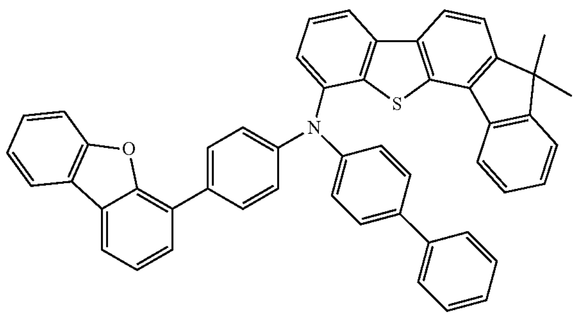
[2-12]
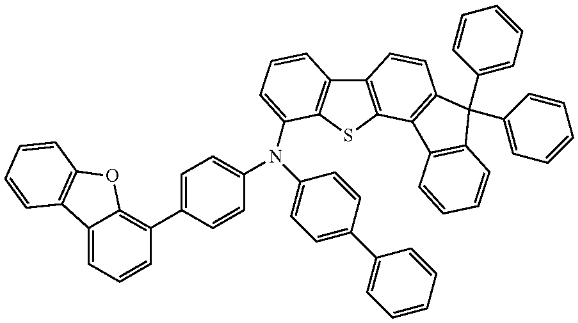
[2-13]
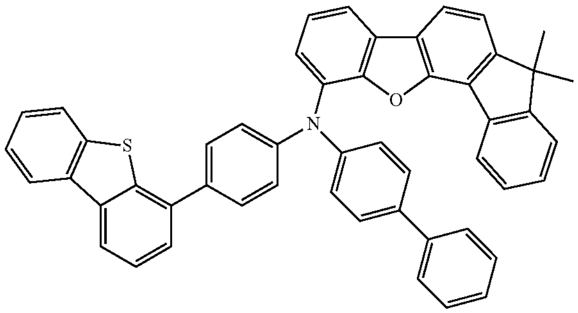
[2-14]
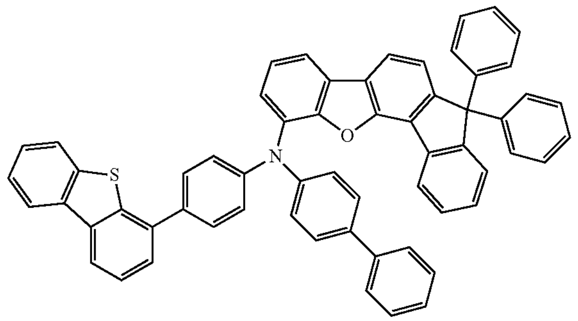

-continued
[2-15]
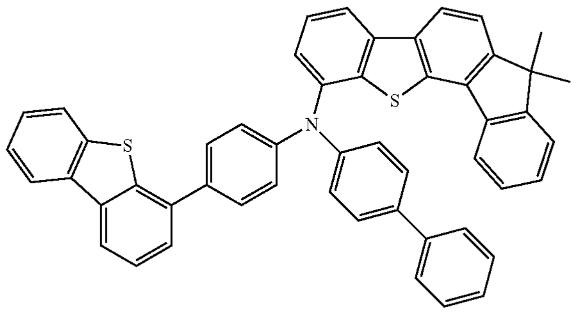
[2-16]
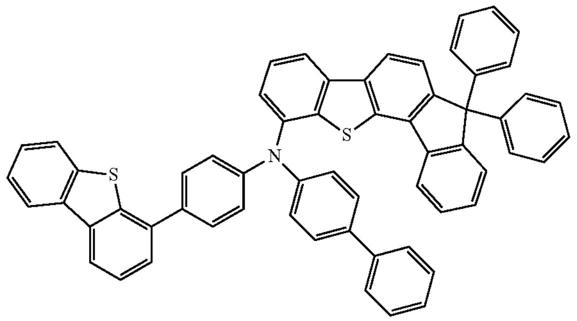
[2-17]
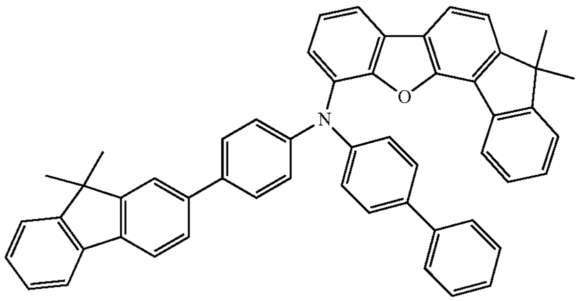
[2-18]
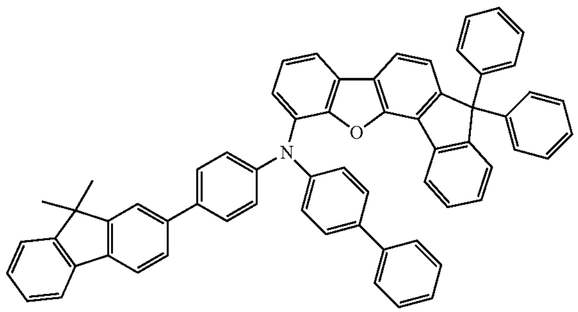
-continued
[2-19]
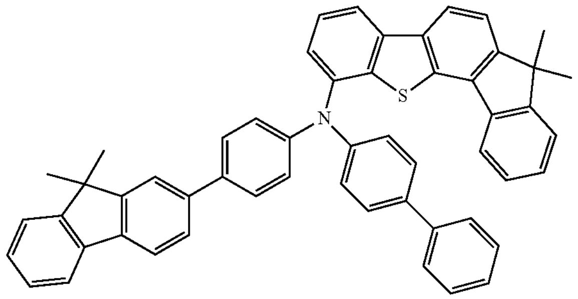
[2-20]
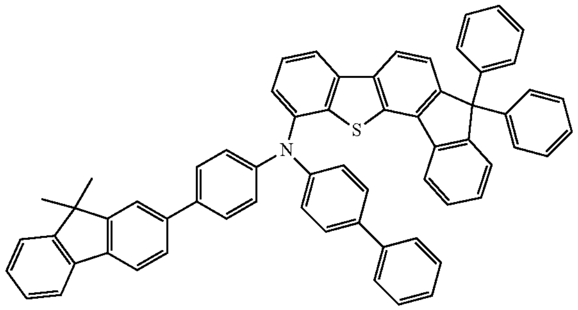
[2-21]
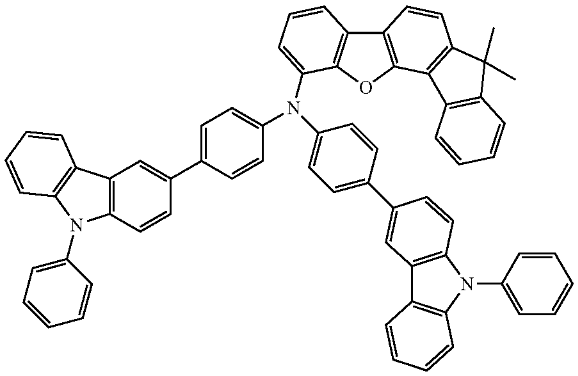
[2-22]
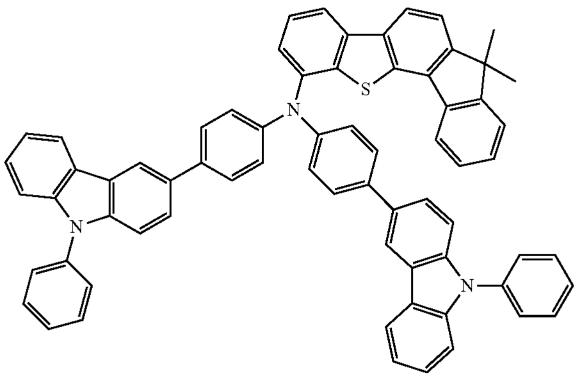

-continued
[2-23]
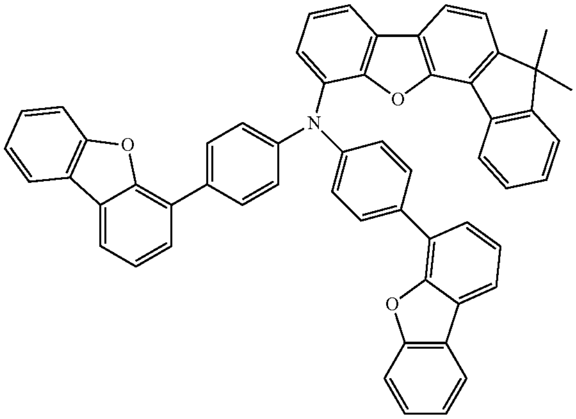
[2-24]
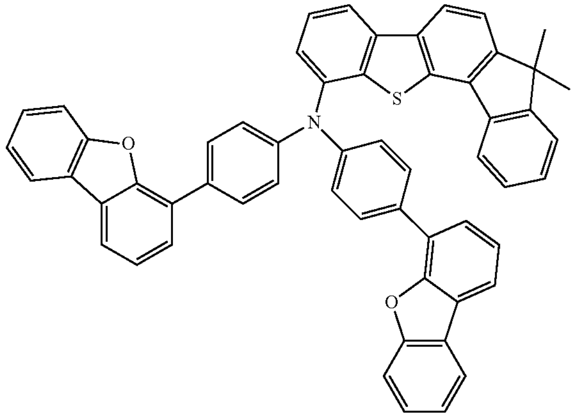
[2-25]
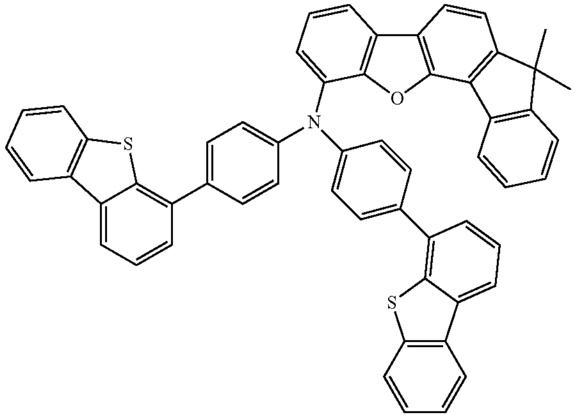
-continued
[2-26]
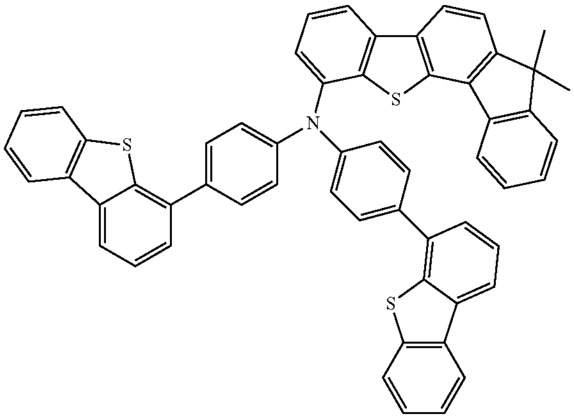
[2-26]
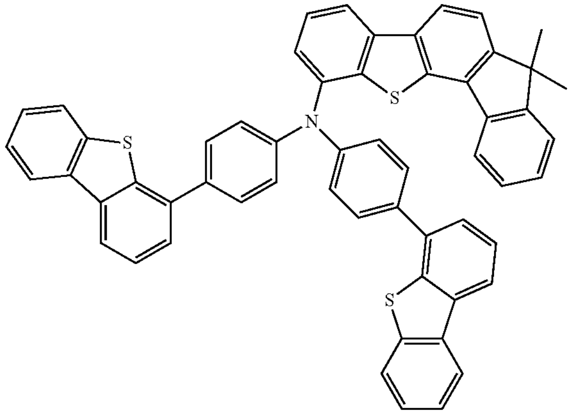
[2-27]
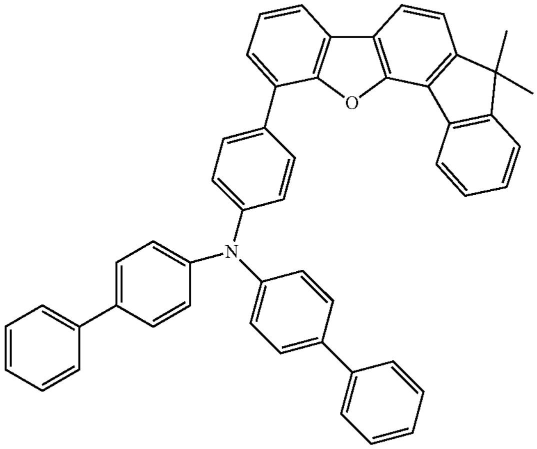

-continued
[2-28]
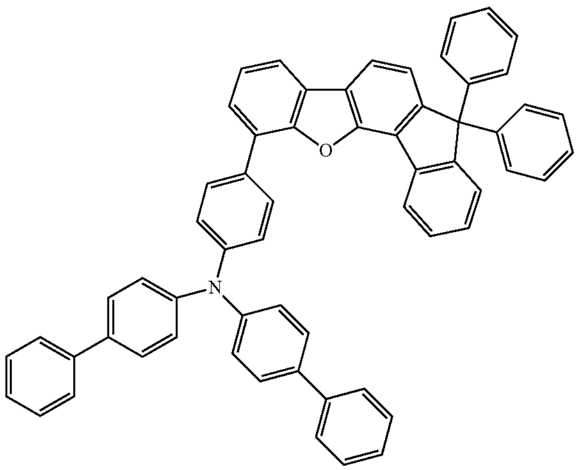
[2-29]
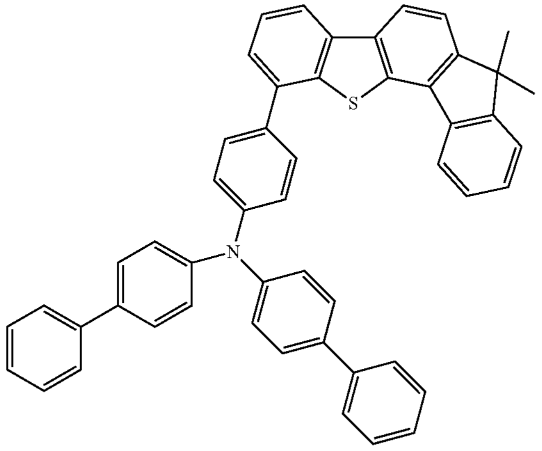
[2-30]
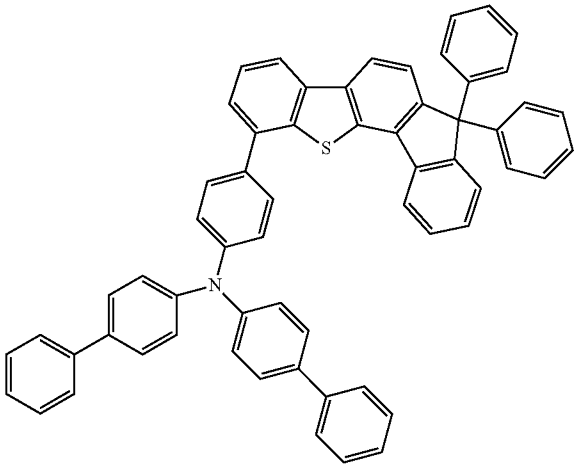
-continued
[2-31]
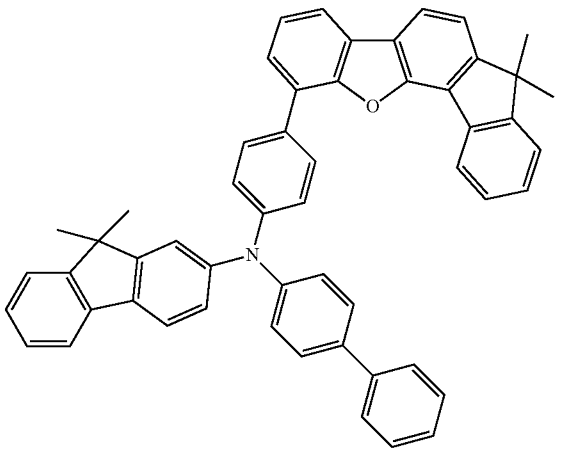
[2-32]
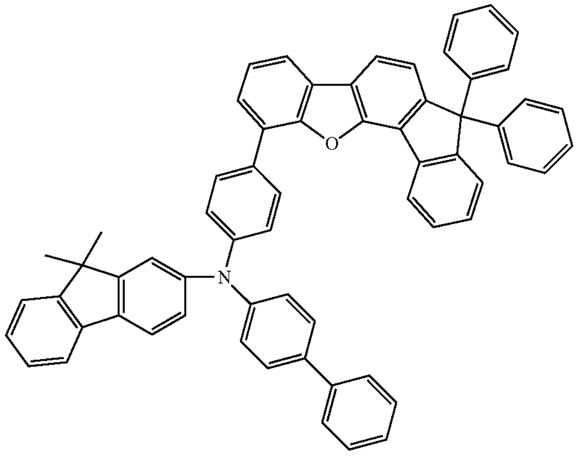
[2-33]
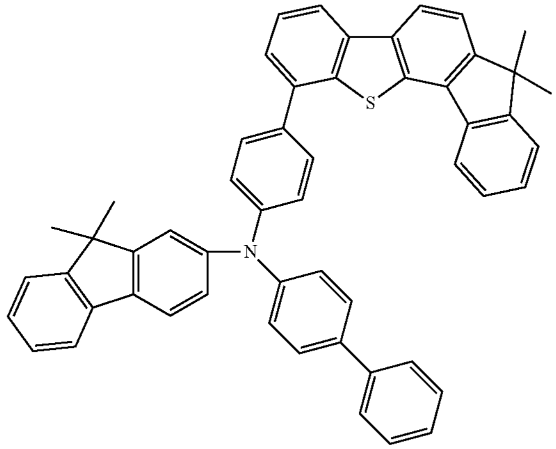

-continued
[2-34]
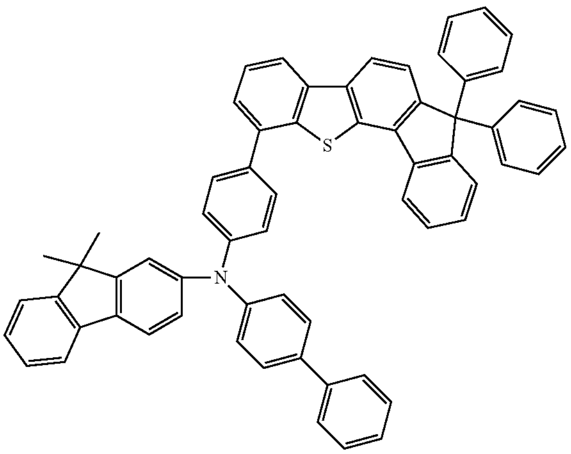
[2-35]
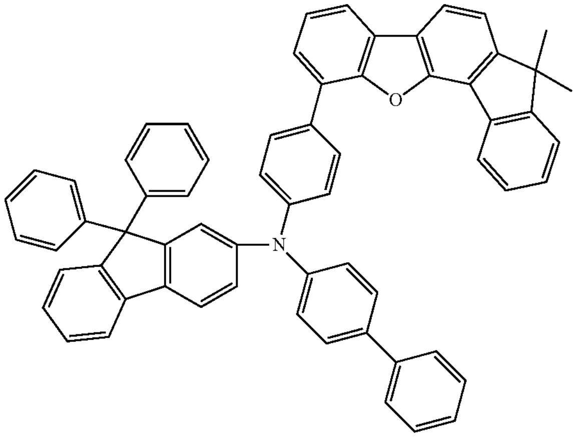
[2-36]
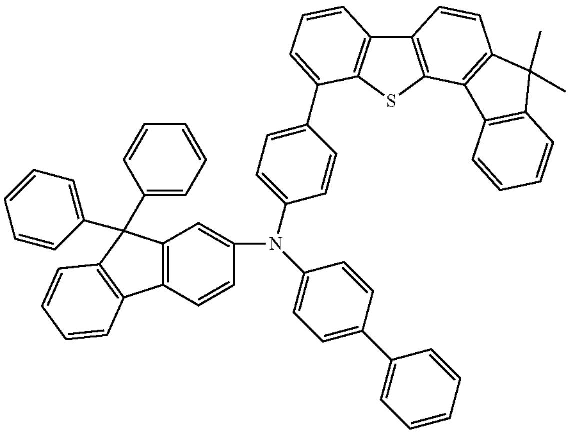
-continued
[2-37]
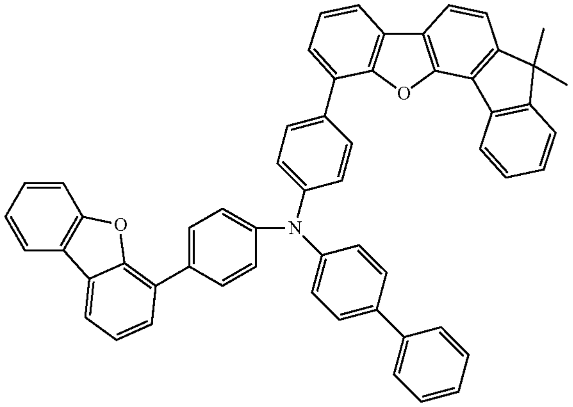
[2-38]
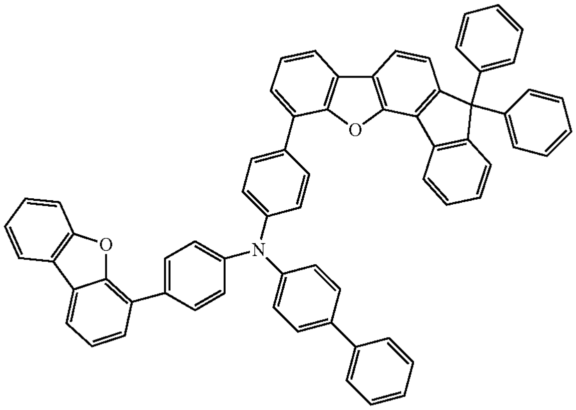
[2-39]
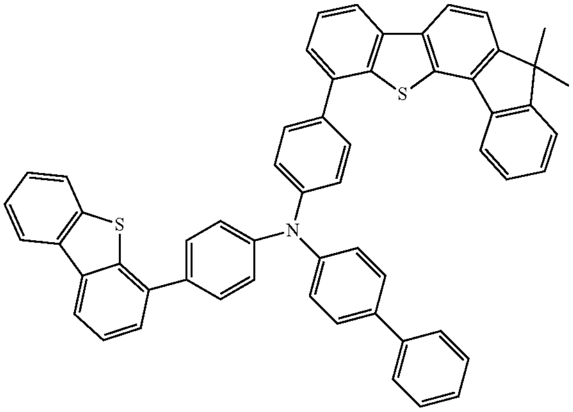

-continued
[2-40]
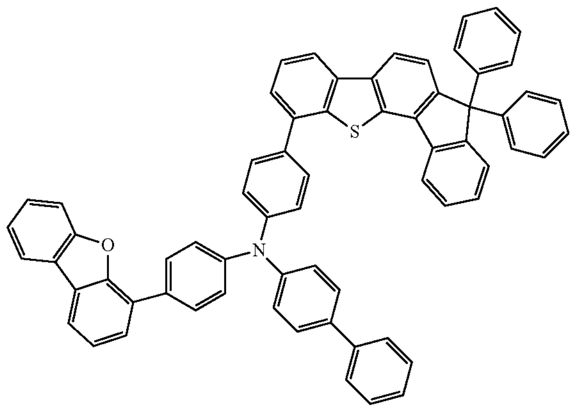
[2-41]
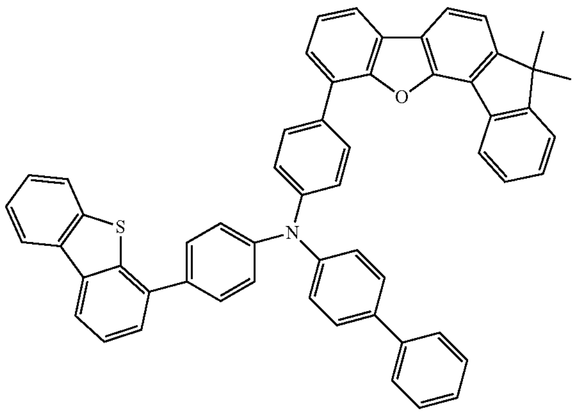
[2-42]
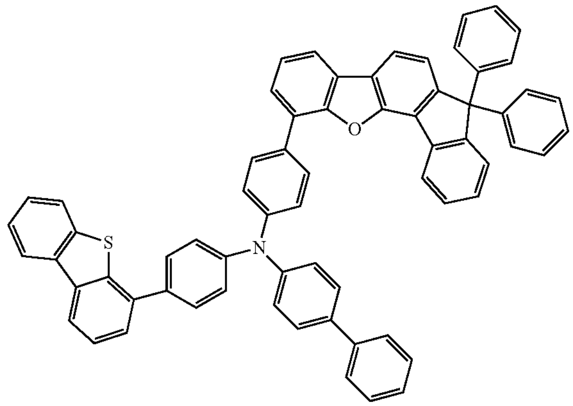
-continued
[2-43]
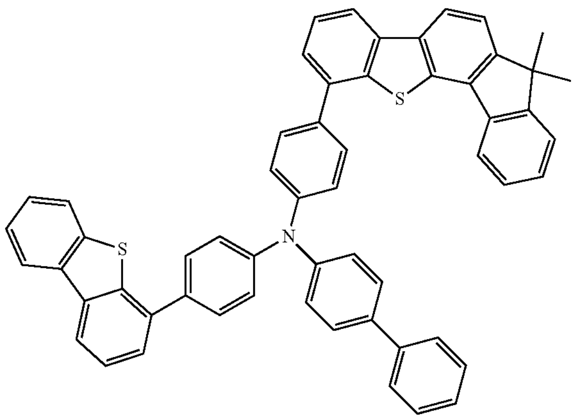
[2-44]
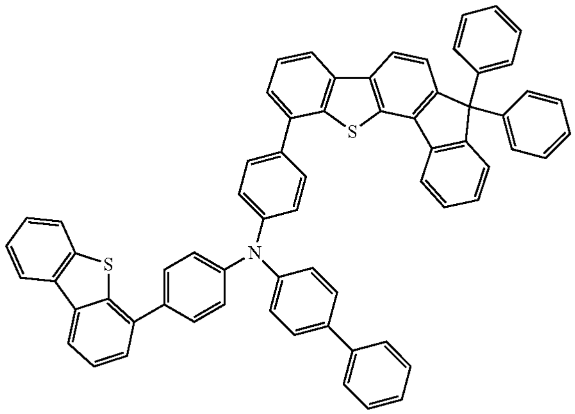
[2-45]
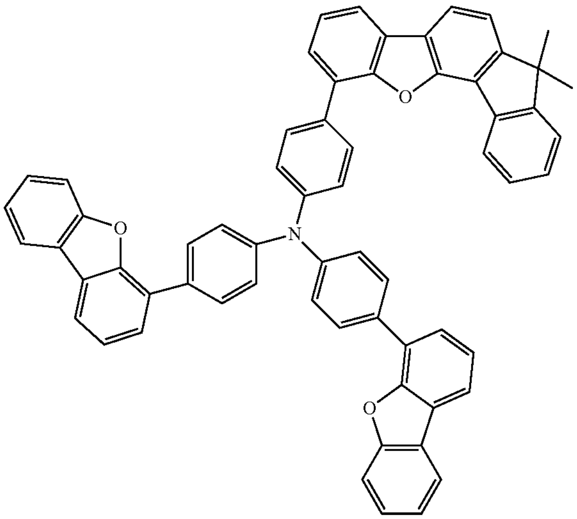

-continued
[2-46]
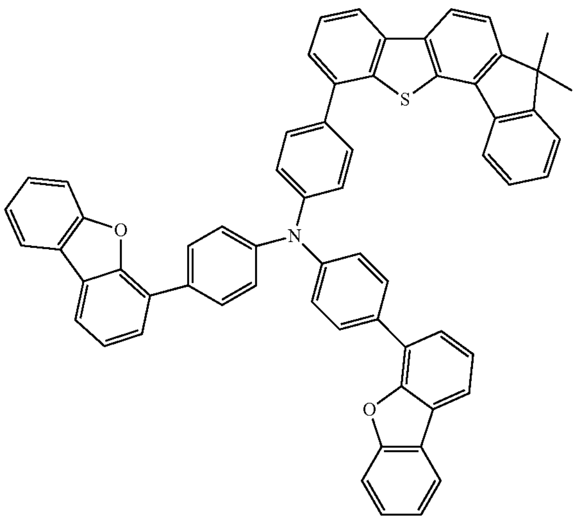
[2-47]
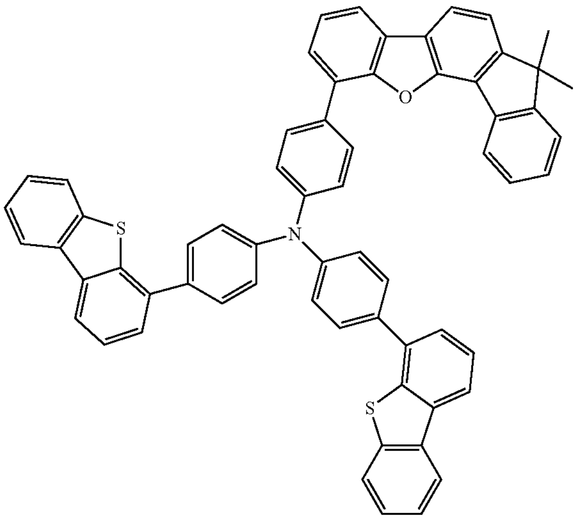
[2-48]
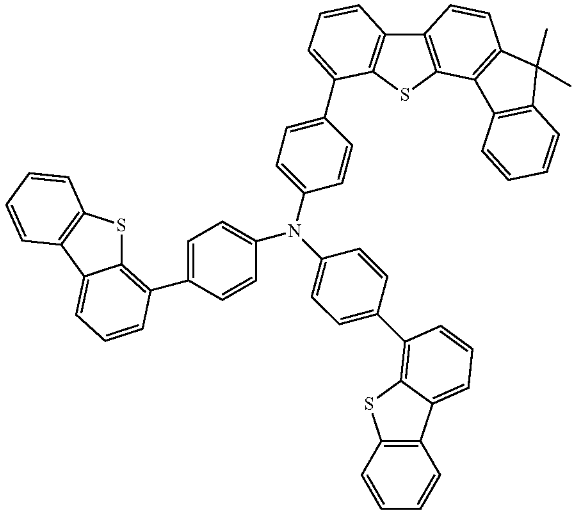
-continued
[2-49]
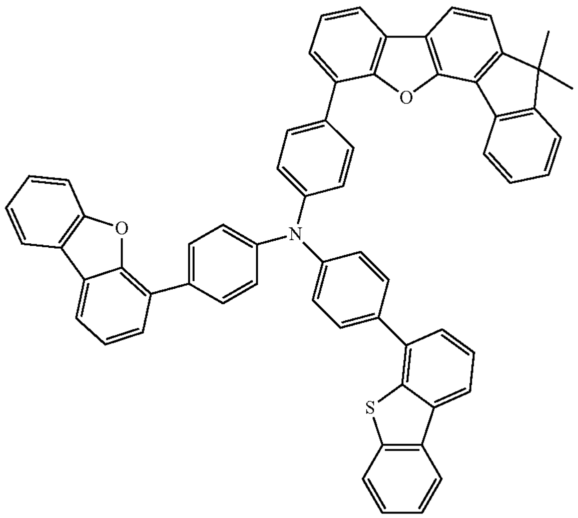
[2-50]
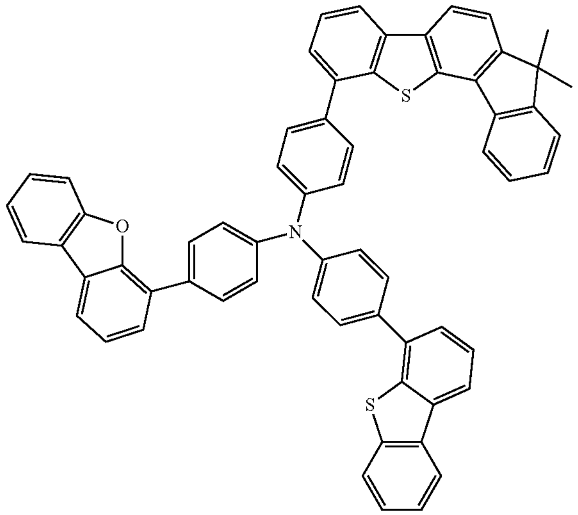
[2-51]
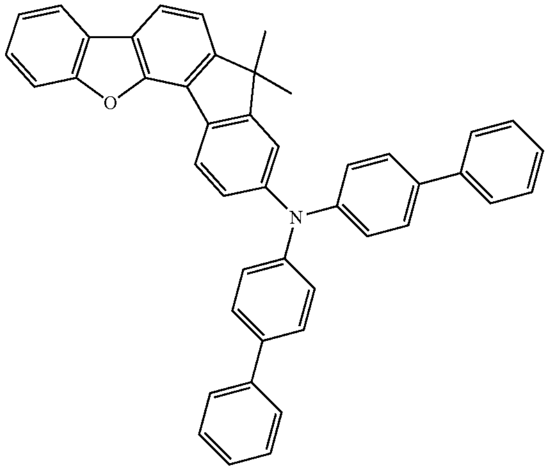

-continued
[2-52]
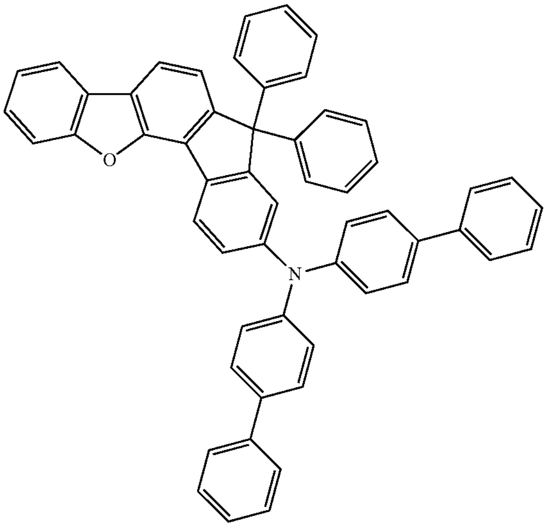
[2-53]
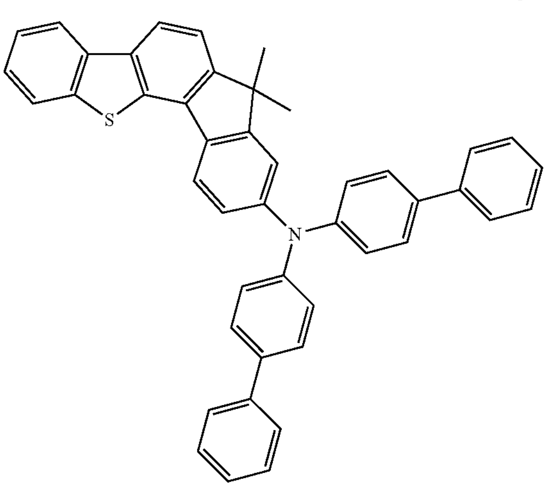
[2-54]
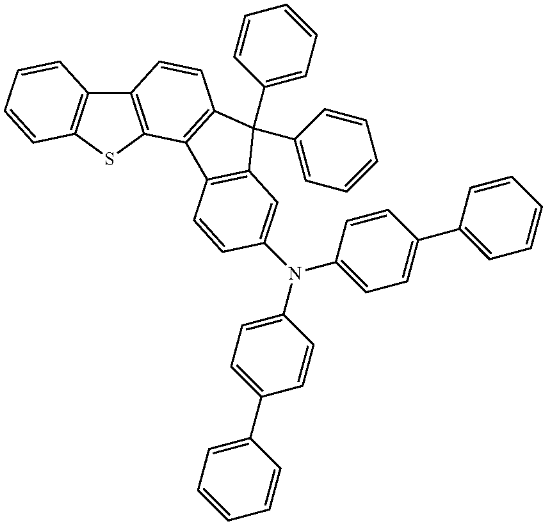
-continued
[2-55]
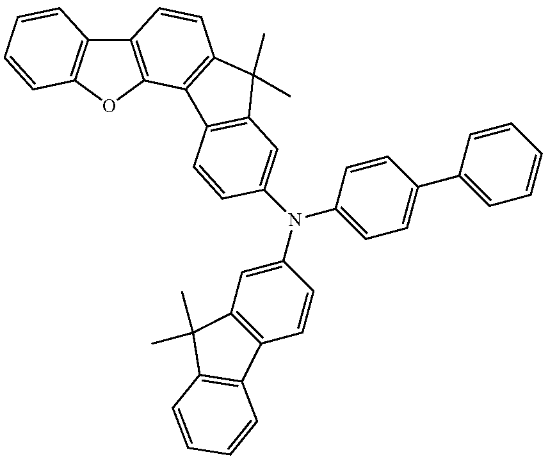
[2-56]
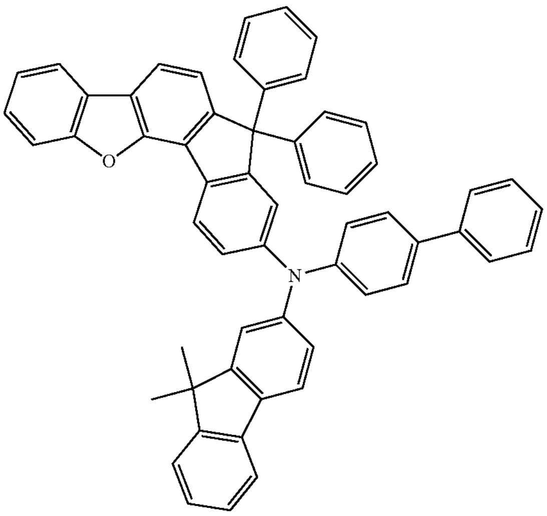
[2-57]
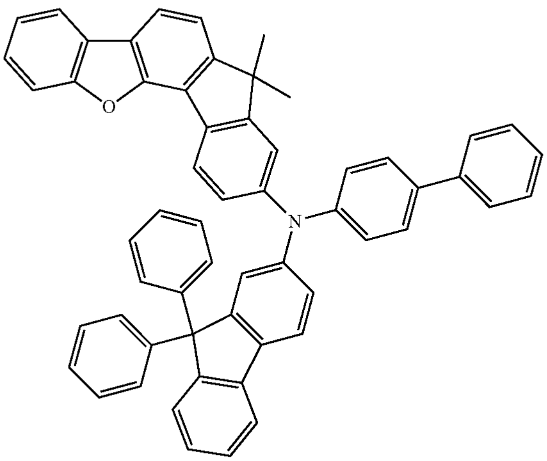

-continued
[2-58]
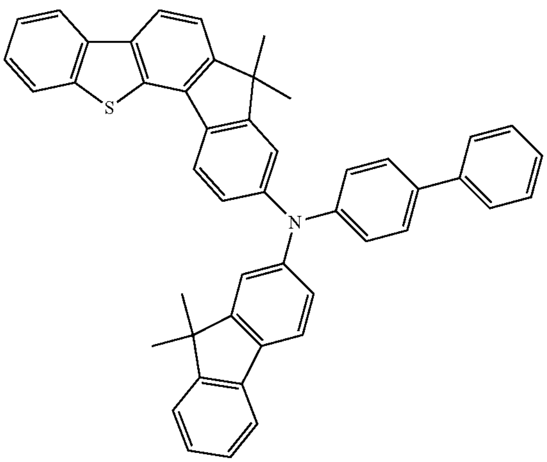
[2-59]
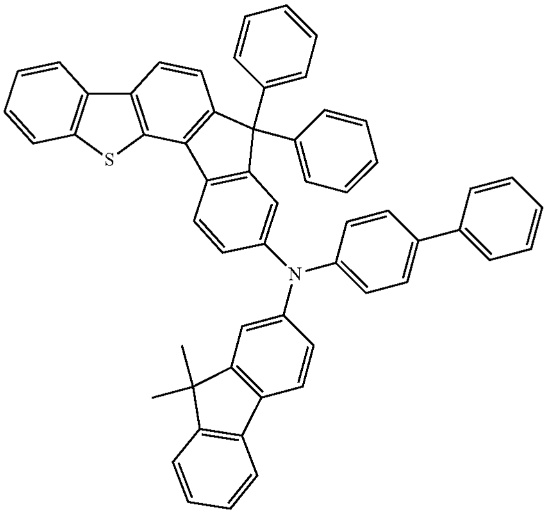
[2-60]
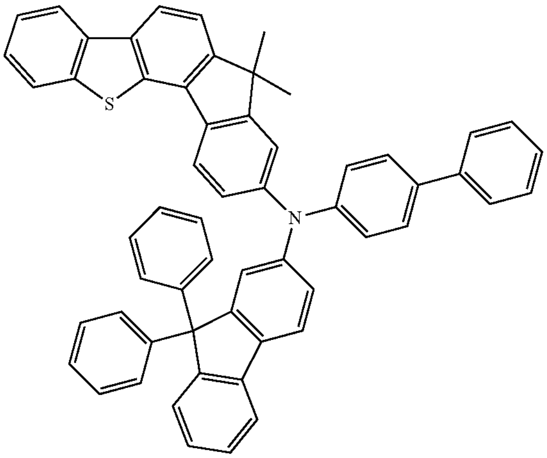
-continued
[2-61]
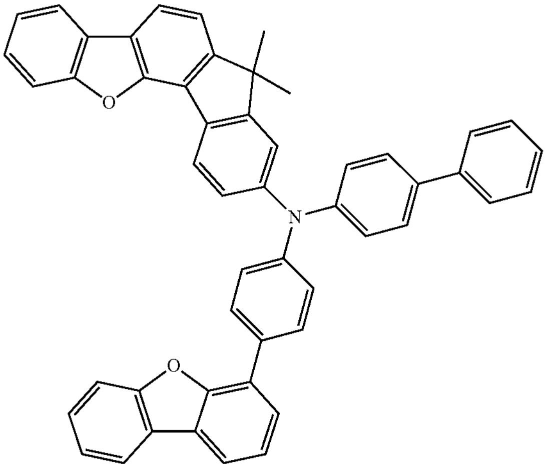
[2-62]
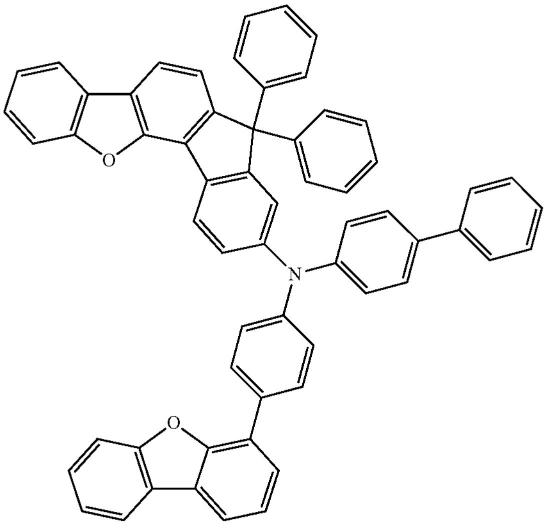
[2-63]
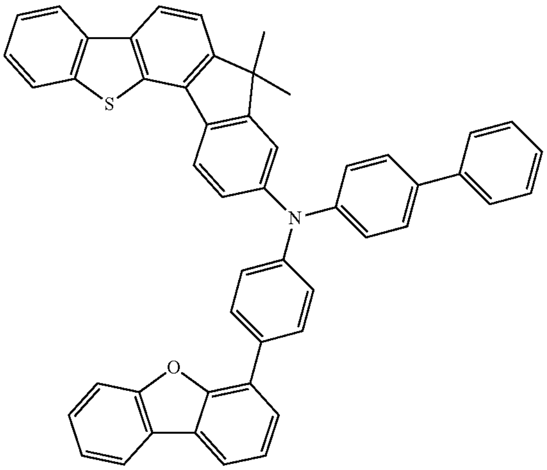

-continued
[2-64]
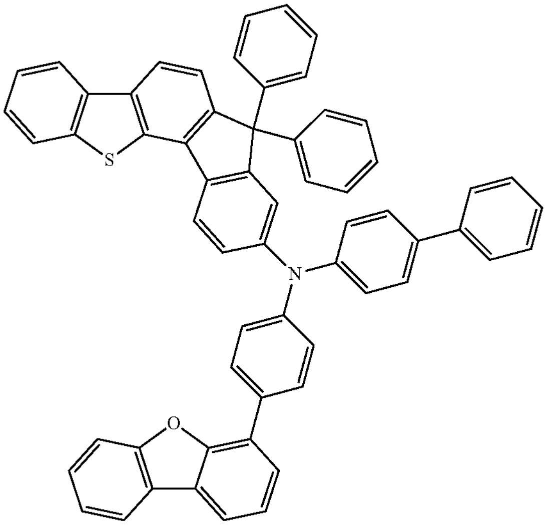
[2-65]
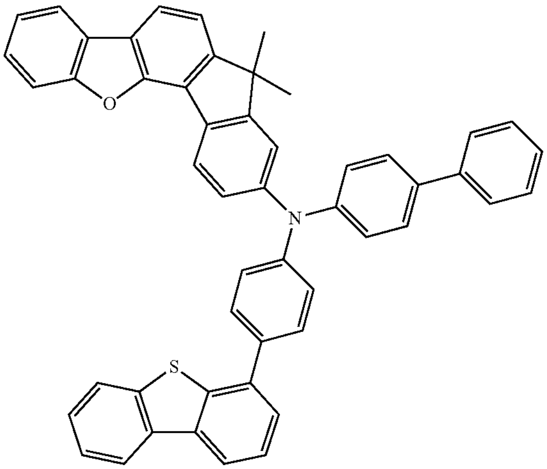
[2-66]
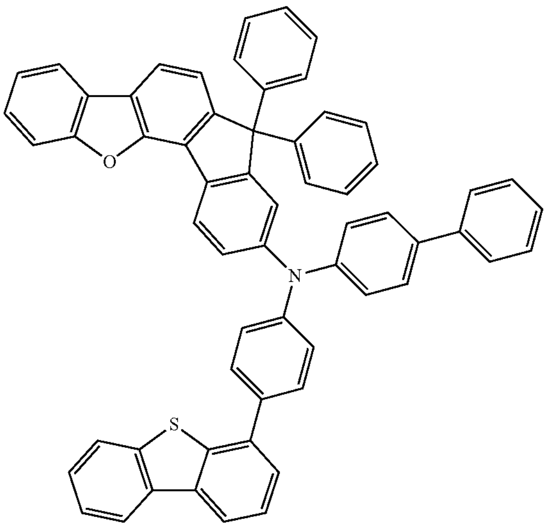
-continued
[2-67]
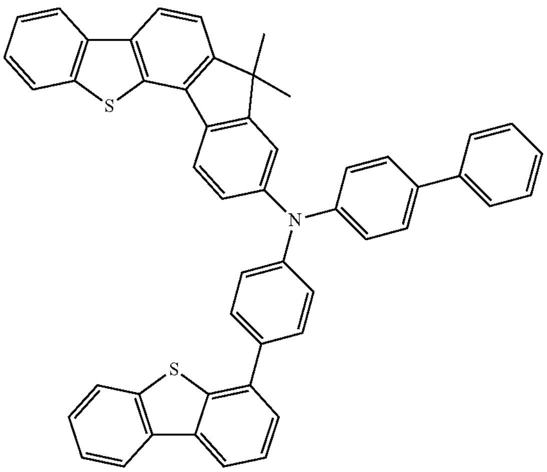
[2-68]
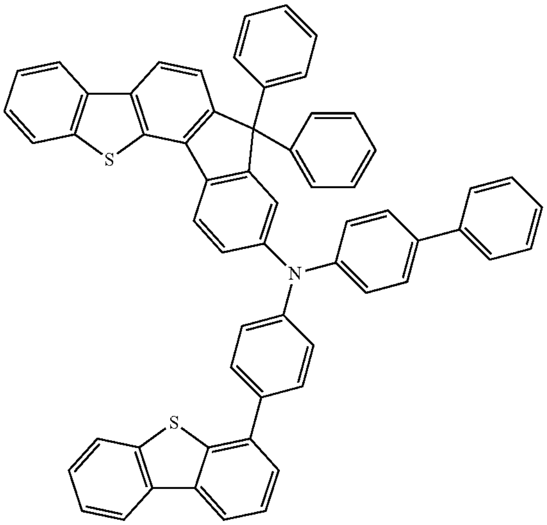
[2-69]
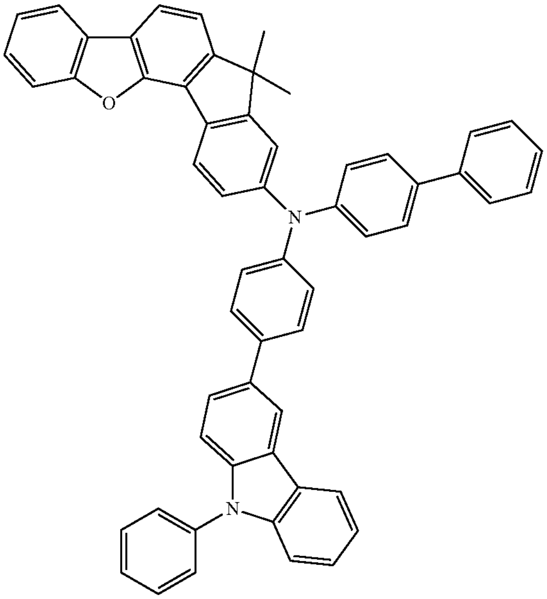

-continued
[2-70]
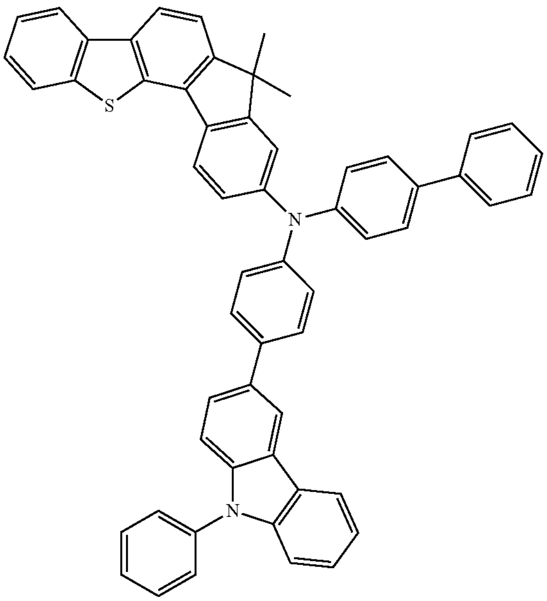
[2-71]
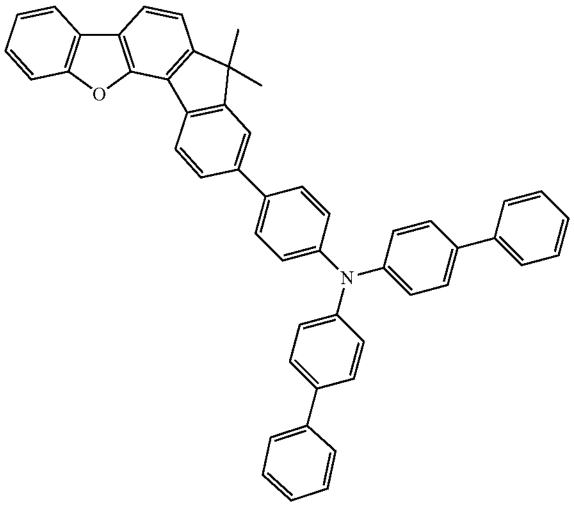
[2-72]
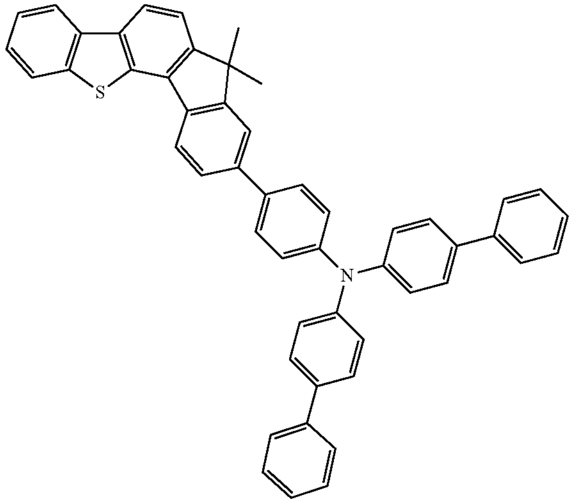
-continued
[2-73]
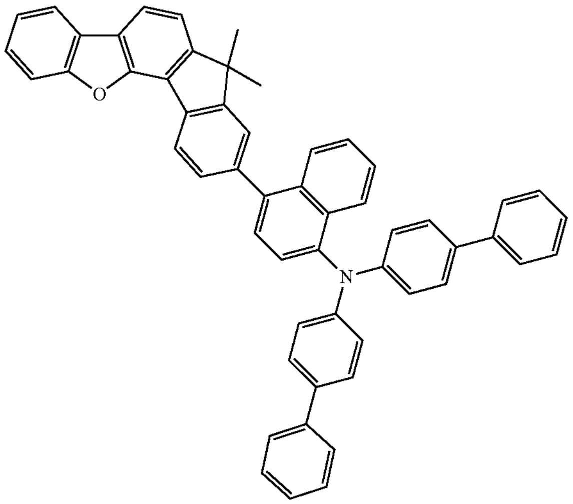
[2-74]
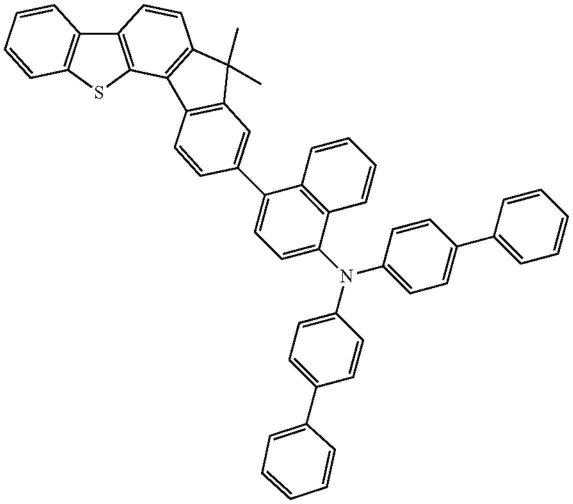
[2-75]
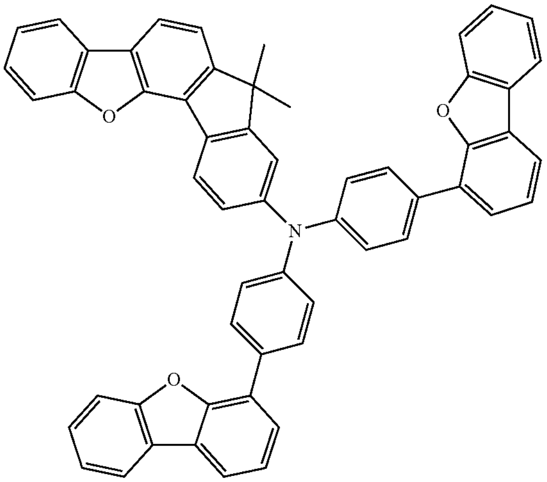

-continued
[2-76]
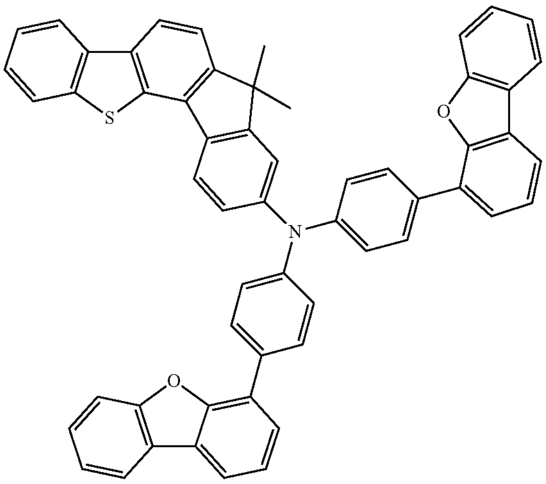
[2-77]
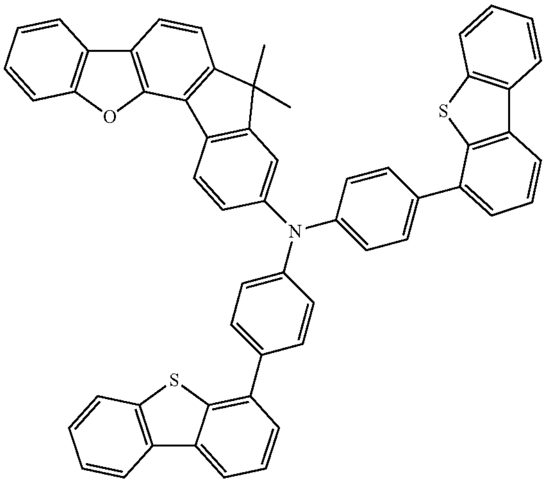
[2-78]
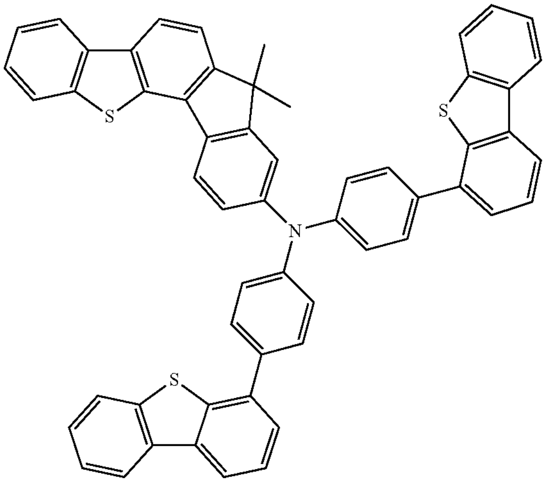
-continued
[2-79]
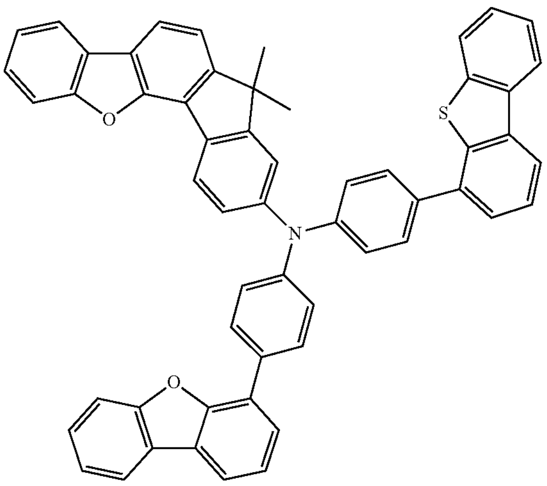
[2-80]
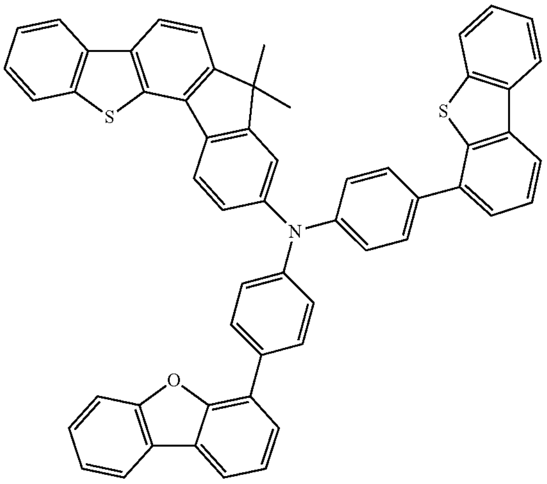
[2-81]
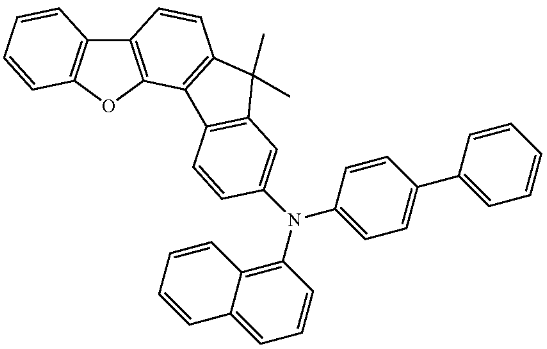

-continued
[2-82]
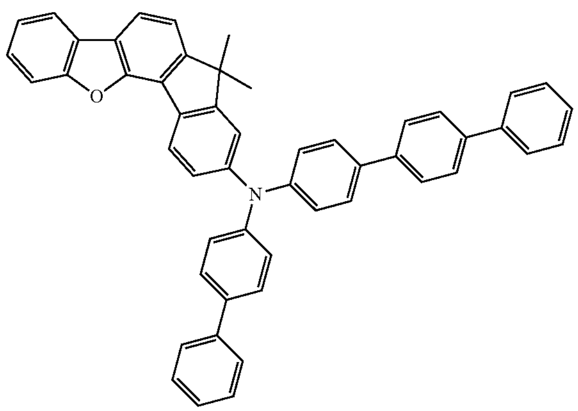
[2-83]
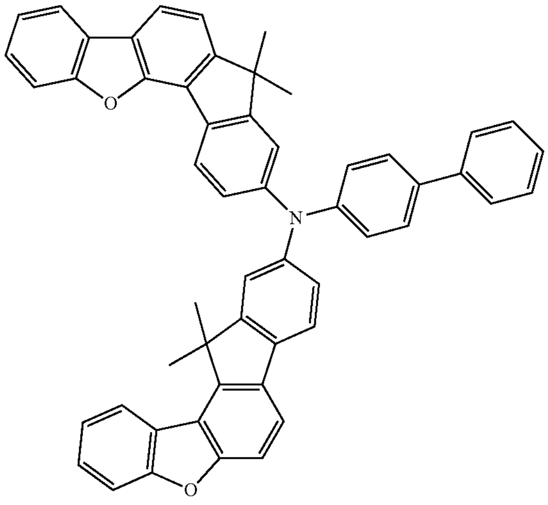
[2-84]
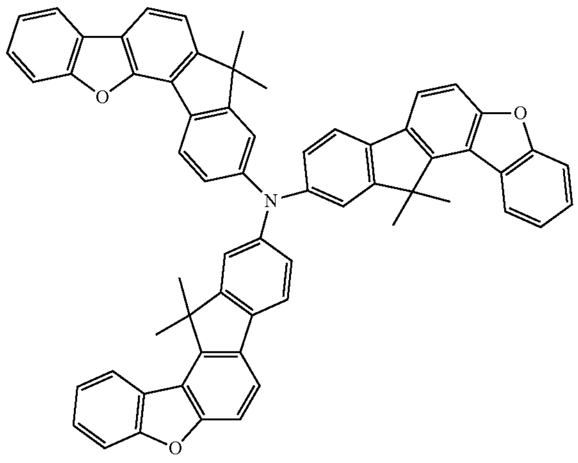
-continued
[2-85]
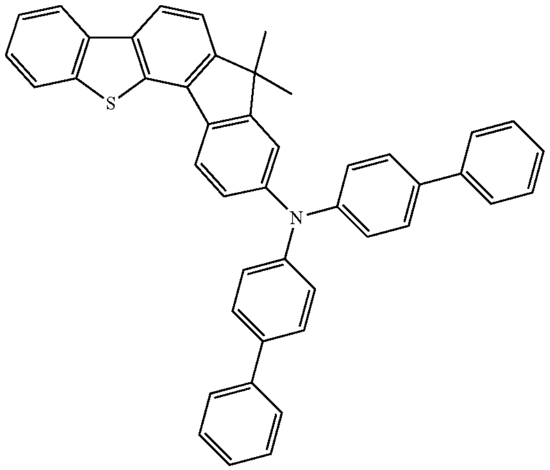
[2-86]
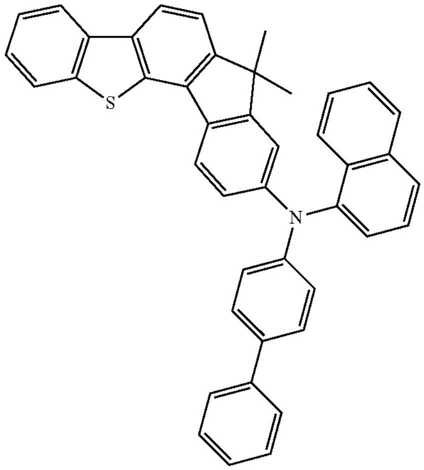
[2-87]
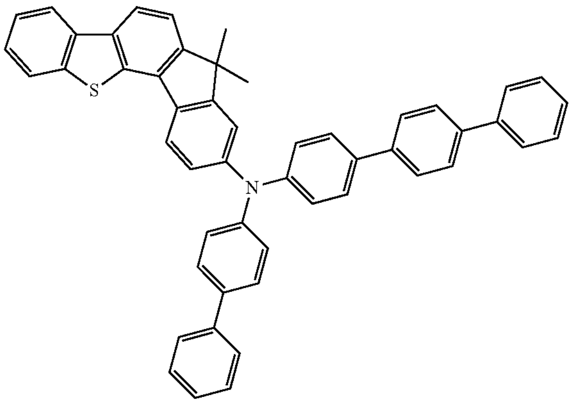

-continued
[2-88]
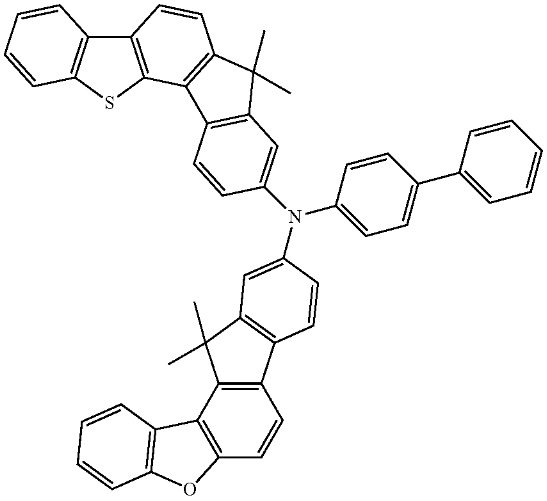
[2-89]
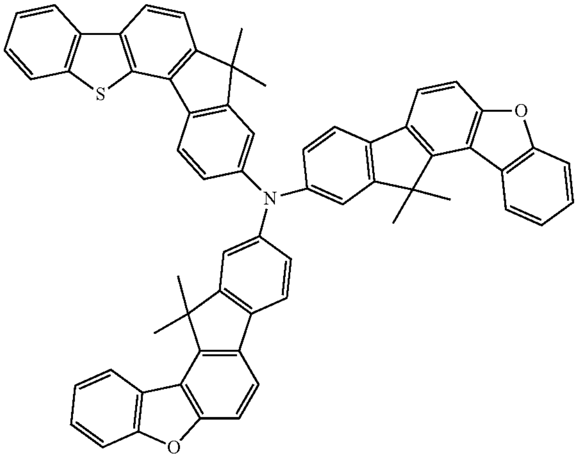
[2-90]
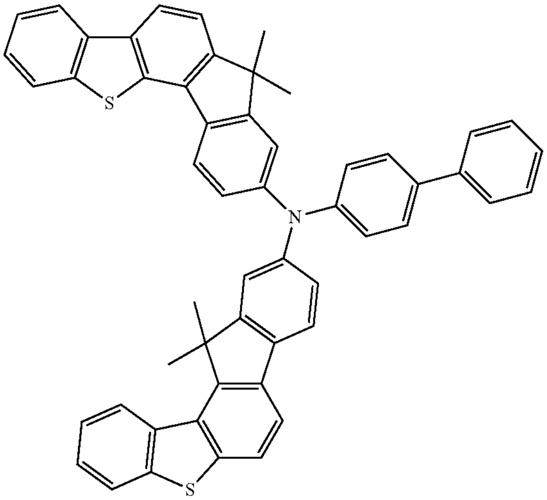
-continued
[2-91]
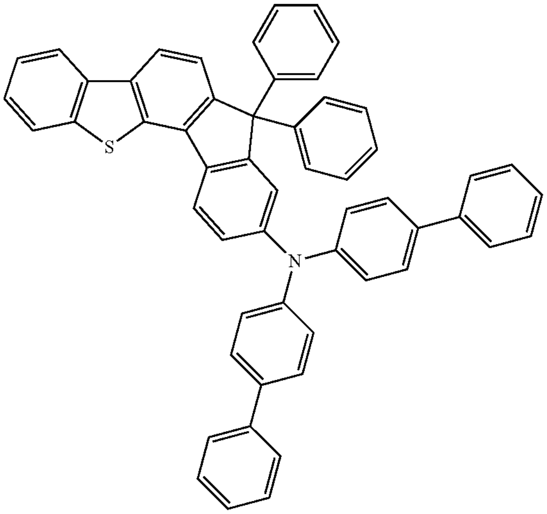
[2-92]
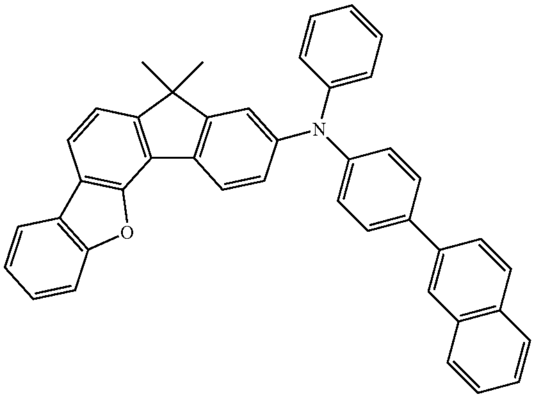
[2-93]
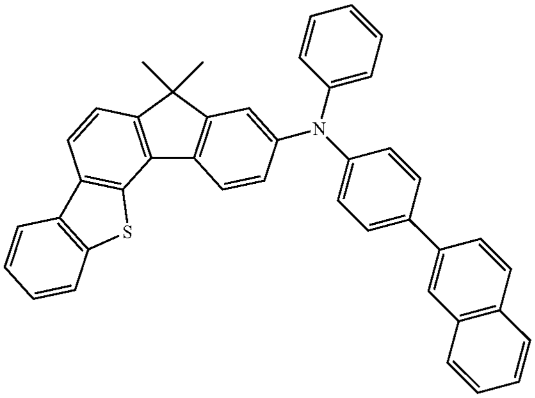

-continued
[2-94]
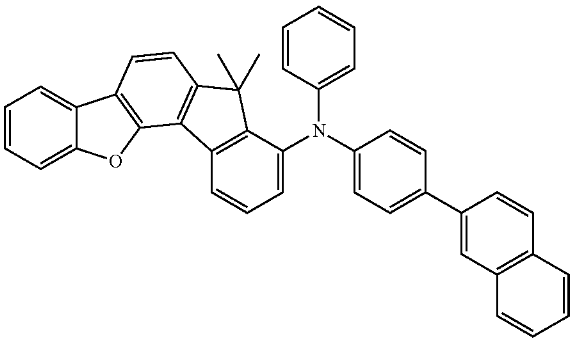
[2-95]
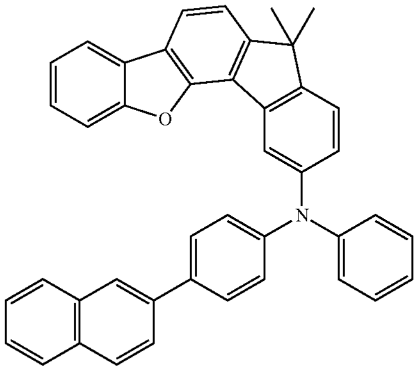
[2-96]
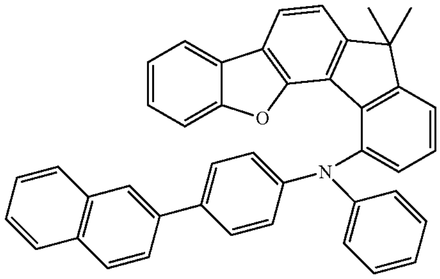
[2-97]
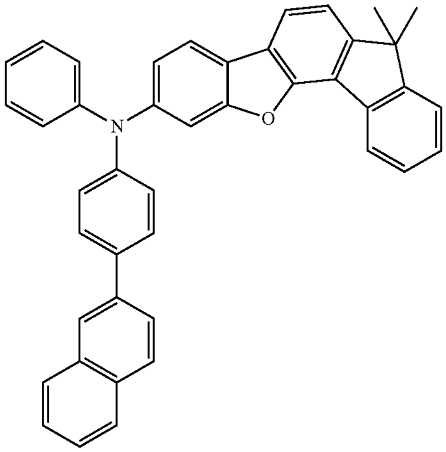
-continued
[2-98]
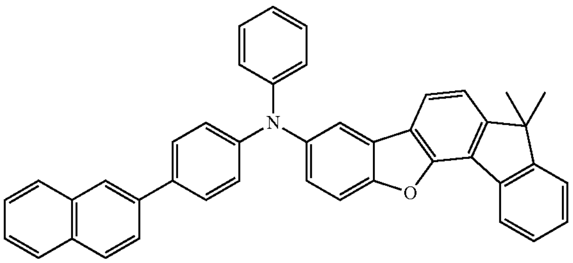
[2-99]
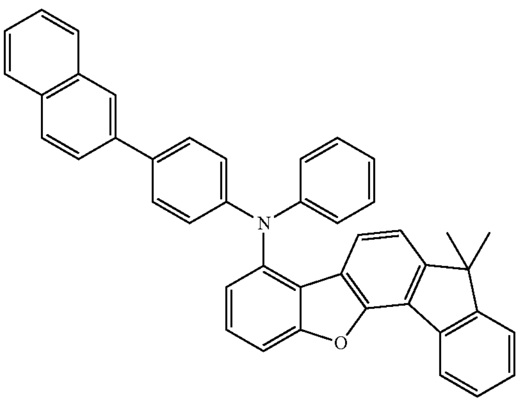
[2-100]
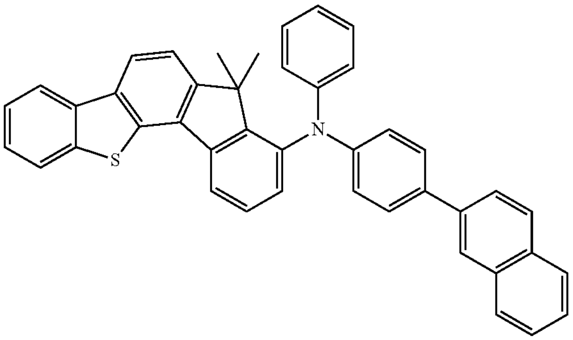
[2-101]
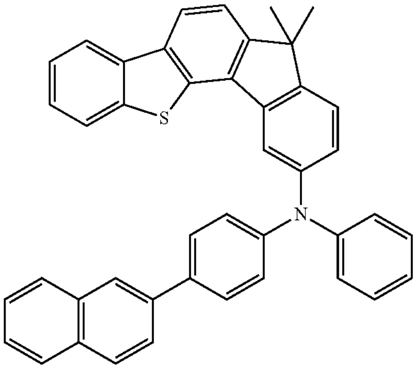

-continued
[2-102]
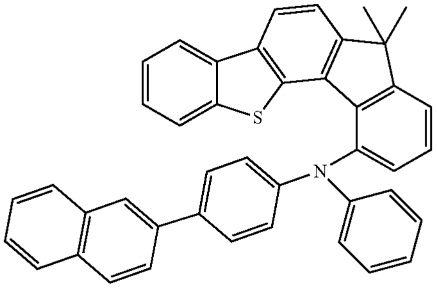
[2-103]
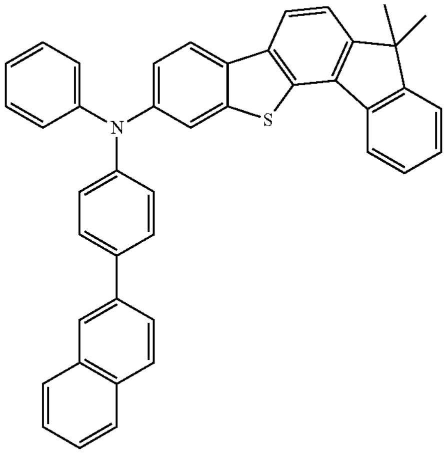
[2-104]
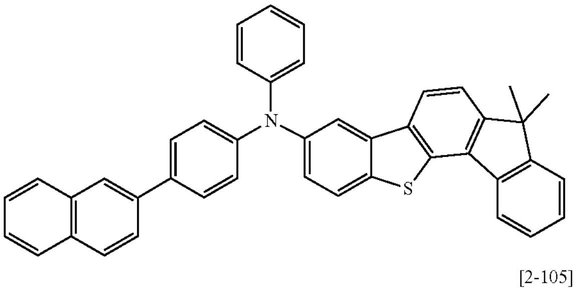
[2-105]
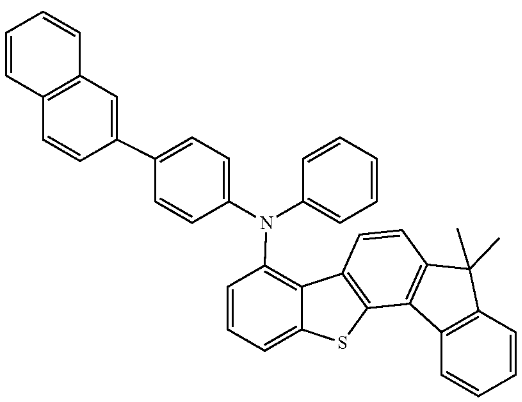
[2-106]
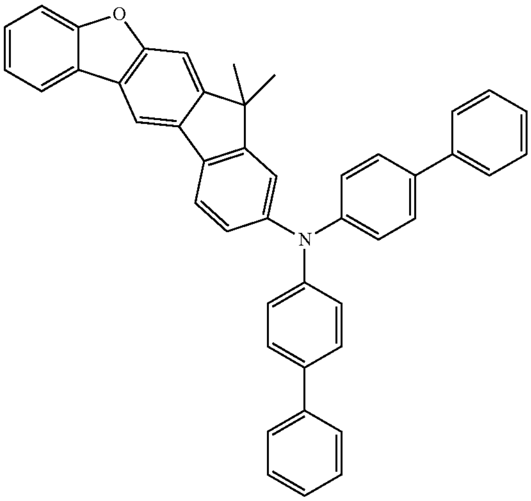
[2-107]
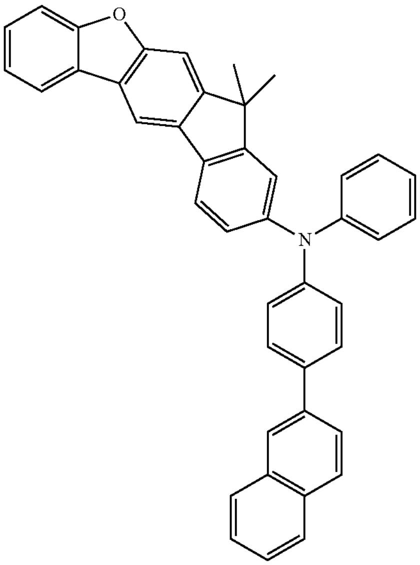
[2-108]
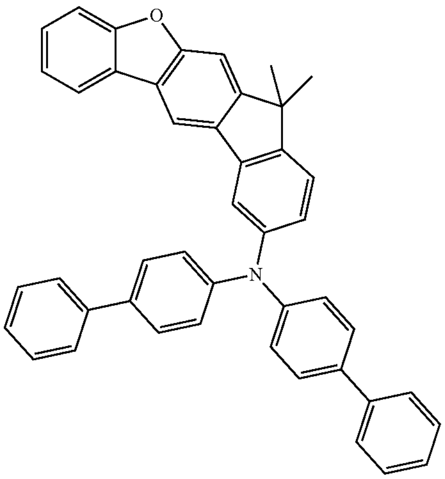

-continued
[2-109]
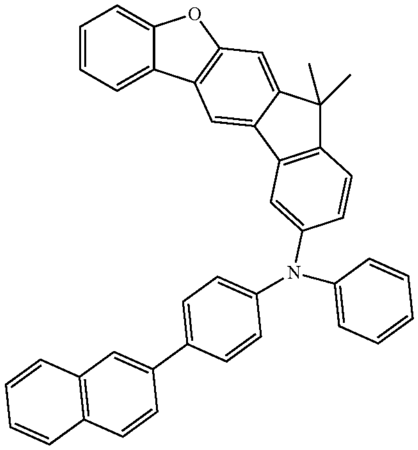
[2-110]
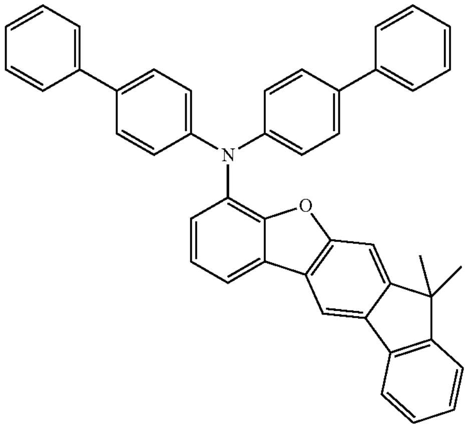
[2-111]
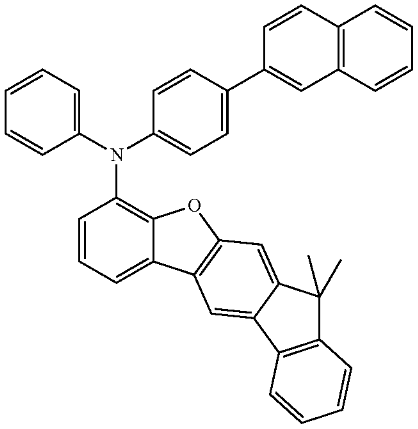
-continued
[2-112]
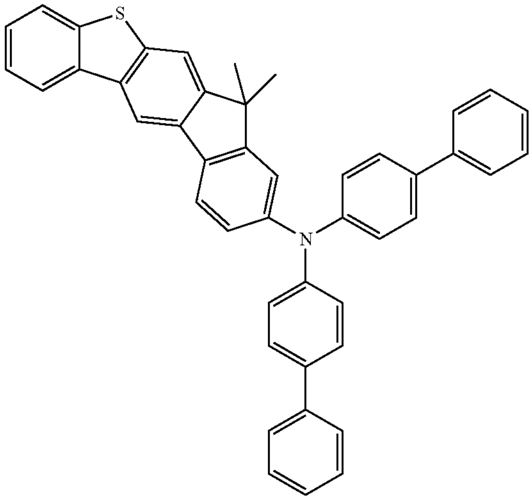
[2-113]
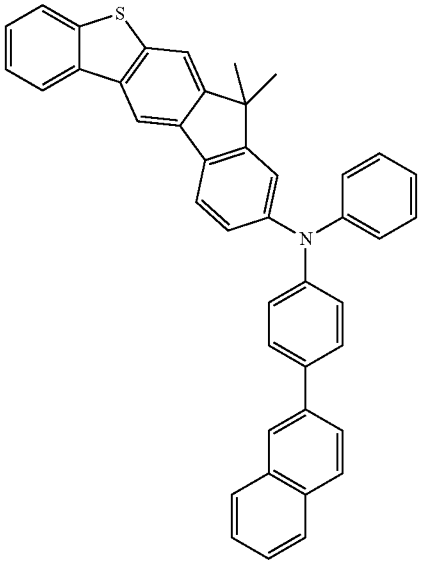
[2-114]
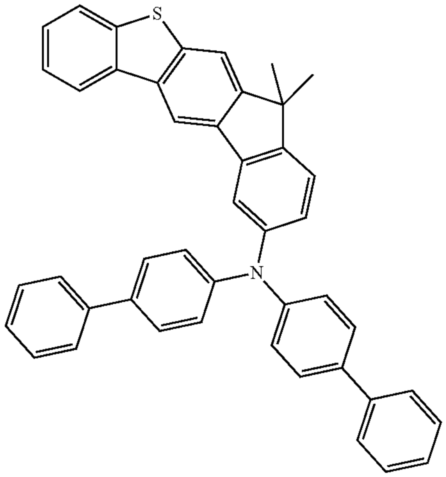

-continued
[2-115]
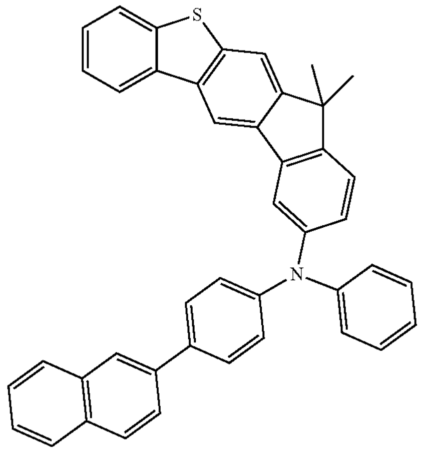
[2-116]
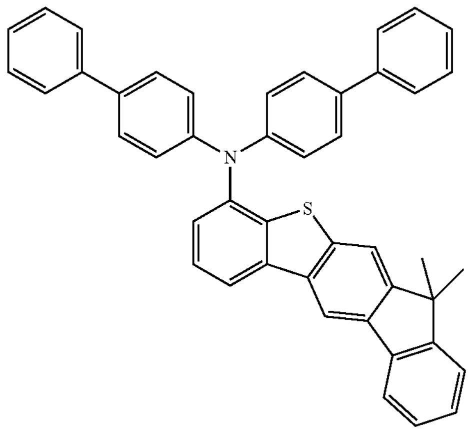
[2-117]
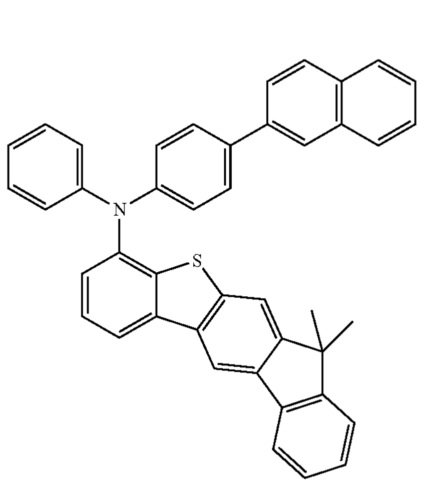
-continued
[2-118]
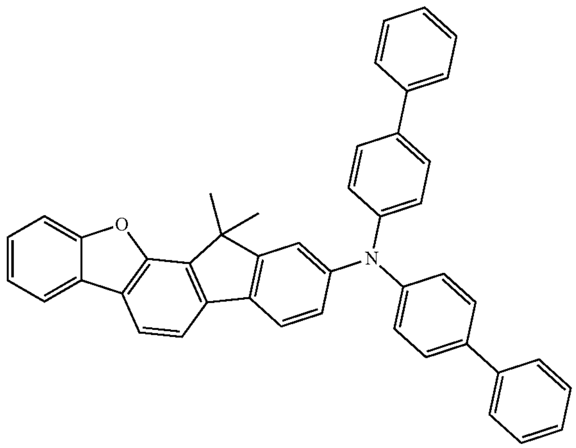
[2-119]
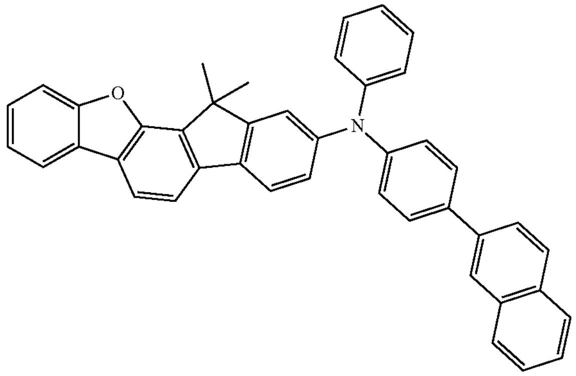
[2-120]
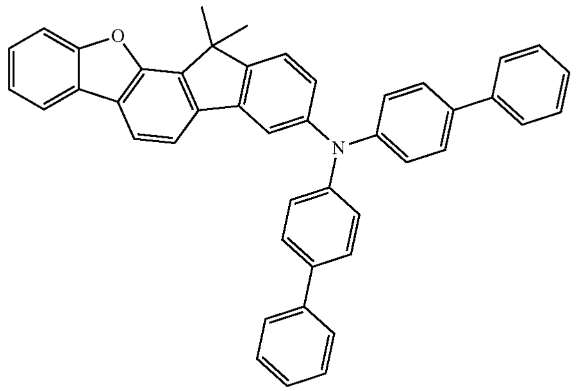

-continued
[2-121]
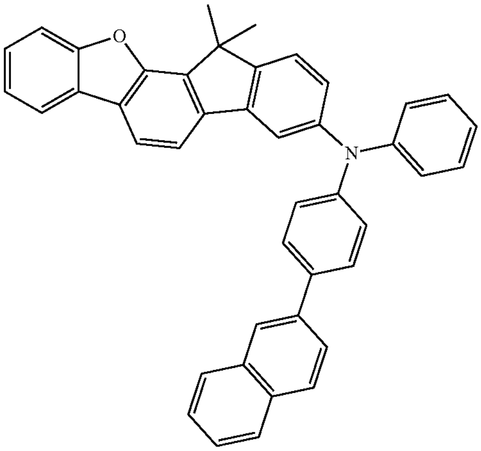
[2-122]
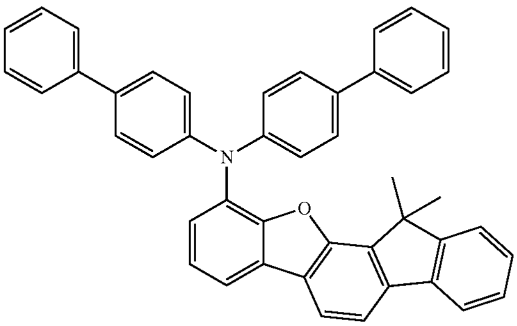
[2-123]
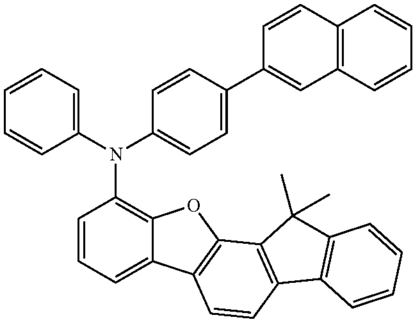
[2-124]
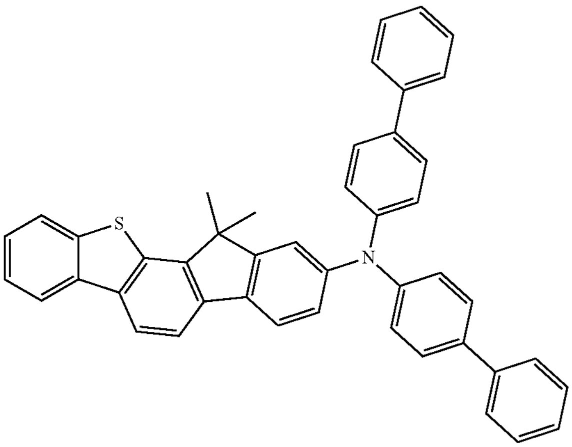
-continued
[2-125]
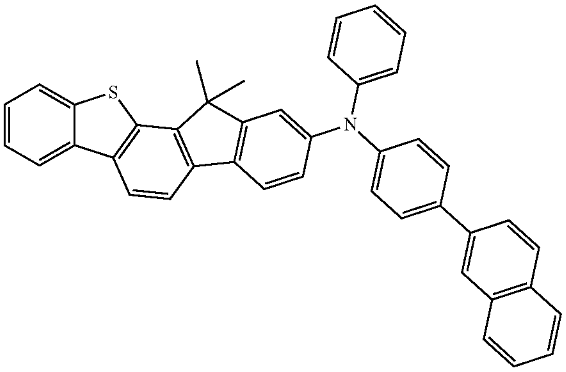
[2-126]
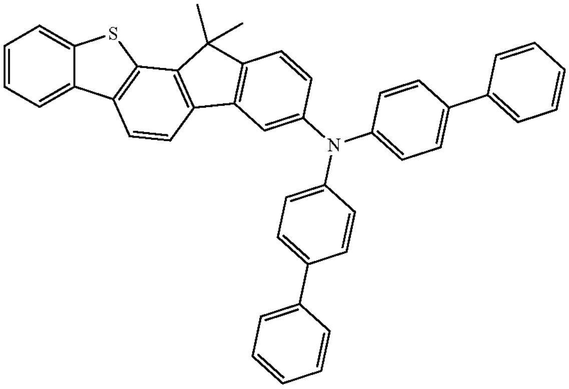
[2-127]
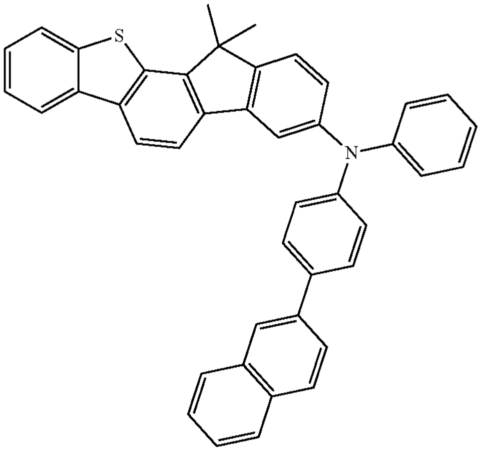
[2-128]
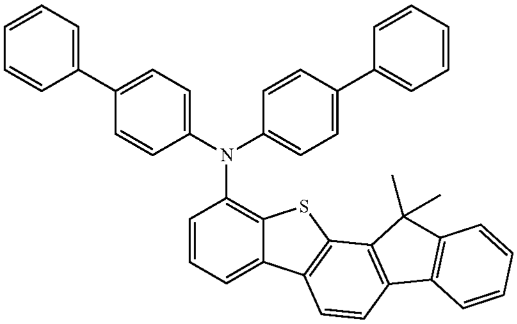

-continued
[2-129]
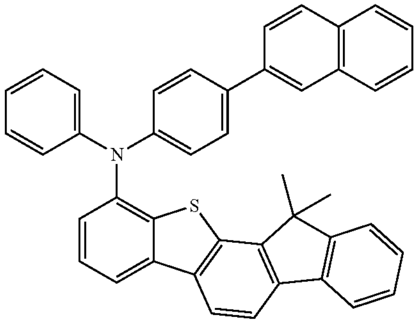
[2-130]
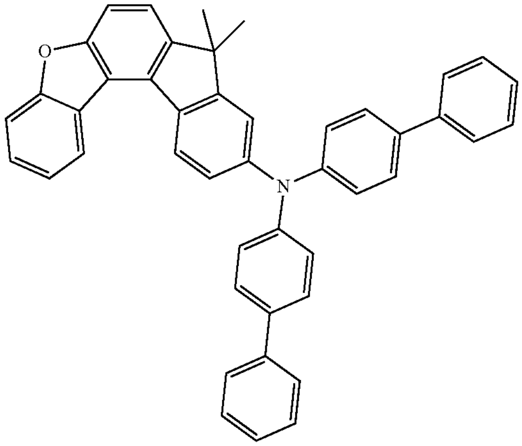
[2-131]
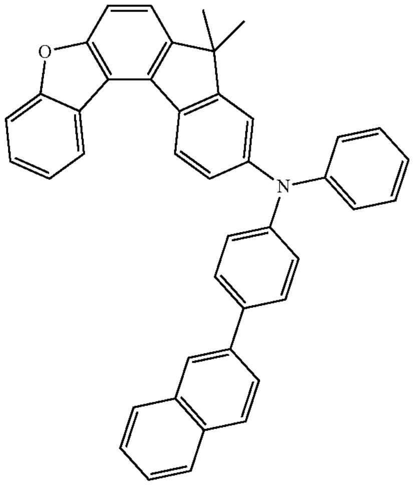
-continued
[2-132]
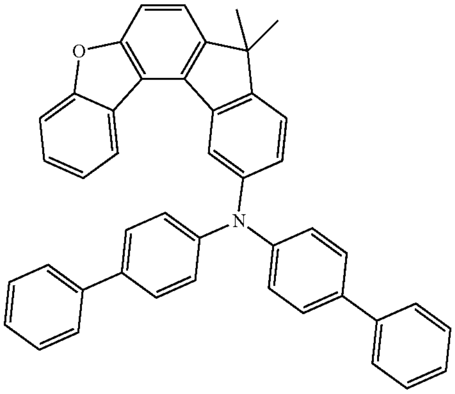
[2-133]
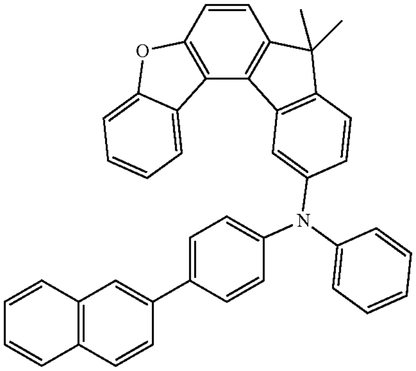
[2-134]
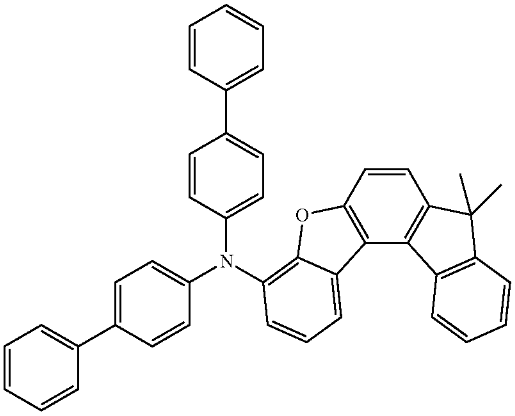
[2-135]
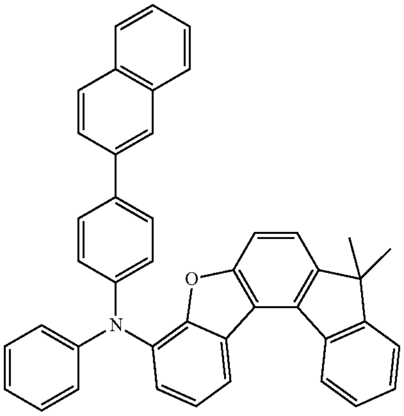

-continued
[2-136]
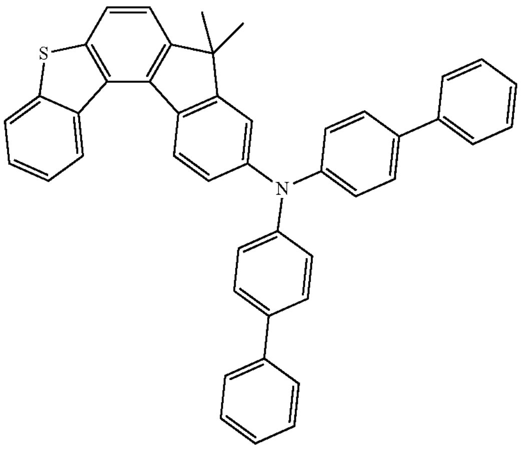
[2-137]
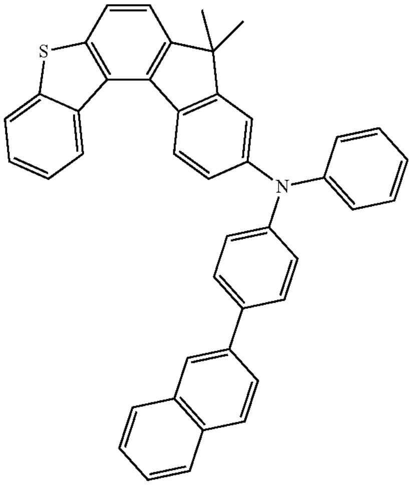
[2-138]
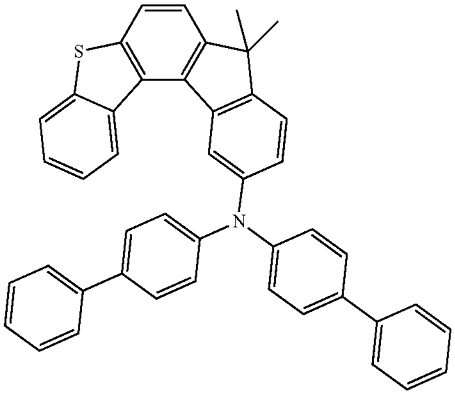
-continued
[2-139]
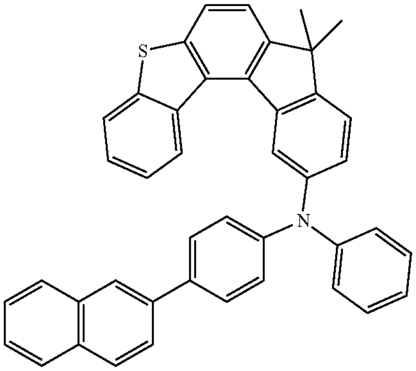
[2-140]
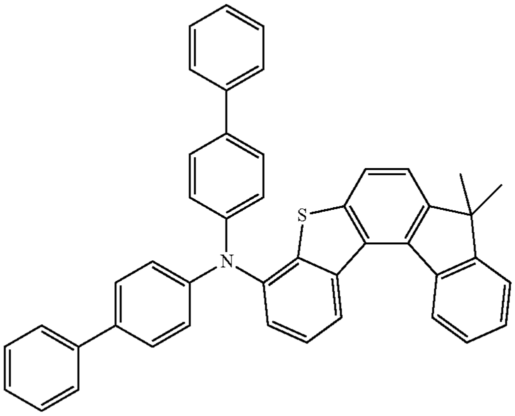
[2-141]
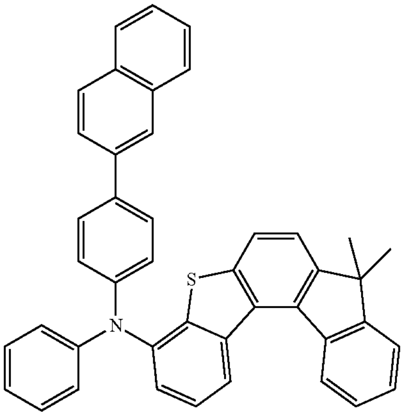

-continued
[2-142]
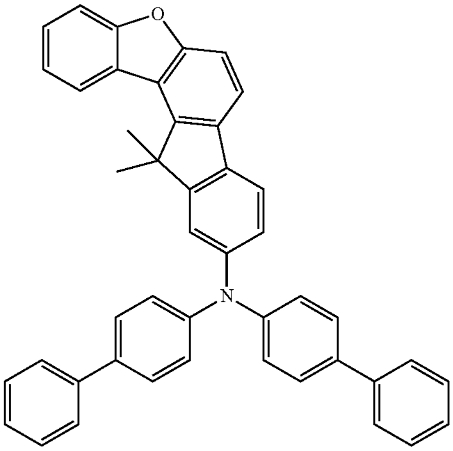
[2-143]
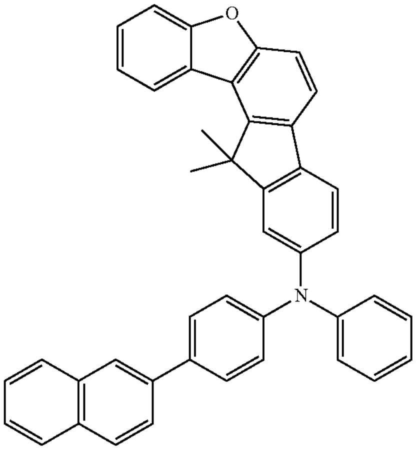
[2-144]
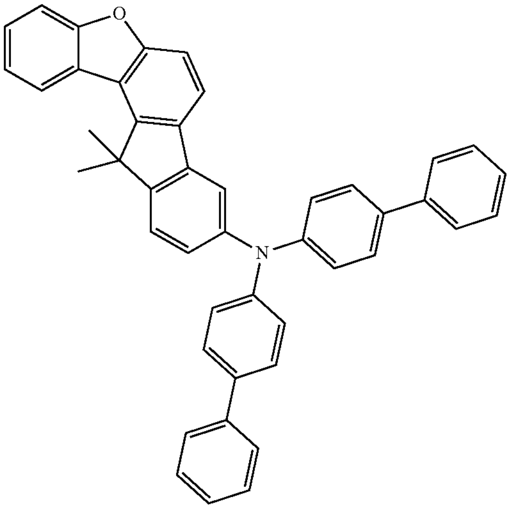
-continued
[2-145]
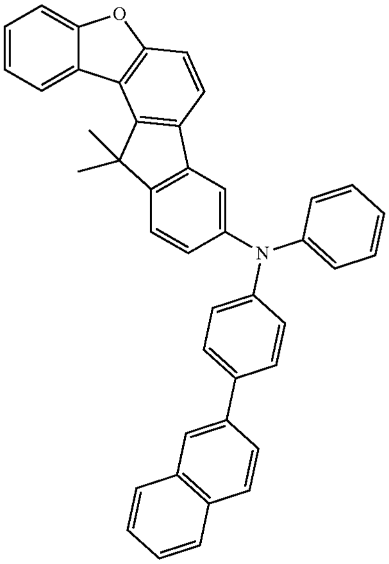
[2-146]
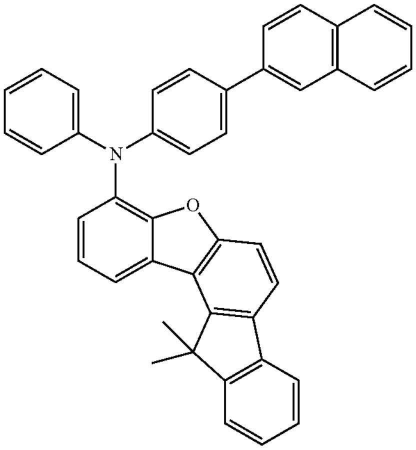
[2-147]
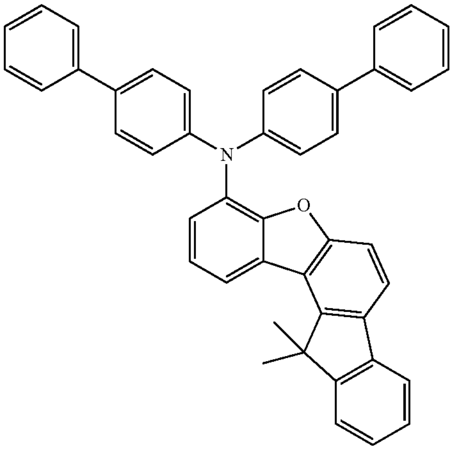

-continued
[2-148]
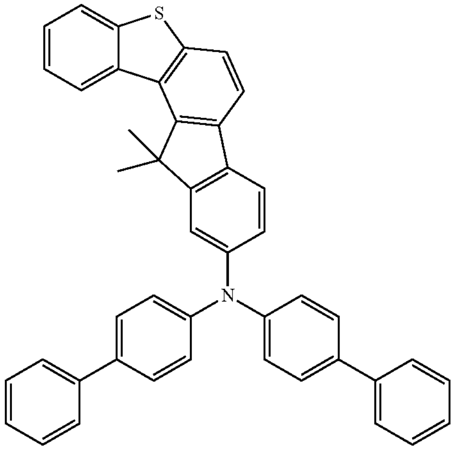
[2-149]
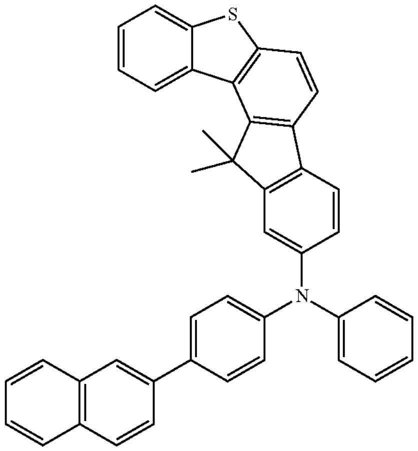
[2-150]
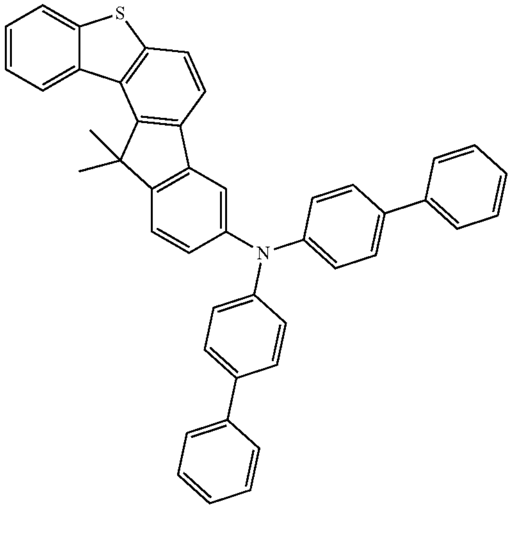
-continued
[2-151]
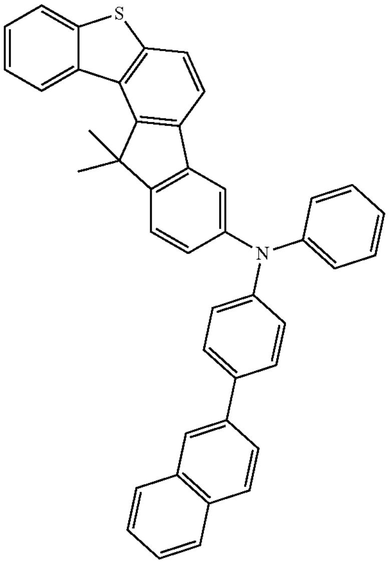
[2-152]
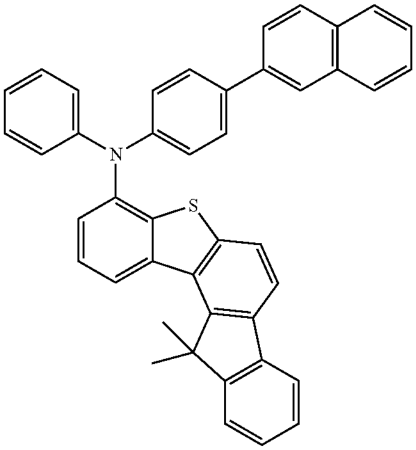
[2-153]
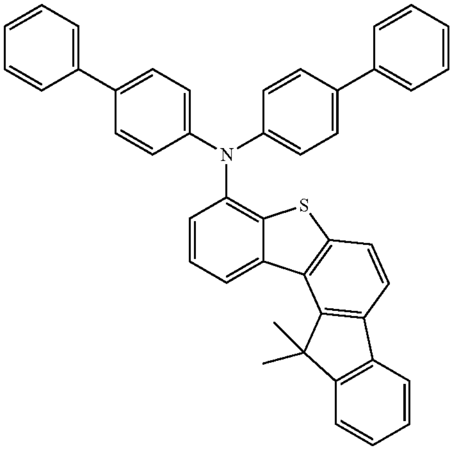

-continued
[2-154]
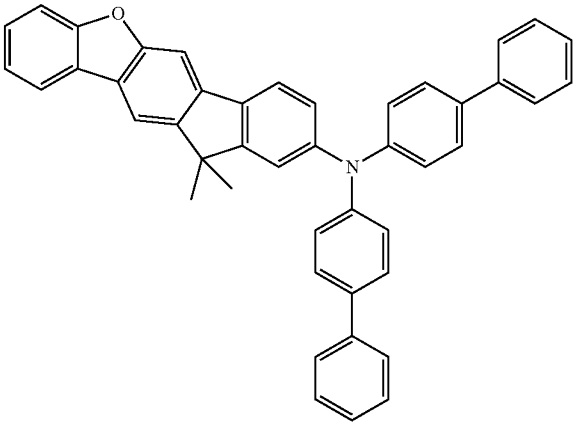
[2-155]
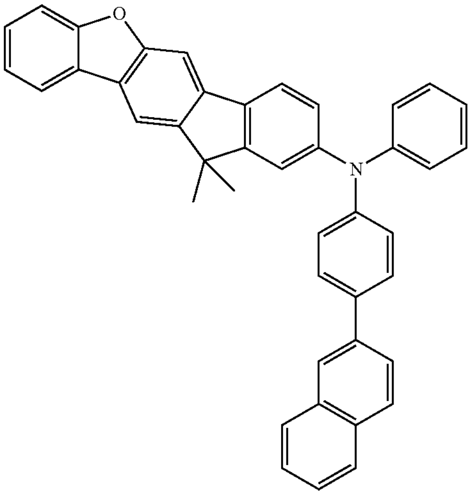
[2-156]
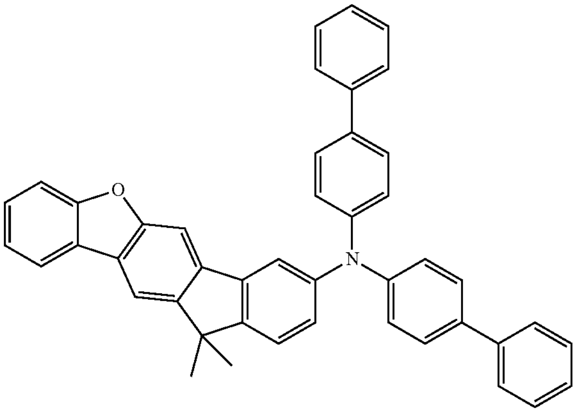
-continued
[2-157]
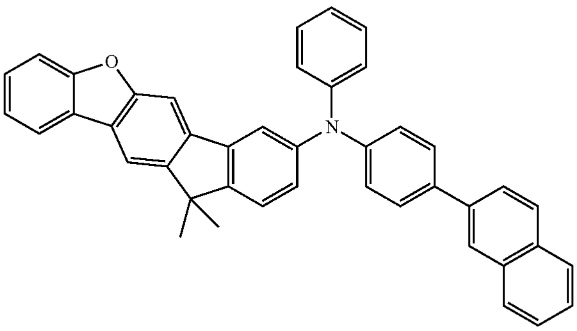
[2-158]
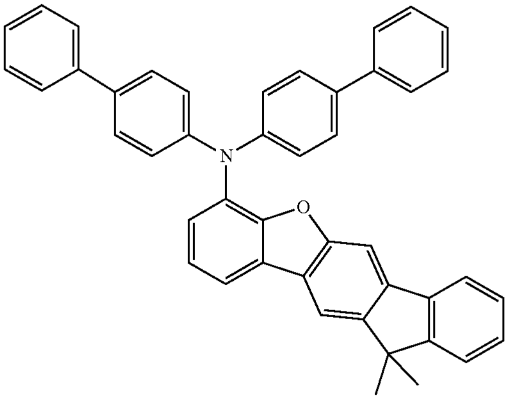
[2-159]
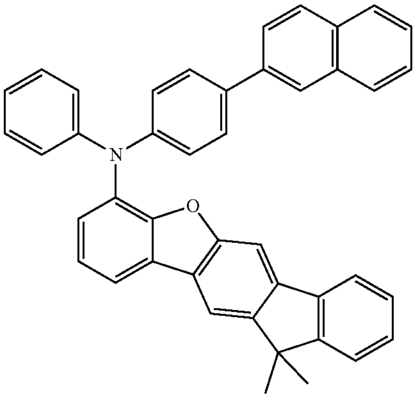
[2-160]
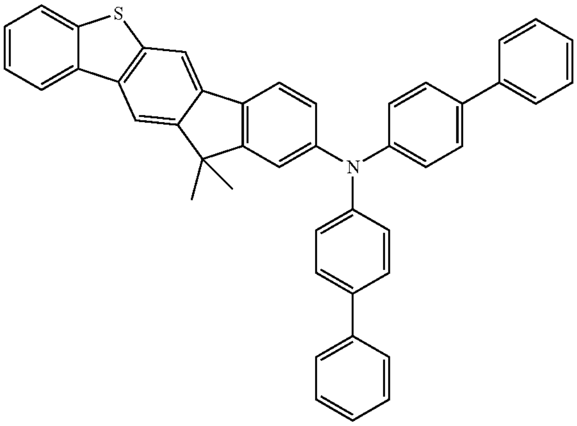

-continued
[2-161]
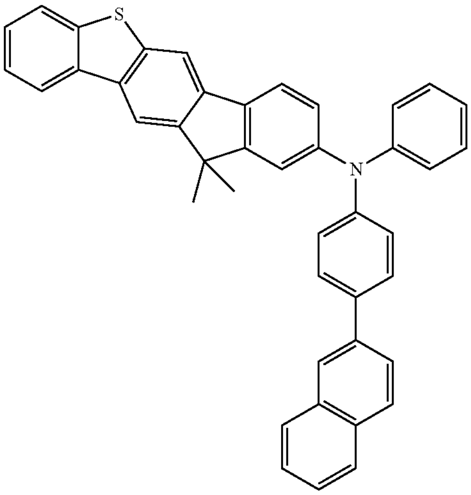
[2-162]
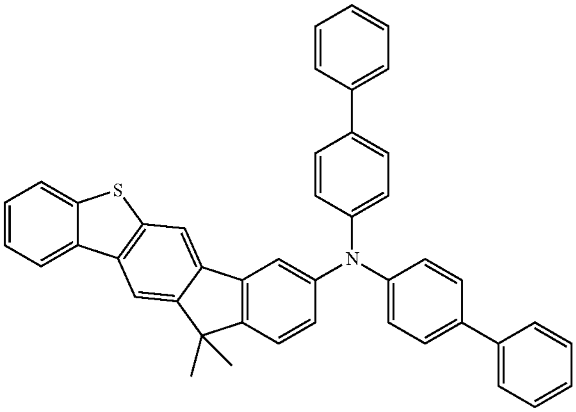
[2-163]
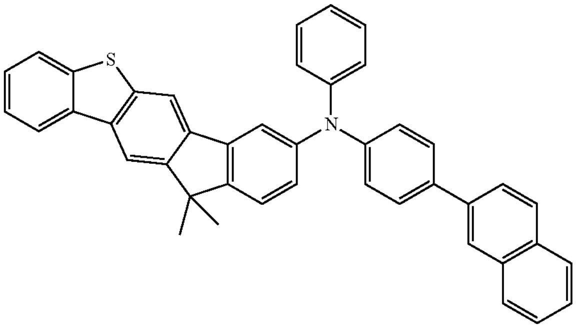
-continued
[2-164]
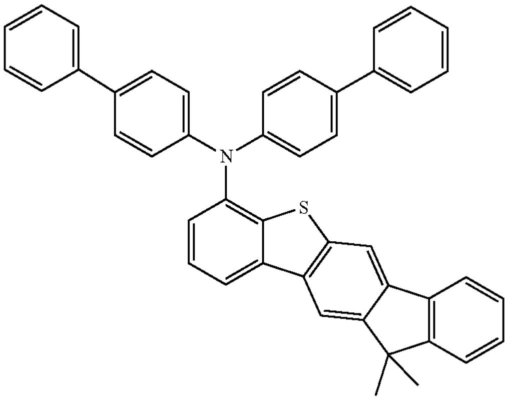
[2-165]
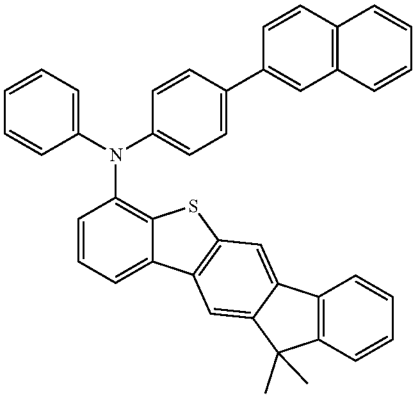
[2-166]
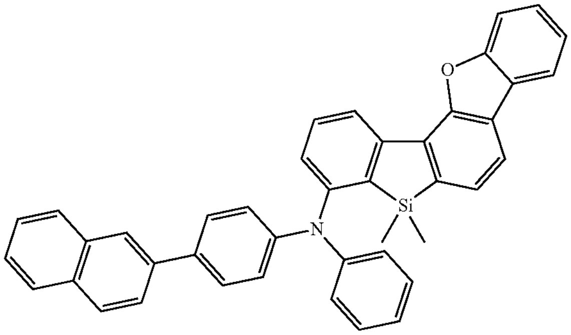
[2-167]
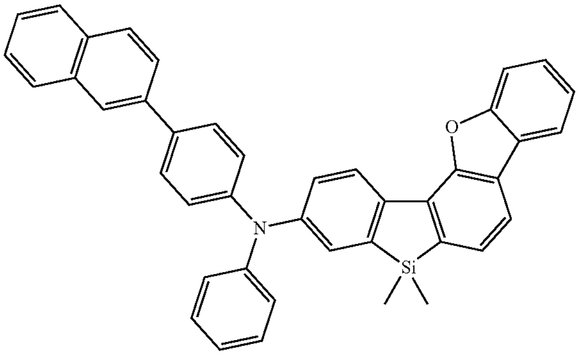

-continued
[2-168]
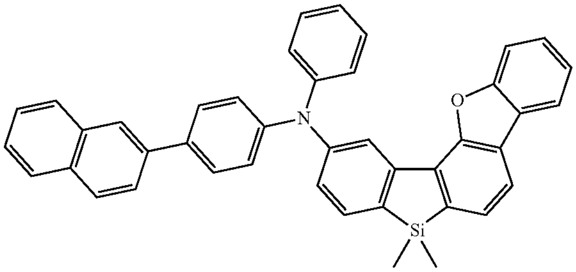
[2-169]
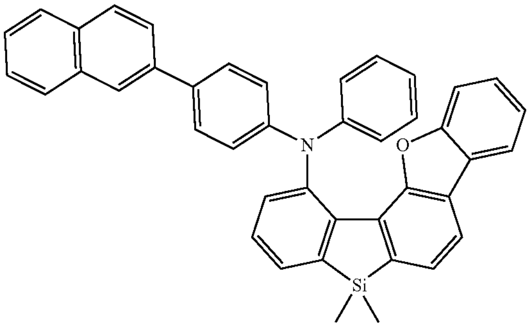
[2-170]
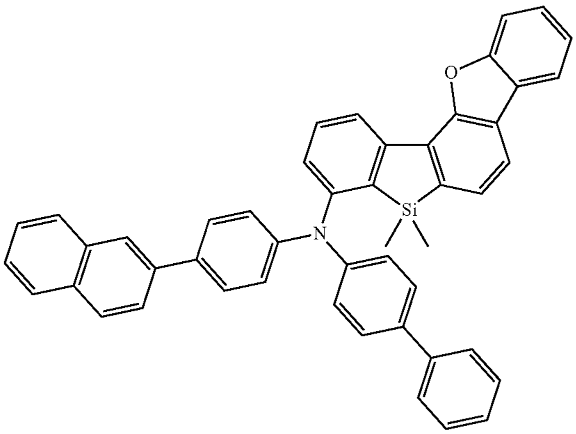
[2-171]
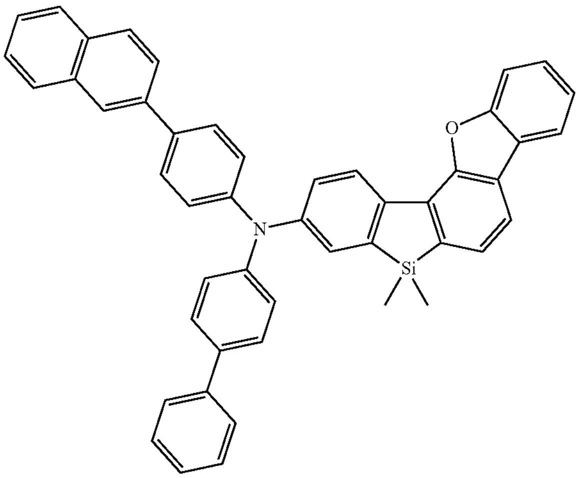
-continued
[2-172]
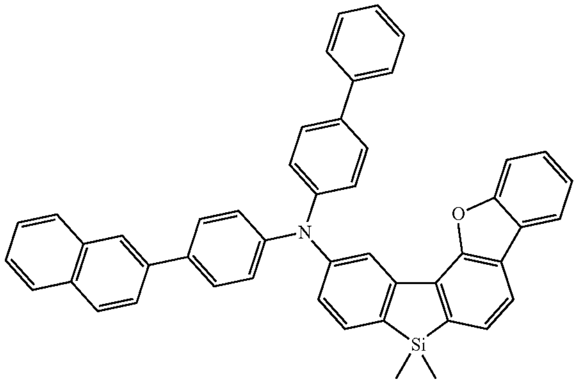
[2-173]
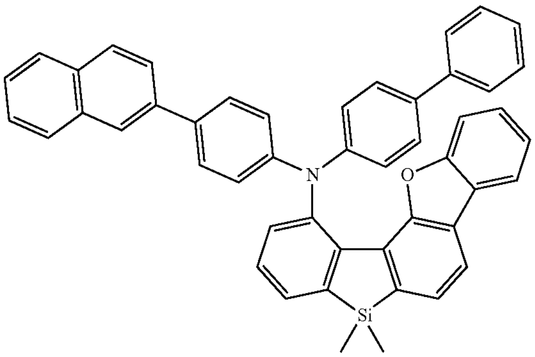
[2-174]
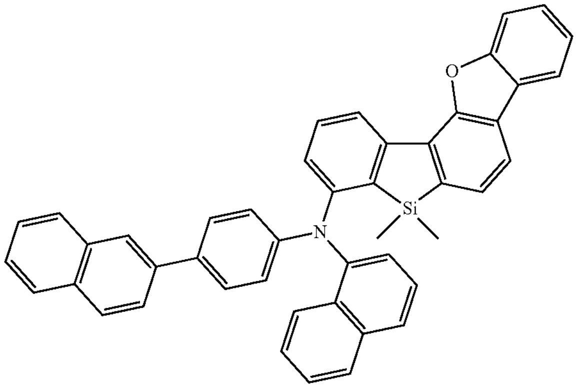
[2-175]
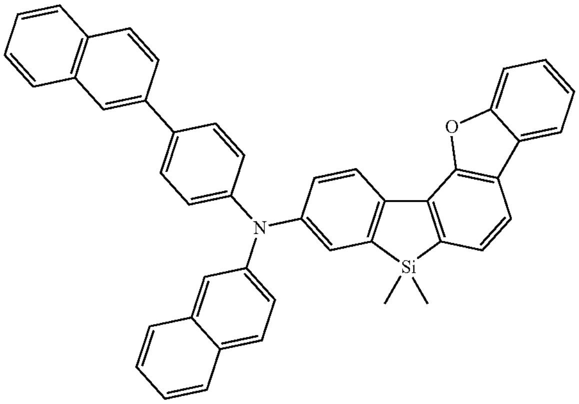

-continued
[2-176]
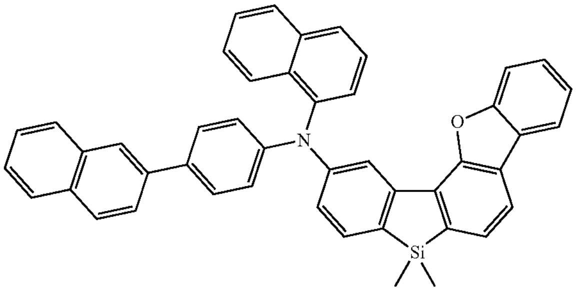
[2-177]
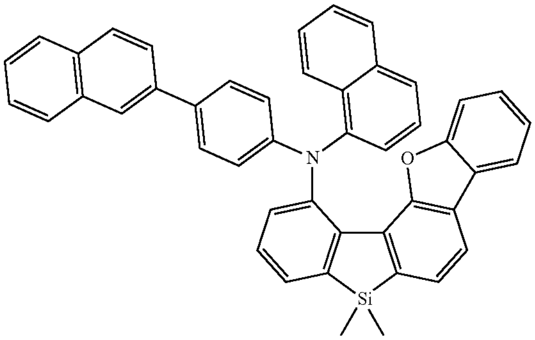
[2-178]
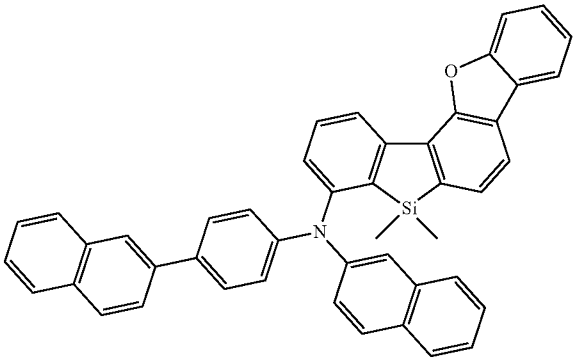
[2-179]
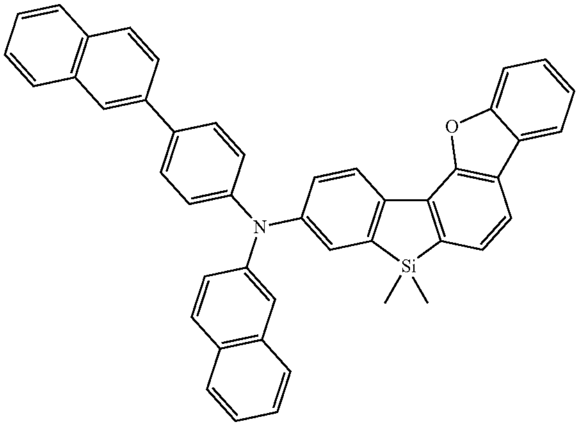
-continued
[2-180]
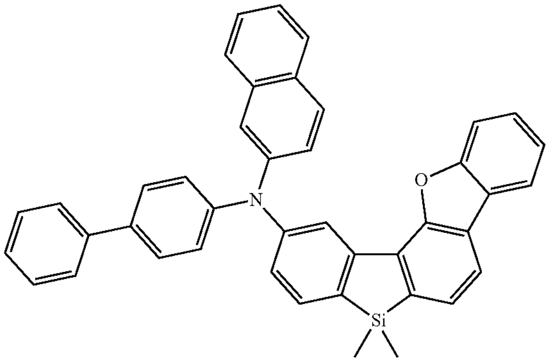
[2-181]
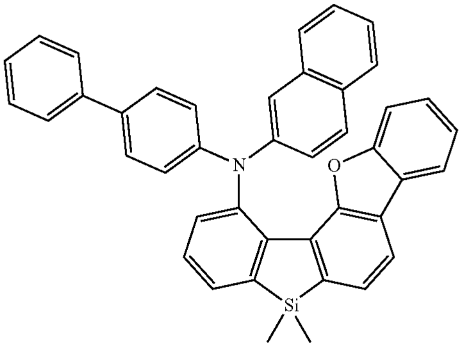
[2-182]
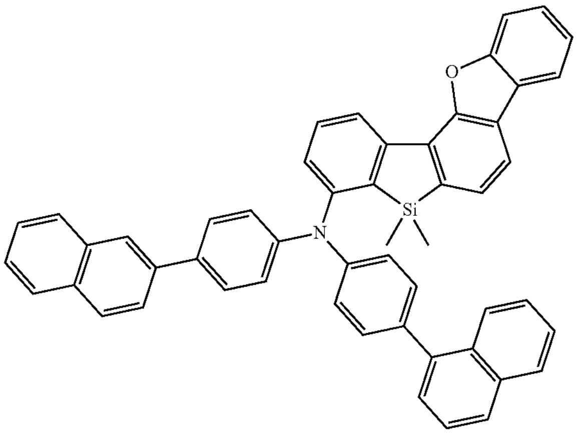

-continued
[2-183]
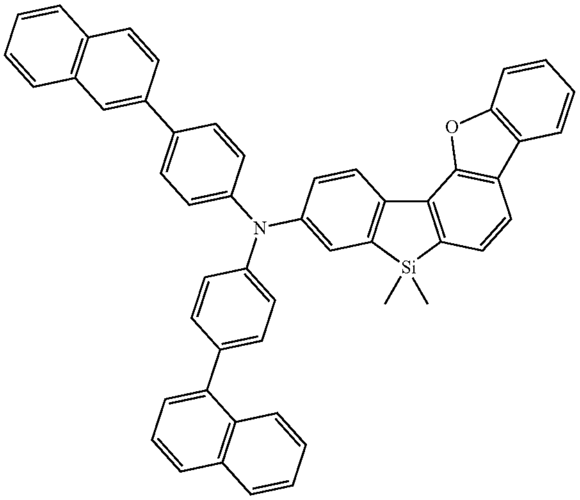
[2-184]
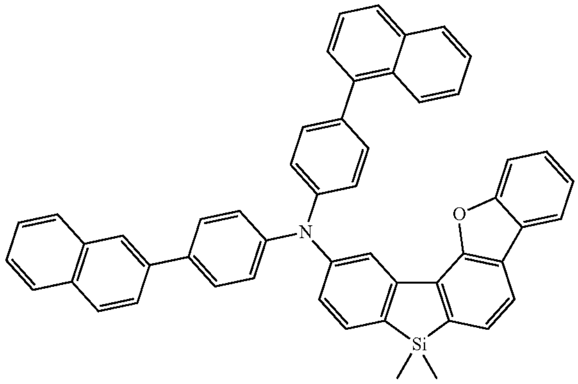
[2-185]
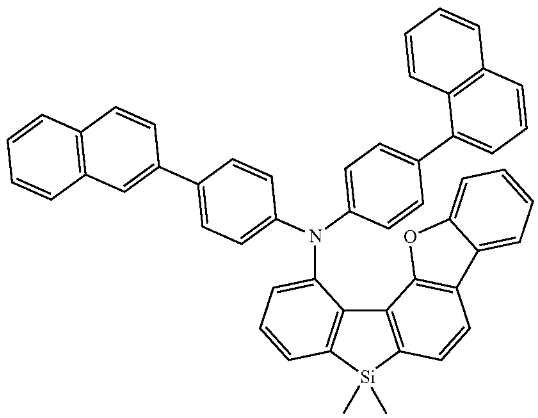
-continued
[2-186]
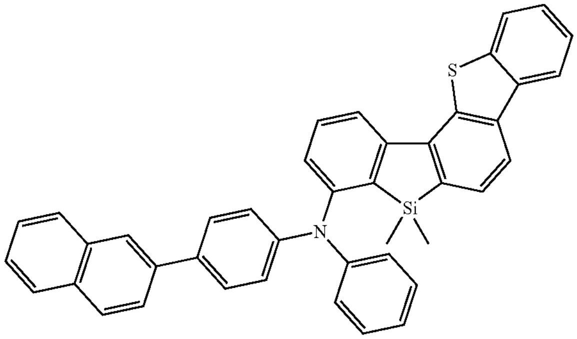
[2-187]
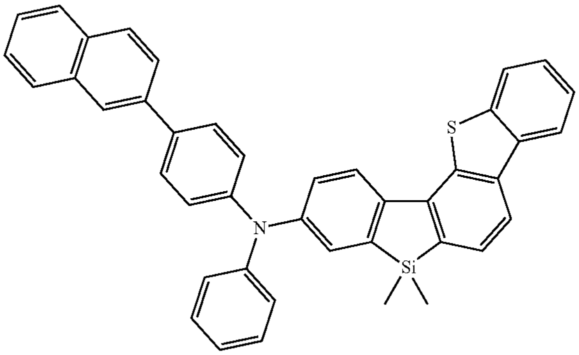
[2-188]
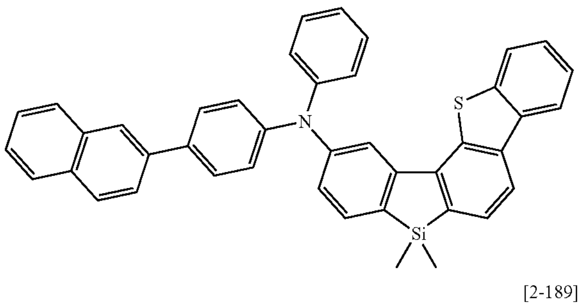
[2-189]
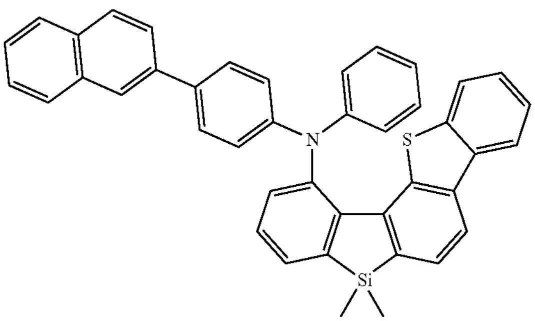

-continued
[2-190]
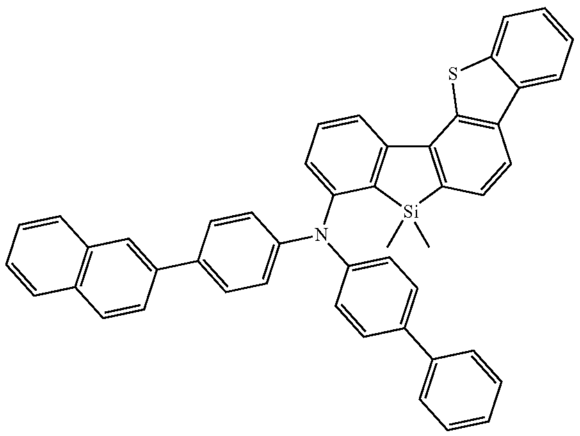
[2-191]
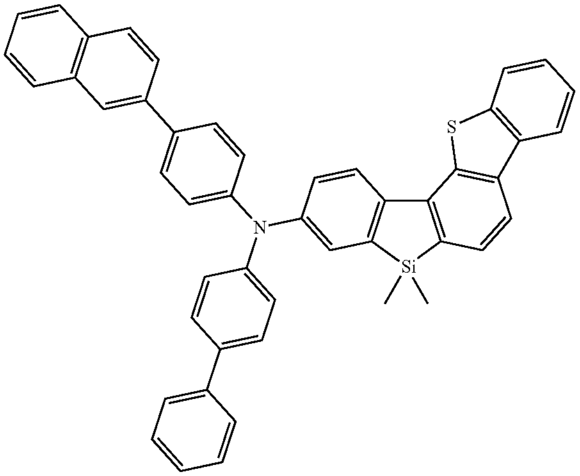
[2-192]
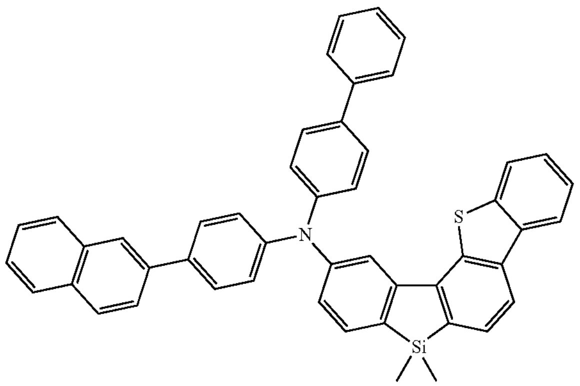
-continued
[2-193]
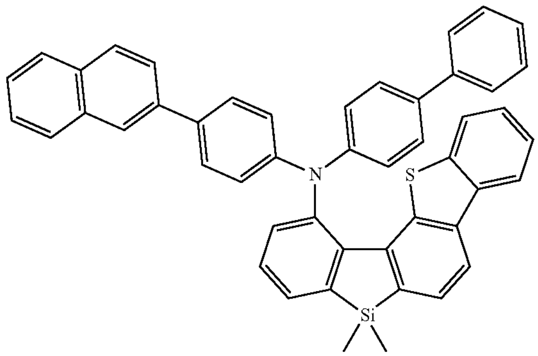
[2-194]
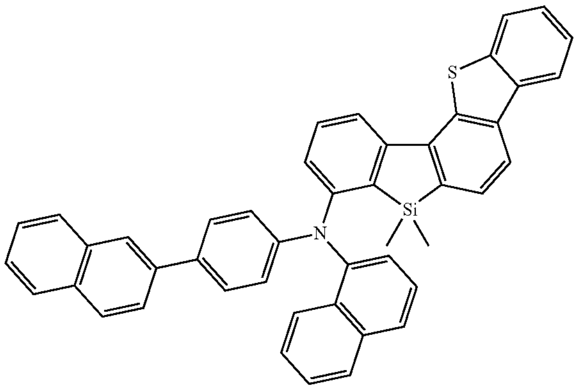
[2-195]
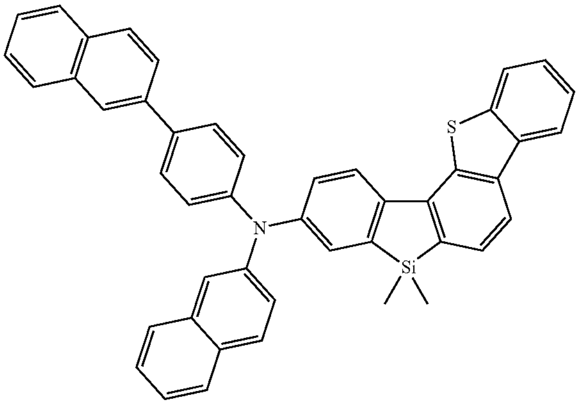
[2-196]
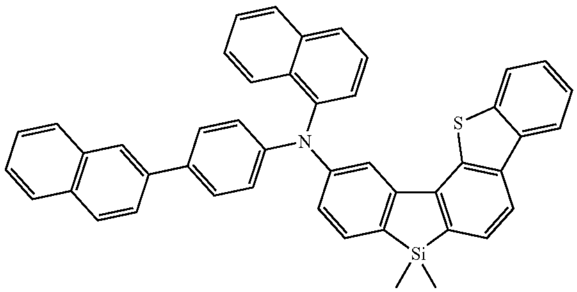

-continued
[2-197]
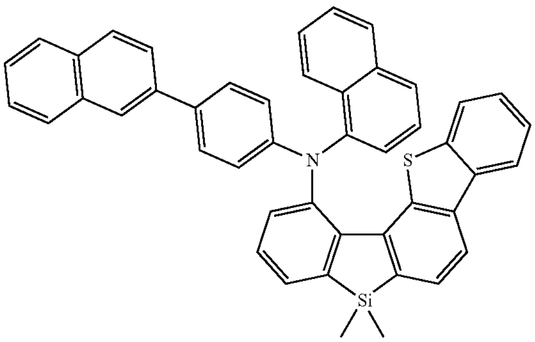
[2-198]
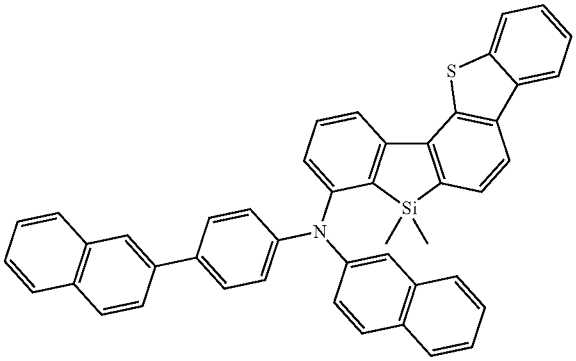
[2-199]
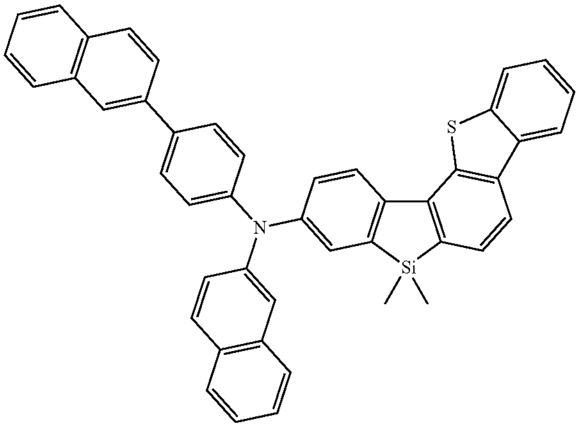
[2-200]
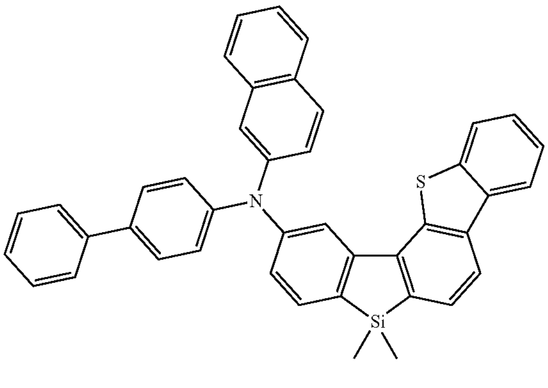
[2-201]
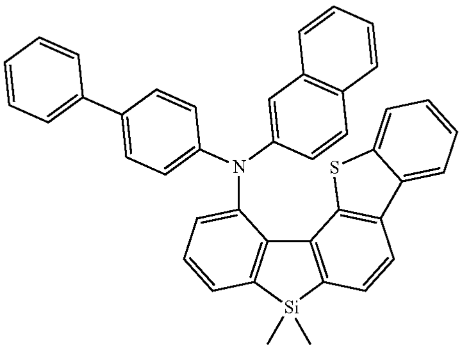
[2-202]
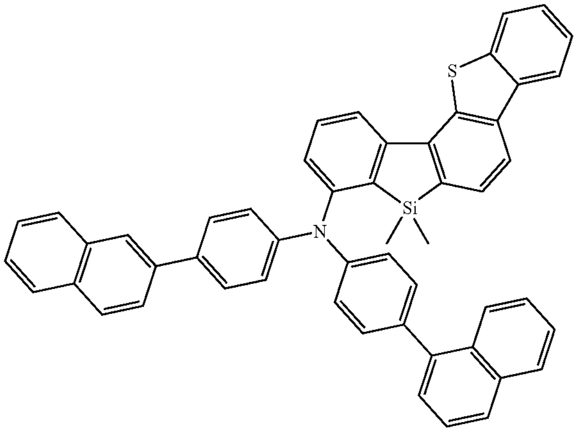
[2-203]
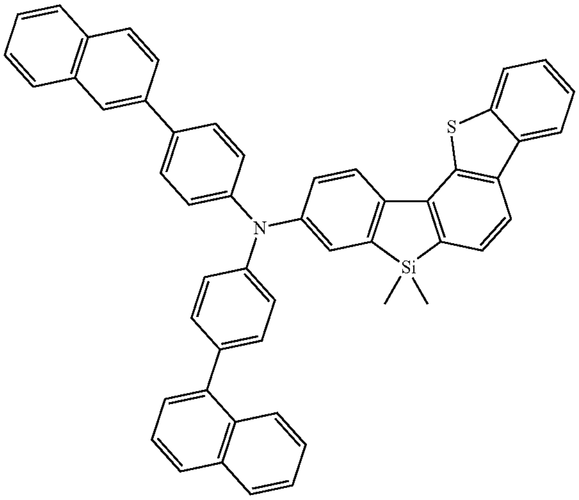

-continued

[2-204]

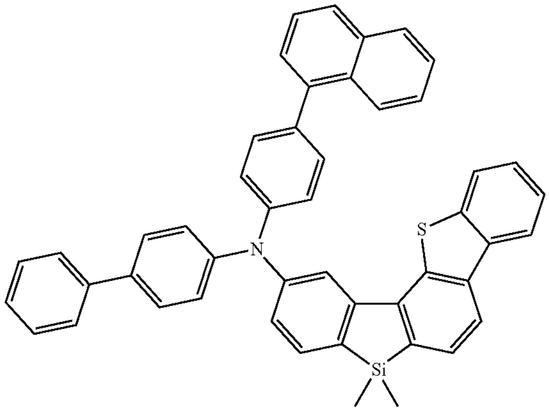

[2-205]

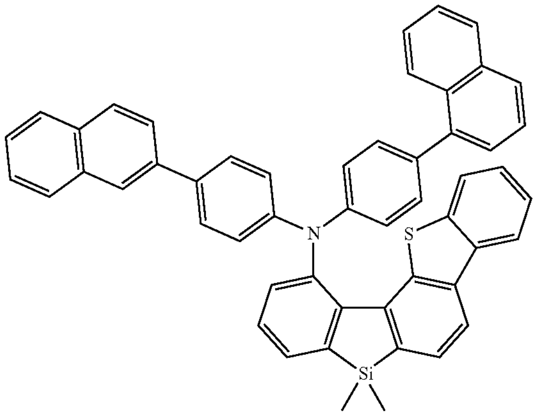

The first compound and the second compound may be included, for example, in a weight ratio of 1:99 to 99:1. Within the range, a desirable weight ratio may be adjusted using an electron transport capability of the first compound and a hole transport capability of the second compound to realize bipolar characteristics and thus to improve efficiency and life-span. Within the range, they may be for example included in a weight ratio of about 10:90 to 90:10, about 20:80 to 80:20, for example about 20:80 to about 70:30, about 20:80 to about 60:40, or about 30:70 to about 60:40. For example, they may be included in a weight ratio of 40:60, 50:50, or 60:40.

In addition to the aforementioned first compound and second compound, one or more compounds may be further included.

The aforementioned compound for an organic optoelectronic device or composition for an organic optoelectronic device may be a composition further including a dopant.

The dopant may be for example a phosphorescent dopant, for example a red, green or blue phosphorescent dopant, for example a red or green phosphorescent dopant.

The dopant is a material mixed with the compound or composition for an organic optoelectronic device in a trace amount to cause light emission, and may be generally a material such as a metal complex that emits light by multiple excitation into a triplet or more. The dopant may be, for example, an inorganic, organic, or organic-inorganic compound, and one or more types thereof may be used.

Examples of the dopant may be a phosphorescent dopant and examples of the phosphorescent dopant may be an organic metal compound including Ir, Pt, Os, Ti, Zr, Hf, Eu, Tb, Tm, Fe, Co, Ni, Ru, Rh, Pd, or a combination thereof. The phosphorescent dopant may be, for example, a compound represented by Chemical Formula Z, but is not limited thereto.

$L^5MX$ [Chemical Formula Z]

In Chemical Formula Z, M is a metal, and $L^5$ and X are the same or different, and are a ligand to form a complex compound with M.

The M may be for example Ir, Pt, Os, Ti, Zr, Hf, Eu, Tb, Tm, Fe, Co, Ni, Ru, Rh, Pd, or a combination thereof, and $L^5$ and X may be, for example a bidendate ligand.

Hereinafter, an organic optoelectronic device including the aforementioned compound for an organic optoelectronic device or composition for an organic optoelectronic device is described.

The organic optoelectronic device may be any device to convert electrical energy into photoenergy and vice versa without particular limitation, and may be, for example an organic photoelectric device, an organic light emitting diode, an organic solar cell, and an organic photoconductor drum.

Herein, an organic light emitting diode as one example of an organic optoelectronic device is described referring to drawings.

FIGS. 1 to 4 are cross-sectional views showing organic light emitting diodes according to embodiments.

Referring to FIG. 1, an organic light emitting diode 100 according to an embodiment includes an anode 120 and a cathode 110 facing each other and an organic layer 105 disposed between the anode 120 and cathode 110.

The anode 120 may be made of a conductor having a large work function to help hole injection, and may be for example a metal, a metal oxide and/or a conductive polymer. The anode 120 may be, for example a metal such as nickel, platinum, vanadium, chromium, copper, zinc, gold, and the like or an alloy thereof, a metal oxide such as zinc oxide, indium oxide, indium tin oxide (ITO), indium zinc oxide (IZO), and the like; a combination of a metal and an oxide such as ZnO and Al or $SnO_2$ and Sb; a conductive polymer such as poly(3-methylthiophene), poly(3,4-(ethylene-1,2-dioxy)thiophene) (PEDOT), polypyrrole, and polyaniline, but is not limited thereto.

The cathode 110 may be made of a conductor having a small work function to help electron injection, and may be for example a metal, a metal oxide, and/or a conductive polymer. The cathode 110 may be for example a metal such as magnesium, calcium, sodium, potassium, titanium, indium, yttrium, lithium, gadolinium, aluminum silver, tin, lead, cesium, barium, and the like, or an alloy thereof; a multi-layer structure material such as LiF/Al, $LiO_2$/Al, LiF/Ca, LiF/Al, and $BaF_2$/Ca, but is not limited thereto.

The organic layer 105 may include the aforementioned compound for an organic optoelectronic device or composition for an organic optoelectronic device.

The organic layer 105 may include the light emitting layer 130, and the light emitting layer 130 may include the aforementioned compound for an organic optoelectronic device or composition for an organic optoelectronic device.

The composition for an organic optoelectronic device further including a dopant may be, for example, a red light-emitting composition.

The light emitting layer 130 may include, for example, the aforementioned first compound for an organic optoelectronic device and second for an organic optoelectronic device, respectively, as a phosphorescent host.

The organic layer may further include a charge transport region in addition to the light emitting layer.

The auxiliary layer may be, for example, the hole auxiliary layer 140.

Referring to FIG. 2, an organic light emitting diode 200 further includes a hole transport region 140 in addition to the light emitting layer 130. The hole transport region 140 may further increase hole injection and/or hole mobility between the anode 120 and the light emitting layer 130 and block electrons. Specifically, the hole transport region 140 may include a hole transport layer between the anode 120 and the light emitting layer 130, and a hole transport auxiliary layer between the light emitting layer 130 and the hole transport layer, and at least one of the compounds of Group E may be included in at least one of the hole transport layer and the hole transport auxiliary layer.

[Group E]

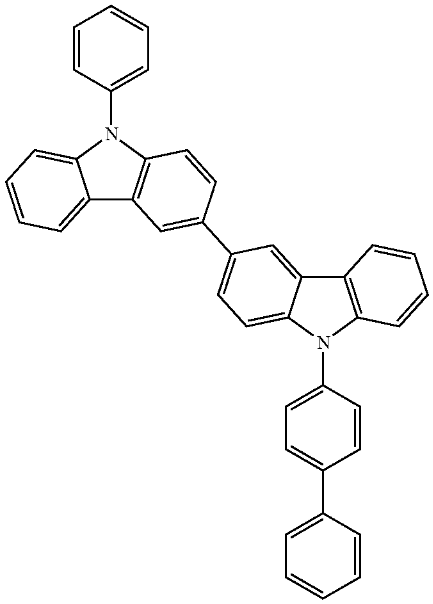

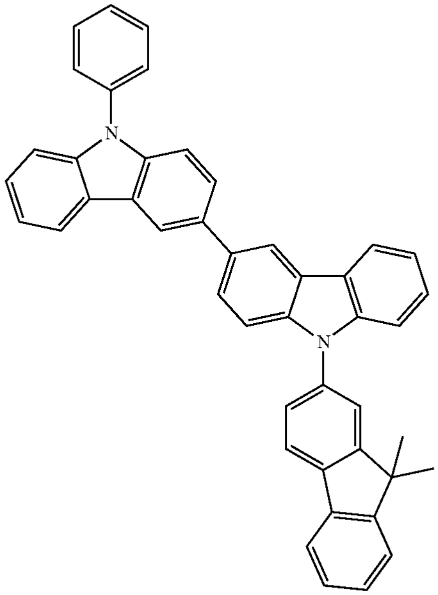

-continued

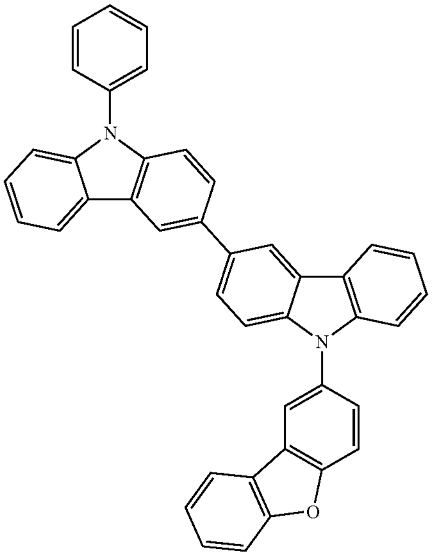

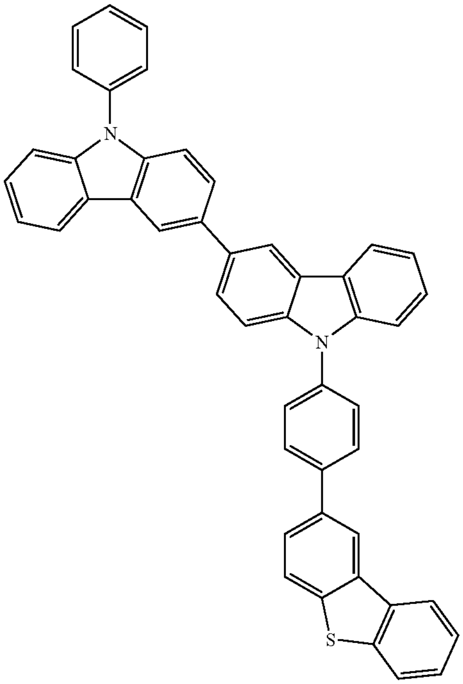

-continued
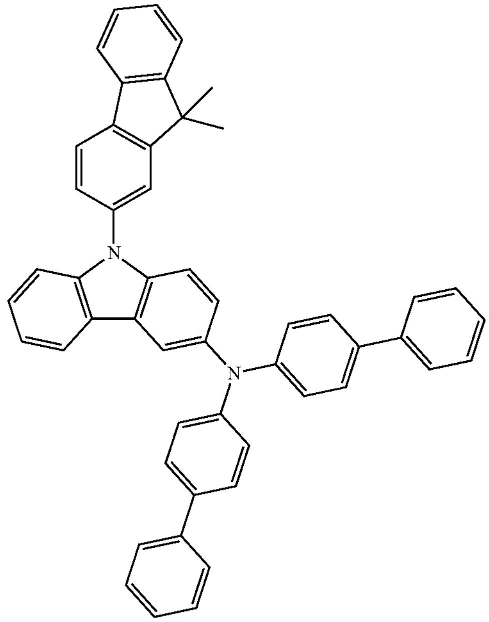
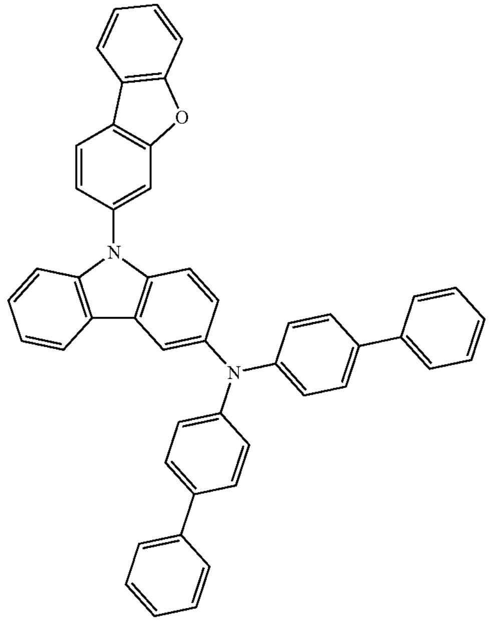
-continued
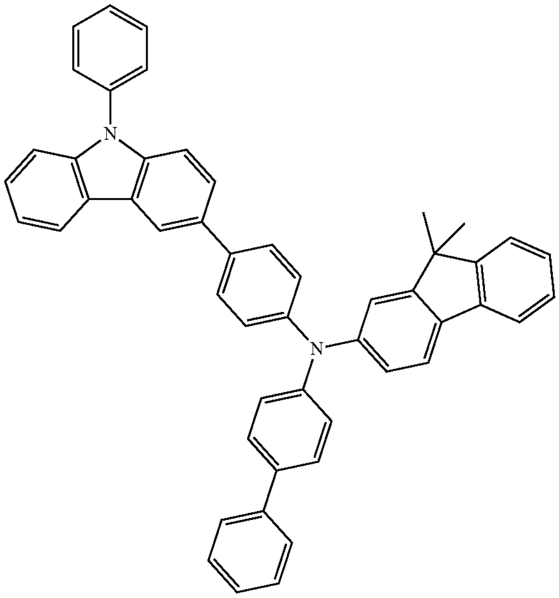
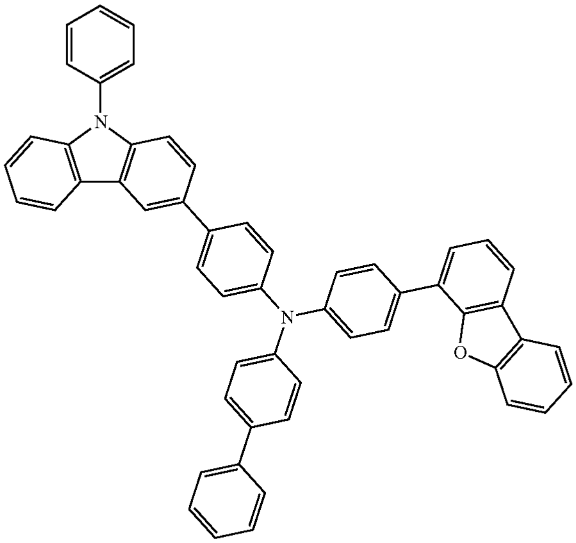
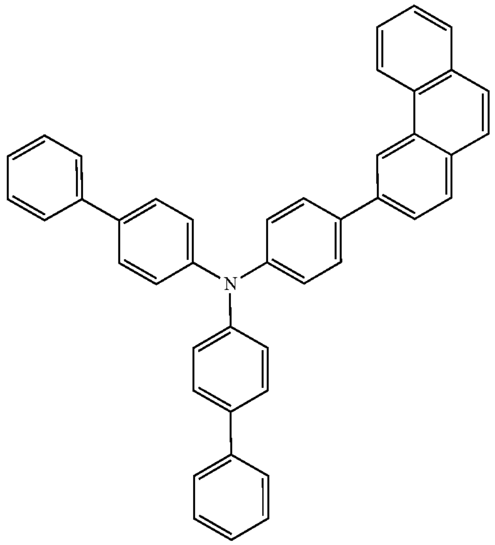

-continued
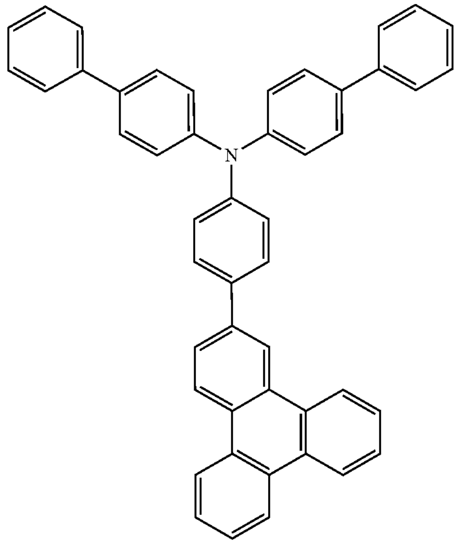
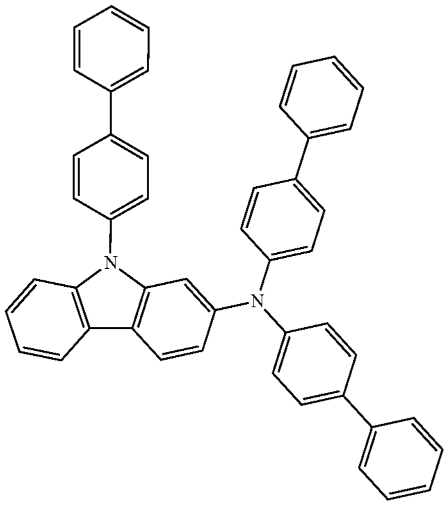
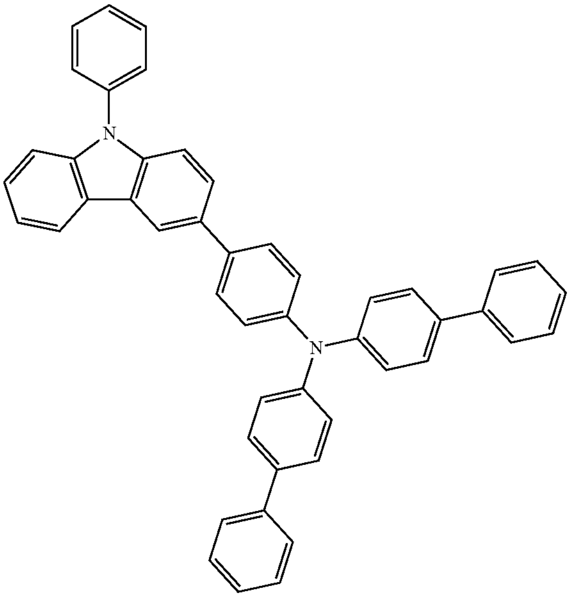
-continued
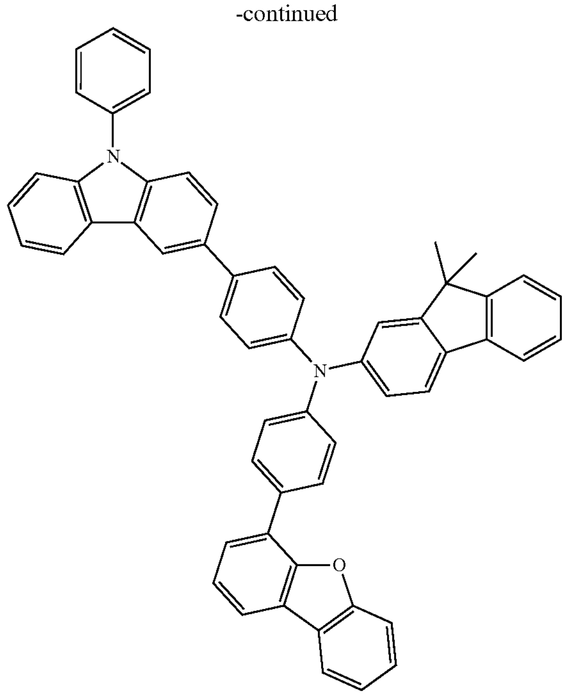
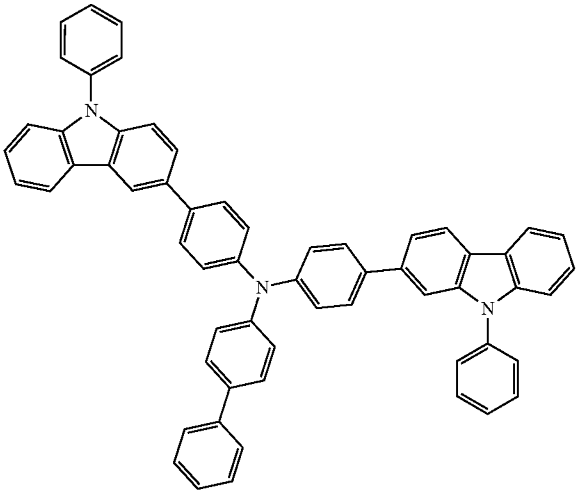
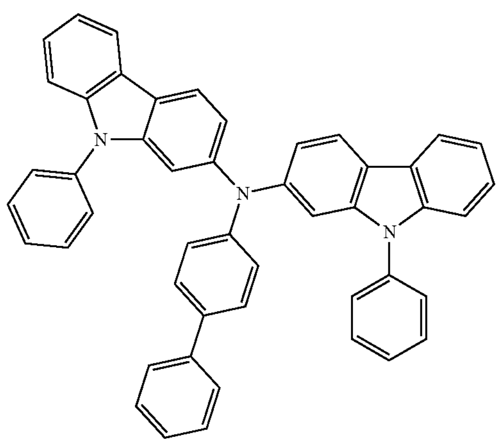

-continued
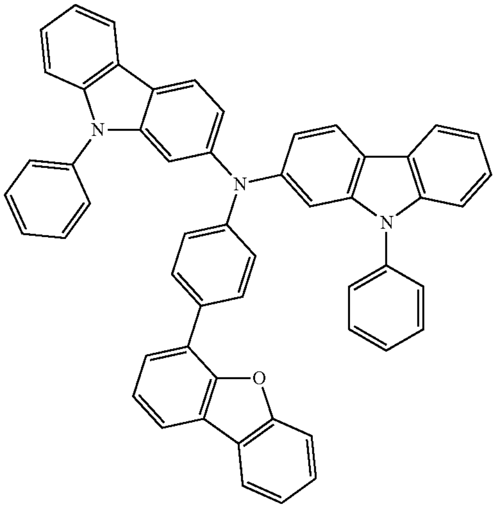
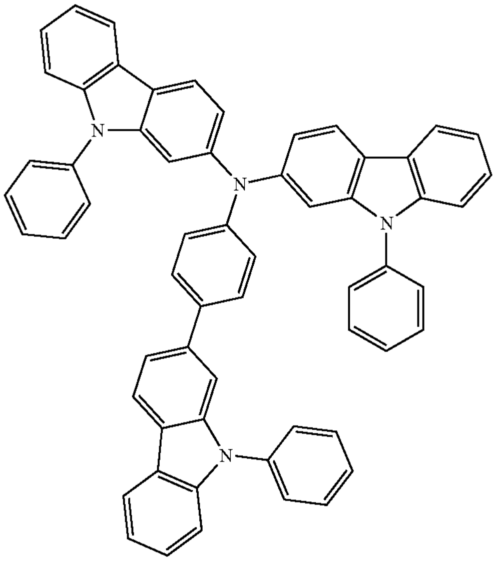
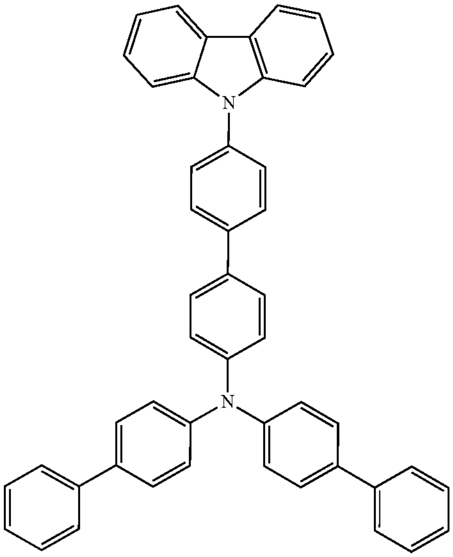
-continued
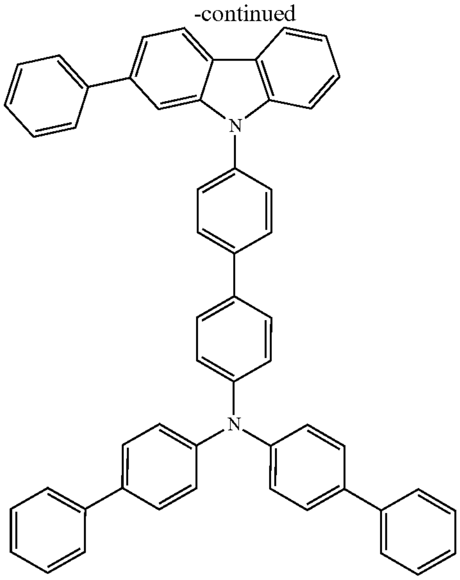
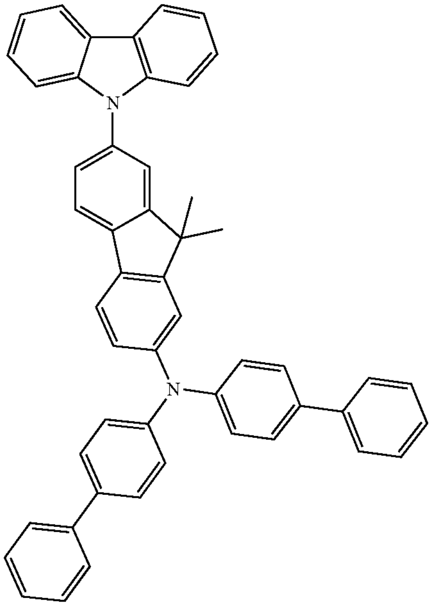
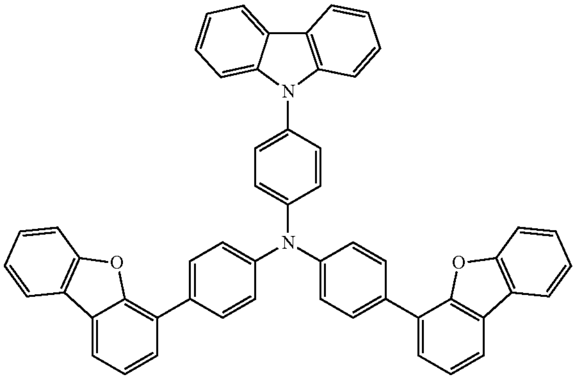

-continued
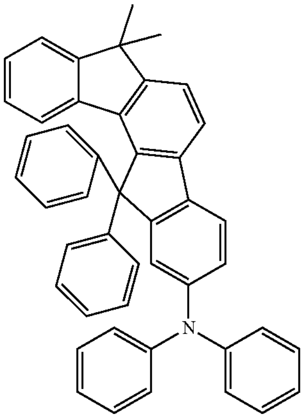
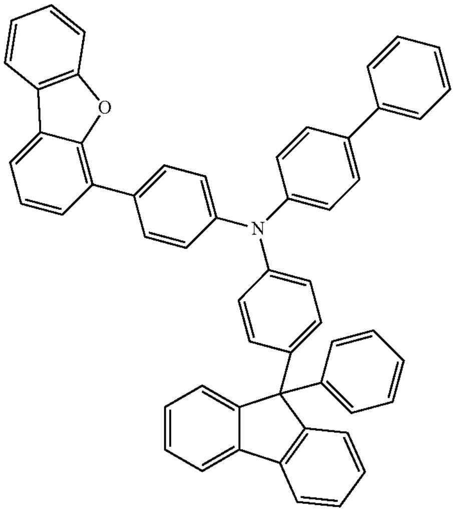
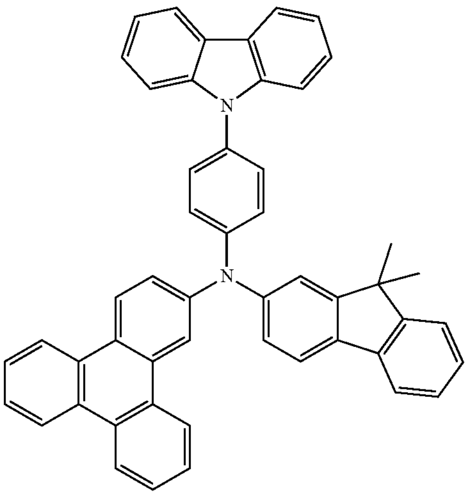
-continued
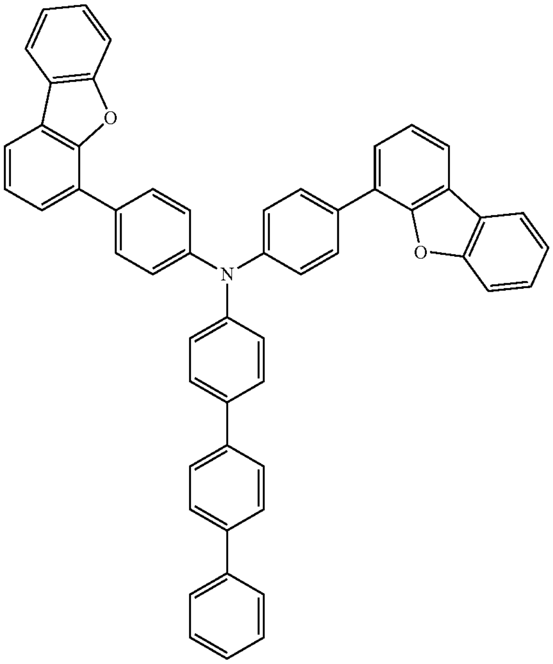
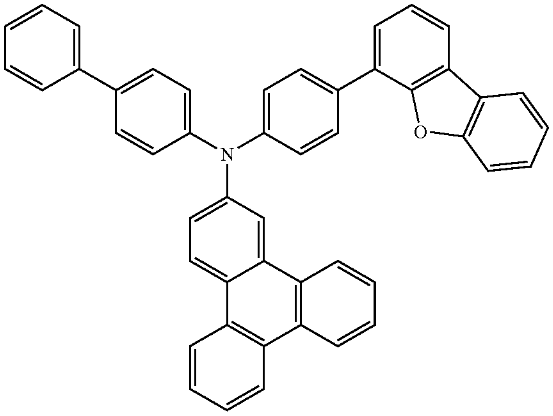
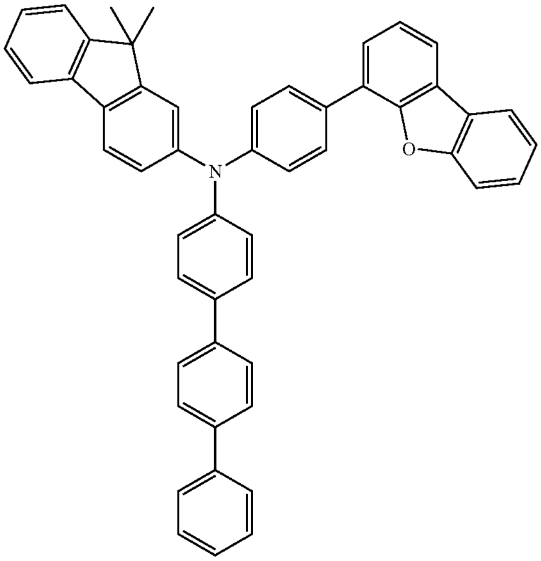

-continued
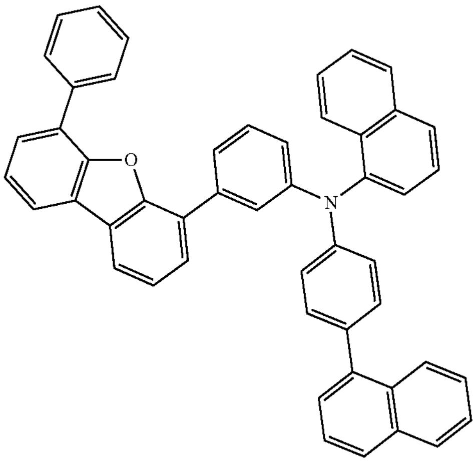
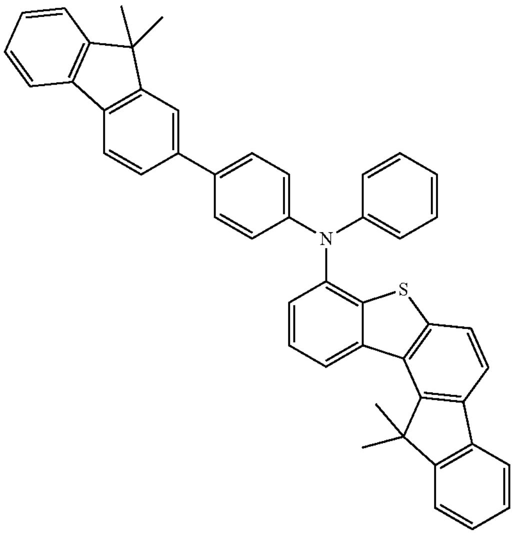
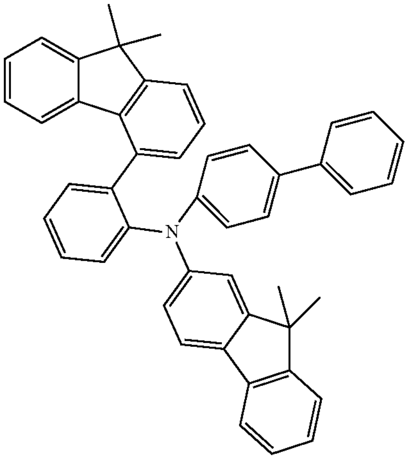
-continued
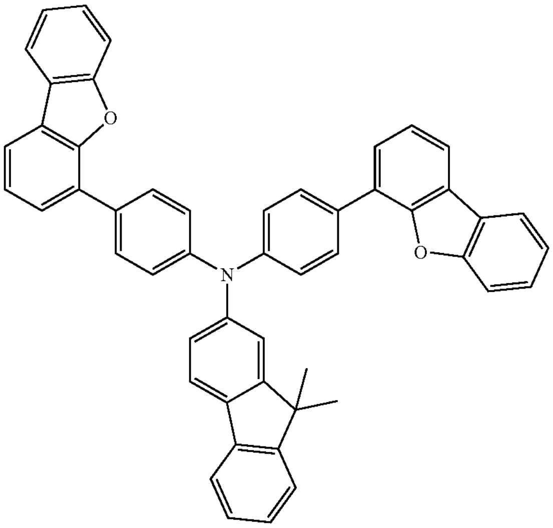
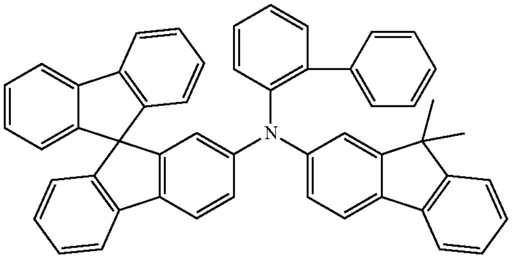
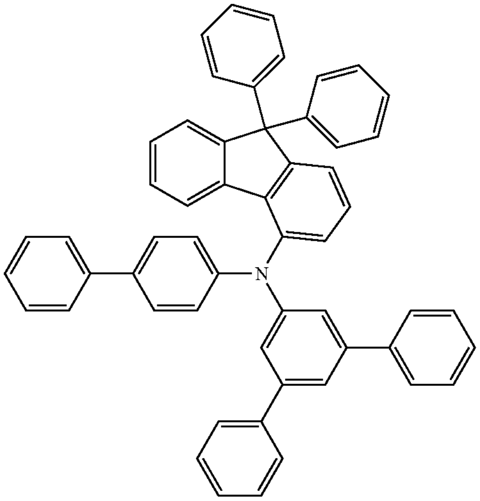
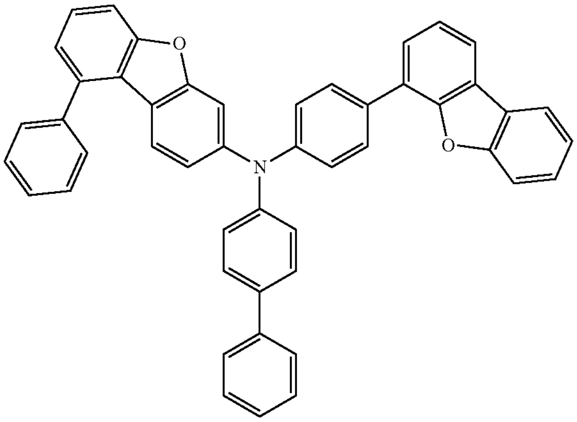

-continued
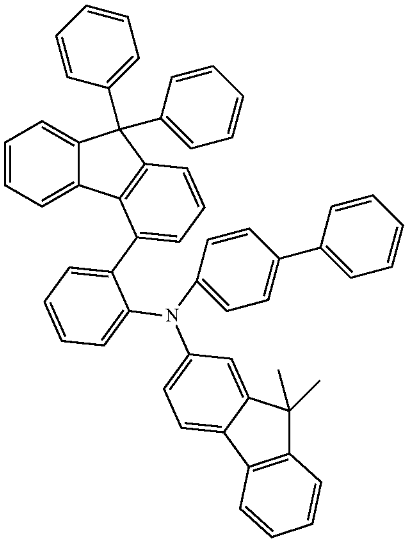
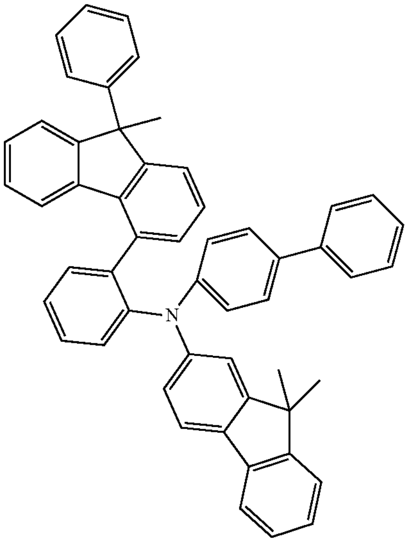
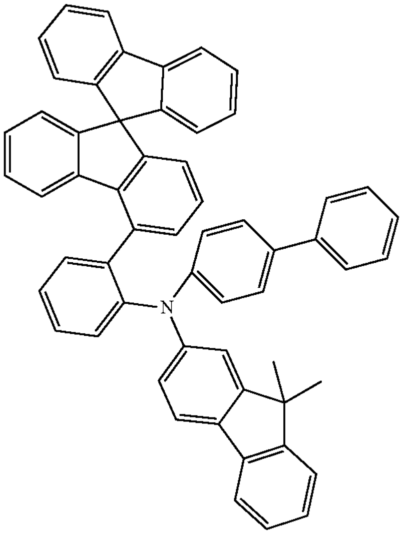
-continued
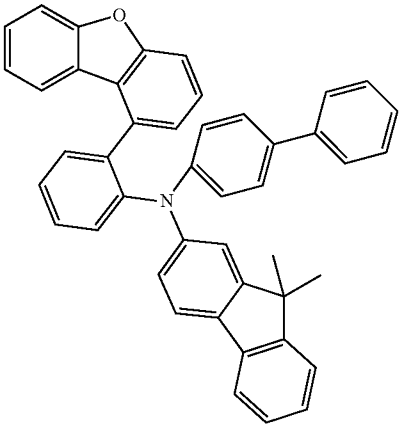
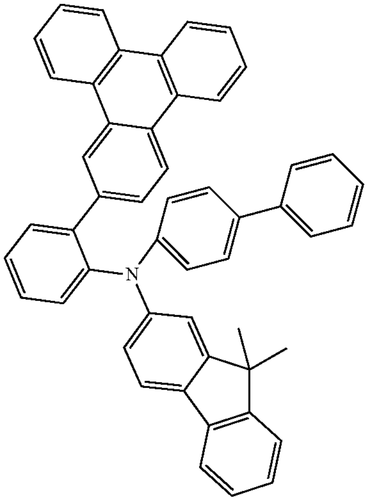
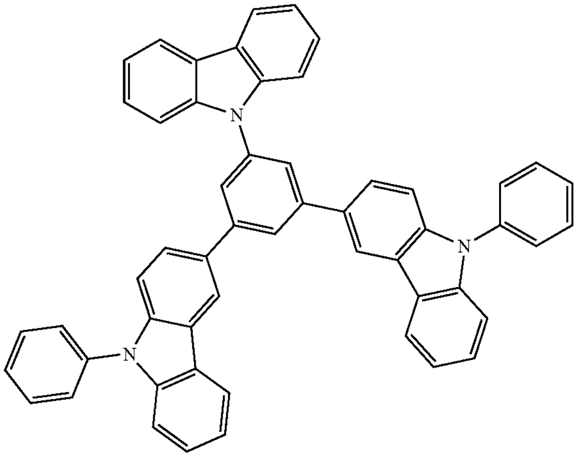
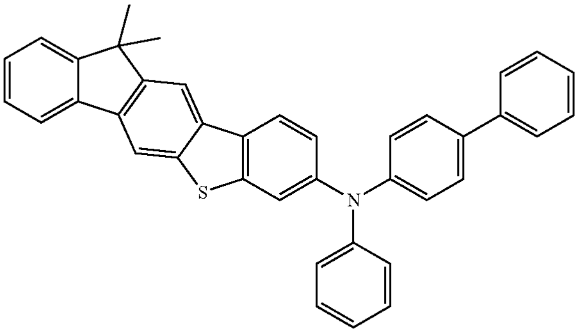

-continued
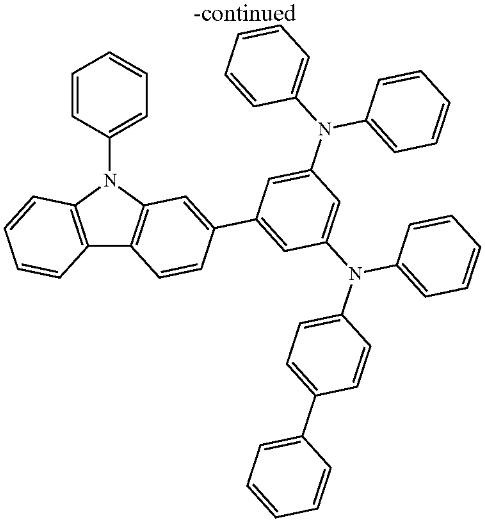
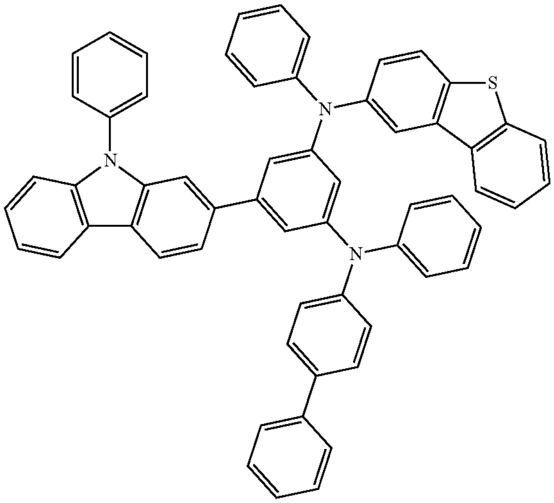
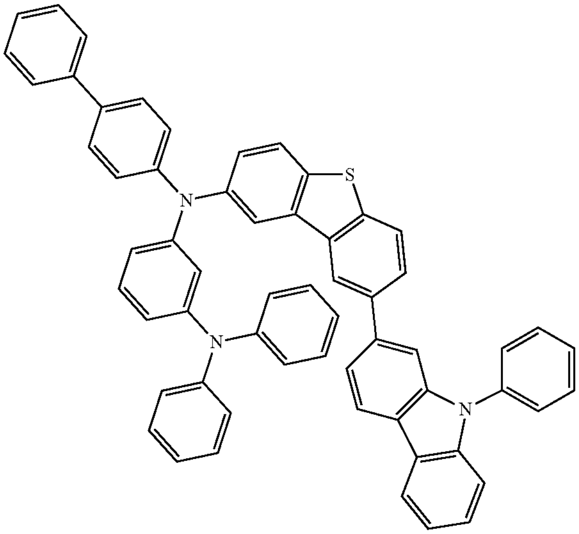
-continued
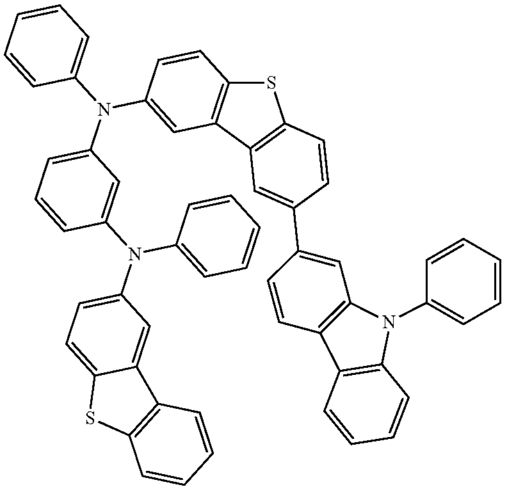
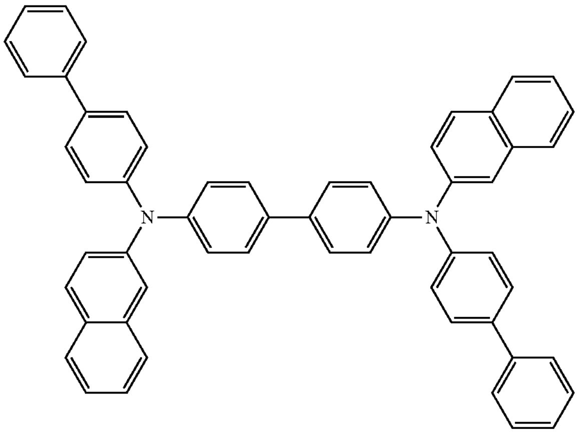
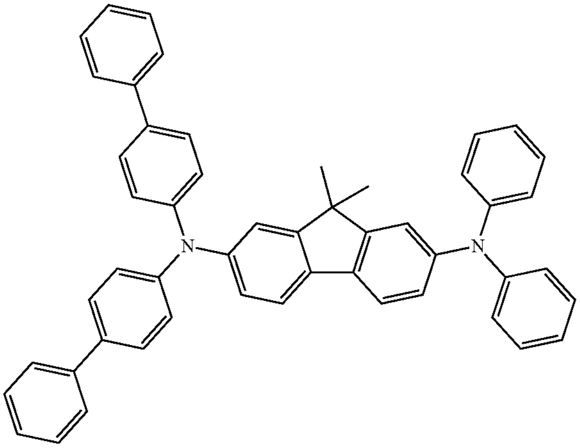

-continued
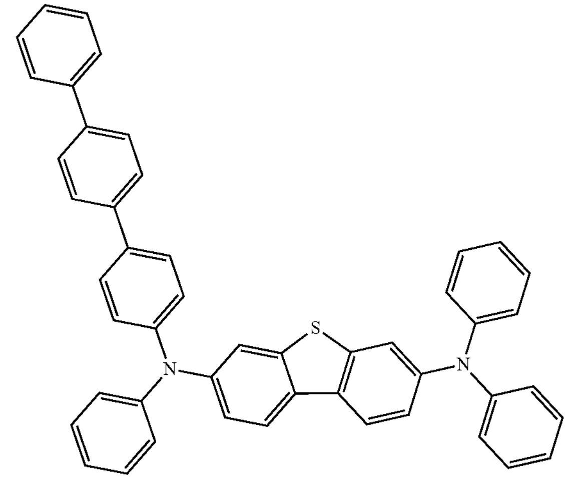
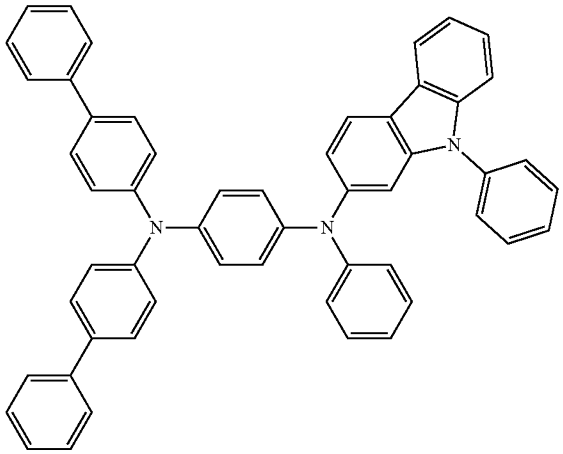
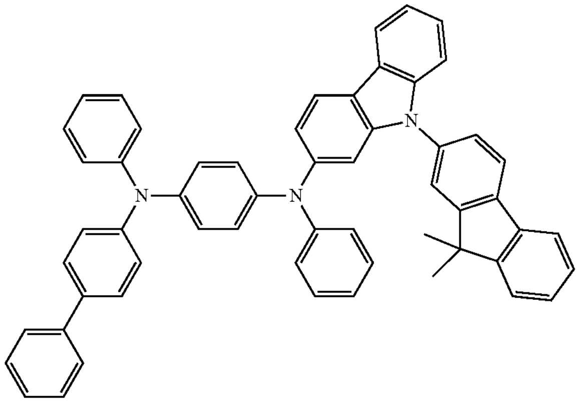
-continued
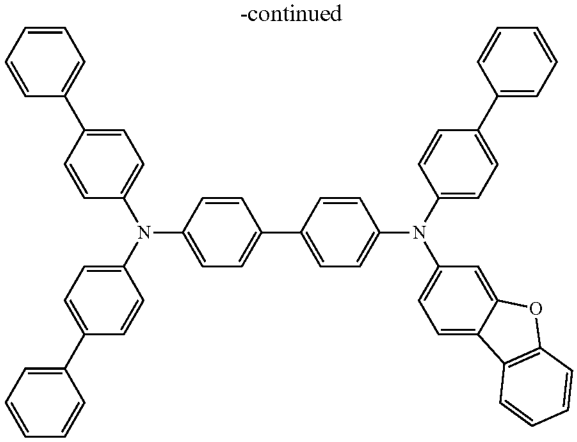
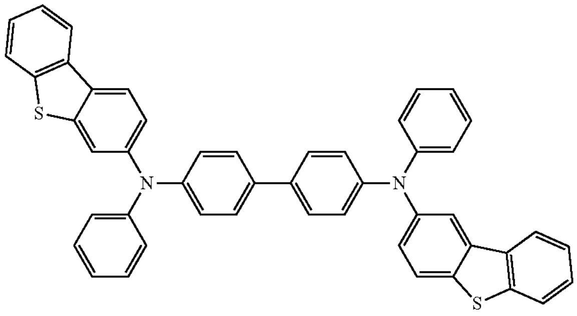
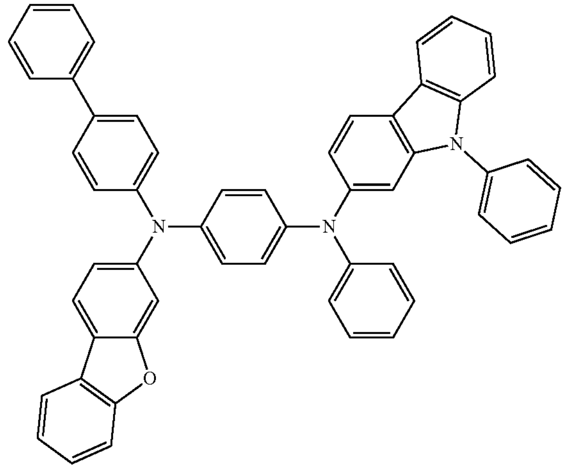
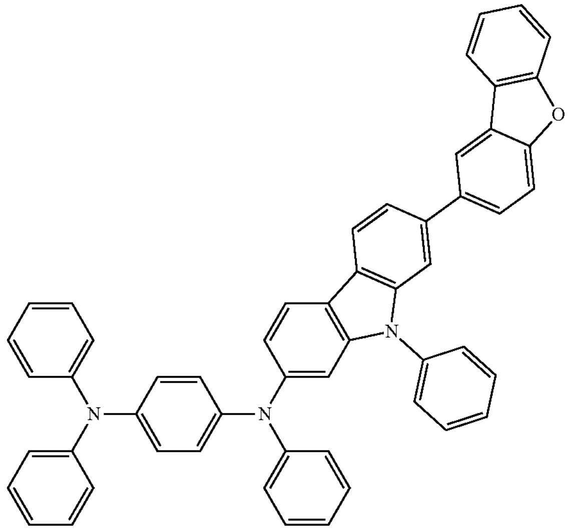

-continued
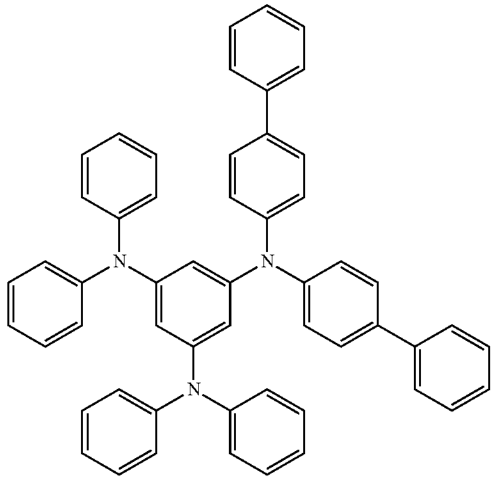
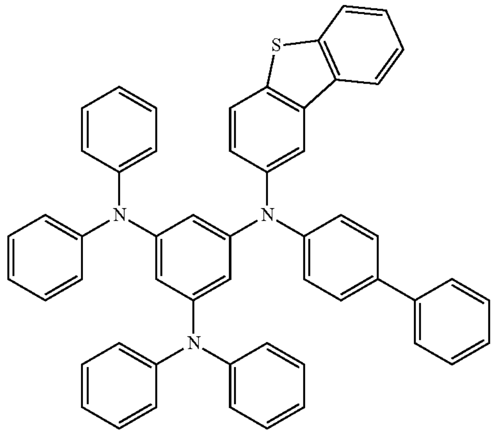
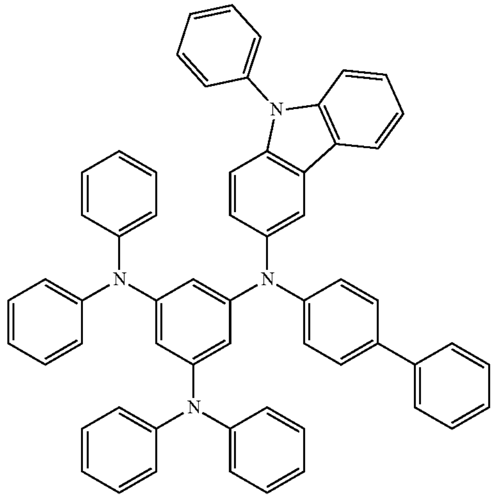
-continued
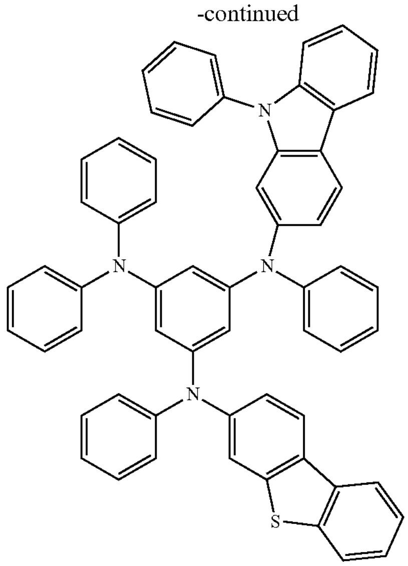
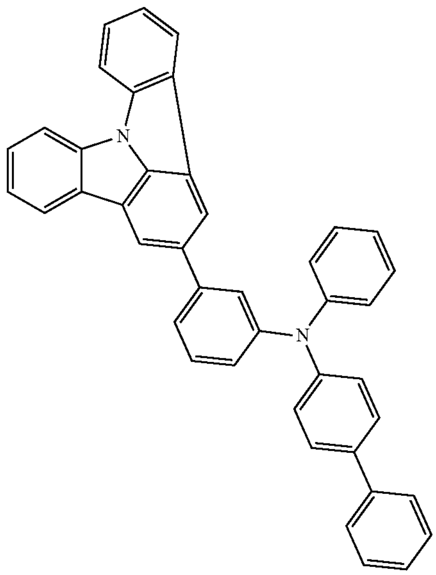
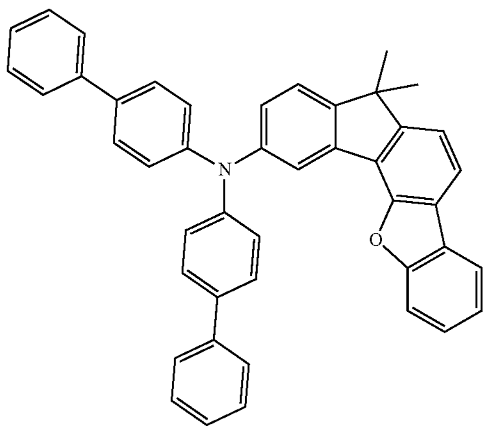

-continued
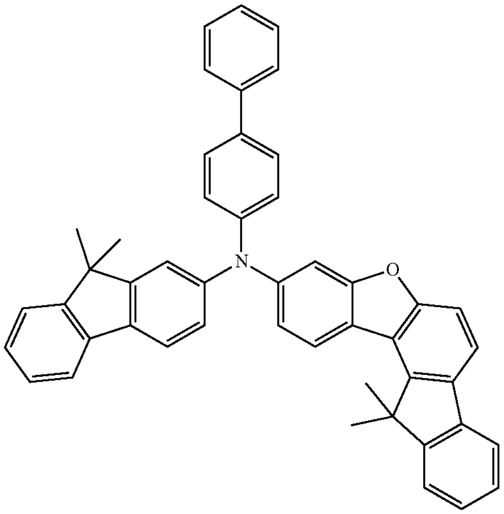
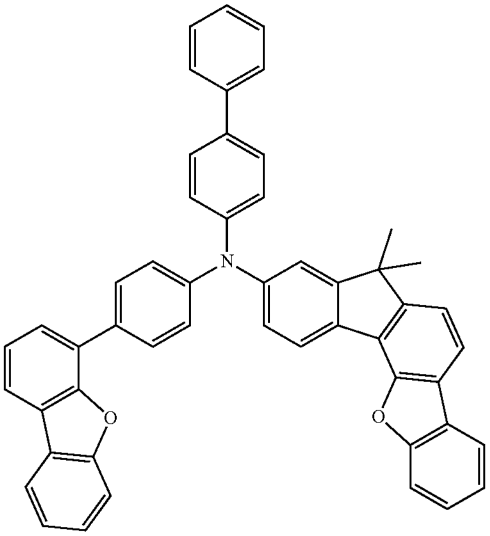
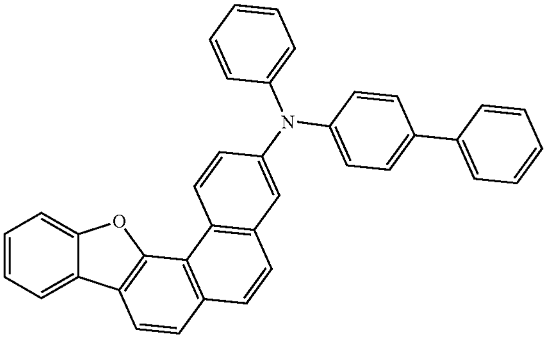
-continued
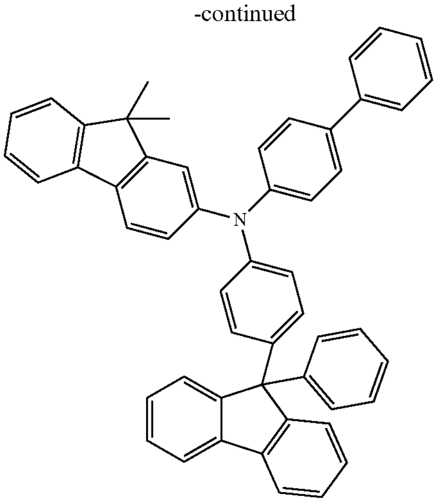
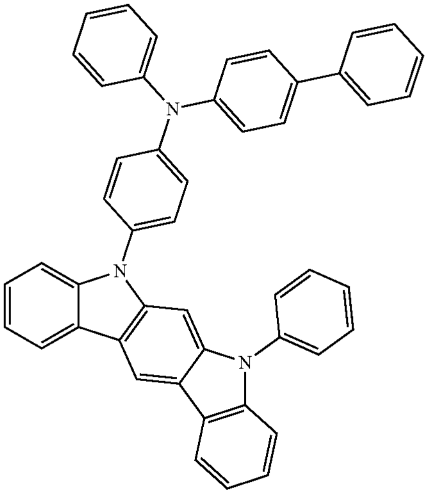
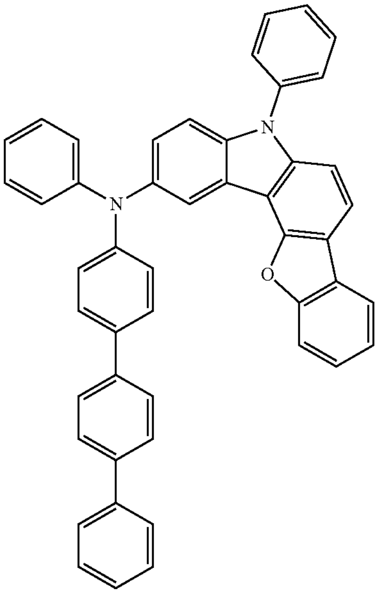

-continued
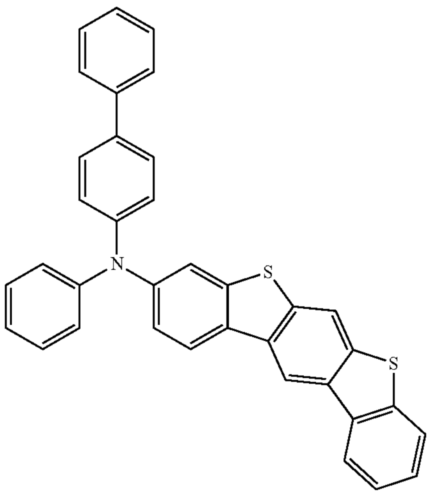
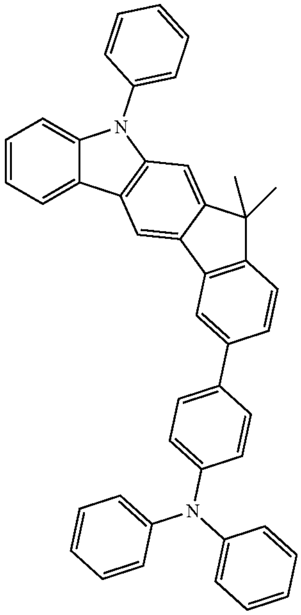
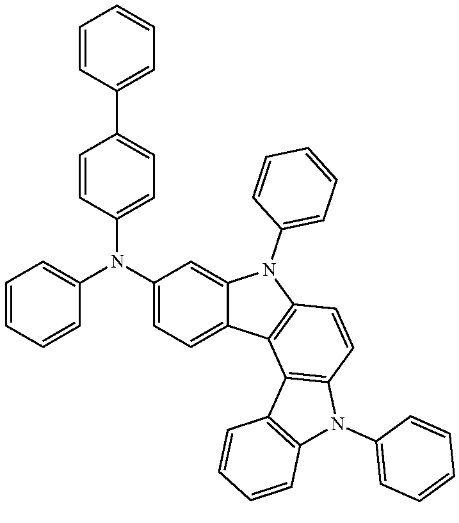
-continued
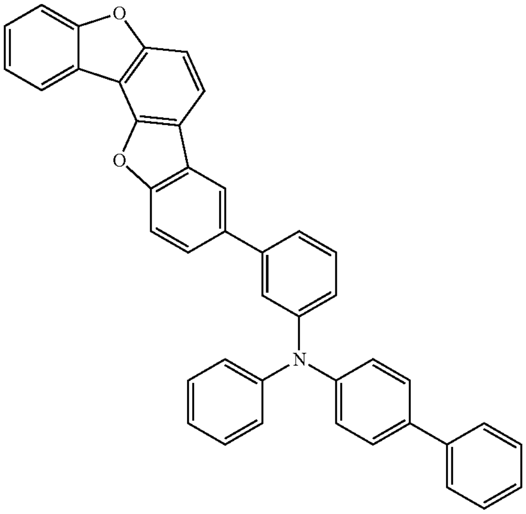
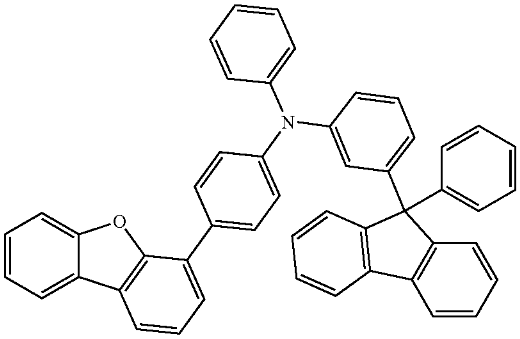
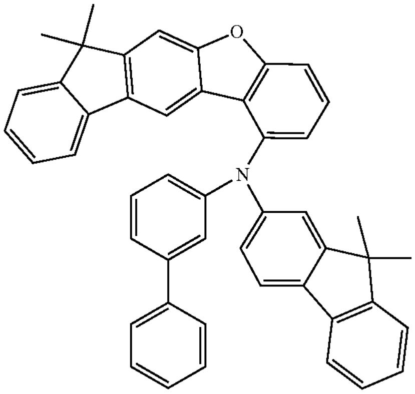
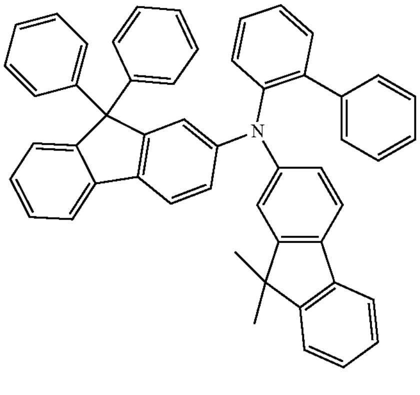

-continued
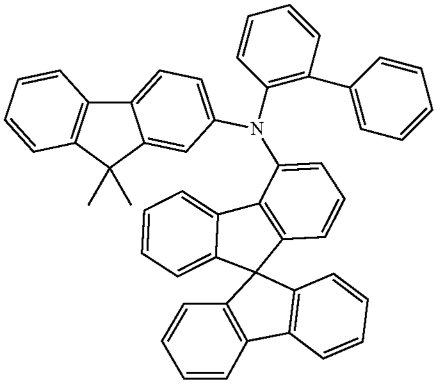
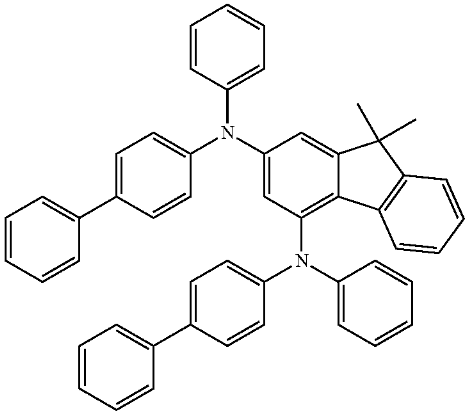
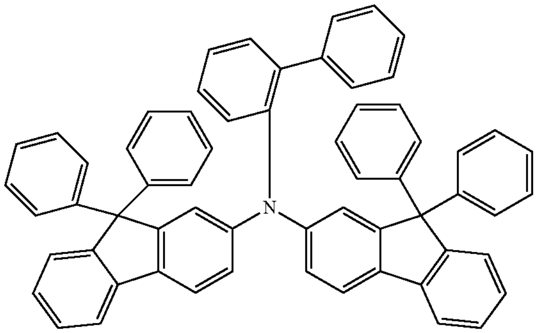
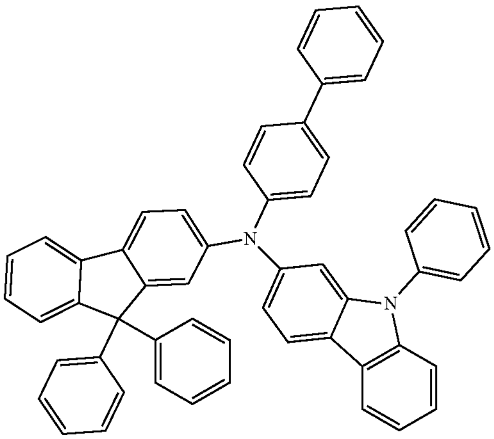
-continued
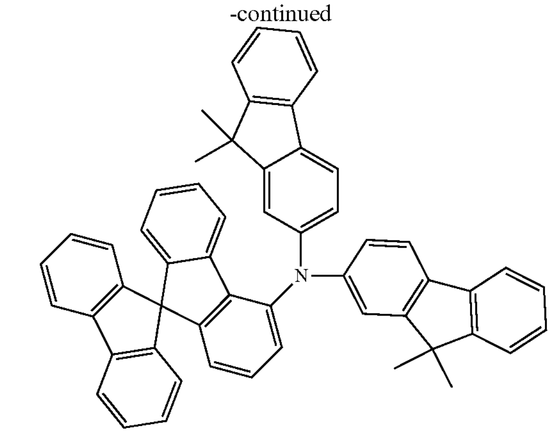
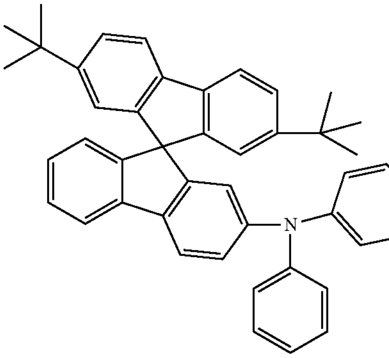
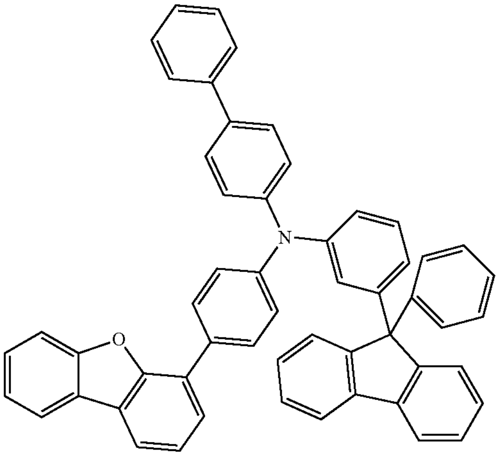
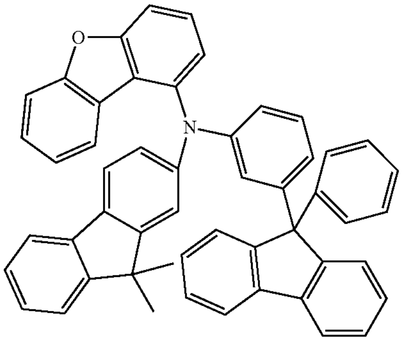

-continued
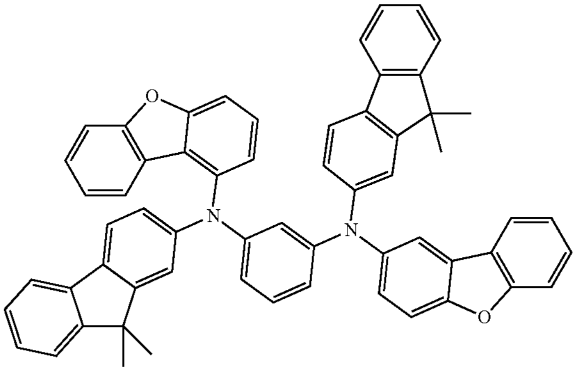
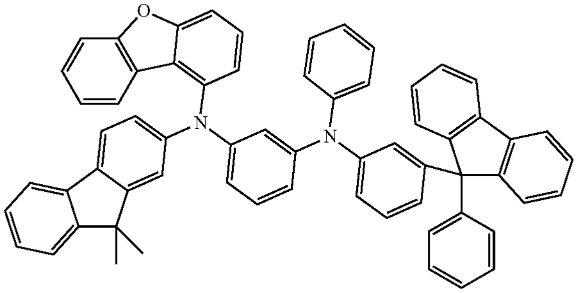
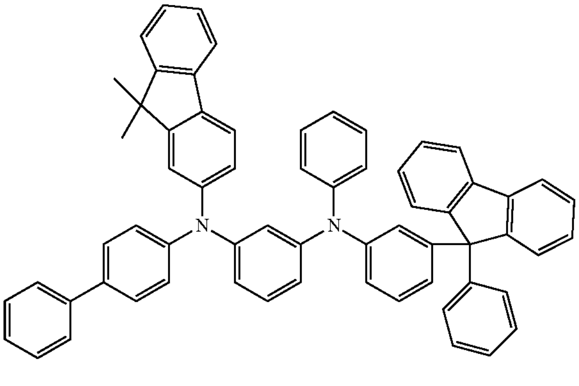
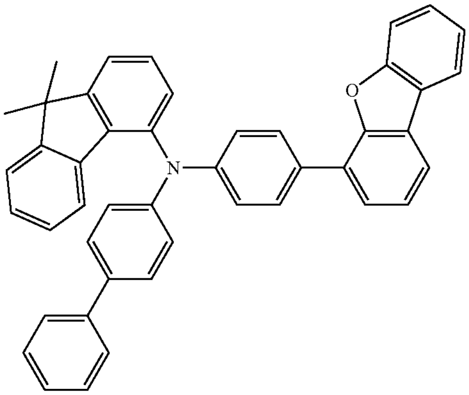
-continued
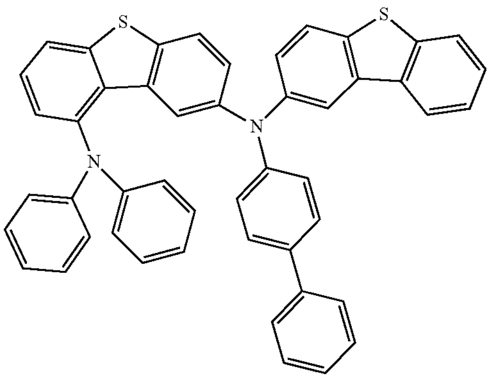
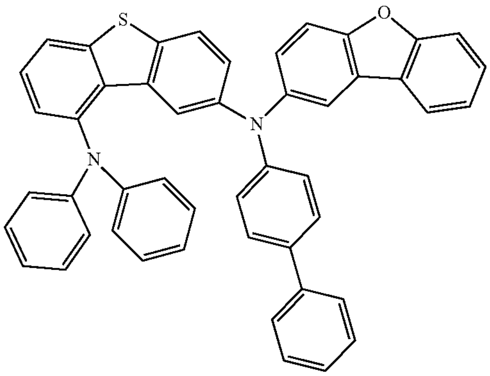
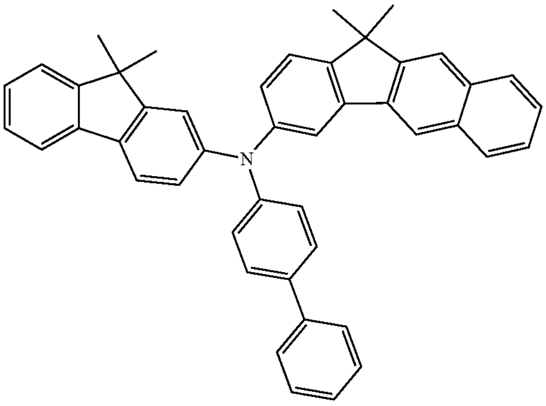

-continued

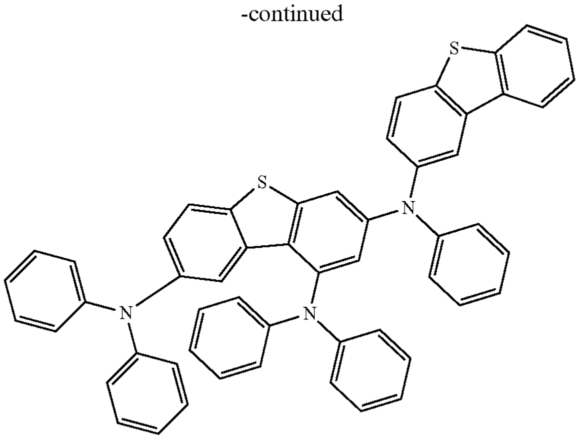

-continued

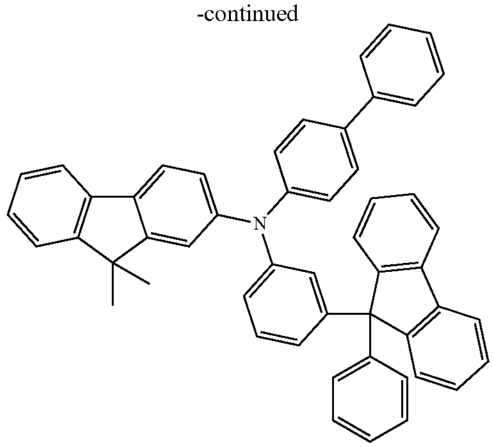

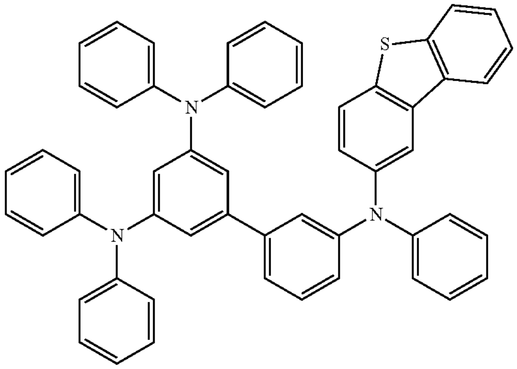

In the hole transport region, in addition to the compounds described above, known compounds disclosed in U.S. Pat. No. 5,061,569A, JP1993-009471A, WO1995-009147A1, JP1995-126615A, JP1998-095973A, etc. and compounds having a similar structure may also be used.

Also, the charge transport region may be, for example, the electron transport region 150.

Referring to FIG. 3, the organic light emitting diode 300 further includes an electron transport region 150 in addition to the light emitting layer 130. The electron transport region 150 may further increase electron injection and/or electron mobility between the cathode 110 and the light emitting layer 130 and block holes.

Specifically, the electron transport region 150 may include an electron transport layer between the cathode 110 and the light emitting layer 130, and an electron transport auxiliary layer between the light emitting layer 130 and the electron transport layer, and at least one of the compounds of Group F may be included in at least one of the electron transport layer and the electron transport auxiliary layer.

[Group F]

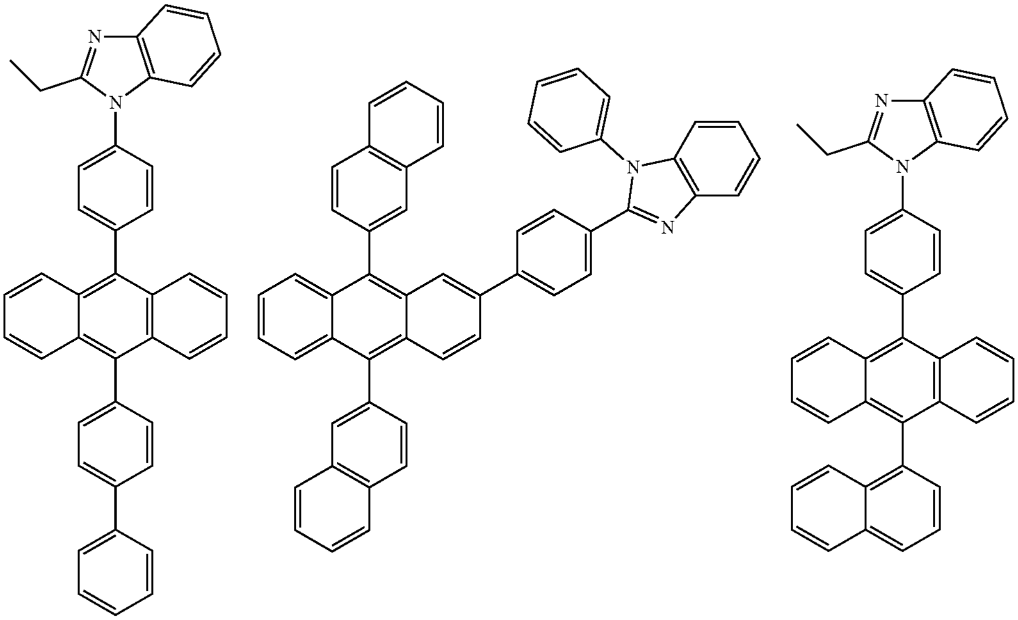

-continued
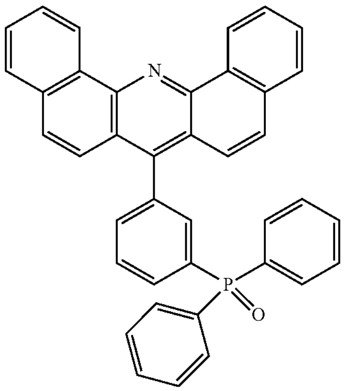
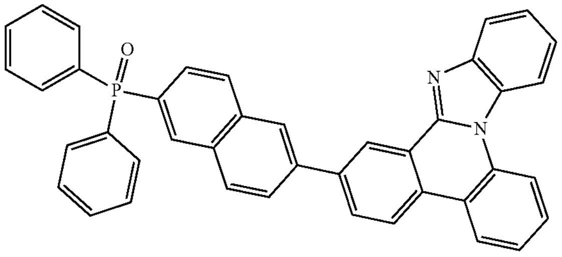
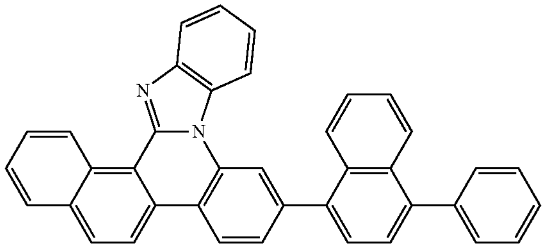
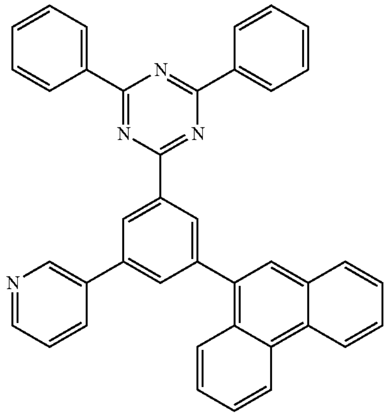
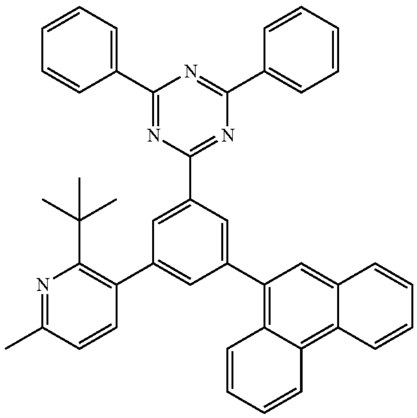
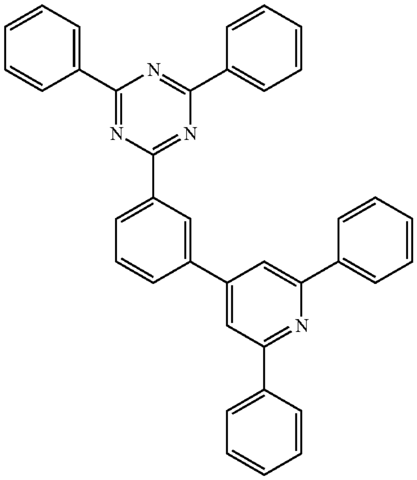
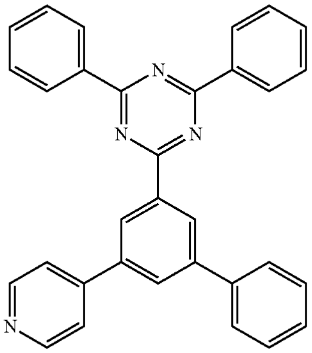
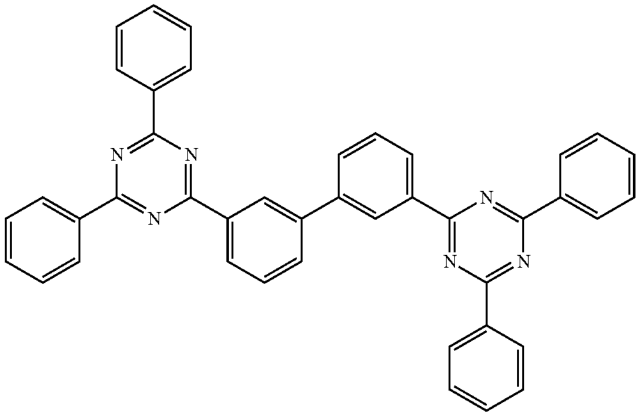

-continued
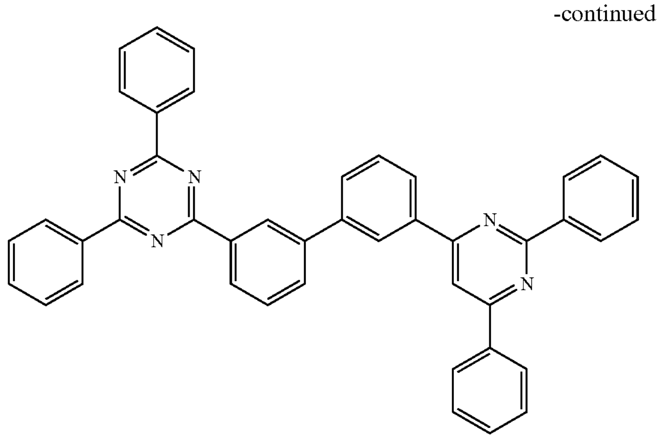
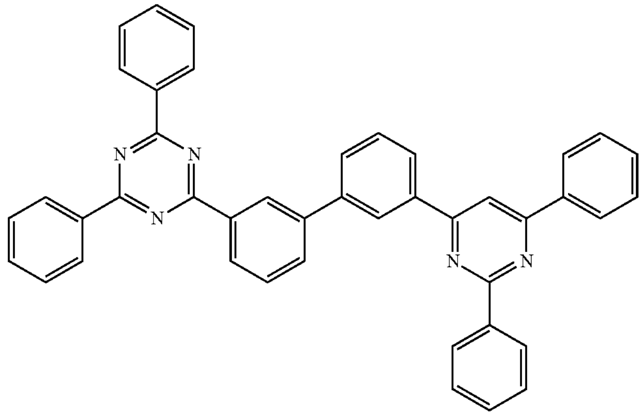
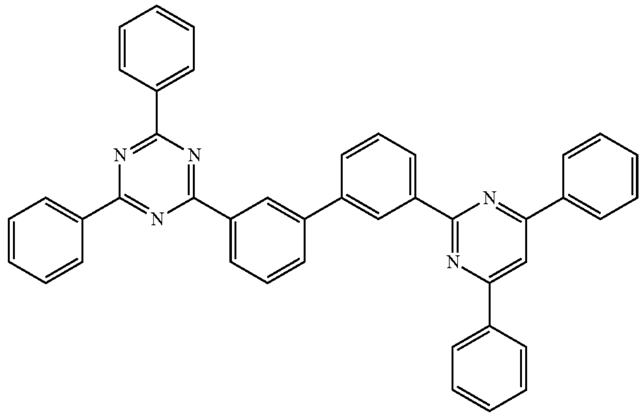
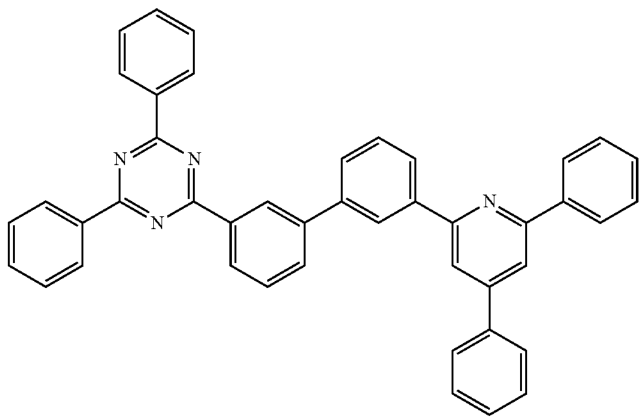

-continued
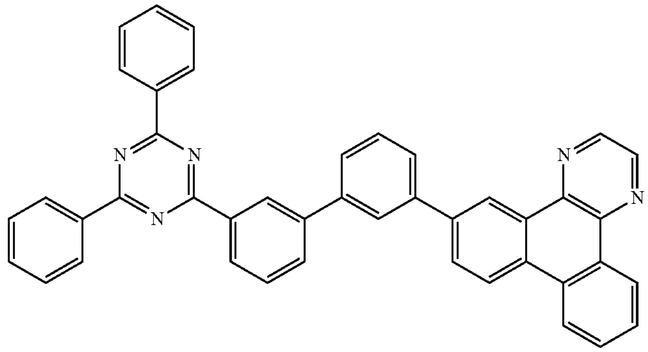
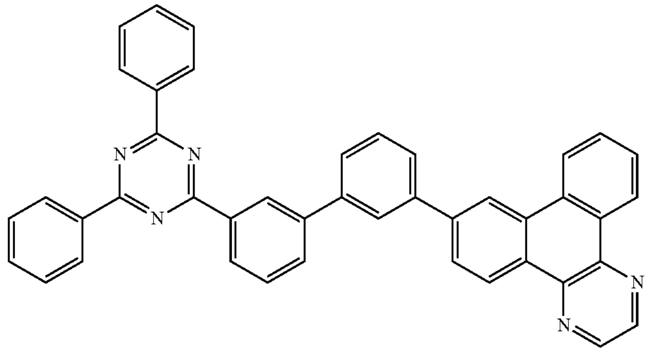
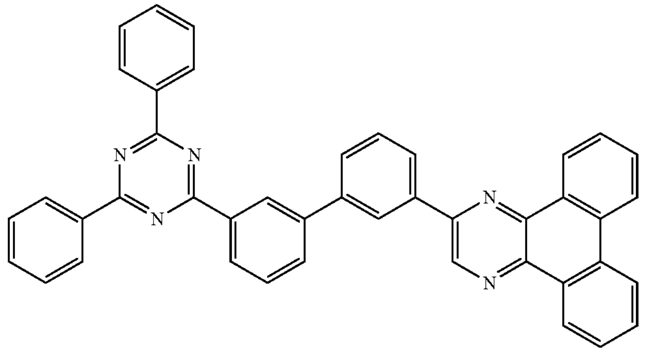
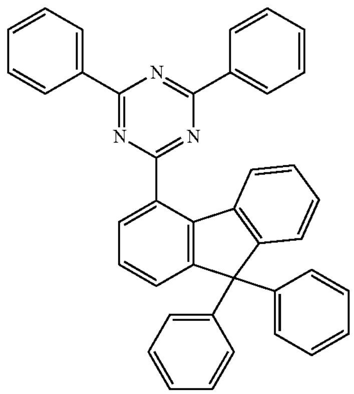
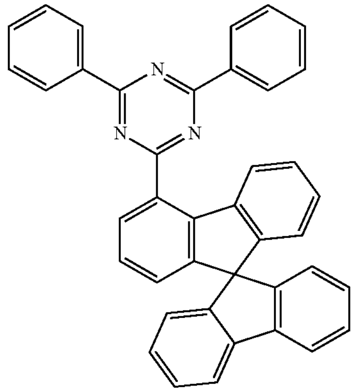
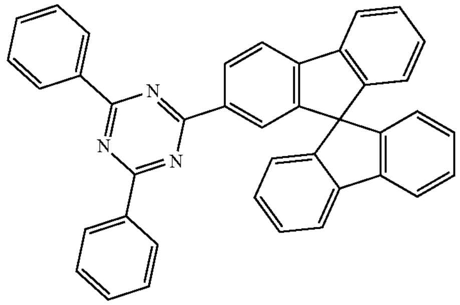

-continued
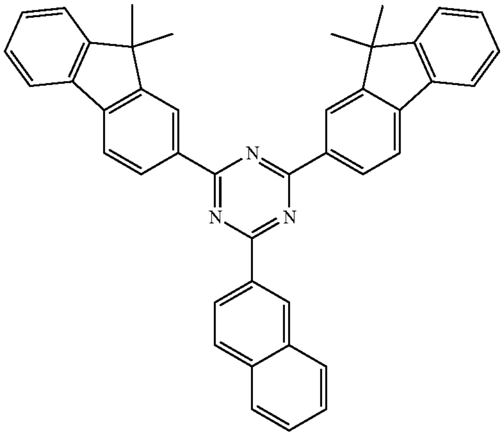
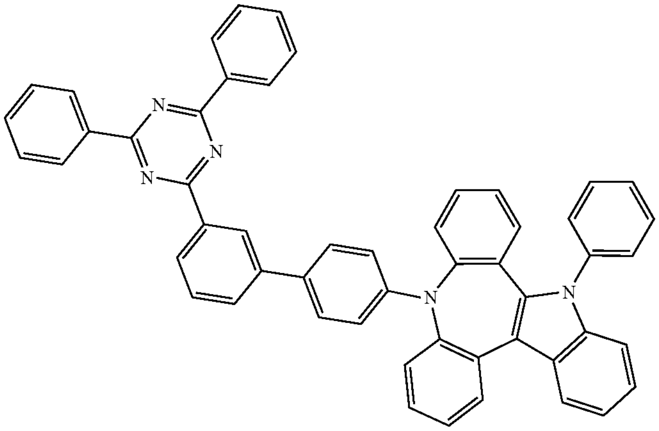
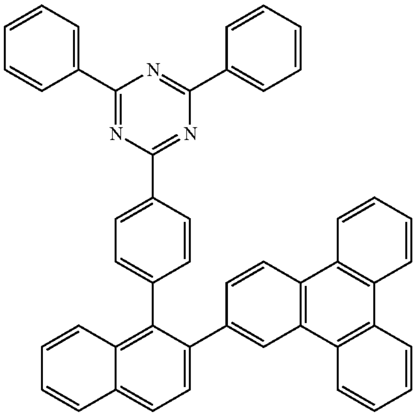
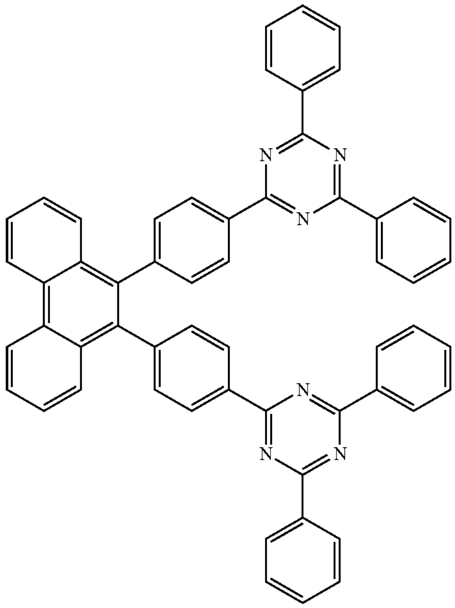
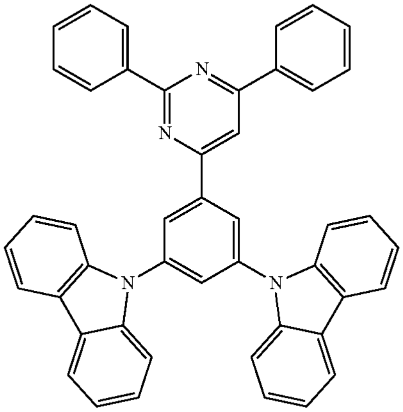
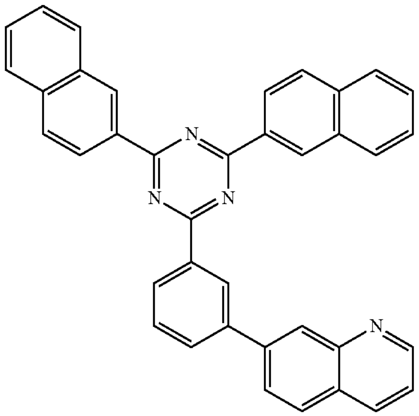

-continued
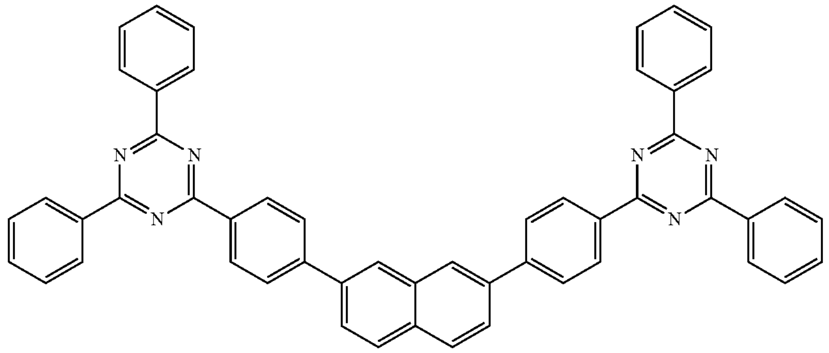
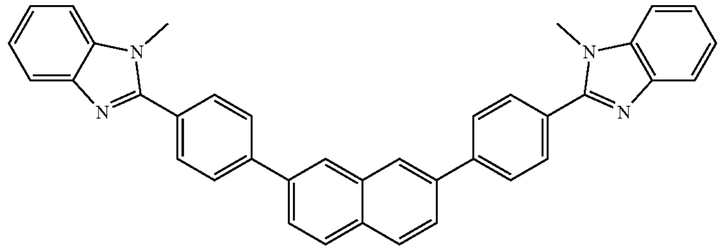
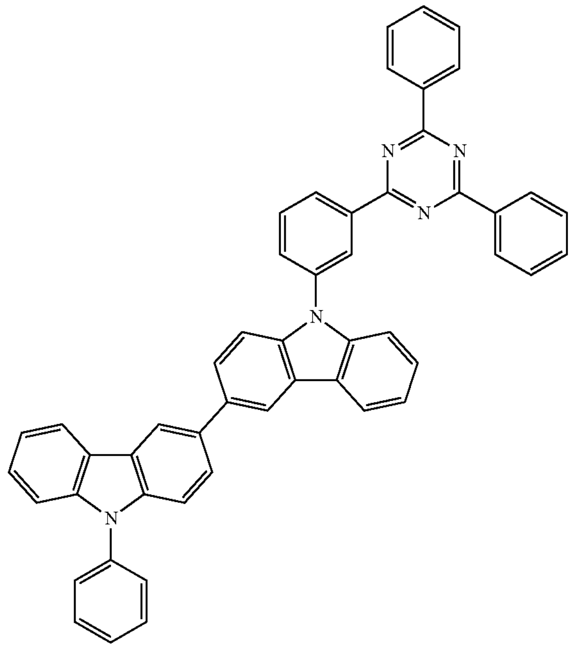
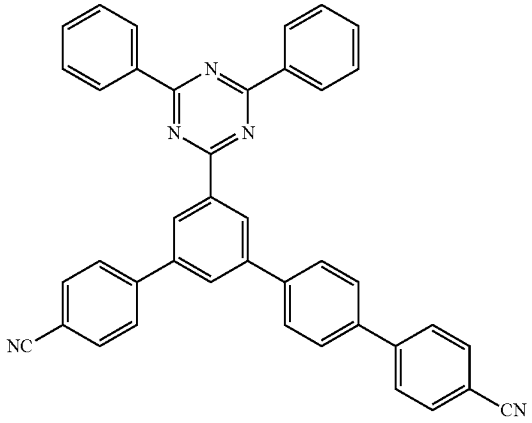

-continued
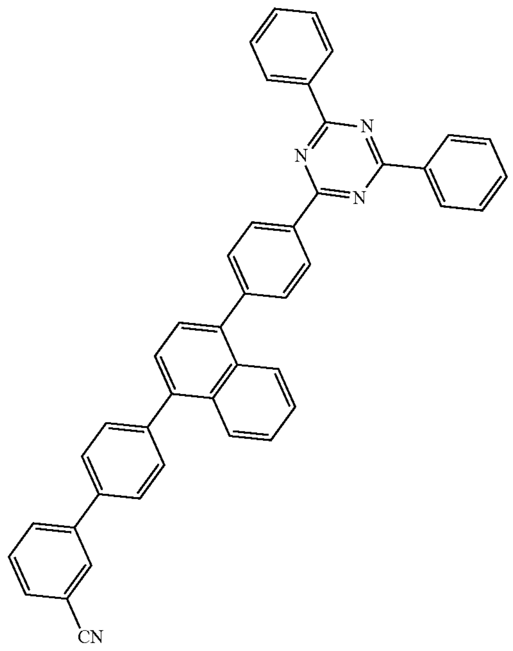
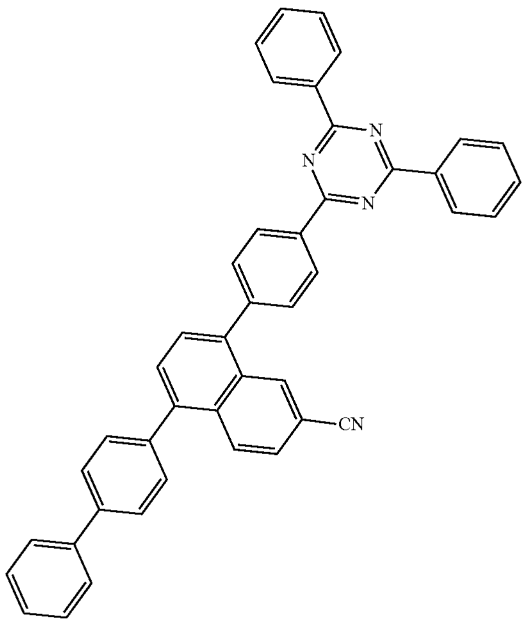
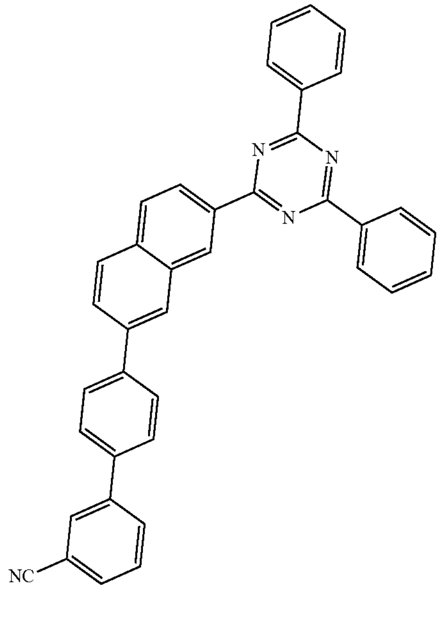
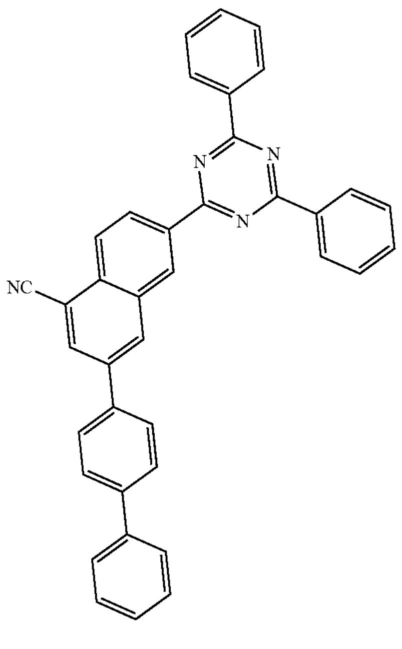

-continued
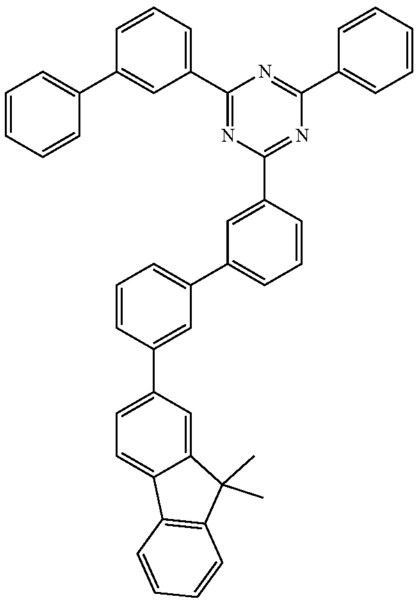
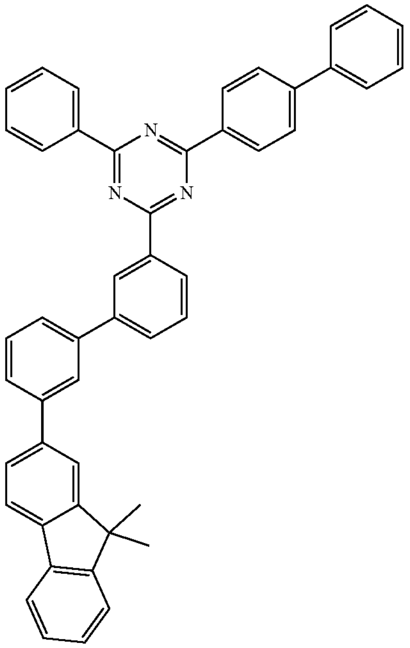
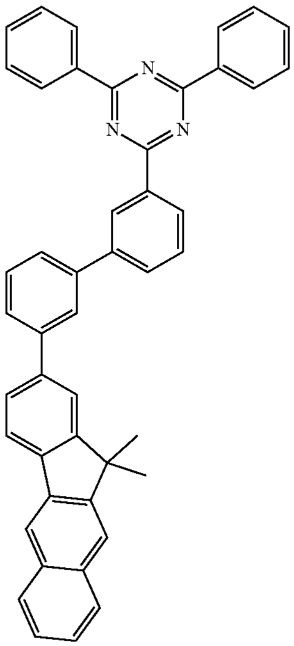
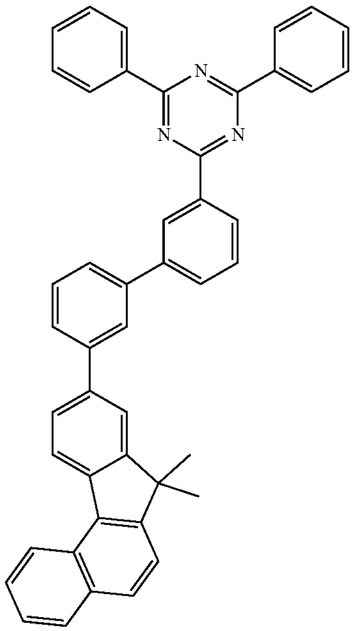
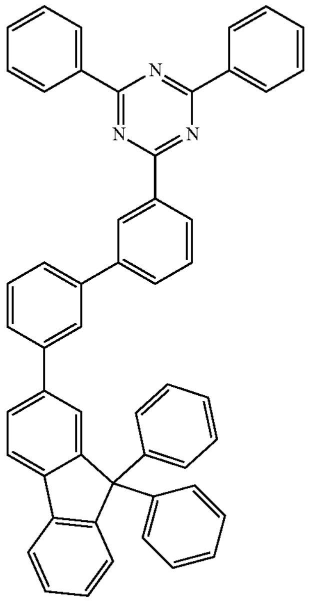
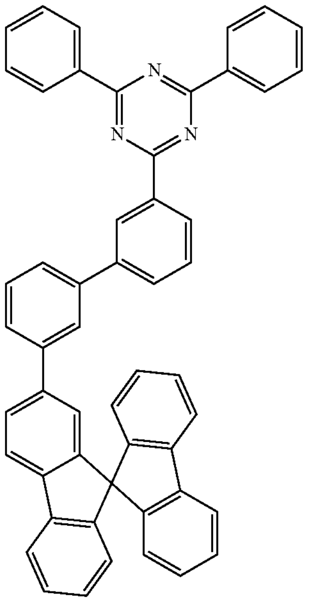
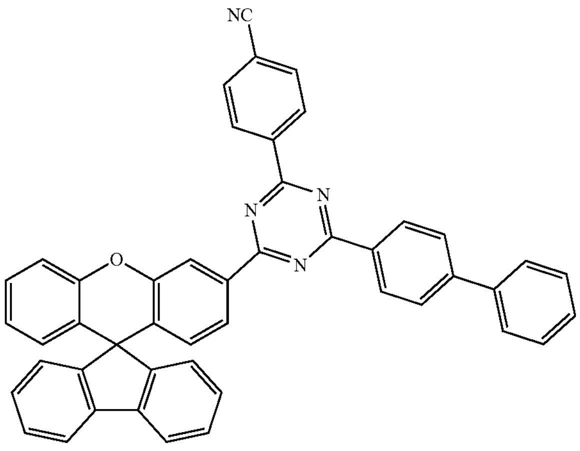
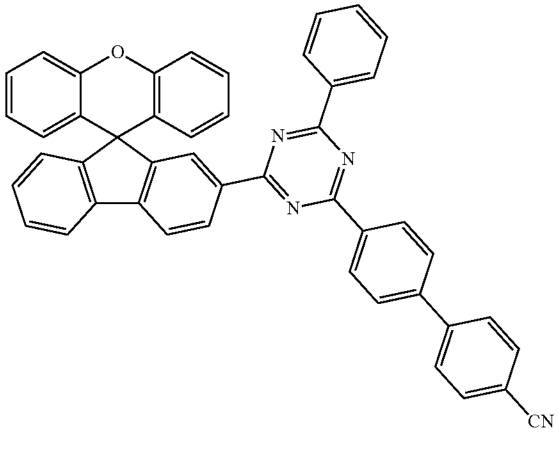

-continued

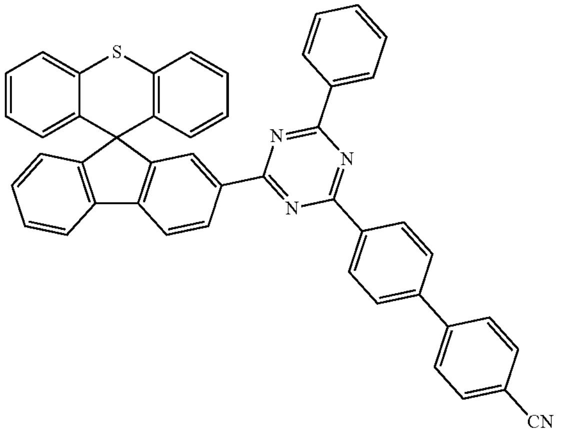

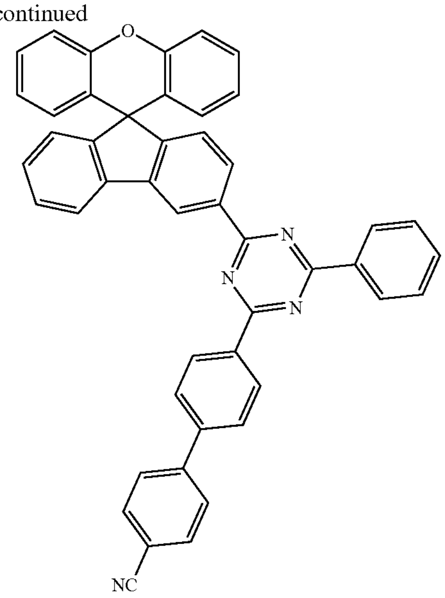

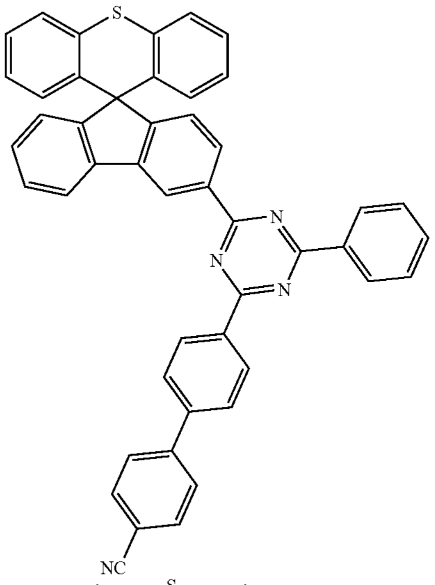

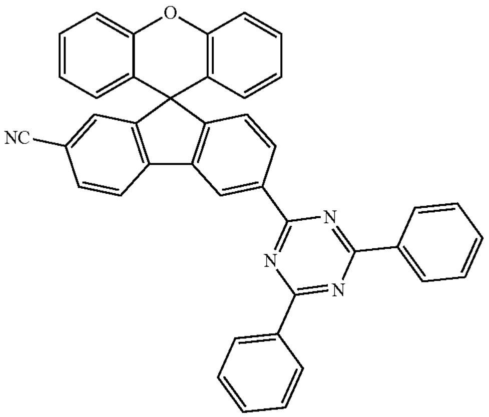

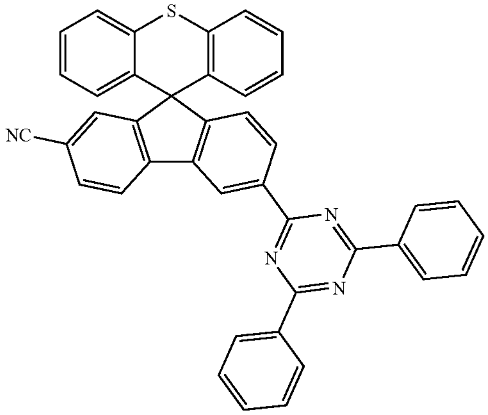

An embodiment of the present invention may provide an organic light emitting diode including the light emitting layer 130 as the organic layer 105 as shown in FIG. 1.

Another embodiment of the present invention may provide an organic light emitting diode including a hole transport region 140 in addition to the light emitting layer 130 as the organic layer 105, as shown in FIG. 2.

Another embodiment of the present invention may provide an organic light emitting diode including an electron transport region 150 in addition to the light emitting layer 130 as the organic layer 105 as shown in FIG. 3.

Another embodiment of the present invention may provide an organic light emitting diode including a hole transport region 140 and an electron transport region 150 in addition to the light emitting layer 130 as the organic layer 105, as shown in FIG. 4.

In another embodiment of the present invention, an organic light emitting diode may further include an electron injection layer (not shown), a hole injection layer (not shown), etc. in addition to the light emitting layer 130 as the organic layer 105 in each of FIGS. 1 to 4.

The organic light emitting diodes 100, 200, 300, and 400 may be manufactured by forming an anode or a cathode on a substrate, and then forming an organic layer by a dry film method such as vacuum deposition, sputtering, plasma plating and ion plating, and forming a cathode or an anode thereon.

The organic light emitting diode may be applied to an organic light emitting display device.

MODE FOR INVENTION

Hereinafter, the embodiments are illustrated in more detail with reference to examples. However, these examples are exemplary, and the scope of claims is not limited thereto.

Hereinafter, starting materials and reactants used in examples and synthesis examples were purchased from Sigma-Aldrich Co. Ltd., TCI Inc., Tokyo chemical industry or P&H tech as far as there is no particular comment or were synthesized by known methods.

(Preparation of Compound for Organic Optoelectronic Device)

The compounds presented as more specific examples of the compounds of the present invention were synthesized through the following steps.

Synthesis Example 1: Synthesis of Int 1

[Reaction Scheme 1]

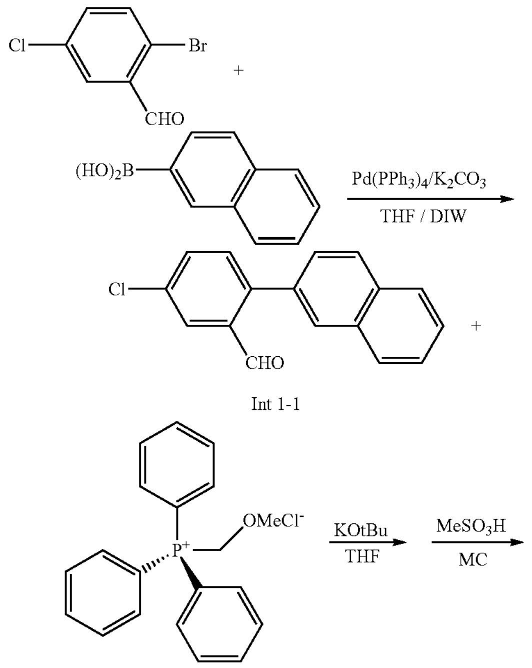

Int 1-1

-continued

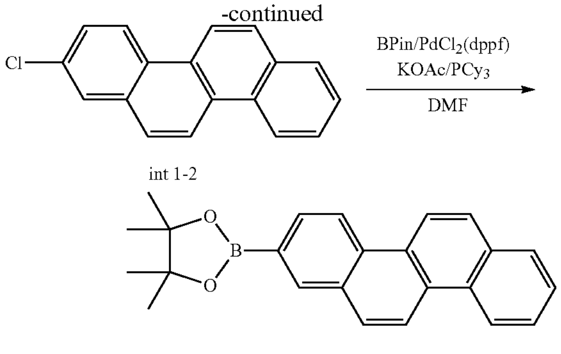

int 1-2 int 1 a) Synthesis of Int 1-1

2-bromo-5-chlorobenzaldehyde (20.0 g, 91.1 mmol), 2-naphthaleneboronic acid (17.2 g, 100.2 mmol), $Pd(PPh_3)_4$(5.3 g, 4.6 mmol), and $K_2CO_3$ (37.8 g, 273.4 mmol) were dissolved in 450 mL of a mixed solution of tetrahydrofuran: distilled water=2:1 in a volume ratio and then, stirred under reflux at 80° C. for 12 hours. When a reaction was completed, the resultant was purified through column chromatography (dichloromethane:n-hexane), obtaining 17.6 g (72.6%) of int 1-1.

b) Synthesis of Int 1-2 int 1-1 (17.6 g, 66 mmol) and (methoxymethyl)triphenylphosphonium chloride (24.9 g, 73 mmol) were dissolved in 130 mL of tetrahydrofuran, and potassium tert-butoxide (8.9 g, 79 mmol) was slowly added thereto and stirred at 0° C. When a reaction was completed, the solvent was all removed by using a rotation evaporator. Subsequently, an organic layer obtained therefrom through twice extraction with dichloromethane and distilled water was dried. Without separate additional purification, the dried organic layer was dissolved in 130 mL of dichlromethane, and methanesulfonic acid (12.7 g, 132 mmol) was slowly added thereto and then, stirred at 0° C. When a reaction was completed, a solid precipitated by adding methyl alcohol to the reaction solution was primarily filtered and then, dissolved in toluene and silica gel-filtered/purified, obtaining 8.9 g (51.4%) of int 1-2.

c) Synthesis of Int 1 int 1-2 (8.9 g, 34 mmol), bis(pinacolato)diboron (11.2 g, 44 mmol), potassium acetate (10.0 g, 102 mmol), tricyclohexylphosphine (1.9 g, 7 mmol), and [1,1'-bis(diphenylphosphino)ferrocene]-dichloropalladium (II) (1.4 g, 2 mmol) were added to 170 mL of N,N-dimethylformamide and then, stirred under reflux at 150° C. for 12 hours. When a reaction was completed, the reaction solution was added to an excessive amount of DIW, forming precipitates. The precipitates were filtered and then, boiled and dissolved in toluene and silica gel-filtered. The filtered solution was recrystallized as it was, obtaining 7.1 g (63.1%) of int 1.

Synthesis Example 2: Synthesis of Int 2

[Reaction Scheme 2]

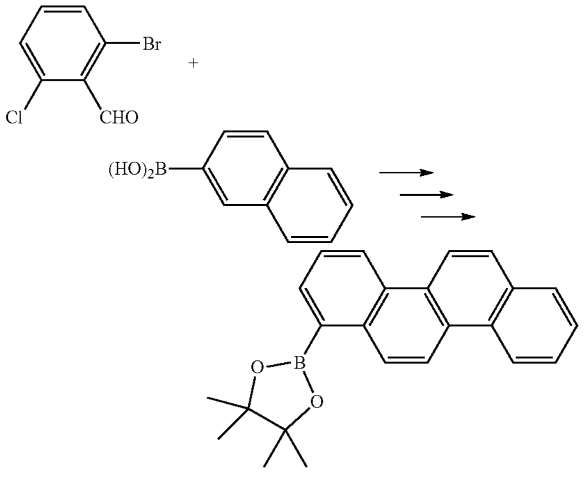

int 2 a) Synthesis of Int 2 int 2 was synthesized according to the same method as the 3rd step of the synthesis method of int 1 according to Synthesis Example 1 except that 2-bromo-6-chlorobenzaldehyde was used instead of the 2-bromo-5-chlorobenzaldehyde.

Synthesis Example 3: Synthesis of Int 3

[Reaction Scheme 3]

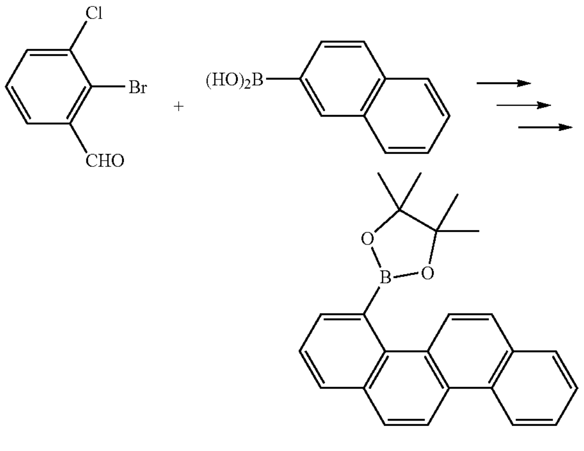

int 3 a) Synthesis of Int 3 int 3 was synthesized according to the same method as the 3rd step of the synthesis method of int 1 according to Synthesis Example 1 except that 2-bromo-3-chlorobenzaldehyde was used instead of the 2-bromo-5-chlorobenzaldehyde.

Synthesis of Synthesis Examples 4 to 10

Each compound according to Synthesis Examples 4 to 10 was synthesized by using Intermediate A and Intermediate B shown in Table 1, which were synthesized through the same Suzuki reaction as the synthesis method of int 1-1.

TABLE 1

| Synthesis Examples | Intermediate A | Intermediate B | Final product | Yield amount (yield) |
|---|---|---|---|---|
| Synthesis Example 4 | 2-([1,1'-biphenyl]-4-yl)-4-chloro-6-phenyl-1,3,5-triazine | int 2 | compound 1 | 12.3 g (87.0%) |
| Synthesis Example 5 | 2-([1,1'-biphenyl]-3-yl)-4-chloro-6-phenyl-1,3,5-triazine | int 2 | compound 3 | 6.9 g (75.4%) |
| Synthesis Example 6 | 2-chloro-4-(dibenzo[b,d]furan-1-yl)-6-phenyl-1,3,5-triazine | int 2 | compound 9 | 9.7 g (67.3%) |
| Synthesis Example 7 | 2-([1,1'-biphenyl]-4-yl)-4-chloro-6-phenyl-1,3,5-triazine | int 3 | compound 59 | 11.8 g (75.9%) |
| Synthesis Example 8 | 2-([1,1'-biphenyl]-3-yl)-4-chloro-6-phenyl-1,3,5-triazine | int 1 | compound 82 | 9.7 g (88.2%) |
| Synthesis Example 9 | 2-chloro-4-(dibenzo[b,d]furan-1-yl)-6-phenyl-1,3,5-triazine | int 1 | compound 88 | 16.3 g (75.1%) |
| Synthesis Example 10 | 2-(4-bromophenyl)-4,6-diphenyl-1,3,5-triazine | int 2 | compound 120 | 10.1 g (69.3%) |

Comparative Synthesis Example 1: Synthesis of Compound B-1

[Reaction Scheme 4]

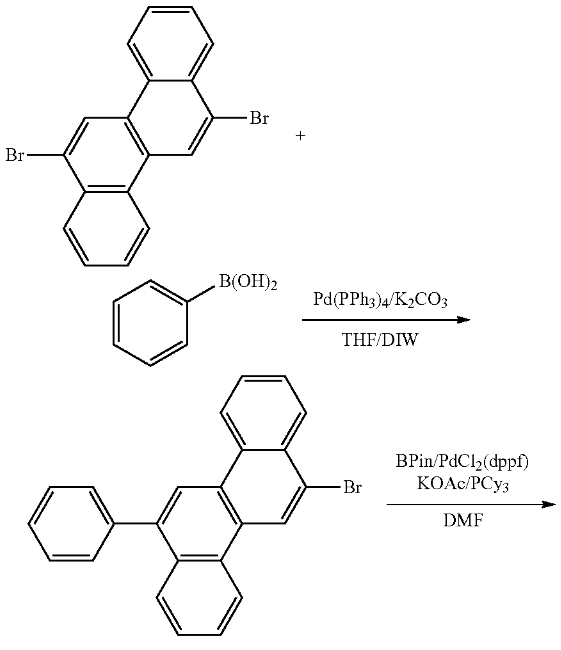

B-1-1

-continued

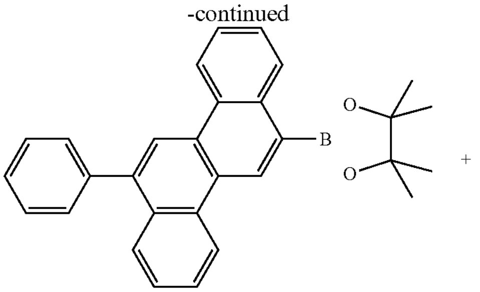

B-1-2

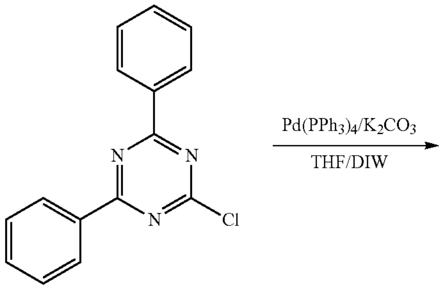

B-1-1

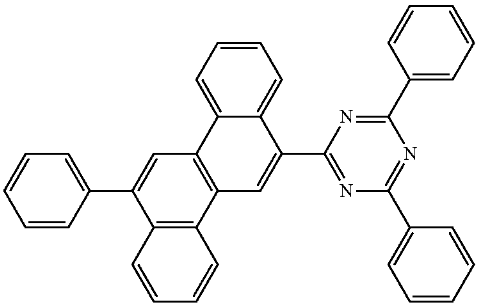

B-1 a) Synthesis of Intermediate B-1-1

Intermediate B-1-1 was synthesized according to the same method as the synthesis method of int 1 according to Synthesis Example 1 except that 6,12-dibromochrysene and phenylboronic acid were used as a starting material and then, recrystallized with toluene.

b) Synthesis of Intermediate B-1-2

Intermediate B-1-2 was synthesized according to the same method as the synthesis method of int 1 according to Synthesis Example 1 except that Intermediate B-1-1 was used as a starting material 1 and then, recrystallized with toluene.

c) Synthesis of Compound B-1

Compound B-1 was synthesized according to the same method as the synthesis method of int 1-1 according to Synthesis Example 1 except that Intermediate B-1-2 and 2-chloro-4,6-diphenyl-1,3,5-triazine were used as a starting material 1 and then, recrystallized with monochlorobenzene.

Comparative Synthesis Example 2: Synthesis of Compound B-2

[Reaction Scheme 5]

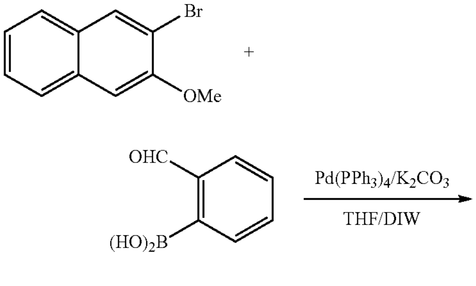

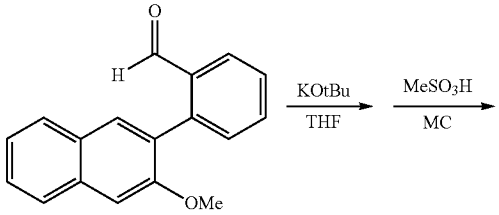

B-2-1

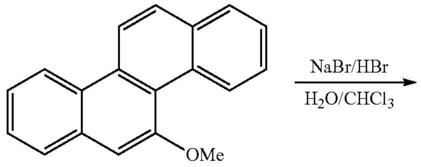

B-2-2

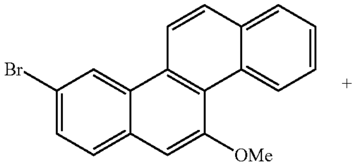

B-2-3

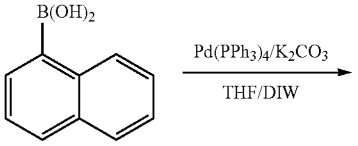

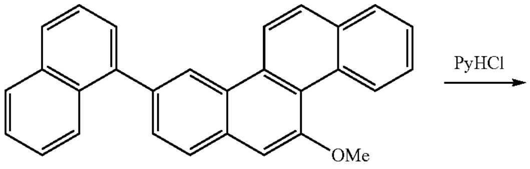

B-2-4

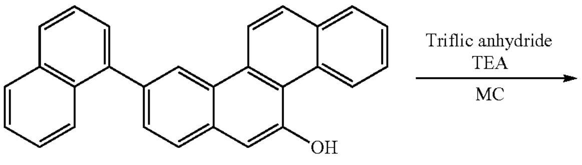

B-2-5

-continued

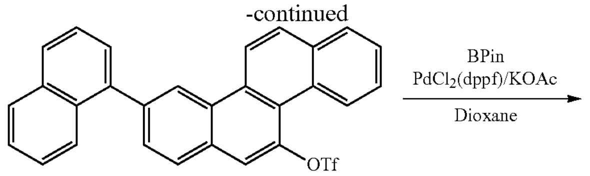

B-2-6

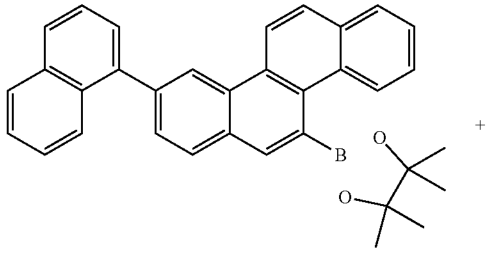

B-2-7

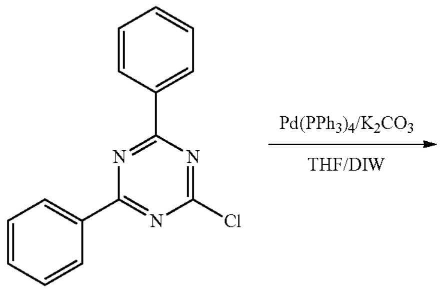

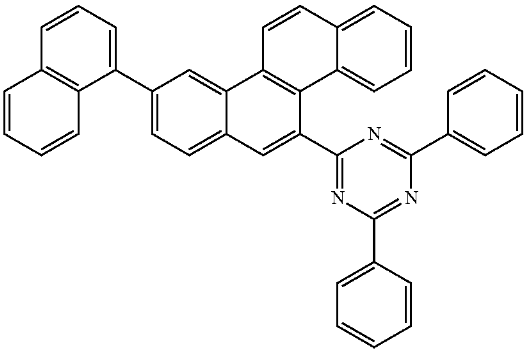

B-2 a) Synthesis of Intermediate B-2-1

Intermediate B-2-1 was synthesized according to the same method as the synthesis method of int 1-1 according to Synthesis Example 1 except that 3-methoxy-2-bromonaphthalene and 2-formylphenylboronic acid were used as a starting material 1 and then, recrystallized with toluene.

b) Synthesis of Intermediate B-2-2

Intermediate B-2-2 was synthesized according to the same method as the synthesis method of int 1-2 according to Synthesis Example 1 except that Intermediate B-2-1 was used as a starting material 1 and then, recrystallized with monochlorobenzene.

c) Synthesis of Intermediate B-2-3

Intermediate B-2-3 was synthesized according to the same method as bromination of 2-methoxynaphthalene, which was described in Tetrahedron Letters, 47(27), 4581-4584; 2006 except that Intermediate B-2-2 was used as a starting material 1, and toluene was used for recrystallization.

d) Synthesis of Intermediate B-2-4

Intermediate B-2-4 was synthesized according to the same method as the synthesis method of int 1-1 according to Synthesis Example 1 except that Intermediate B-2-3 and 1-naphthaleneboronic acid were used as a starting material 1 and then, recrystallized with monochlorobenzene.

e) Synthesis of Intermediate B-2-5

Intermediate B-2-4 (22.0 g, 57 mmol) and pyridine hydrochloride (66 g, 572 mmol) were mixed and then, stirred under reflux at 200° C. for 12 hours. When a reaction was completed, the resultant was cooled down to a predetermined temperature and then, completely cooled down to room temperature by adding distilled water thereto. The resultant was twice extracted with ethyl acetate and distilled water and then, silica gel-filtered, obtaining 16.9 g (79.7%) of Intermediate B-2-5.

f) Synthesis of Intermediate B-2-6

Intermediate B-2-5 (16 g, 43 mmol) and triethylamine (6.6 g, 65 mmol) were dissolved in 85 mL of dichloromethane, and triflic anhydride (14.0 g, 50 mmol) was slowly added thereto at 0° C. When the addition was completed, the mixture was heated up to room temperature and then, stirred for 12 hours. When a reaction was completed, ice water was added thereto and then, twice extracted with dichloromethane, and an organic layer therefrom was silica gel-filtered therefrom. Methyl alcohol was added thereto to produce precipitates, and the precipitates were filtered, obtaining 20.1 g (92.6%) of Intermediate B-2-6.

g) Synthesis of Intermediate B-2-7

Intermediate B-2-7 was synthesized according to the same method as the synthesis method of int 1 of Synthesis Example 1 except that Intermediate B-2-6 was used as a starting material, and the solvent alone was changed into dioxane and then, recrystallized with toluene.

h) Synthesis of Compound B-2

Compound B-2 was synthesized according to the same method as the synthesis method of int 1-1 of Synthesis Example 1 except that Intermediate B-2-7 and 2-chloro-4,6-diphenyl-1,3,5-triazine were used as a starting material and then, recrystallized with monochlorobenzene.

Comparative Synthesis Example 3: Synthesis of Compound B-3

[Reaction Scheme 6]

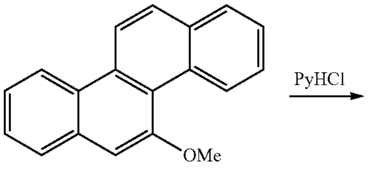

B-2-2

-continued

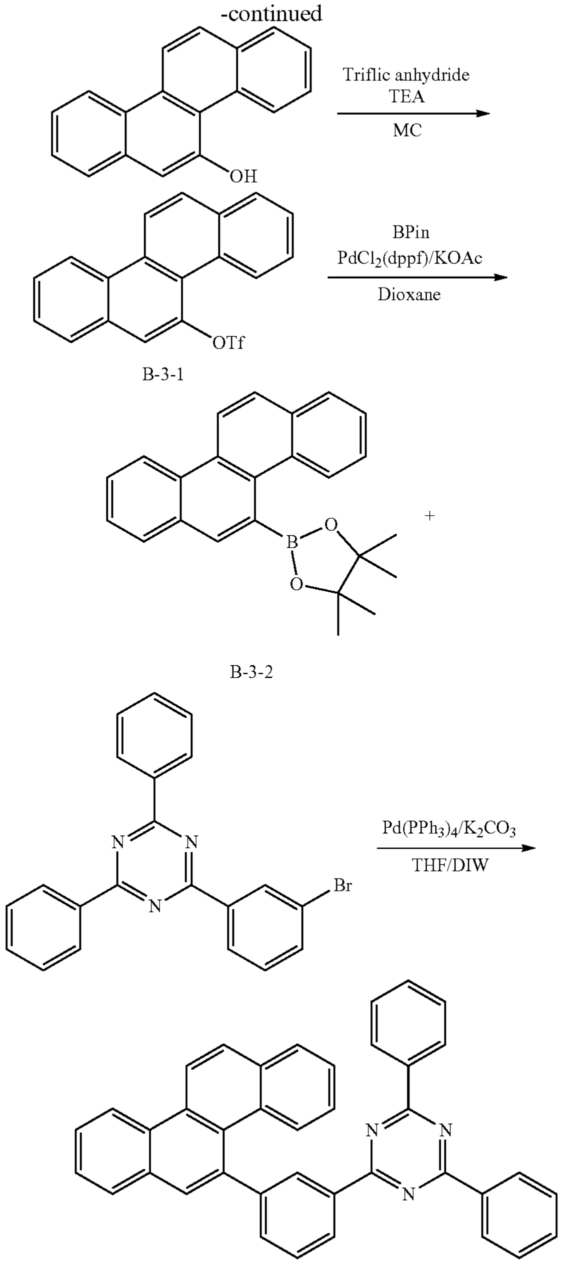

B-3 a) Synthesis of Intermediate B-3-1

Intermediate B-3-1 was synthesized/purified according to the same method as the synthesis method of Intermediate B-2-5 of Comparative Synthesis Example 2 except that Intermediate B-2-2 was used as a starting material.

b) Synthesis of Intermediate B-3-2

Intermediate B-3-2 was synthesized/purified according to the same method as the synthesis method of Intermediate B-2-6 of Comparative Synthesis Example 2 except that Intermediate B-3-1 was used as a starting material.

c) Synthesis of Compound B-3

Compound B-3 was synthesized/purified according to the same method as the synthesis method of int 1-1 of Synthesis Example 1 except that Intermediate B-3-2 and 2-(3-bromophenyl)-4,6-diphenyl-1,3,5-triazine were used as a starting material and then, recrystallized with monochlorobenzene.

Synthesis of Second Compound

Synthesis Example 11: Synthesis of Compound A-84

[Reaction Scheme 7]

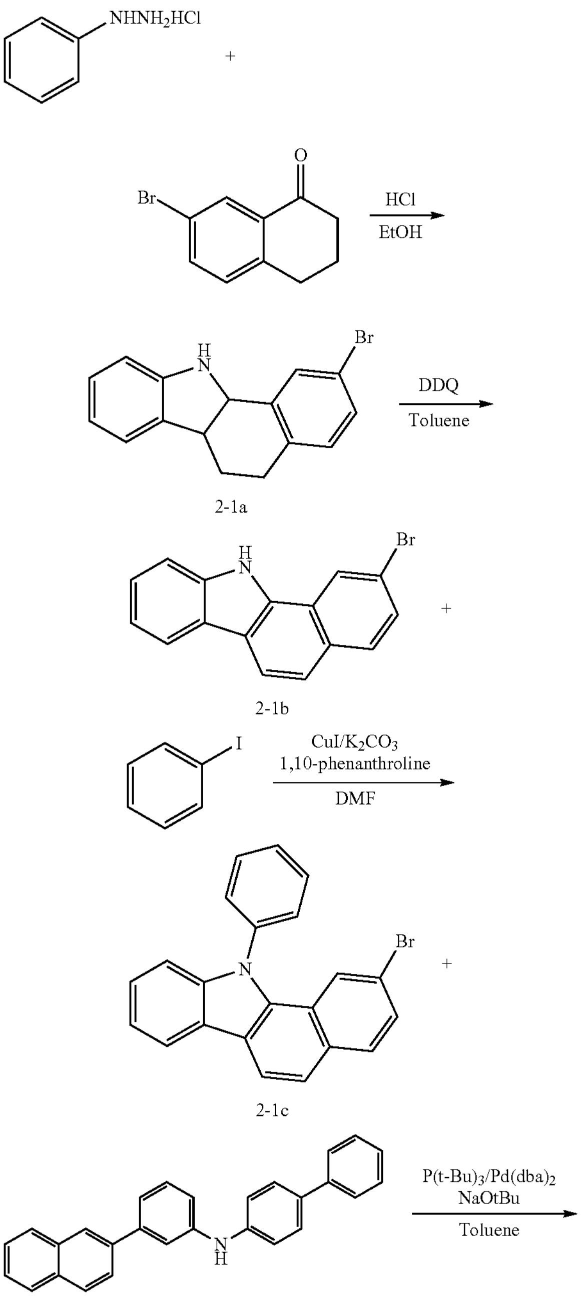

-continued

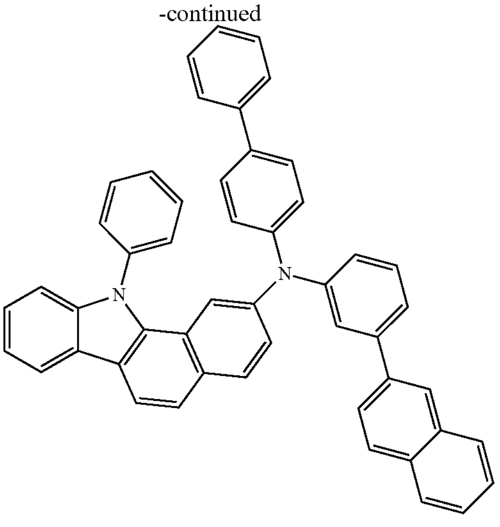

A-84 a) Synthesis of Intermediate 2-1a

Phenylhydrazinehydrochloride (70.0 g, 484.1 mmol) and 7-bromo-3,4-dihydro-2H-naphthalen-1-one (108.9 g, 484.1 mmol) were put in a round-bottomed flask and then, dissolved in ethanol (1200 ml). At room temperature, 60 mL of hydrochloric acid was slowly added thereto in a dropwise fashion and then, stirred at 90° C. for 12 hours. When a reaction was completed, after removing the solvent under a reduced pressure, an excessive amount of EA was used for extraction. After removing an organic solvent under a reduced pressure, the residue was stirred in a small amount of methanol and then, filtered, obtaining 95.2 g (66%) of Intermediate 2-1a.

b) Synthesis of Intermediate 2-1b

Intermediate 2-1a (95.2 g, 319.3 mmol) and 2,3-dichloro-5,6-dicyano-1,4-benzoquinone (108.7 g, 478.9 mmol) were put in a round-bottomed flask and then, dissolved in 600 ml of toluene. The solution was stirred at 80° C. for 12 hours. When a reaction was completed, after removing the reaction solvent, the residue was treated through column chromatography, obtaining 41.3 g (44%) of Intermediate 2-1b.

c) Synthesis of Intermediate 2-1c

Intermediate 2-1b (41.3 g, 139.0 mmol), iodobenzene (199.2 g, 976.0 mmol), CuI (5.31 g, 28.0 mmol), $K_2CO_3$ (28.9 g, 209.0 mmol), and 1,10-phenanthroline (5.03 g, 28.0 mmol) were put in a round-bottomed flask and dissolved in 500 ml of DMF. The solution was stirred at 180° C. for 12 hours. When a reaction was completed, after removing the reaction solvent under a reduced pressure, the residue was dissolved in dichloromethane and then, silica gel-filtered. After concentrating the dichloromethane, the resultant was recrystallized with hexane, obtaining 39.0 g (75%) of Intermediate 2-1c.

d) Synthesis of Compound A-84

5.0 g (13.46 mmol) of Intermediate 2-1c, 4.41 g (13.46 mmol) of an amine intermediate 2-1d, 1.94 g (20.19 mmol) of sodium t-butoxide, and 0.54 g (1.35 mmol) of tri-tert-butylphosphine were dissolved in 100 ml of toluene, and 0.37 g (0.4 mmol) of $Pd(dba)_2$ was added thereto and then, stirred under reflux for 12 hours under a nitrogen atmosphere. When a reaction was completed, an organic layer obtained through extraction with toluene and distilled water was dried with anhydrous magnesium sulfate and filtered, and a filtrate therefrom was concentrated under a reduced pressure. A product therefrom was purified through silica gel column chromatography with normal hexane/dichloro methane (in a volume ratio of 2:1), obtaining 6.4 g (Yield: 82.0%) of Compound A-84.

Synthesis Example 12: Synthesis of Compound 2-92

[Reaction Scheme 8]

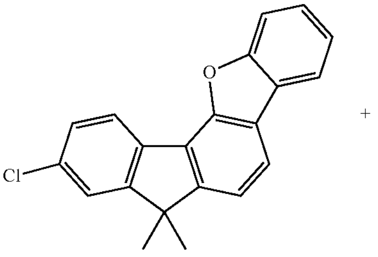

2-92a

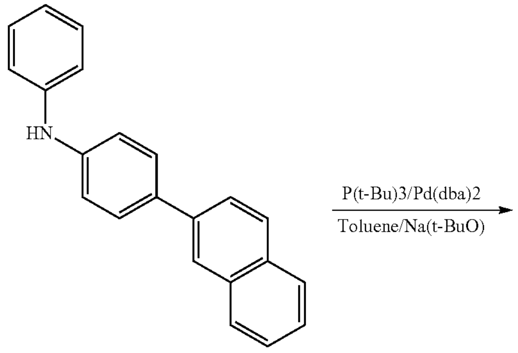

2-92b

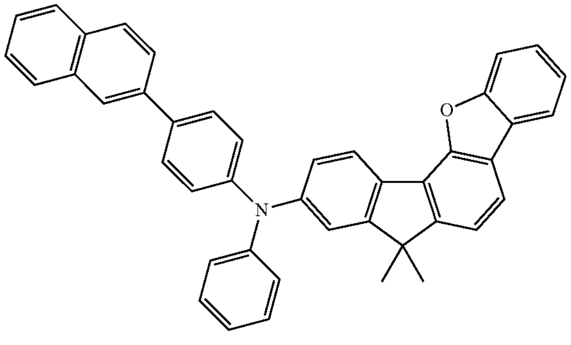

2-92 a) Synthesis of Intermediate 2-92a

It was synthesized with reference to the KR10-1423173 B1.

b) Synthesis of Compound 2-92

5.0 g (16.93 mmol) of Intermediate 2-92a, 5.4 g (16.93 mmol) of an amine intermediate 2-92b, 2.44 g (25.39 mmol) of sodium t-butoxide, and 0.68 g (1.69 mmol) of tri-tert-butylphosphine were dissolved in 100 ml of toluene, and 0.47 g (0.51 mmol) of $Pd(dba)_2$ was added thereto and then, stirred under reflux for 12 hours under a nitrogen atmosphere. When a reaction was completed, an organic layer extracted with toluene and distilled water was dried with anhydrous magnesium sulfate and filtered, and a filtrate therefrom was concentrated under a reduced pressure. A product therefrom was purified through silica gel column chromatography with normal hexane/dichloromethane (in a volume ratio of 2:1), obtaining 8.2 g (Yield: 84.0%) of Compound 2-92.

(Manufacture of Organic Light Emitting Diode)

Example 1

The glass substrate coated with ITO (Indium tin oxide) was washed with distilled water and ultrasonic waves. After washing with the distilled water, the glass substrate was washed with a solvent such as isopropyl alcohol, acetone, methanol, and the like ultrasonically and dried and then, moved to a plasma cleaner, cleaned by using oxygen plasma for 10 minutes, and moved to a vacuum depositor. This obtained ITO transparent electrode was used as an anode, Compound A doped with 1% NDP-9 (available from Novaled GmbH) was vacuum-deposited on the ITO substrate to form a 1400 Å-thick hole transport layer, and Compound B was deposited on the hole transport layer to form a 350 Å-thick hole transport auxiliary layer. On the hole transport auxiliary layer, 400 Å-thick light emitting layer was formed by using Compound 1 of Synthesis Example 4 and doping 2 wt % of $[Ir(piq)_2acac]$ as a dopant by a vacuum-deposition. Subsequently, Compound C was deposited on the light emitting layer to form a 50 Å-thick electron transport auxiliary layer, and Compound D and Liq were simultaneously vacuum-deposited at a weight ratio of 1:1 to form a 300 Å-thick electron transport layer. LiQ (15 Å) and Al (1200 Å) were sequentially vacuum-deposited on the electron transport layer to form a cathode, thereby manufacturing an organic light emitting diode.

The organic light emitting diode had a five-layered organic thin layer, and specifically the following structure.

ITO/Compound A (1% NDP-9 doping, 1400 Å)/Compound B (350 Å)/EML [Compound 1: $[Ir(piq)_2acac]$ (2 wt %)] (400 Å)/Compound C (50 Å)/Compound D: Liq (300 Å)/LiQ (15 Å)/Al (1200 Å).

Compound A: N-(biphenyl-4-yl)-9,9-dimethyl-N-(4-(9-phenyl-9H-carbazol-3-yl)phenyl)-9H-fluoren-2-amine Compound B: N,N-di([1,1'-biphenyl]-4-yl)-7,7-dimethyl-7H-fluoreno[4,3-b]benzofuran-10-amine Compound C: 2-(3-(3-(9,9-dimethyl-9H-fluoren-2-yl)phenyl)phenyl)-4,6-diphenyl-1,3,5-triazine Compound D: 8-(4-(4,6-di(naphthalen-2-yl)-1,3,5-triazin-2-yl)phenyl)quinoline Example 2 and Comparative Examples 1 and 2

Diodes of Example 2, Comparative Example 1, and Comparative Example 2 were manufactured in the same manner as in Example 1, except that the host was changed as shown in Table 2.

Examples 3 to 12 and Comparative Examples 3 to 5

Diodes of Examples 3 to 12 and Comparative Example 3 to Comparative Example 5 were manufactured in the same manner as in Example 1, except that the host was changed as shown in Table 3 and the first host and the second host were mixed in a weight ratio of 5:5.

Evaluation

Luminous efficiency and life-span characteristics of the organic light emitting diodes according to Example 1 to Example 12, Comparative Example 1 to Comparative Example 5 were evaluated. Specific measurement methods are as follows, and the results are shown in Tables 2 and 3.

(1) Measurement of Current Density Change Depending on Voltage Change

The obtained organic light emitting diodes were measured regarding a current value flowing in the unit device, while increasing the voltage from 0 V to 10 V using a current-voltage meter (Keithley 2400), and the measured current value was divided by area to provide the results.

(2) Measurement of Luminance Change Depending on Voltage Change

Luminance was measured by using a luminance meter (Minolta Cs-1000A), while the voltage of the organic light emitting diodes was increased from 0 V to 10 V.

(3) Measurement of Luminous Efficiency

Luminous efficiency (cd/A) at the same current density (10 $mA/cm^2$) were calculated by using the luminance, current density, and voltage from the items (1) and (2).

The relative values evaluated relative to the luminous efficiency of Comparative Example 1 and Comparative Example 3 are shown in Tables 2 and 3.

(4) Measurement of Life-Span

T95 life-spans of the organic light emitting diodes according to Example 1 to 12 and Comparative Example 1 to Comparative Example 5 were measured as a time when their luminance decreased down to 95% relative to the initial luminance ($cd/m^2$) after emitting light with 6,000 $cd/m^2$ as the initial luminance ($cd/m^2$) and measuring their luminance decrease depending on a time with a Polanonix life-span measurement system.

The relative values evaluated relative to the T95 life-span of Comparative Example 1 and Comparative Example 3 are shown in Tables 2 and 3.

TABLE 2

| | Single host | T95 life-span (%) | Efficiency (%) |
|---|---|---|---|
| Example 1 | Compound 1 | 160 | 115 |
| Example 2 | Compound 88 | 220 | 110 |
| Comparative Example 1 | B-1 | 100 | 100 |
| Comparative Example 2 | B-3 | 55 | 102 |

TABLE 3

| | Host | | T95 life-span (%) | Efficiency (%) |
|---|---|---|---|---|
| | First host | Second host | | |
| Example 3 | Compound 1 | A-84 | 300 | 120 |
| Example 4 | Compound 3 | A-84 | 330 | 118 |
| Example 5 | Compound 9 | A-84 | 360 | 125 |
| Example 6 | Compound 59 | A-84 | 250 | 105 |
| Example 7 | Compound 82 | A-85 | 450 | 112 |

TABLE 3-continued

| | Host | | T95 life- | Efficiency |
|---|---|---|---|---|
| | First host | Second host | span (%) | (%) |
| Example 8 | Compound 88 | A-84 | 400 | 113 |
| Example 9 | Compound 120 | A-84 | 380 | 105 |
| Example 10 | Compound 1 | Compound 2-92 | 270 | 125 |
| Example 11 | Compound 9 | Compound 2-92 | 320 | 130 |
| Example 12 | Compound 82 | Compound 2-92 | 440 | 115 |
| Comparative Example 3 | B-1 | A-84 | 100 | 100 |
| Comparative Example 4 | B-2 | A-84 | 60 | 85 |
| Comparative Example 5 | B-1 | Compound 2-92 | 85 | 110 |

Referring to Tables 2 and 3, the compound according to the present invention as a single host exhibited improved efficiency and life-span, compared with the comparative compounds, and particularly, when mixed with a second host, exhibited overall greatly improved driving voltage, efficiency, and life-span.

While this invention has been described in connection with what is presently considered to be practical embodiments, it is to be understood that the invention is not limited to the disclosed embodiments, but, on the contrary, is intended to cover various modifications and equivalent arrangements included within the spirit and scope of the appended claims.

The invention claimed is:

1. A composition for an organic optoelectronic device, comprising:

a first compound, and a second compound, wherein:

the first compound is represented by Chemical Formula 1; and the second compound is represented by Chemical Formula 2:

[Chemical Formula 1]

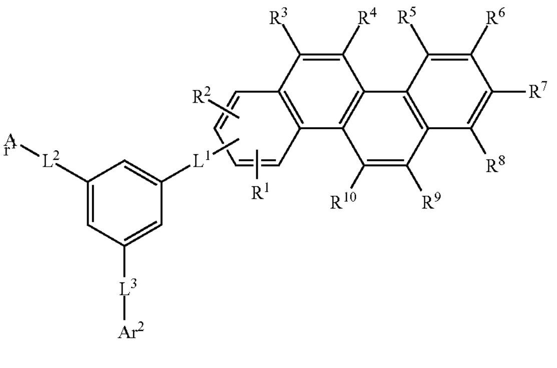

in Chemical Formula 1, $L^1$ to $L^3$ are each independently a single bond, or a substituted or unsubstituted C6 to C30 arylene group, $Ar^1$ and $Ar^2$ are each independently a substituted or unsubstituted C6 to C30 aryl group or a substituted or unsubstituted C2 to C30 heterocyclic group, and $R^1$ to $R^{10}$ are each independently hydrogen, deuterium, a substituted or unsubstituted C1 to C20 alkyl group, or a substituted or unsubstituted C6 to C20 aryl group, and

[Chemical Formula 2]

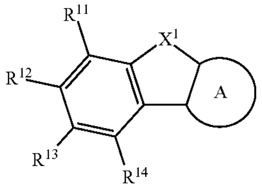

in Chemical Formula 2, $X^1$ is O, S, $NR^a$, $CR^bR^c$, or $SiR^dR^e$, $R^a$, $R^b$, $R^c$, $R^d$, $R^e$, and $R^{11}$ to $R^{14}$ are each independently hydrogen, deuterium, a substituted or unsubstituted amine group, a substituted or unsubstituted C1 to C30 alkyl group, a substituted or unsubstituted C6 to C30 aryl group, or a substituted or unsubstituted C2 to C30 heterocyclic group, and A is any one selected from the rings of Group II and Group III,

[Group II]

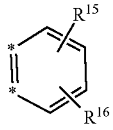

[Group III]

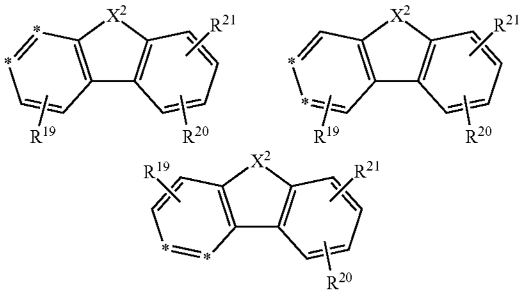

wherein, in Group II and Group III,

* is a linking point, $X^2$ is O, S, $NR^f$, $CR^gR^h$, or $SiR^iR^j$, $R^f$, $R^g$, $R^h$, $R^i$, $R^j$, $R^{15}$, $R^{16}$, and $R^{19}$ to $R^{21}$ are each independently hydrogen, deuterium, a substituted or unsubstituted amine group, a substituted or unsubstituted C1 to C30 alkyl group, a substituted or unsubstituted C6 to C30 aryl group or a substituted or unsubstituted C2 to C30 heterocyclic group, and at least one of $R^{11}$ to $R^{14}$, $R^{15}$, $R^{16}$, and $R^{19}$ to $R^{21}$ is a group represented by Chemical Formula a,

[Chemical Formula a]

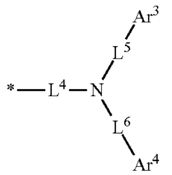

wherein, in Chemical Formula a, $L^4$ to $L^6$ are each independently a single bond, or a substituted or unsubstituted C6 to C30 arylene group, $Ar^3$ and $Ar^4$ are each independently a substituted or unsubstituted amine group, a substituted or unsubstituted C6 to C30 aryl group, or a substituted or unsubstituted C2 to C30 heterocyclic group, and

* is a linking point.

2. The compound composition of claim 1, wherein:

Chemical Formula 1 is represented by one of Chemical Formula 1-1, Chemical Formula 1-2, or Chemical Formula 1-4:

[Chemical Formula 1-1]

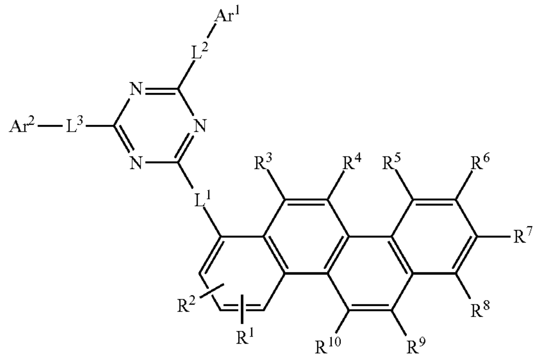

[Chemical Formula 1-2]

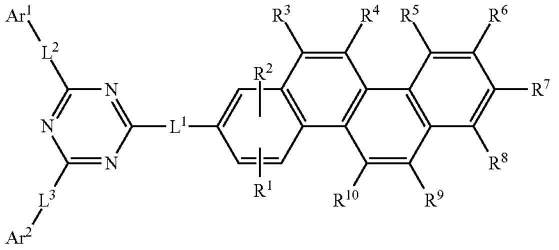

[Chemical Formula 1-4]

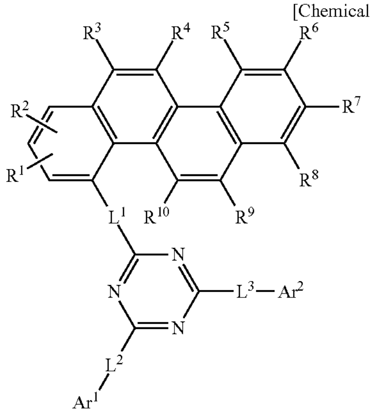

in Chemical Formula 1-1 to Chemical Formula 1-4, $L^1$ to $L^3$, $Ar^1$ and $Ar^2$ and $R^1$ to $R^{10}$ are the same as in claim 1.

3. The compound composition of claim 1, wherein at least one of $Ar^1$ and $Ar^2$ is a substituted or unsubstituted C10 to C30 aryl group, a substituted or unsubstituted dibenzofuranyl group, or a substituted or unsubstituted dibenzothiophenyl group.

4. The compound composition of claim 1, wherein:

$L^1$ is a single bond, $Ar^1$ and $Ar^2$ are each independently a substituted or unsubstituted phenyl group, a substituted or unsubstituted naphthyl group, a substituted or unsubstituted phenanthrenyl group, a substituted or unsubstituted biphenyl group, a substituted or unsubstituted dibenzofuranyl group or a substituted or unsubstituted dibenzothiophenyl group, and at least one of $Ar^1$ and $Ar^2$ is a substituted or unsubstituted naphthyl group, a substituted or unsubstituted phenanthrenyl group, a substituted or unsubstituted biphenyl group, a substituted or unsubstituted dibenzofuranyl group, or a substituted or unsubstituted dibenzothiophenyl group.

5. The compound composition of claim 1, wherein;

$L^1$ is a substituted or unsubstituted phenylene group, and $Ar^1$ and $Ar^2$ are each independently a substituted or unsubstituted phenyl group, a substituted or unsubstituted naphthyl group, a substituted or unsubstituted phenanthrenyl group, a substituted or unsubstituted biphenyl group, a substituted or unsubstituted dibenzofuranyl group, or a substituted or unsubstituted dibenzothiophenyl group.

6. The composition of claim 1, wherein *-$L^2$-$Ar^1$ and *-$L^3$-$Ar^2$ are each independently selected from the substituents of Group I:

[Group I]

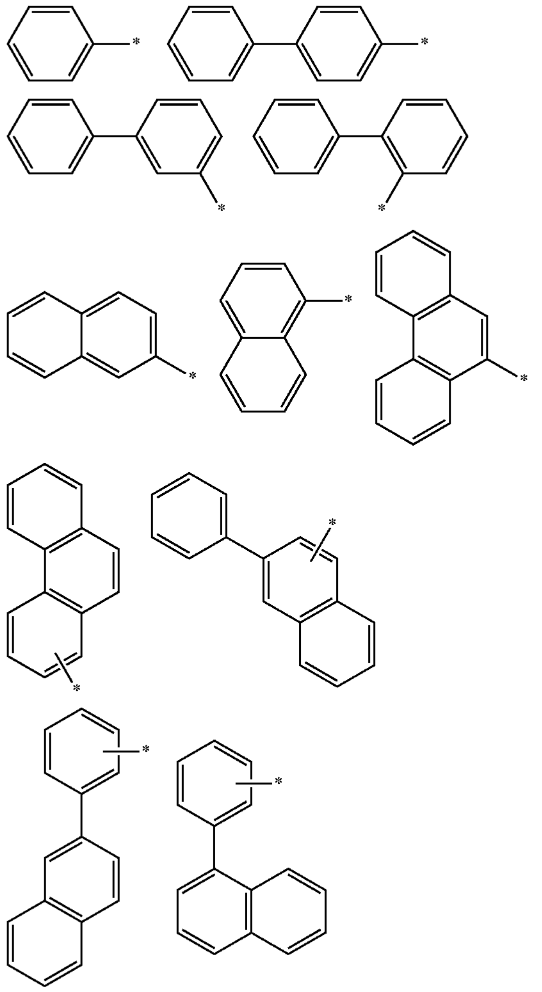

-continued
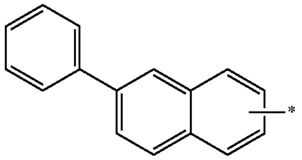
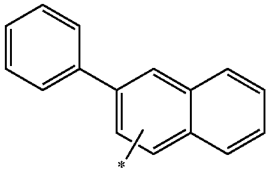
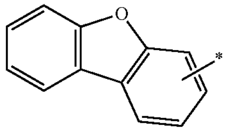
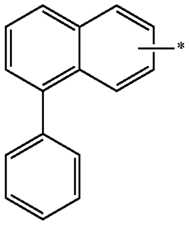
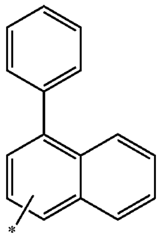
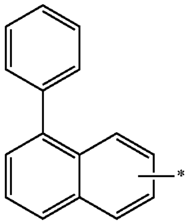
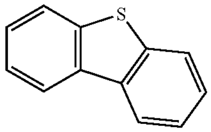
wherein, in Group I, * is a linking point.
7. The composition of claim 1, wherein the first compound is a compound of Group 1:
[Group 1]
[1]
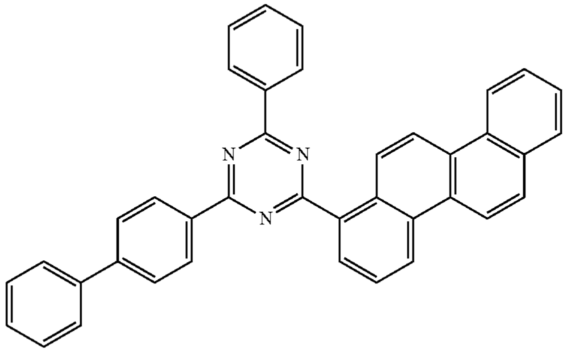
-continued
[2]
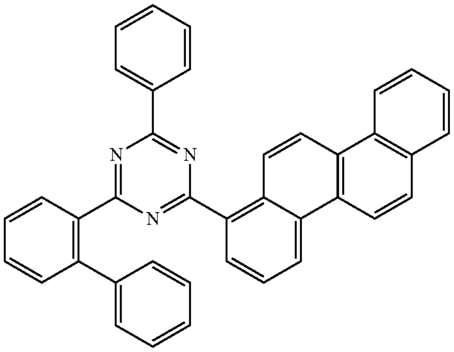
[3]
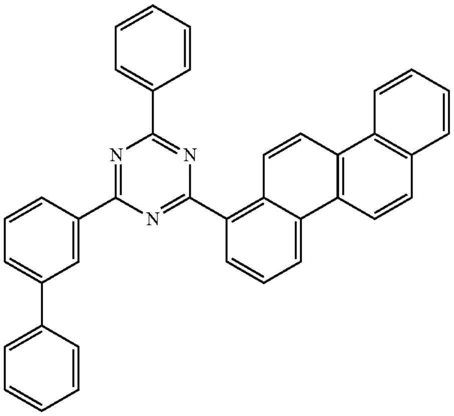
[4]
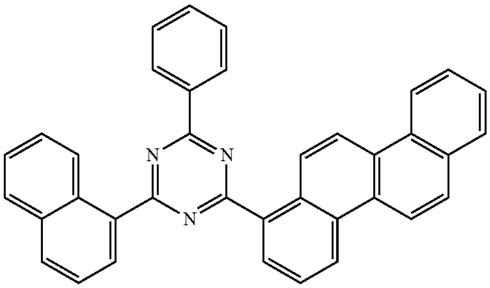
[5]
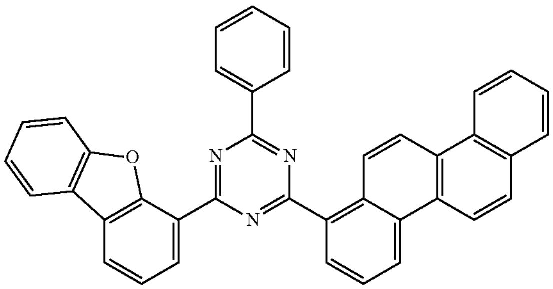

-continued
[6]
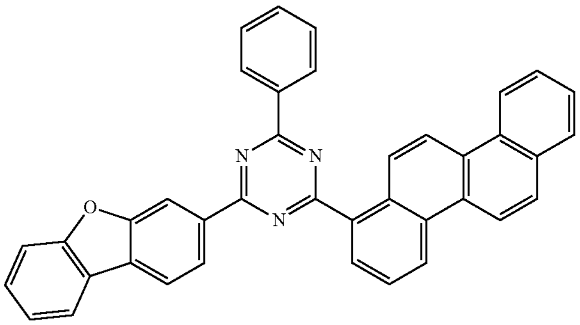
[7]
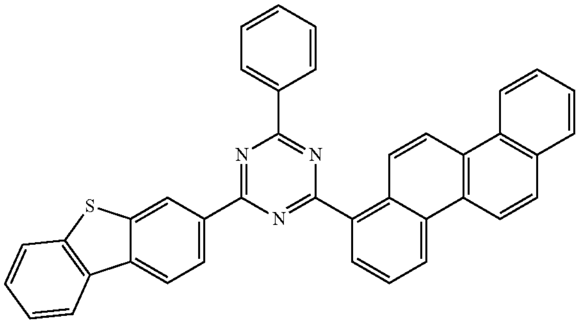
[8]
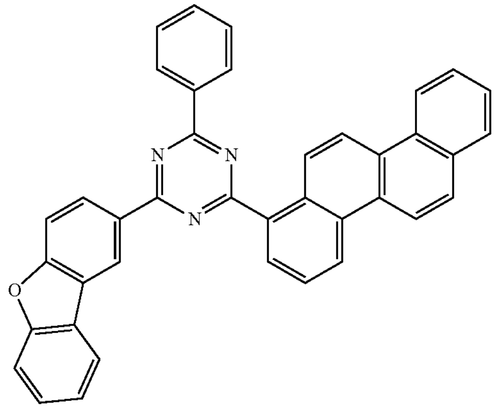
[9]
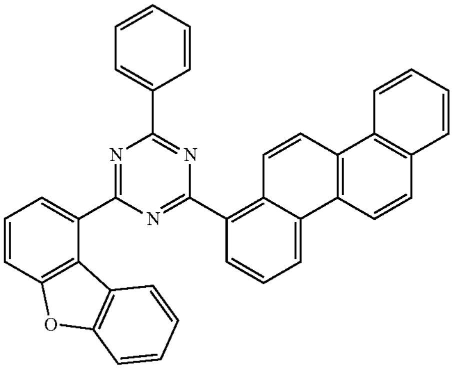
-continued
[10]
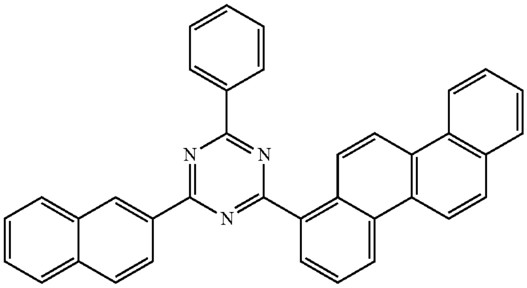
[11]
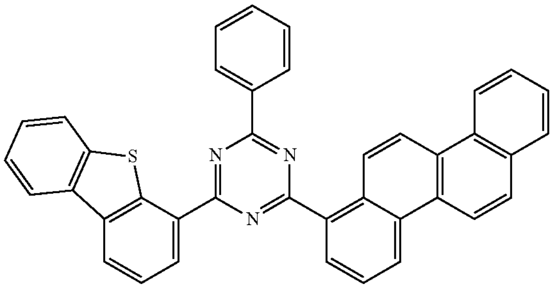
[12]
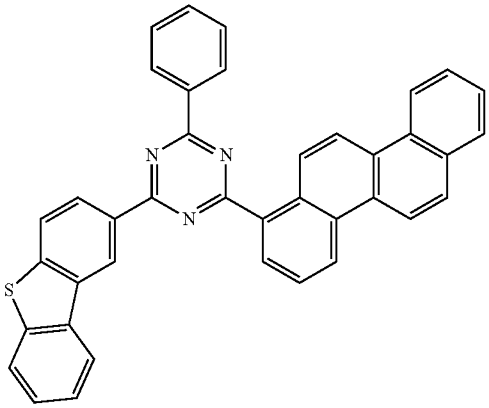
[13]
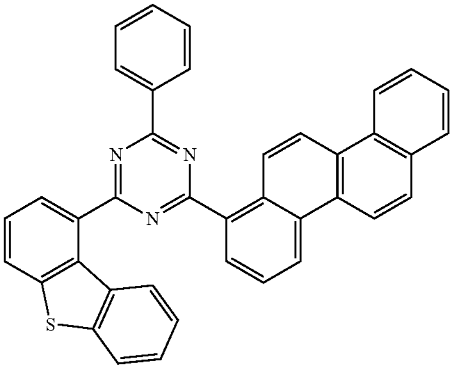

-continued
[14]
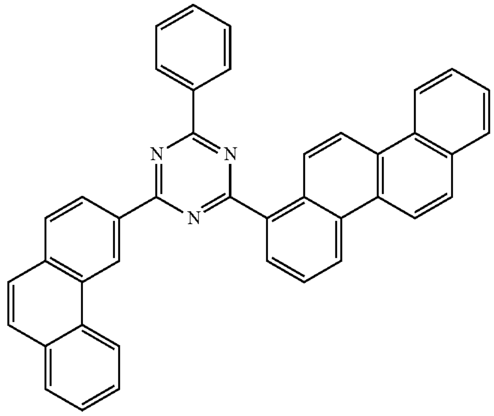
[15]
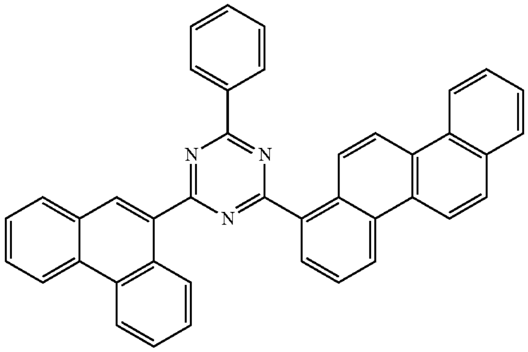
[16]
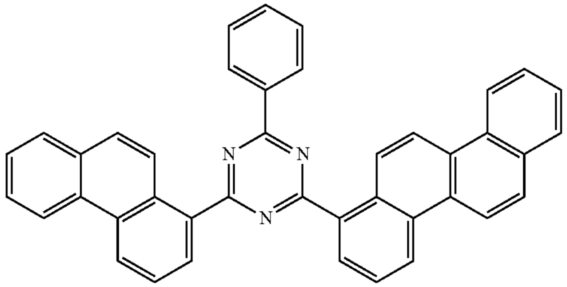
[17]
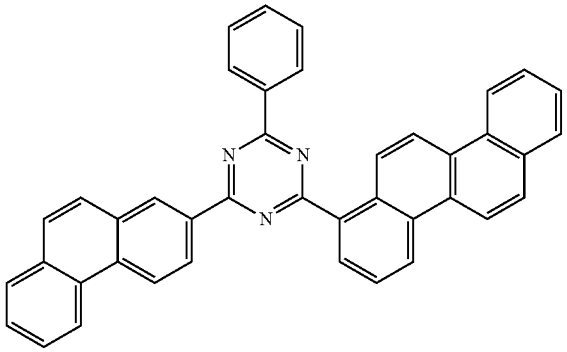
-continued
[18]
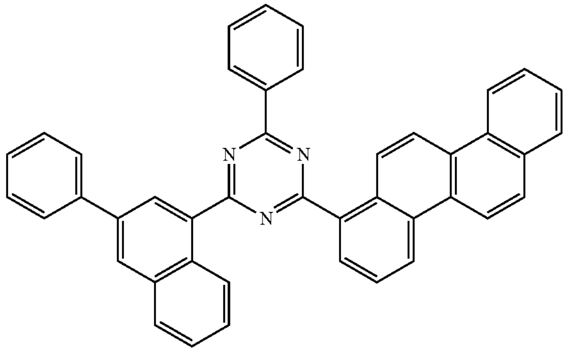
[19]
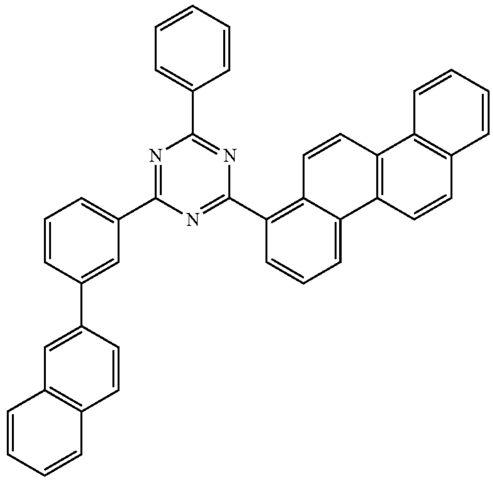
[20]
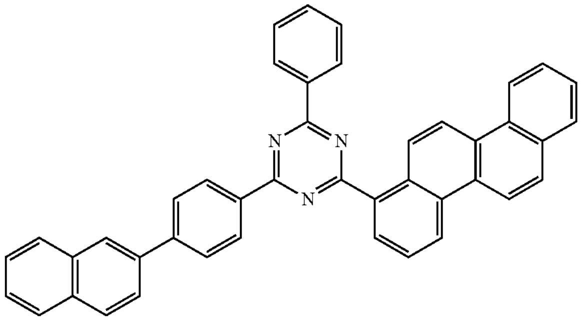
[21]
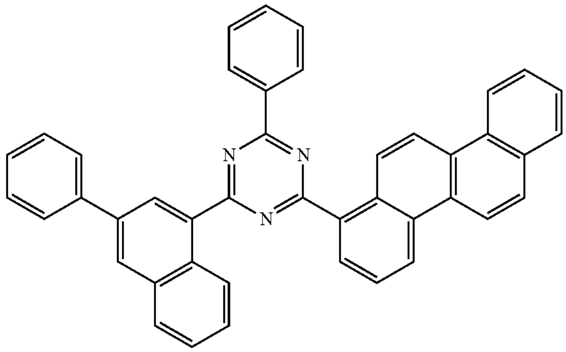

-continued
[22]
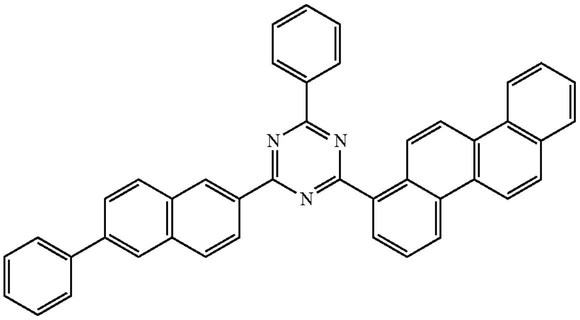
[23]
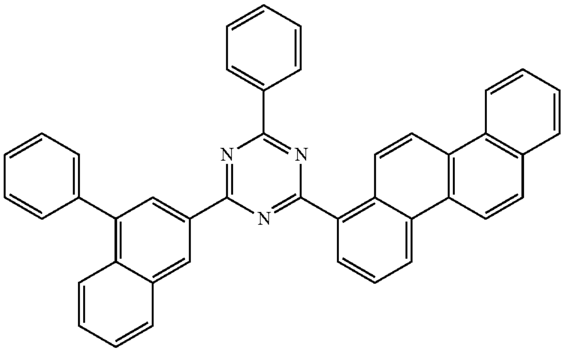
[24]
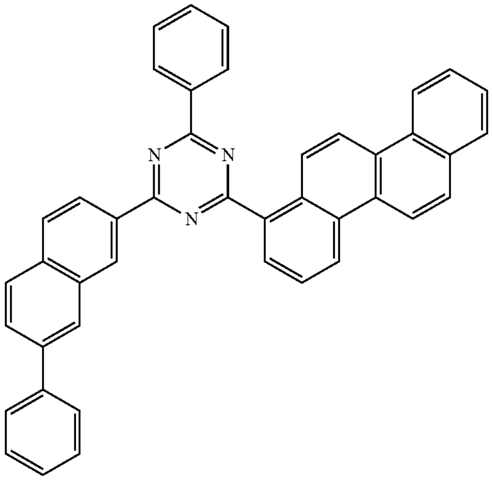
[25]
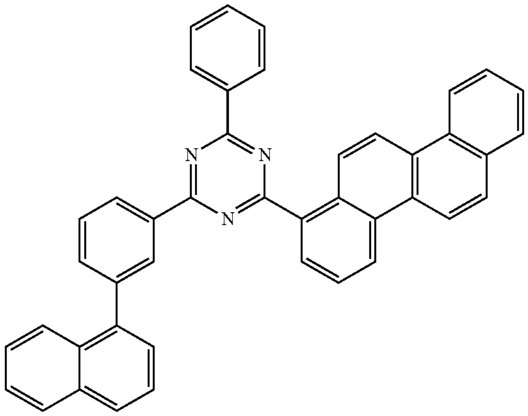
-continued
[26]
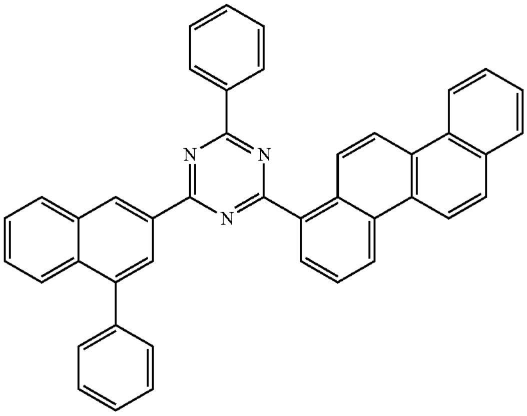
[27]
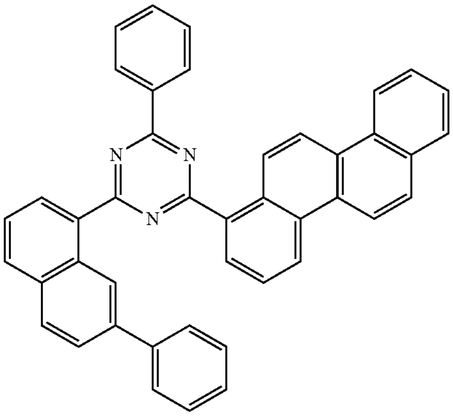
[28]
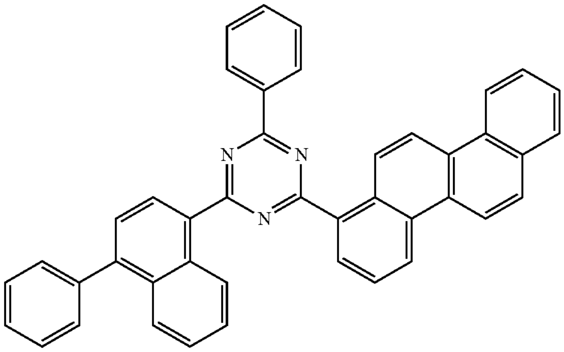
[29]
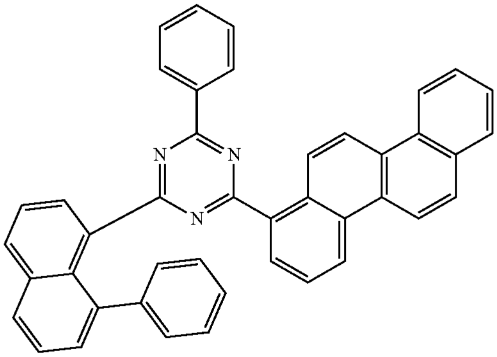

-continued
[30]
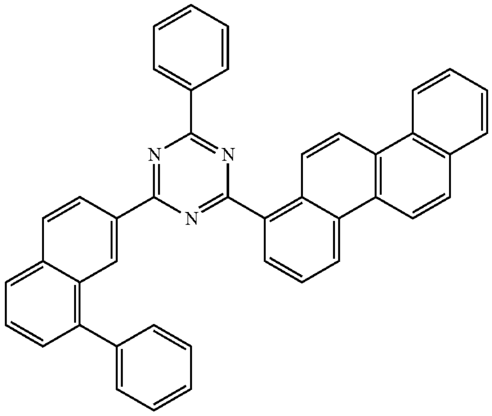
[31]
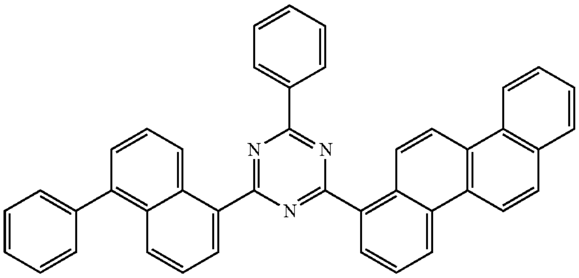
[32]
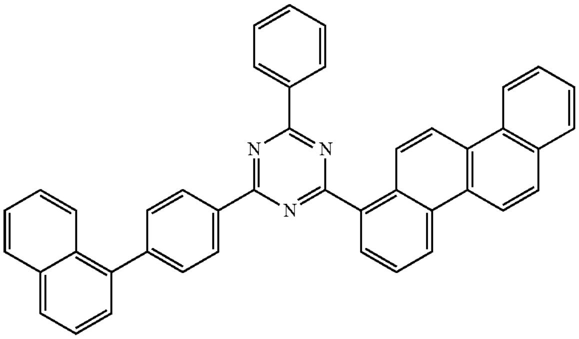
[33]
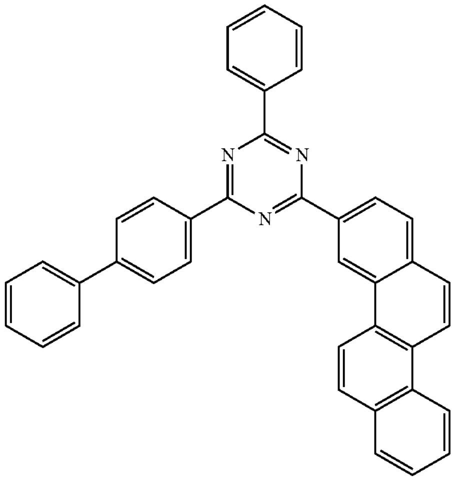
-continued
[34]
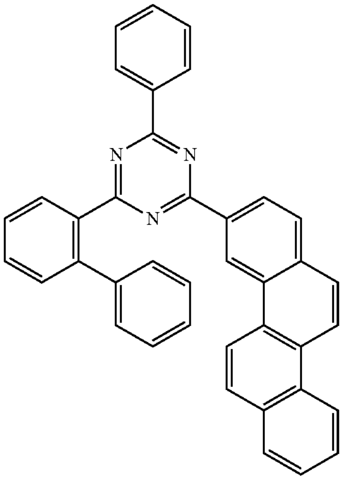
[35]
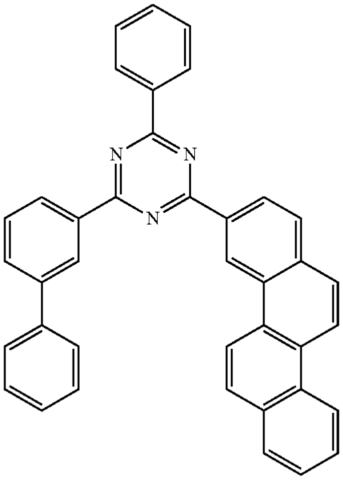
[36]
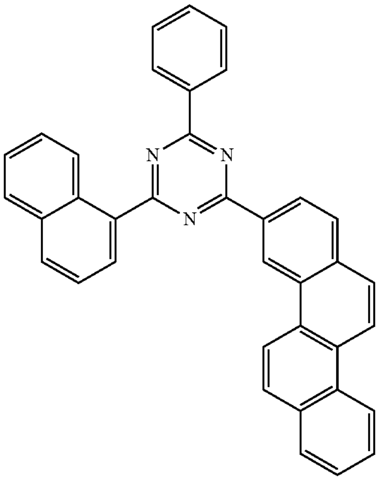

-continued
[37]
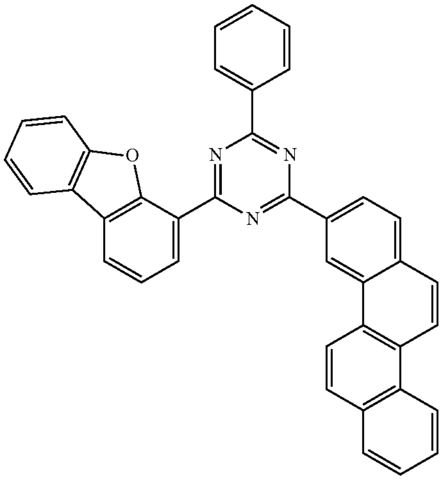
[38]
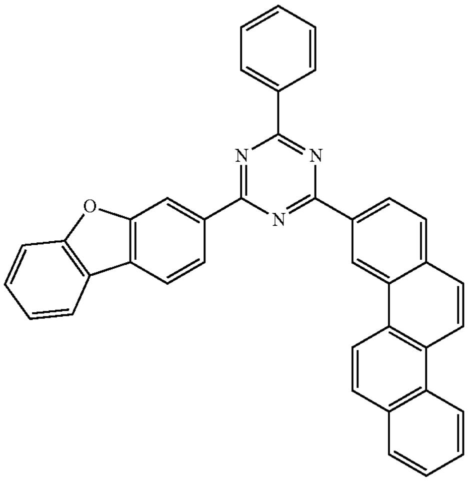
[39]
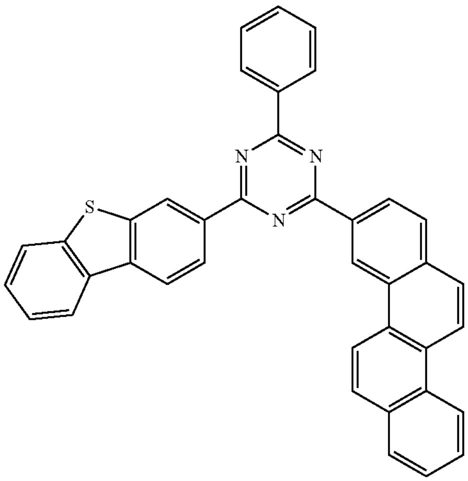
-continued
[40]
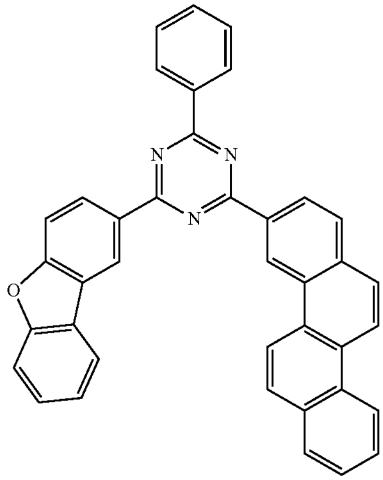
[41]
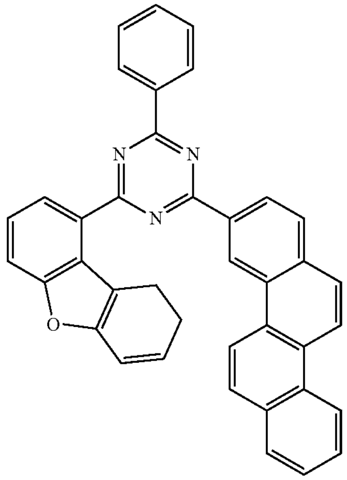
[42]
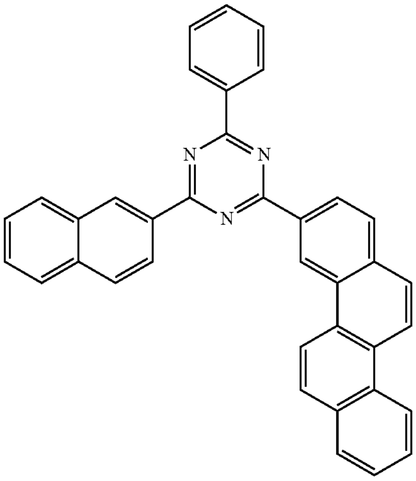

-continued
[43]
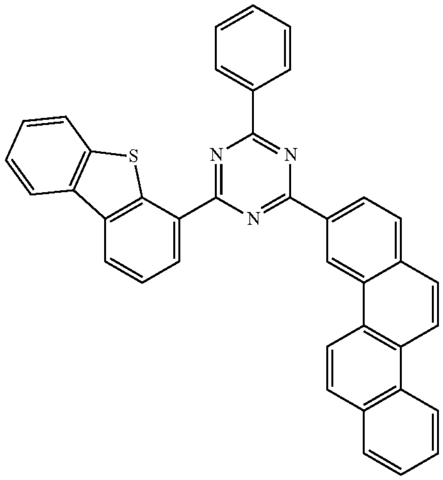
[44]
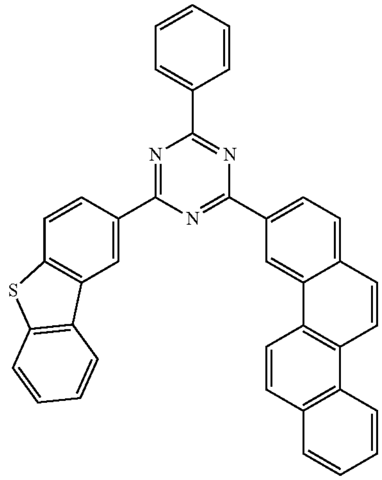
[45]
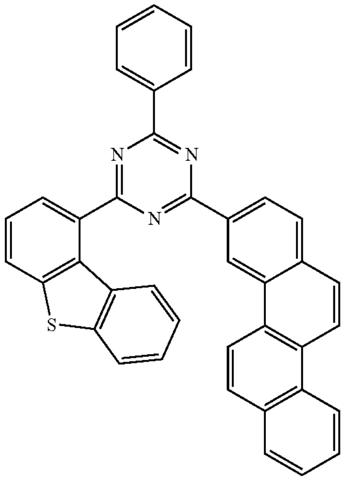
-continued
[46]
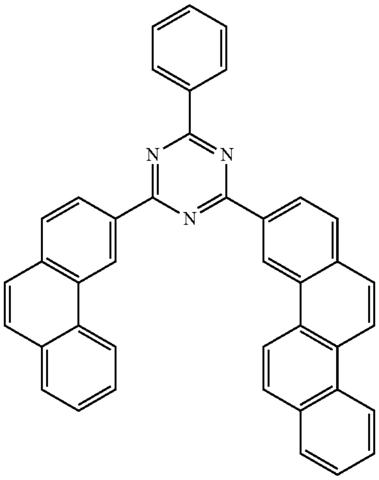
[47]
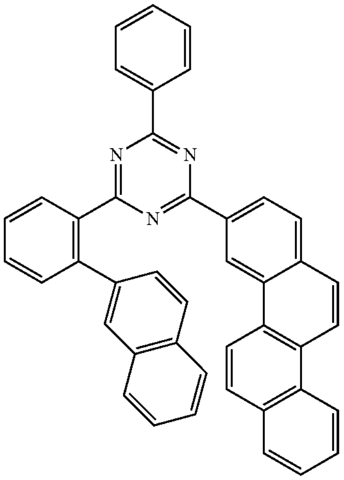
[48]
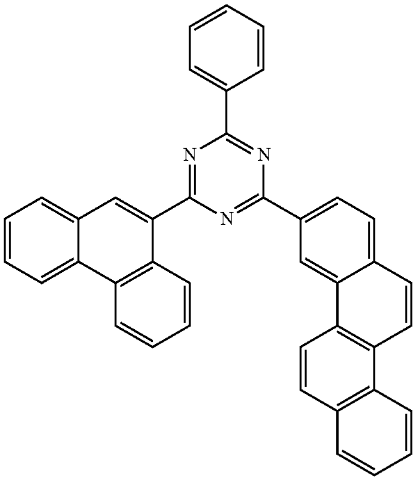

-continued
[49]
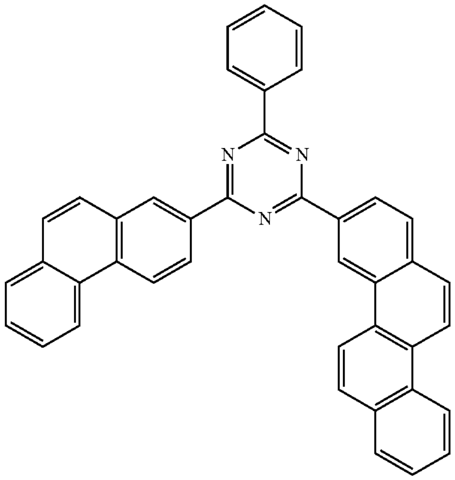
[50]
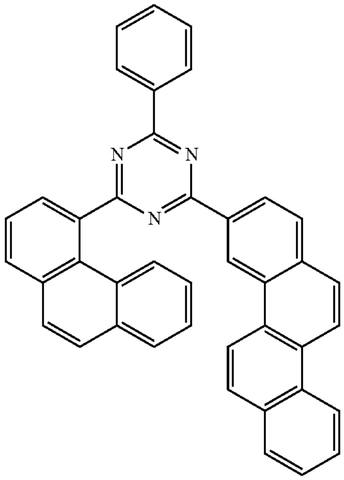
[51]
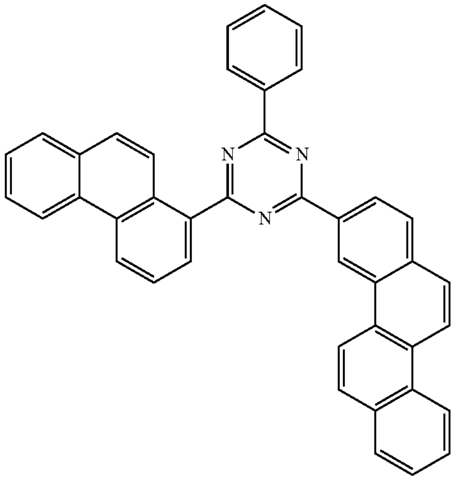
-continued
[52]
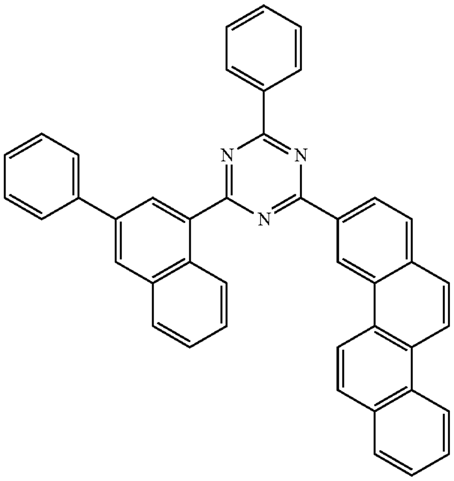
[53]
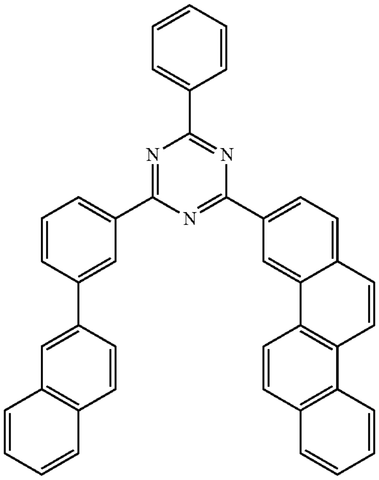
[54]
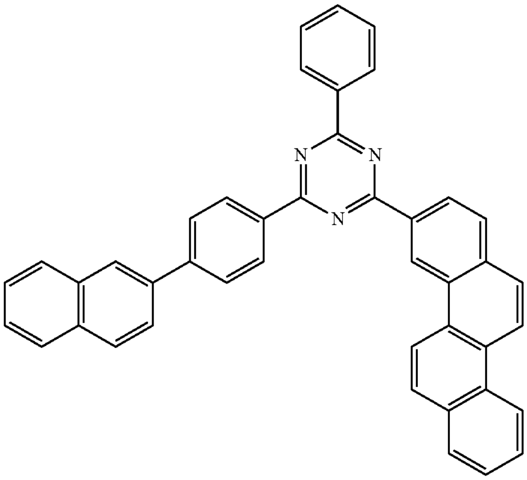

-continued
[55]
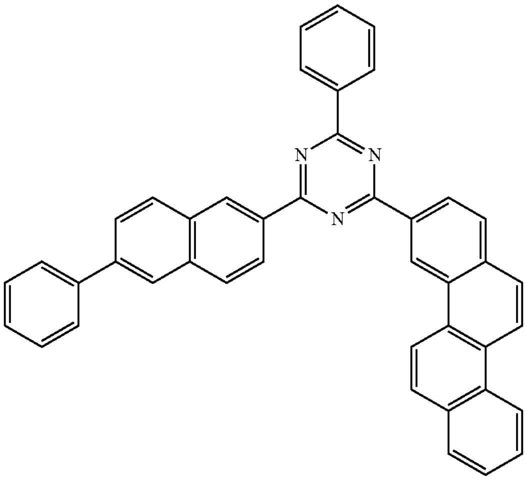
[56]
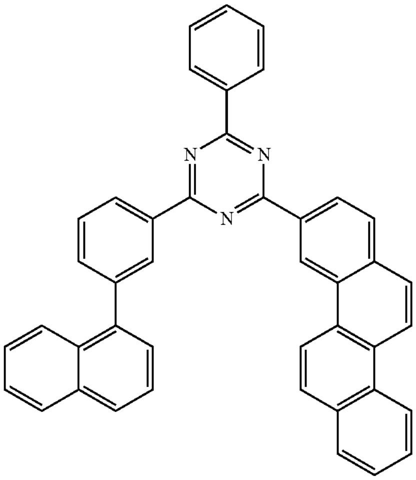
[57]
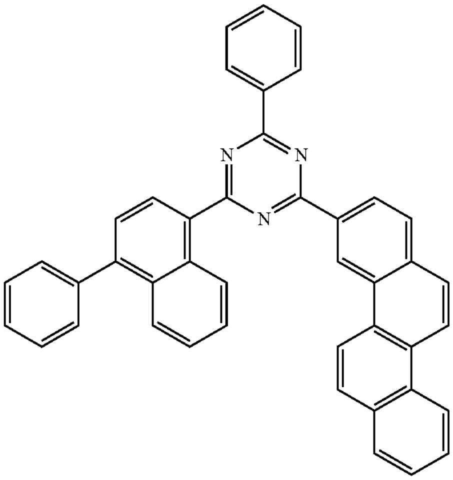
-continued
[58]
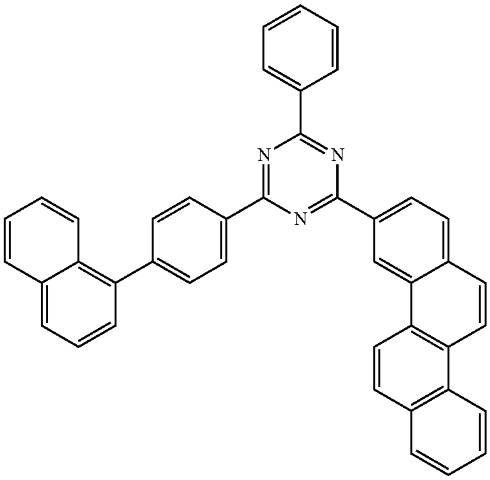
[59]
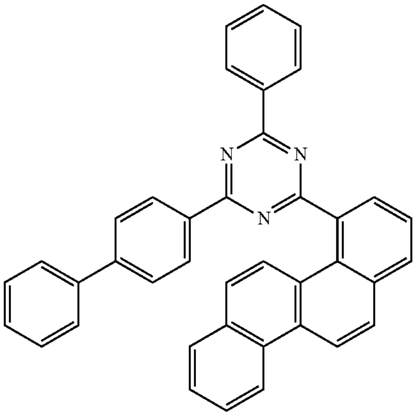
[60]
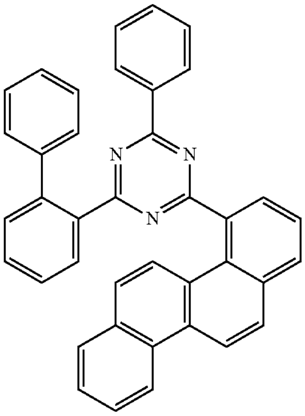

-continued
[61]
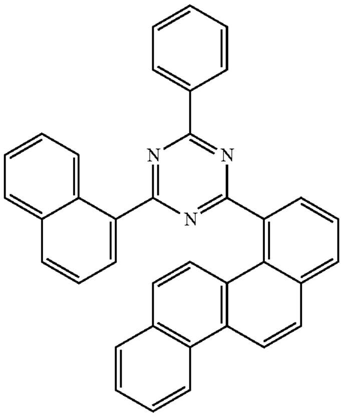
[62]
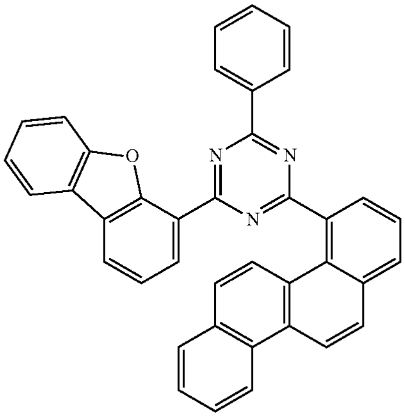
[63]
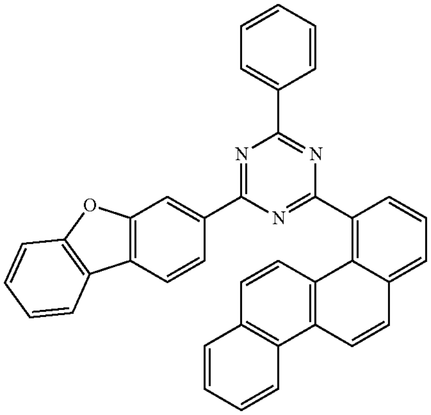
-continued
[64]
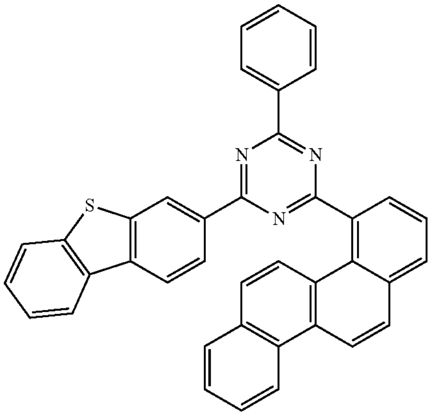
[65]
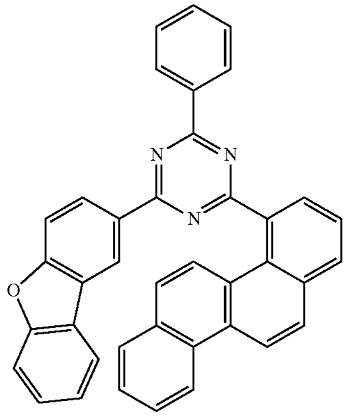
[66]
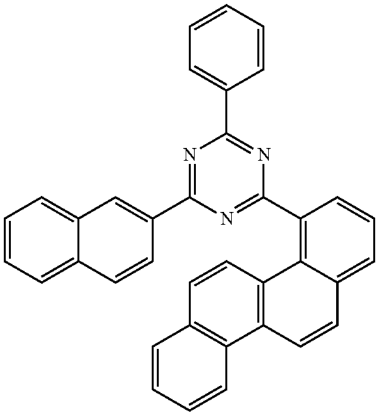

-continued
[67]
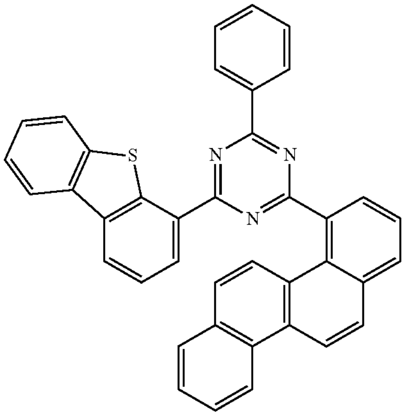
[68]
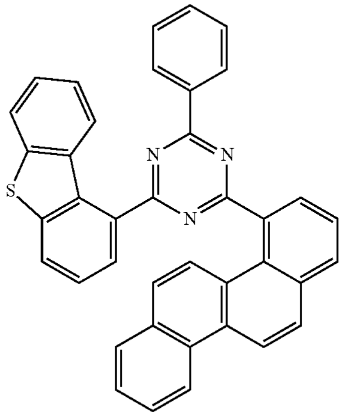
[69]
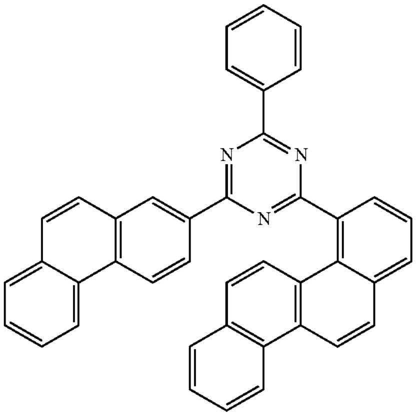
-continued
[70]
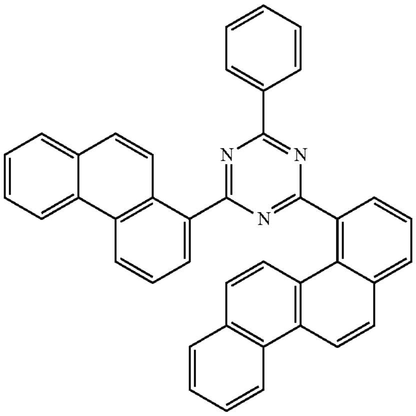
[71]
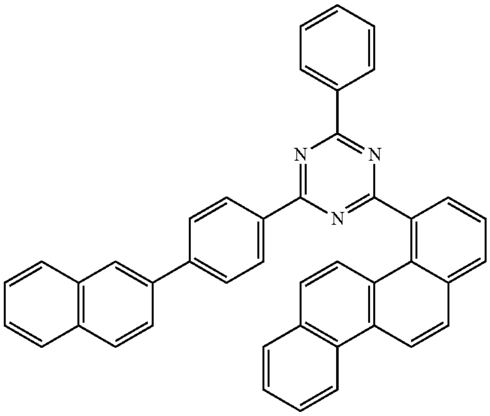
[72]
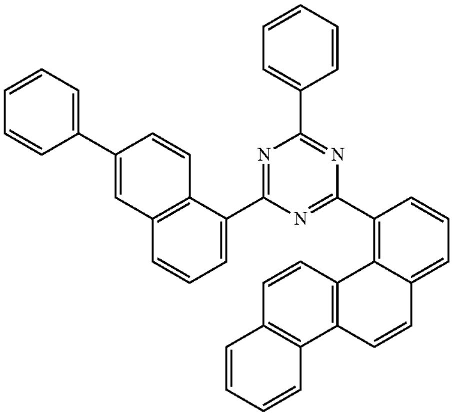

-continued
[73]
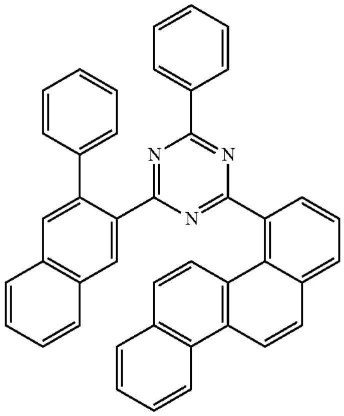
[74]
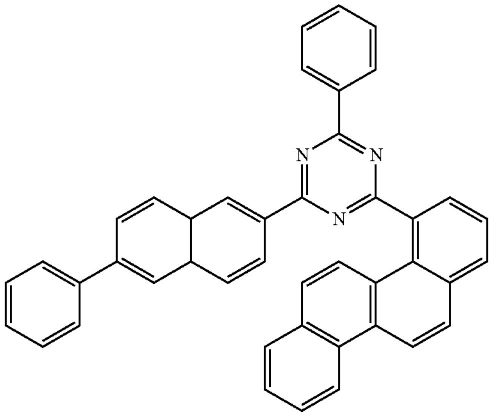
[75]
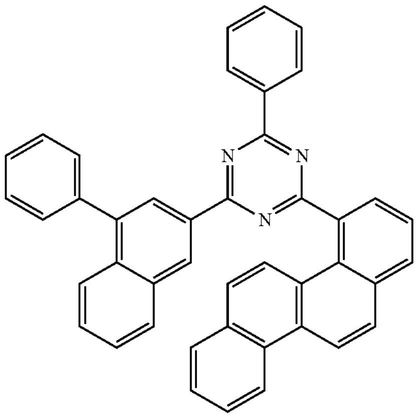
-continued
[76]
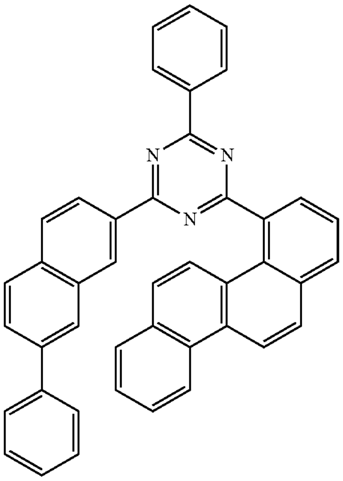
[77]
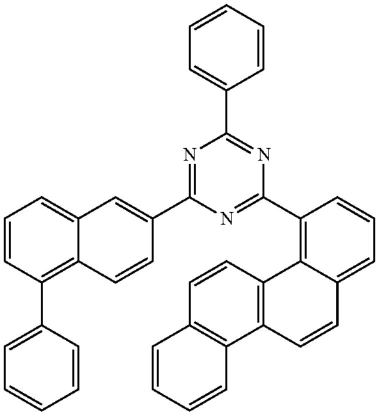
[78]
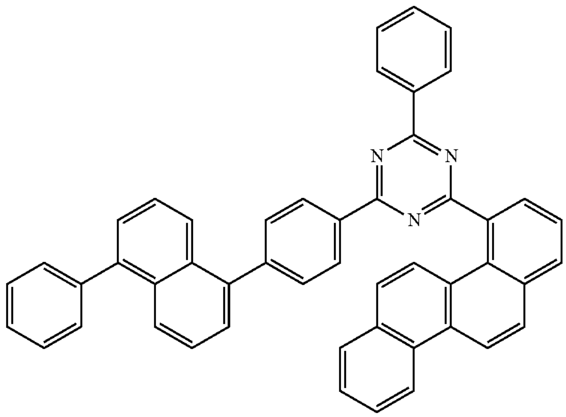

-continued
[79]
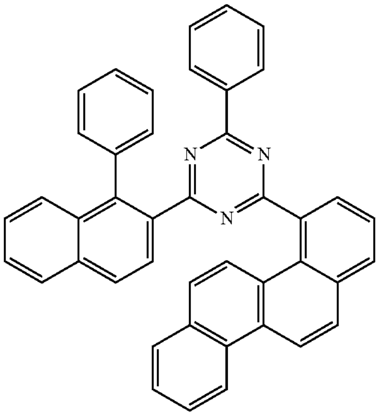
[80]
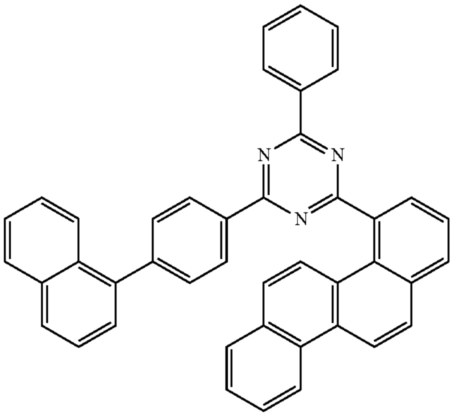
[81]
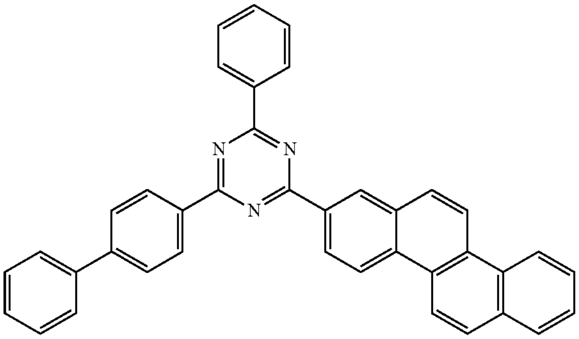
[82]
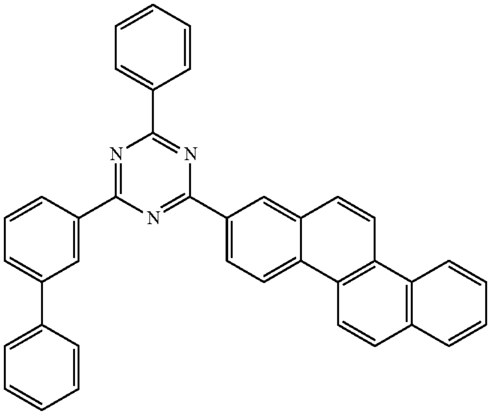
-continued
[83]
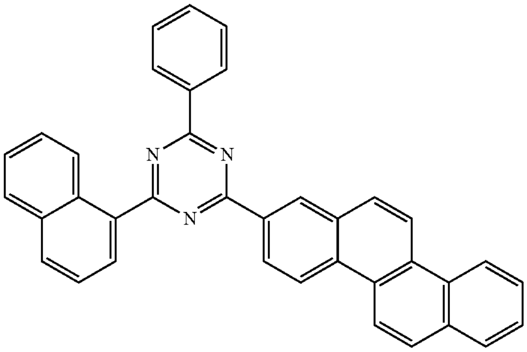
[84]
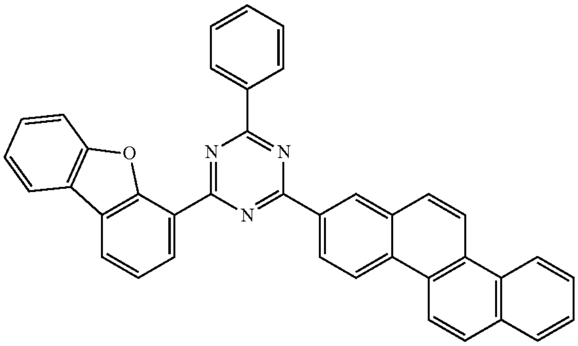
[85]
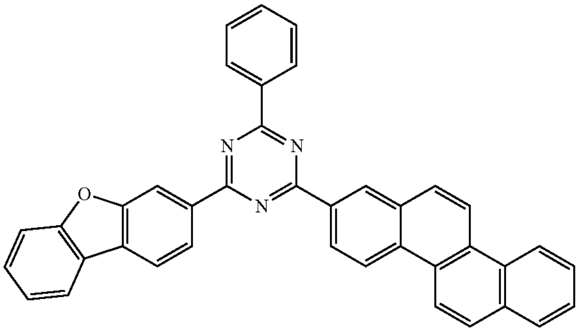
[86]
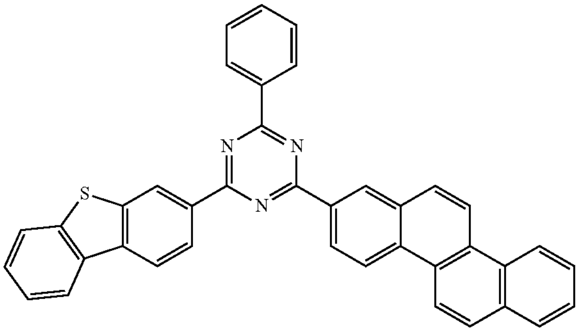

-continued
[87]
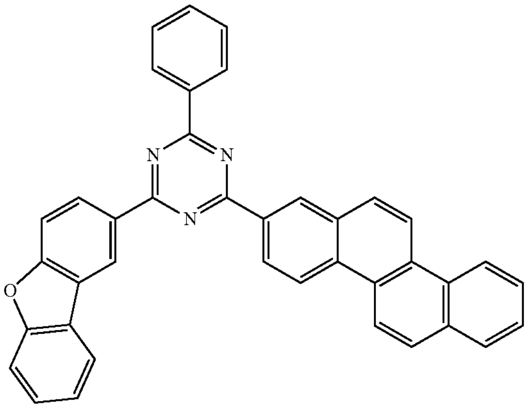
[88]
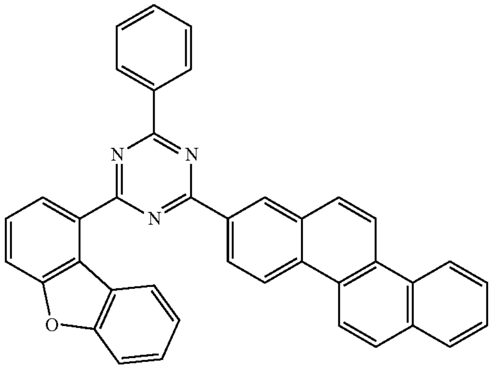
[89]
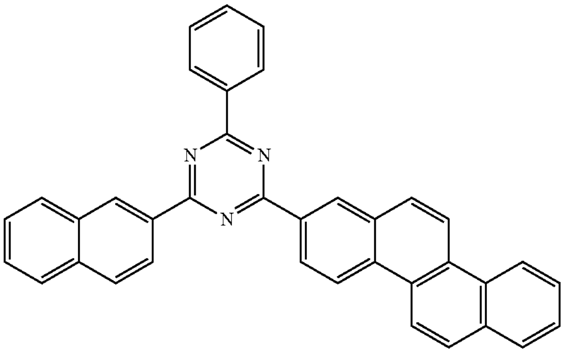
[90]
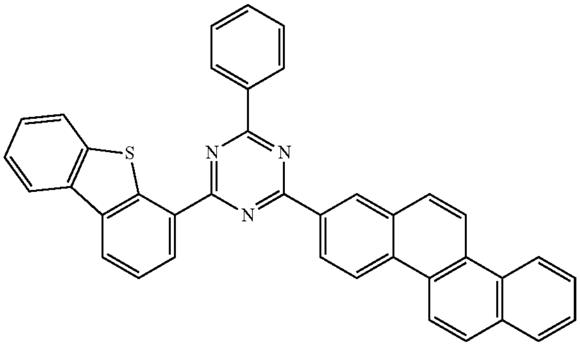
-continued
[91]
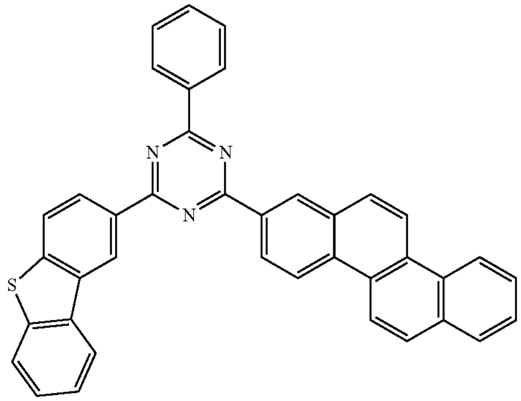
[92]
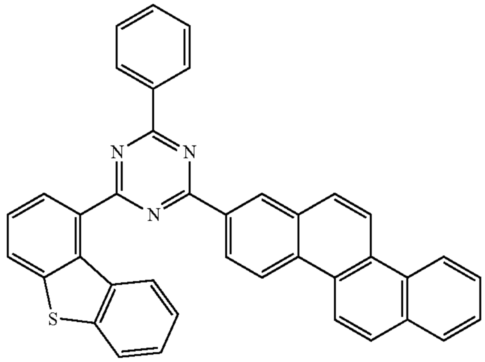
[93]
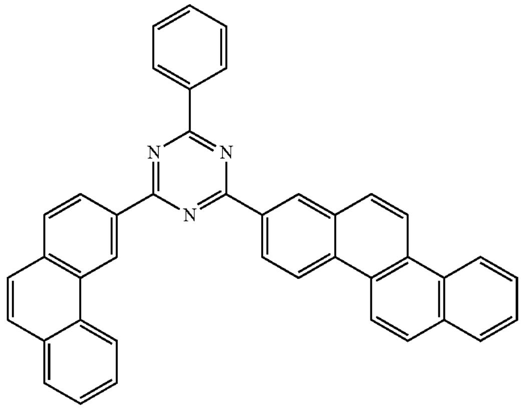
[94]
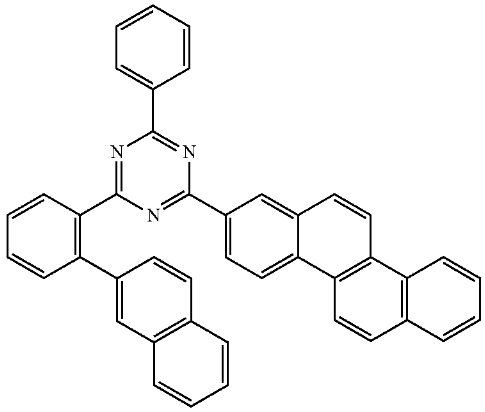

-continued
[95]
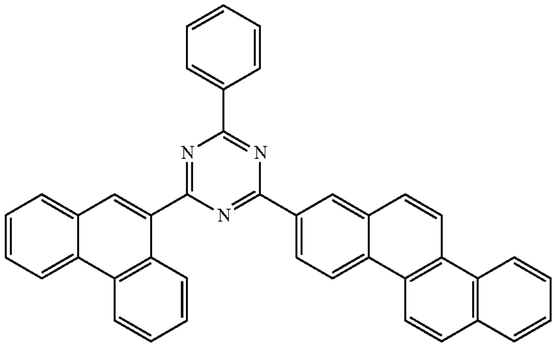
[96]
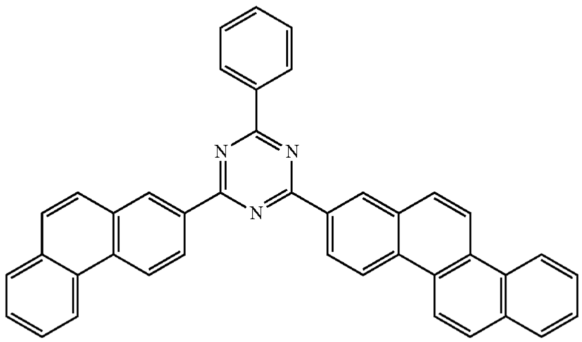
[97]
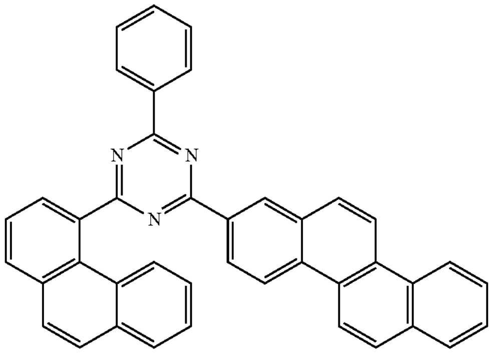
[98]
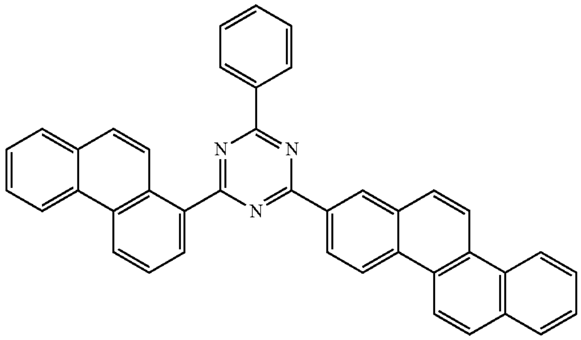
-continued
[99]
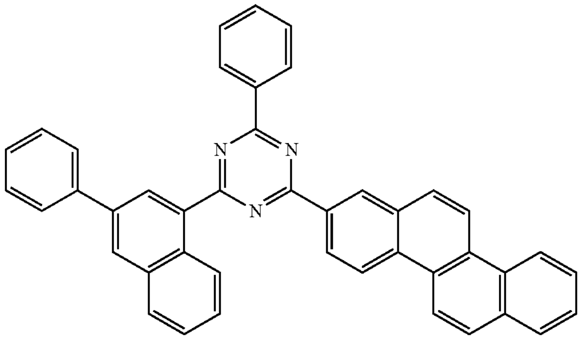
[100]
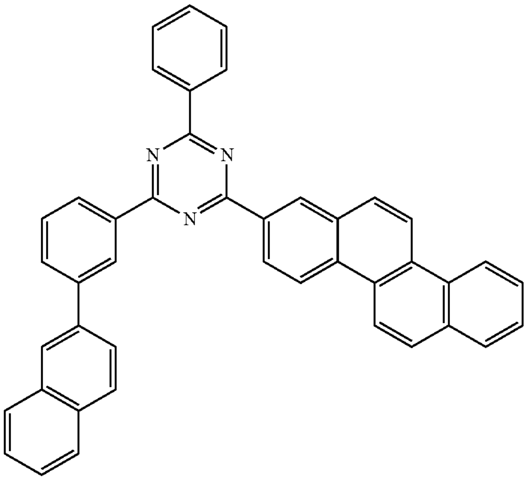
[101]
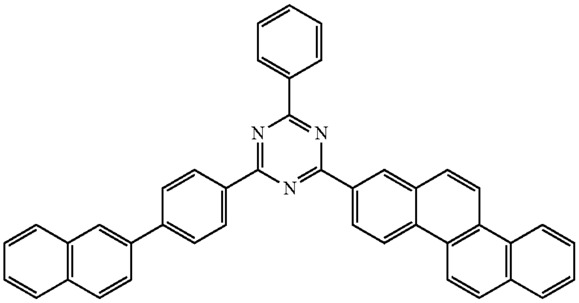
[102]
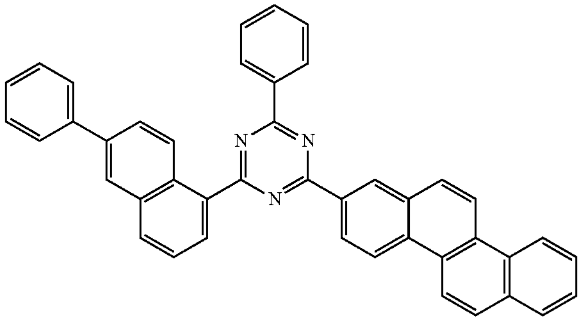

-continued
[103]
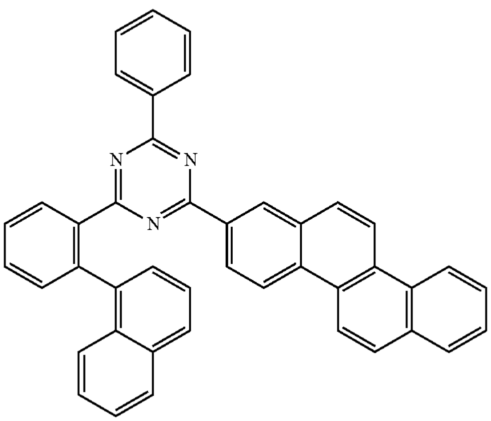
[104]
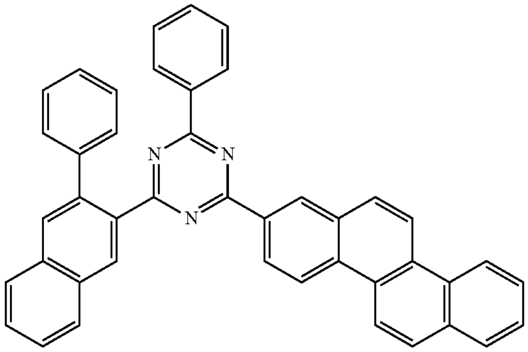
[105]
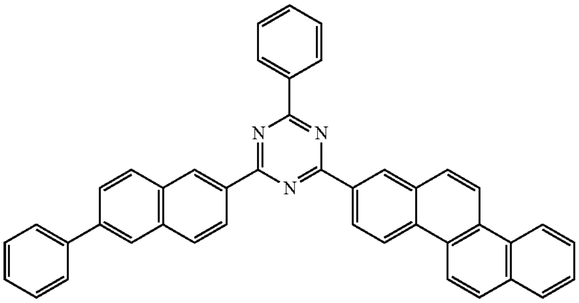
[106]
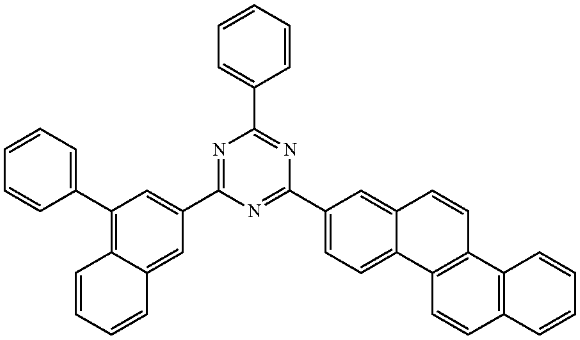
-continued
[107]
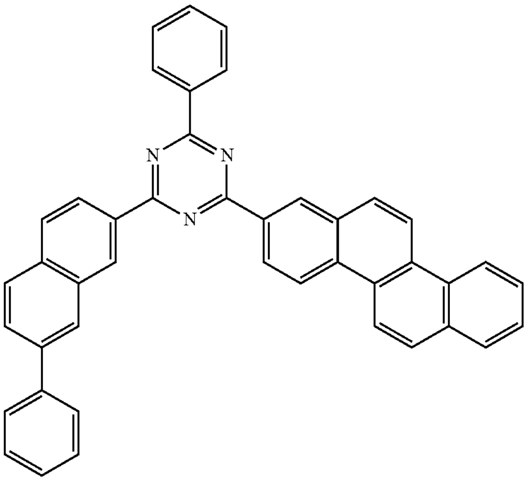
[108]
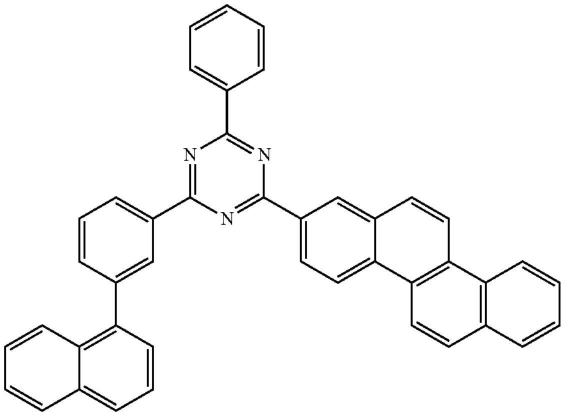
[109]
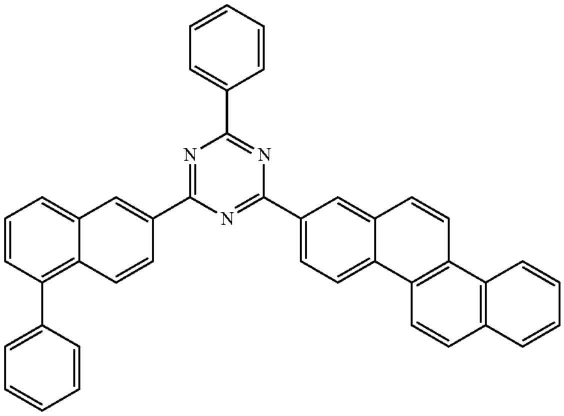

-continued
[110]
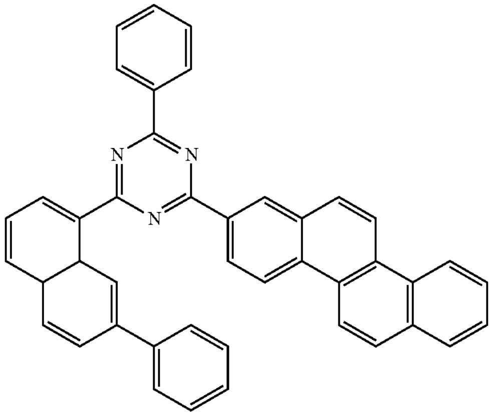
[111]
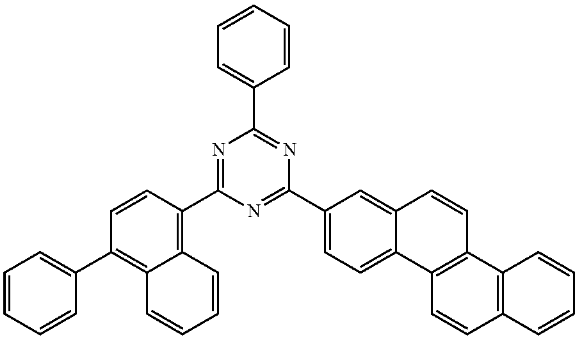
[112]
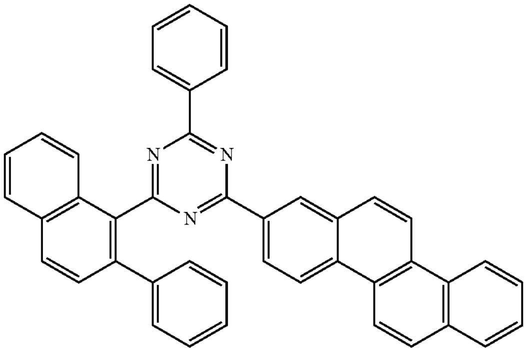
[113]
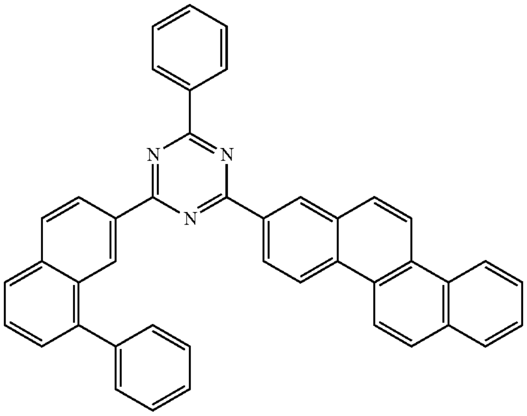
-continued
[114]
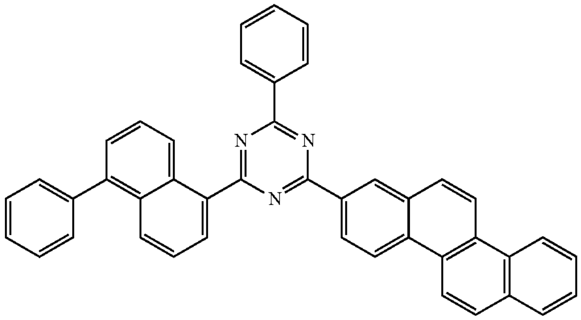
[115]
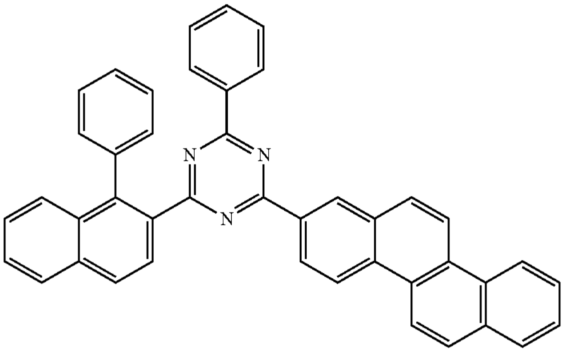
[116]
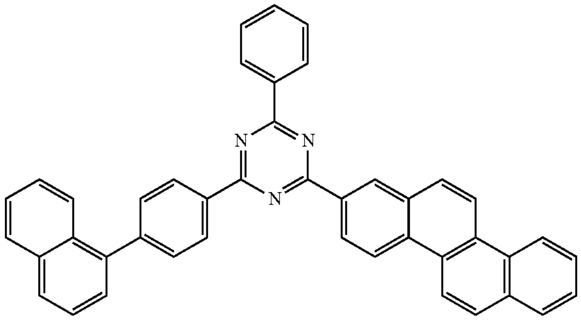
[117]
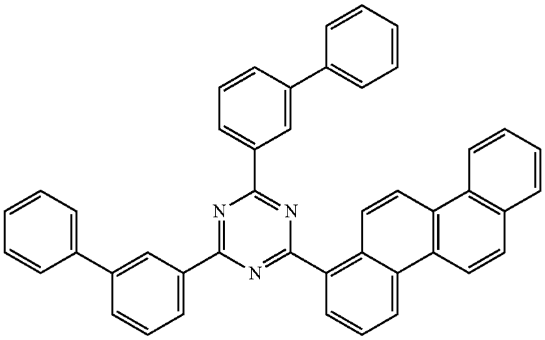

-continued
[118]
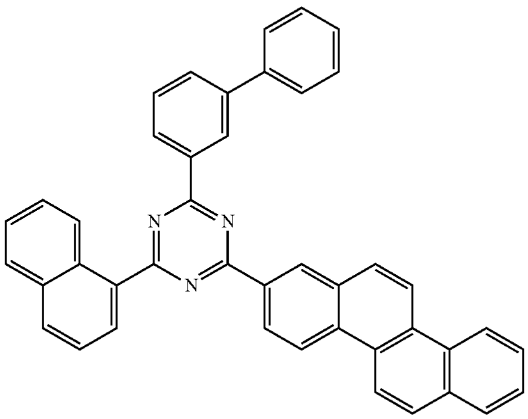
[119]
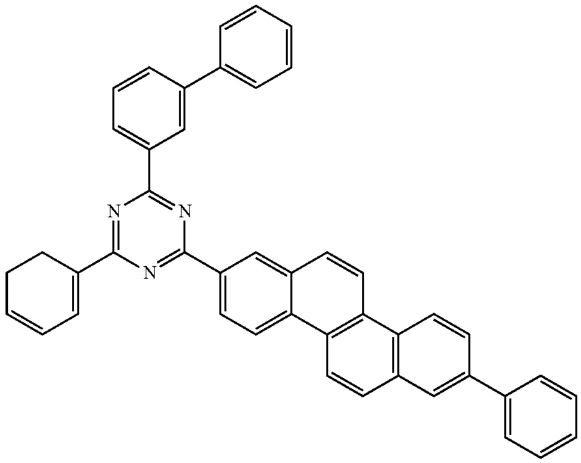
[120]
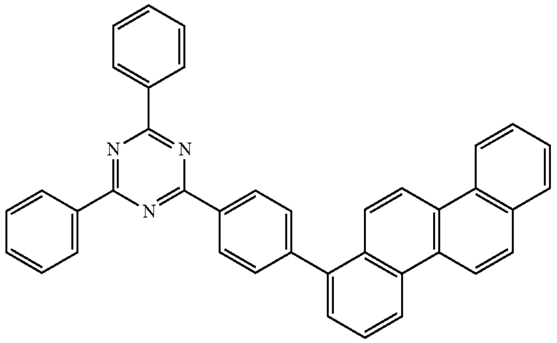
[121]
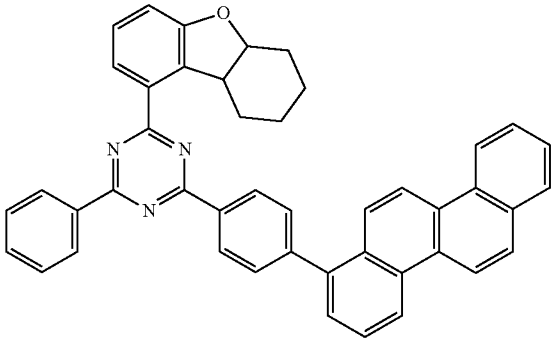
-continued
[122]
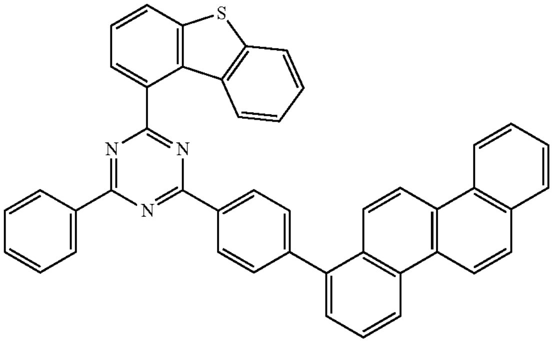
[123]
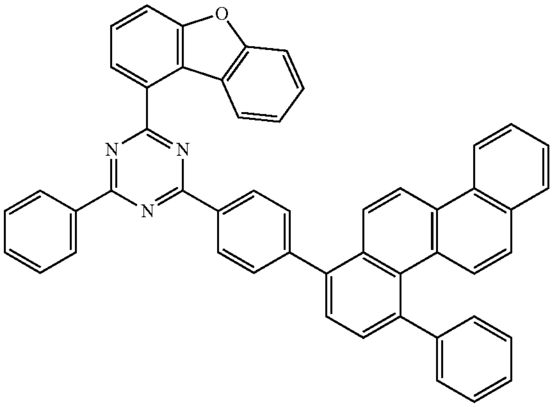
[124]
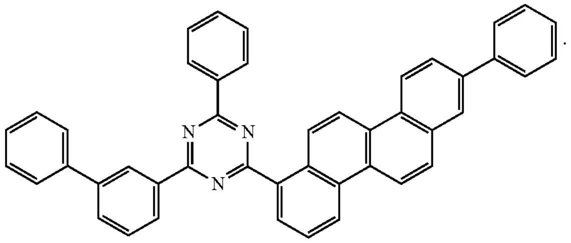
8. The composition of claim 1, wherein;
Chemical Formula 2 is represented by one of Chemical Formula 2-I and Chemical Formula 2-V to Chemical Formula 2-IX:
[Chemical Formula 2-I]
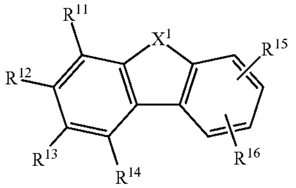

-continued

[Chemical Formula 2-V]

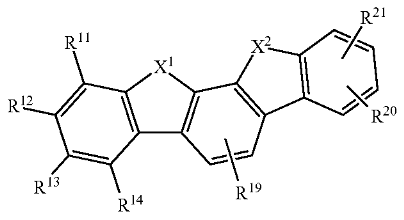

[Chemical Formula 2-VI]

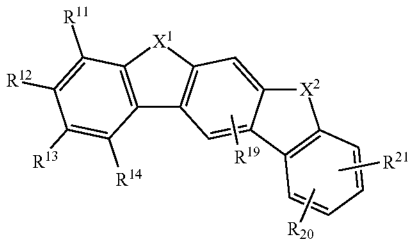

[Chemical Formula 2-VII]

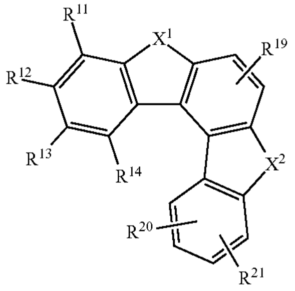

[Chemical Formula 2-VIII]

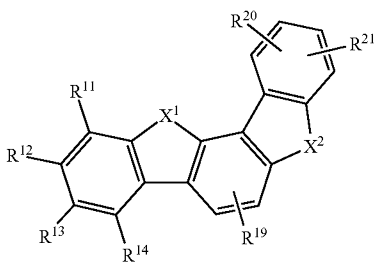

[Chemical Formula 2-IX]

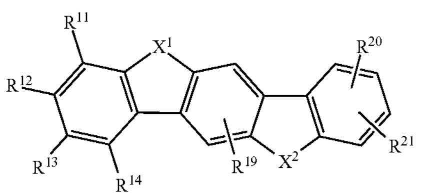

in Chemical Formula 2-I and Chemical Formula 2-V to Chemical Formula 2-IX, $X^1$, $X^2$, $R^{11}$ to $R^{16}$, and $R^{19}$ to $R^{21}$ are the same as in claim 1.

9. The composition of claim 1, wherein:

the second compound is represented by any one of Chemical Formula 2-IA, Chemical Formula 2-VA to Chemical Formula 2-IXA, Chemical Formula 2-IB, and Chemical Formula 2-VB to Chemical Formula 2-IXB

[Chemical Formula 2-IA]

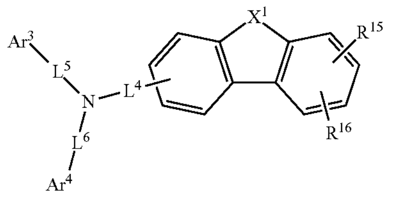

[Chemical Formula 2-VA]

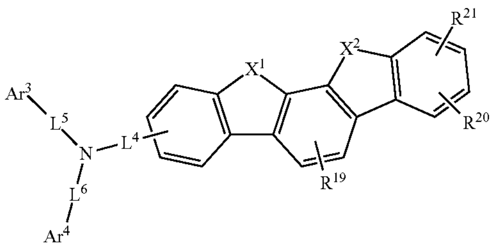

[Chemical Formula 2-VIA]

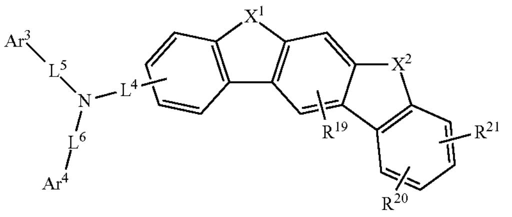

[Chemical Formula 2-VIIA]

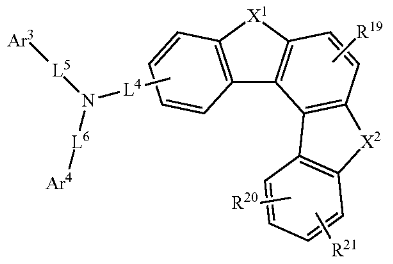

[Chemical Formula 2-VIIIA]

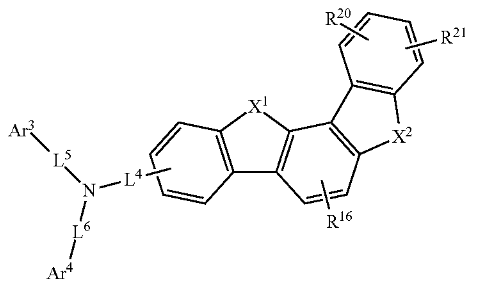

[Chemical Formula 2-IXA]

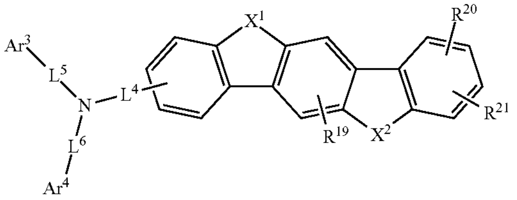

-continued

[Chemical Formula 2-IB]

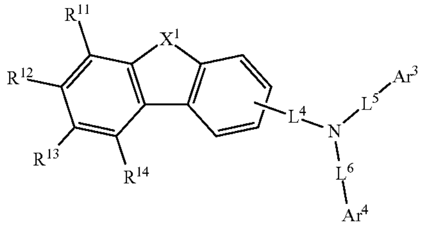

[Chemical Formula 2-VB]

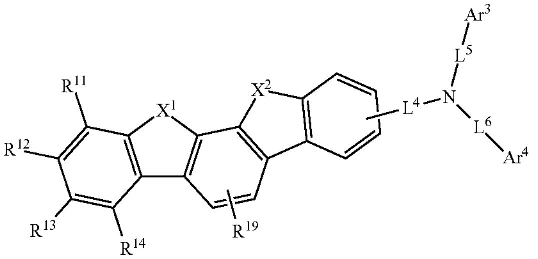

[Chemical Formula 2-VIB]

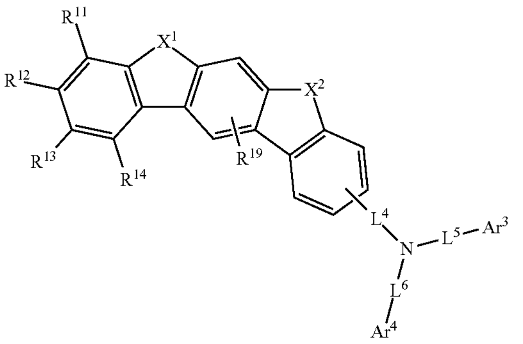

[Chemical Formula 2-VIIB]

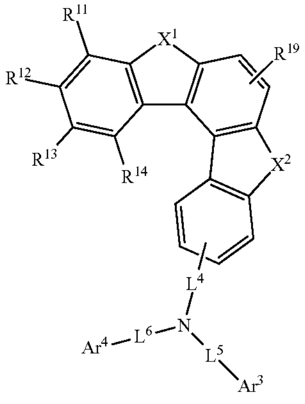

[Chemical Formula 2-IXB]

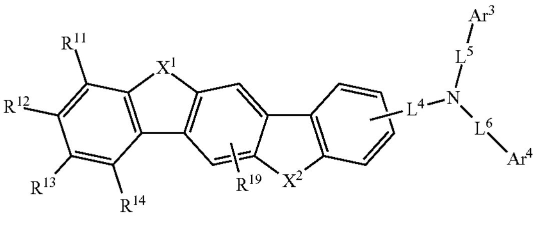

in Chemical Formula 2-IA, Chemical Formula 2-VA to Chemical Formula 2-IXA, Chemical Formula 2-IB, and Chemical Formula 2-VB to Chemical Formula 2-IXB, $X^1$, $X^2$, $L^4$ to $L^6$, $Ar^3$, and $Ar^4$ are the same as in claim 1, and $R^{11}$ to $R^{16}$ and $R^{19}$ to $R^{21}$ are each independently hydrogen, deuterium, a substituted or unsubstituted C1 to C30 alkyl group, or a substituted or unsubstituted C6 to C30 aryl group.

10. The composition of claim 1, wherein:

the second compound is represented by Chemical Formula 2-VIIIA-2 or Chemical Formula 2-VIIIB-2:

[Chemical Formula 2-VIIIA-2]

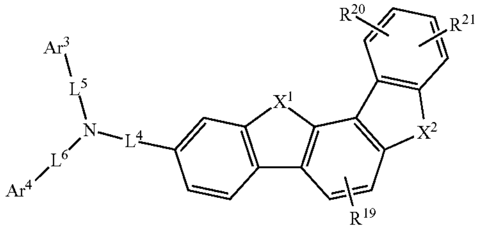

[Chemical Formula 2-VIIIB-2]

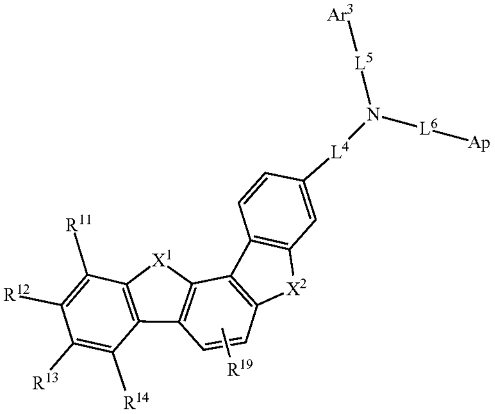

in Chemical Formula 2-VIIIA-2 and Chemical Formula 2-VIIIB-2, $L^4$ to $L^6$ are each independently a single bond or a substituted or unsubstituted phenylene group, $Ar^3$ and $Ar^4$ are each independently a substituted or unsubstituted phenyl group, a substituted or unsubstituted biphenyl group, or a substituted or unsubstituted naphthyl group, $X^1$ is $NR^a$, O, S, $CR^bR^c$, or $SiR^dR^e$, $X^2$ is O, S, $CR^gR^h$, or $SiR^iR^j$, $R^a$, $R^b$, $R^c$, $R^d$, $R^e$, $R^8$, $R^h$, $R^i$, and $R^j$ are each independently a substituted or unsubstituted C1 to C30 alkyl group, or a substituted or unsubstituted C6 to C30 aryl group, and $R^{11}$ to $R^{14}$ and $R^{19}$ to $R^{21}$ are each independently hydrogen, deuterium, a substituted or unsubstituted C1 to C30 alkyl group, a substituted or unsubstituted C6 to C30 aryl group or a substituted or unsubstituted C2 to C30 heterocyclic group.

11. An organic optoelectronic device, comprising an anode and a cathode facing each other, and at least one organic layer between the anode and the cathode, wherein the organic layer comprises a light emitting layer, and the light emitting layer comprises the composition for an organic optoelectronic device of claim 1.

12. The organic optoelectronic device of claim 11, wherein the composition for an organic optoelectronic device is included in the light emitting layer as a host.

13. A display device comprising the organic optoelectronic device of claim 11.

* * * * *